(12) United States Patent
Tilson et al.

(10) Patent No.: US 11,471,653 B2
(45) Date of Patent: Oct. 18, 2022

(54) INFLATABLE MEDICAL DEVICES

(71) Applicant: LOMA VISTA MEDICAL, INC., Tempe, AZ (US)

(72) Inventors: Alexander Quillin Tilson, Burlingame, CA (US); Mark Christopher Scheeff, San Francisco, CA (US)

(73) Assignee: LOMA VISTA MEDICAL, INC., Tempe, AZ (US)

(*) Notice: Subject to any disclaimer, the term of this patent is extended or adjusted under 35 U.S.C. 154(b) by 846 days.

(21) Appl. No.: 16/247,696

(22) Filed: Jan. 15, 2019

(65) Prior Publication Data

US 2019/0192832 A1 Jun. 27, 2019

Related U.S. Application Data

(63) Continuation of application No. 14/406,311, filed as application No. PCT/US2013/044561 on Jun. 6, 2013, now Pat. No. 10,195,403.

(60) Provisional application No. 61/656,404, filed on Jun. 6, 2012.

(51) Int. Cl.
| | |
|---|---|
| *A61M 25/10* | (2013.01) |
| *A61F 2/24* | (2006.01) |
| *A61F 2/958* | (2013.01) |
| *A61B 18/08* | (2006.01) |
| *A61B 18/14* | (2006.01) |
| *A61B 18/00* | (2006.01) |
| *A61M 29/02* | (2006.01) |

(52) U.S. Cl.
CPC ....... *A61M 25/1002* (2013.01); *A61B 18/082* (2013.01); *A61B 18/1492* (2013.01); *A61F 2/2433* (2013.01); *A61F 2/958* (2013.01); *A61M 25/1029* (2013.01); *A61B 2018/0022* (2013.01); *A61B 2018/00488* (2013.01); *A61M 25/104* (2013.01); *A61M 29/02* (2013.01); *A61M 2025/1031* (2013.01); *A61M 2025/1072* (2013.01); *A61M 2025/1079* (2013.01); *A61M 2025/1084* (2013.01); *A61M 2025/1093* (2013.01)

(58) Field of Classification Search
CPC .......... A61M 25/1002; A61M 25/1029; A61B 18/082; A61B 18/1492; A61B 2018/0022; A61F 2/2433; A61F 2/958
USPC .................................................. 604/103.07
See application file for complete search history.

(56) References Cited

U.S. PATENT DOCUMENTS

| | | | | |
|---|---|---|---|---|
| 2009/0038752 A1* | 2/2009 | Weng | ................ | A61M 25/1029 604/103.09 |
| 2011/0172698 A1* | 7/2011 | Davies, Jr | ........... | A61M 25/104 606/194 |

* cited by examiner

*Primary Examiner* — Phillip A Gray
(74) *Attorney, Agent, or Firm* — Dickinson Wright PLLC; Andrew D. Dorisio

(57) ABSTRACT

An inflatable balloon includes a base balloon having a cylindrical section and a conical section and at least one circumferential fiber extending circumferentially around the conical section. The inflatable balloon includes a plurality of reinforcing strips in the conical section over the at least one circumferential fiber. Each reinforcing strip includes a plurality of fibers extending at an angle relative to the at least one fiber. Each reinforcing strip is positioned a set circumferential distance away from a neighboring reinforcing strip.

21 Claims, 78 Drawing Sheets

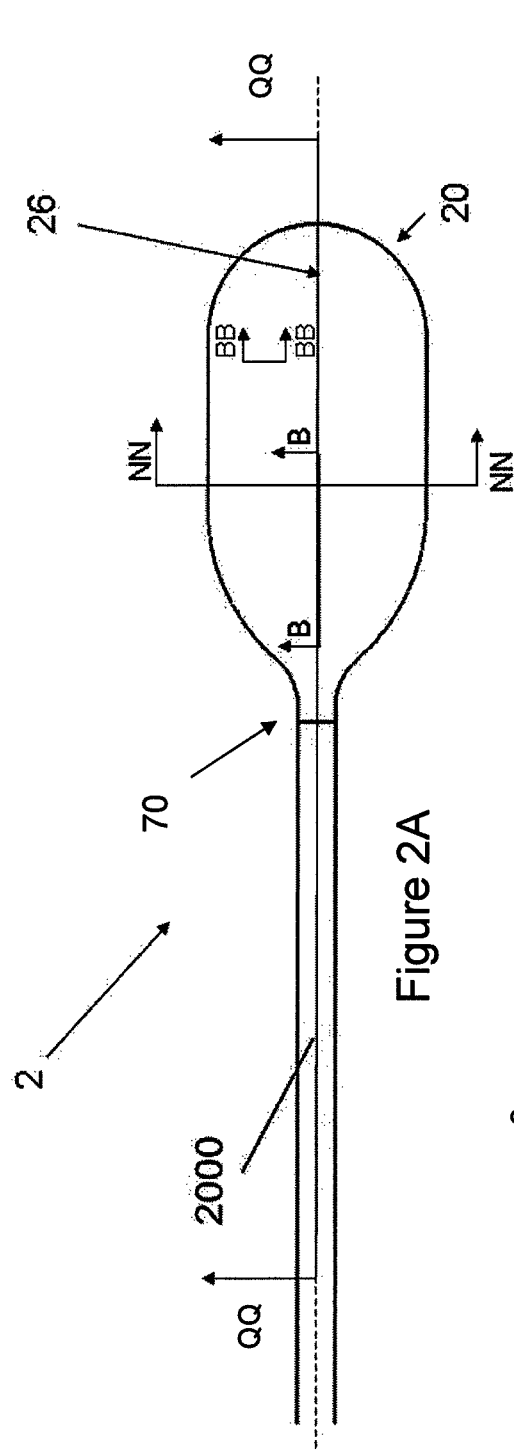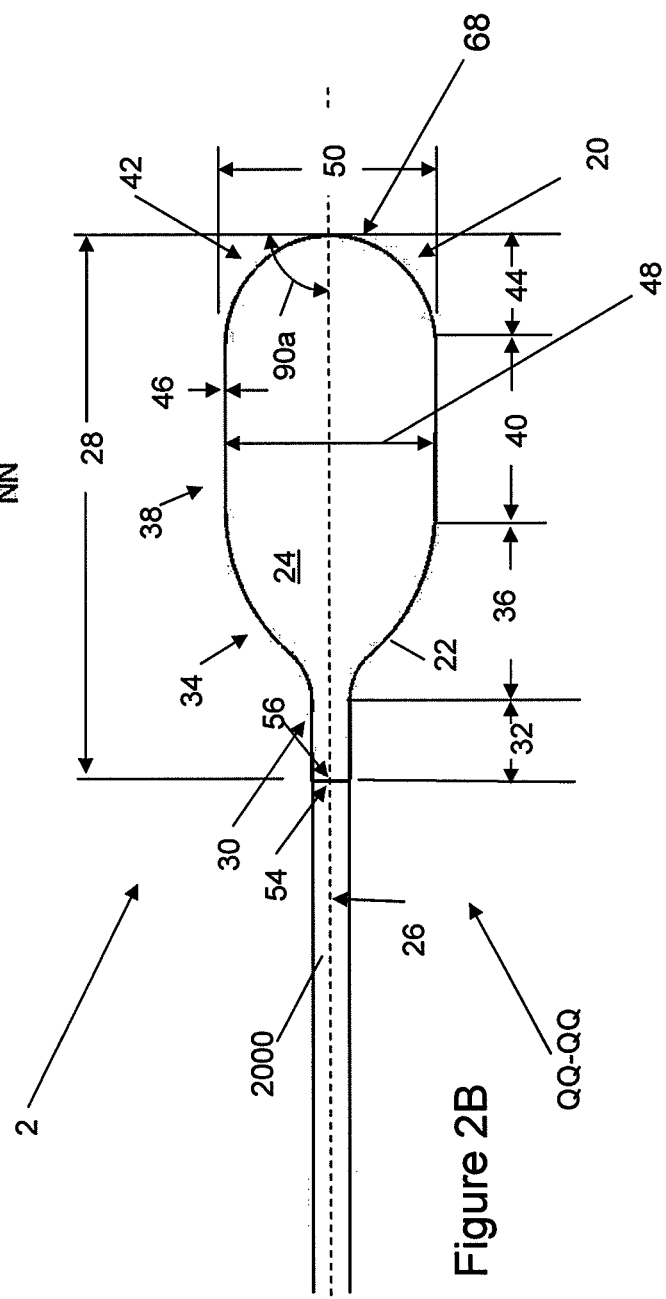
Figure 2A
Figure 2B

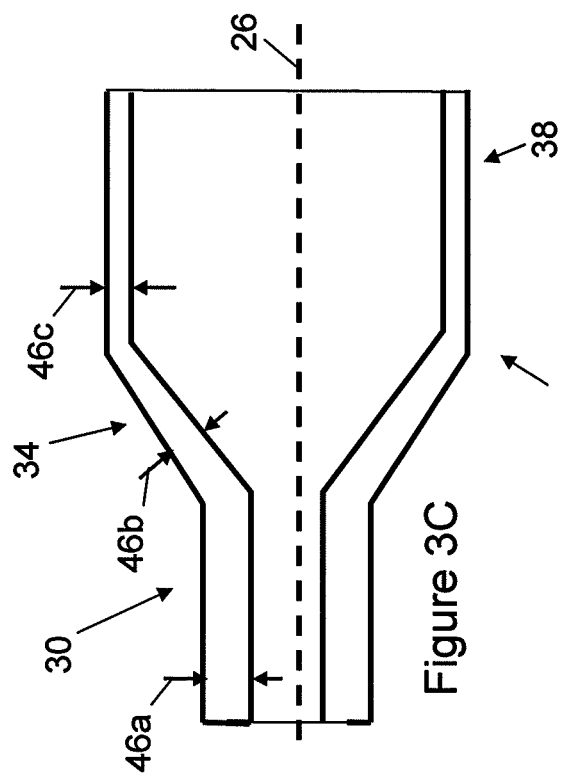
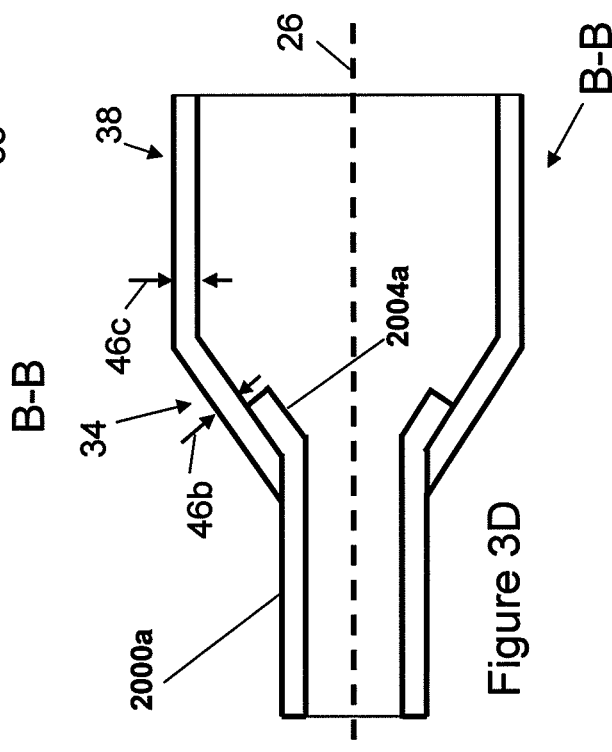
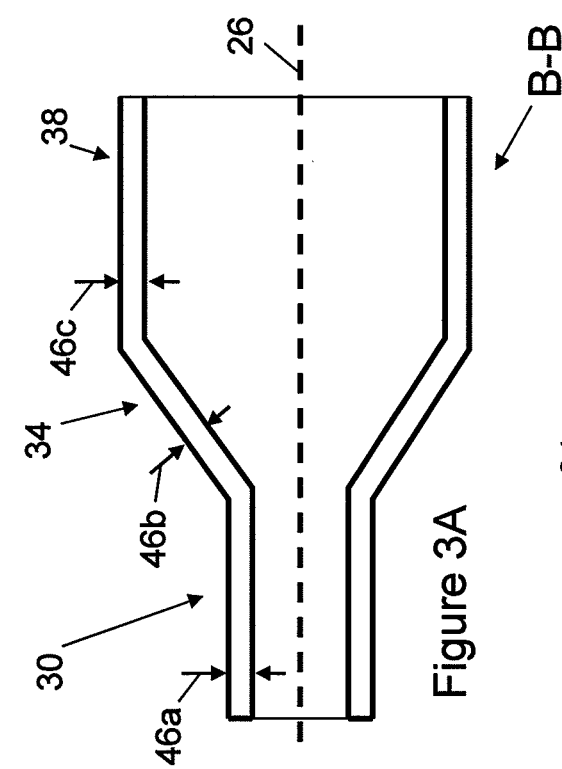
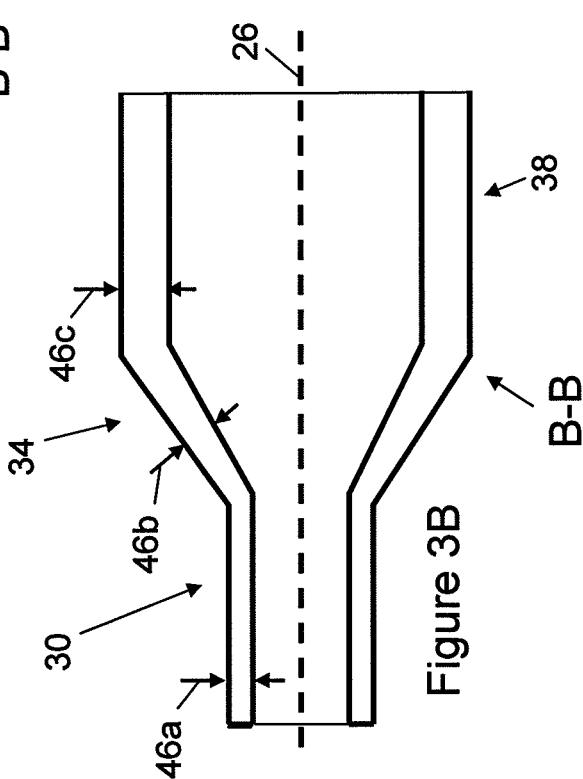

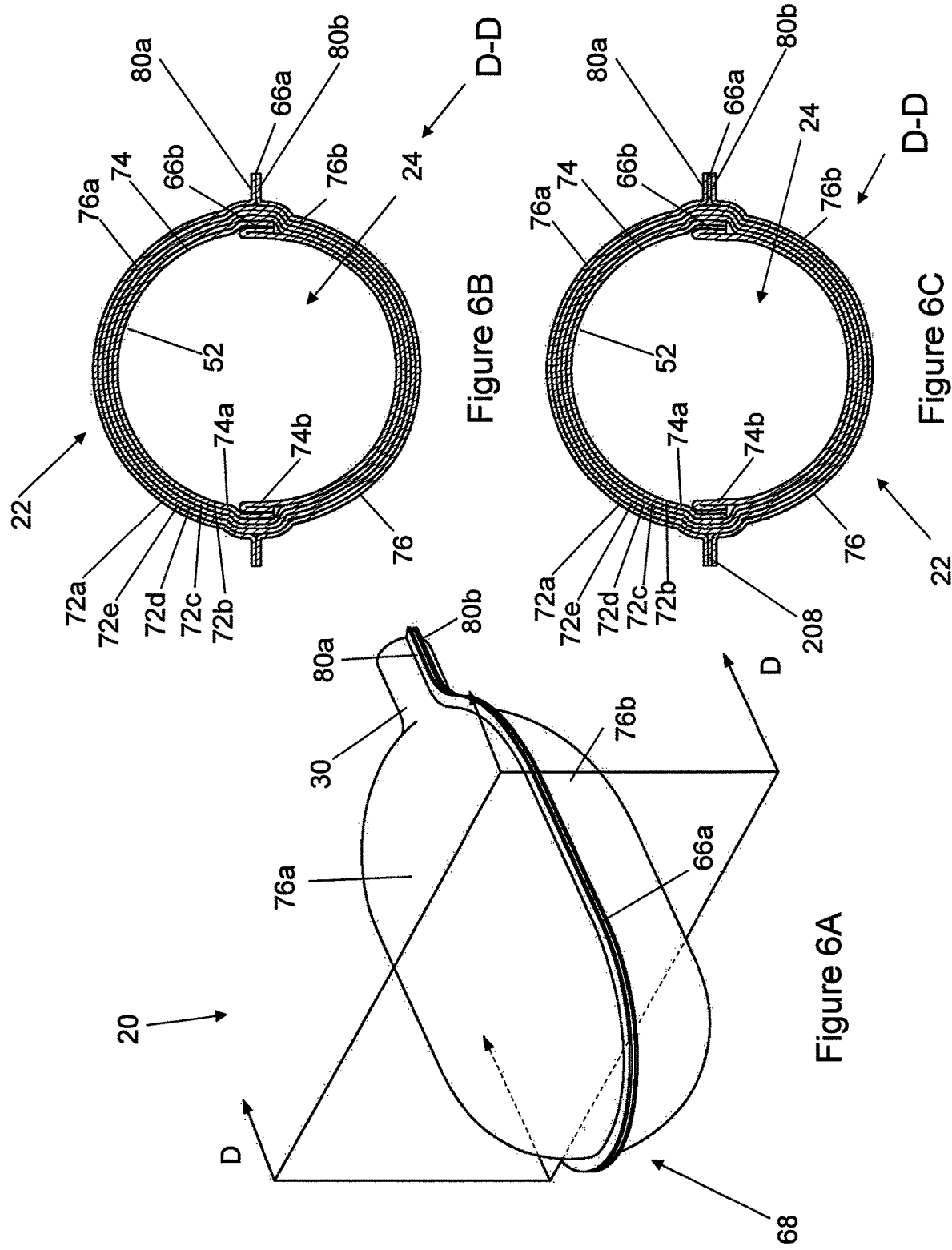

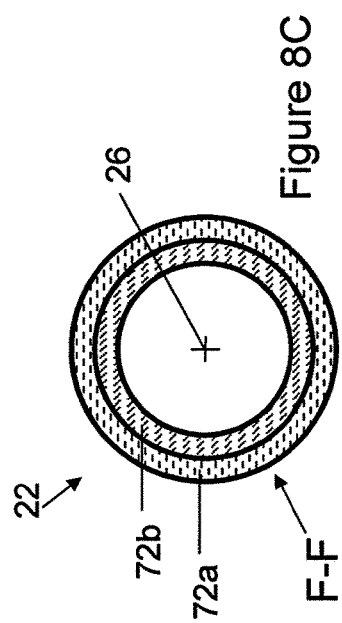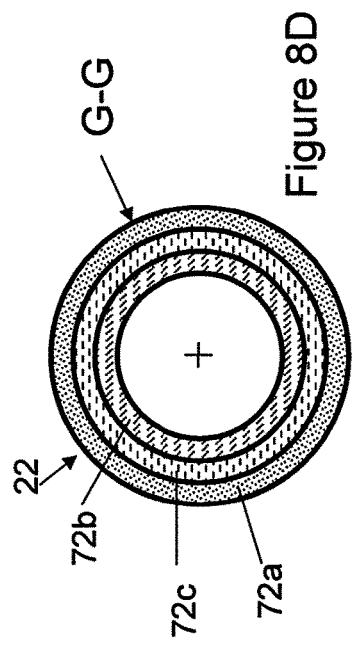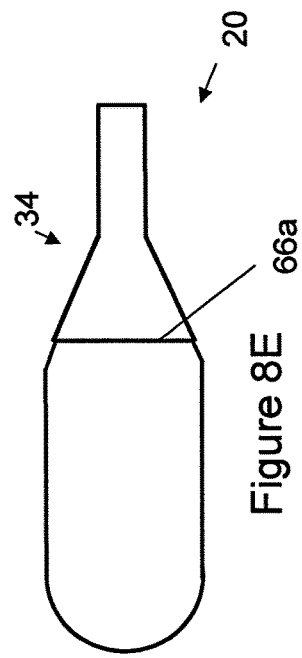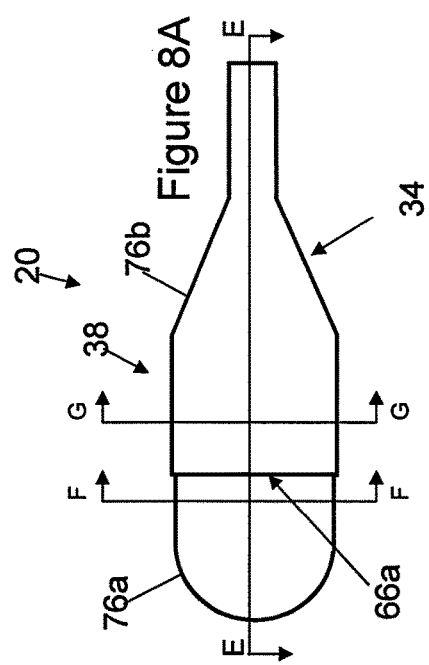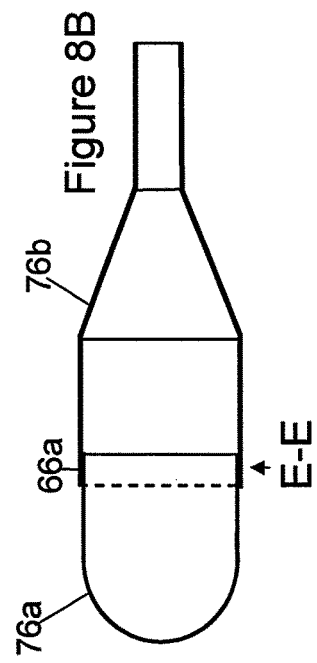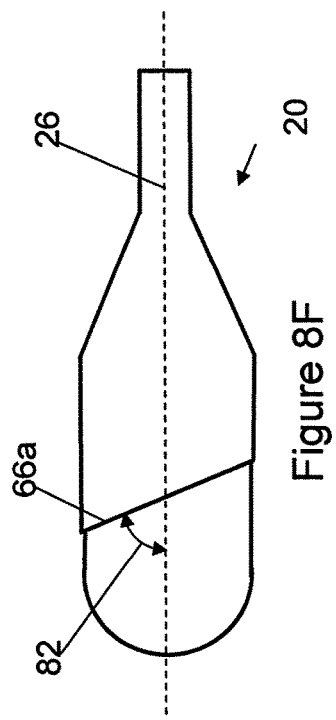

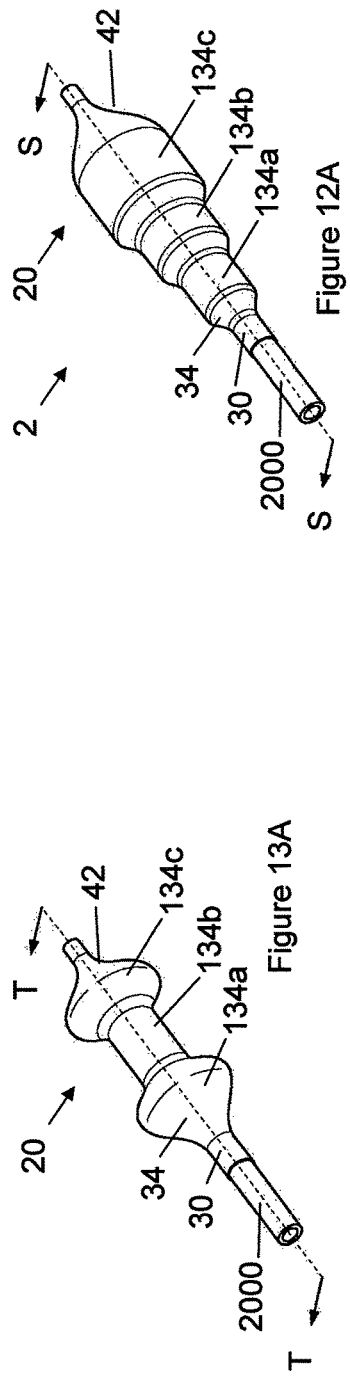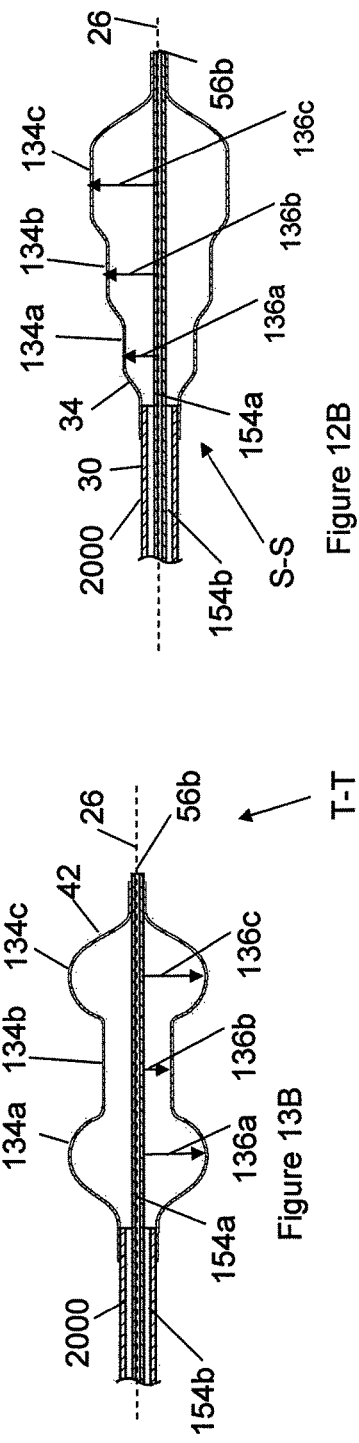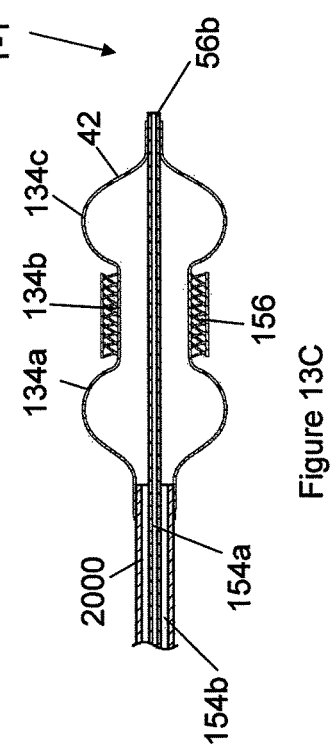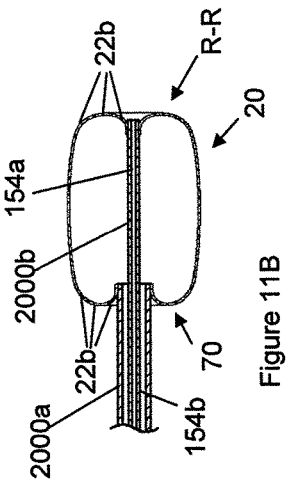

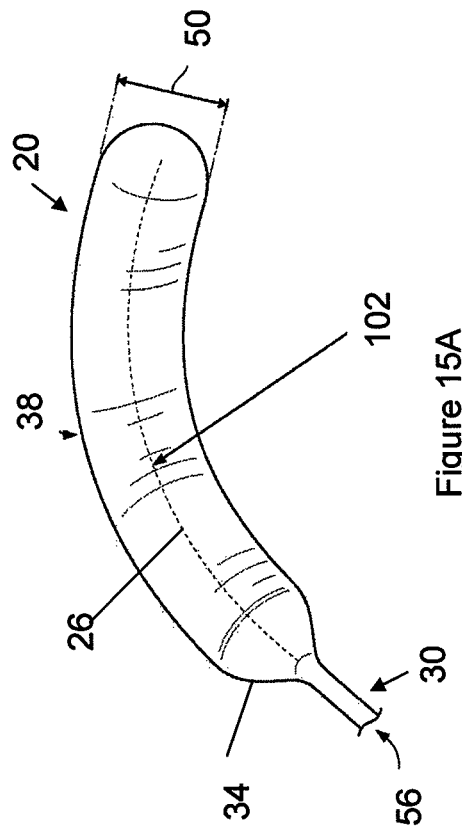
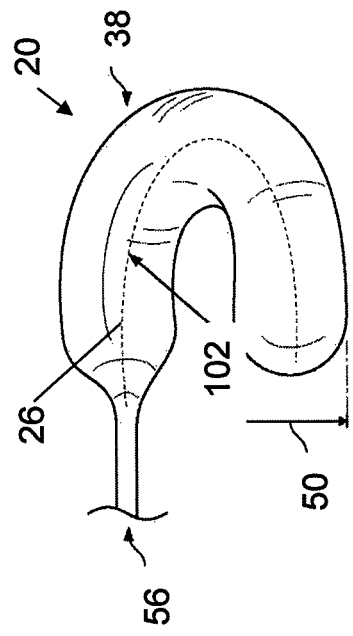
Figure 15A
Figure 15B
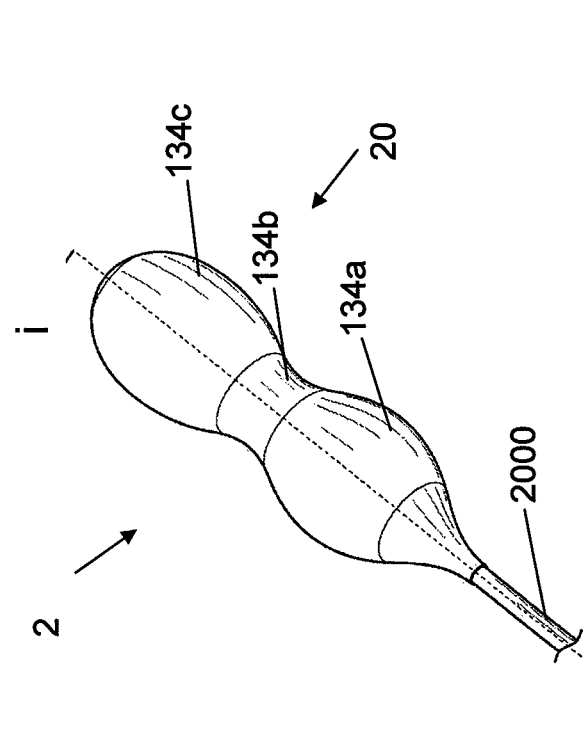
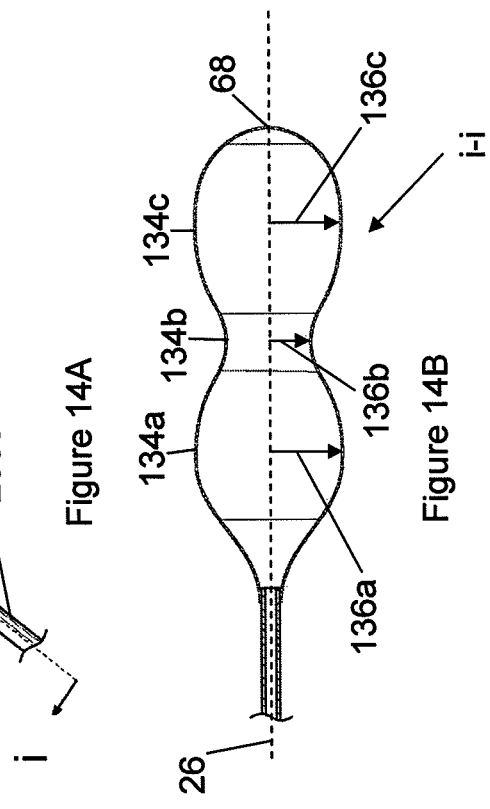
Figure 14A
Figure 14B

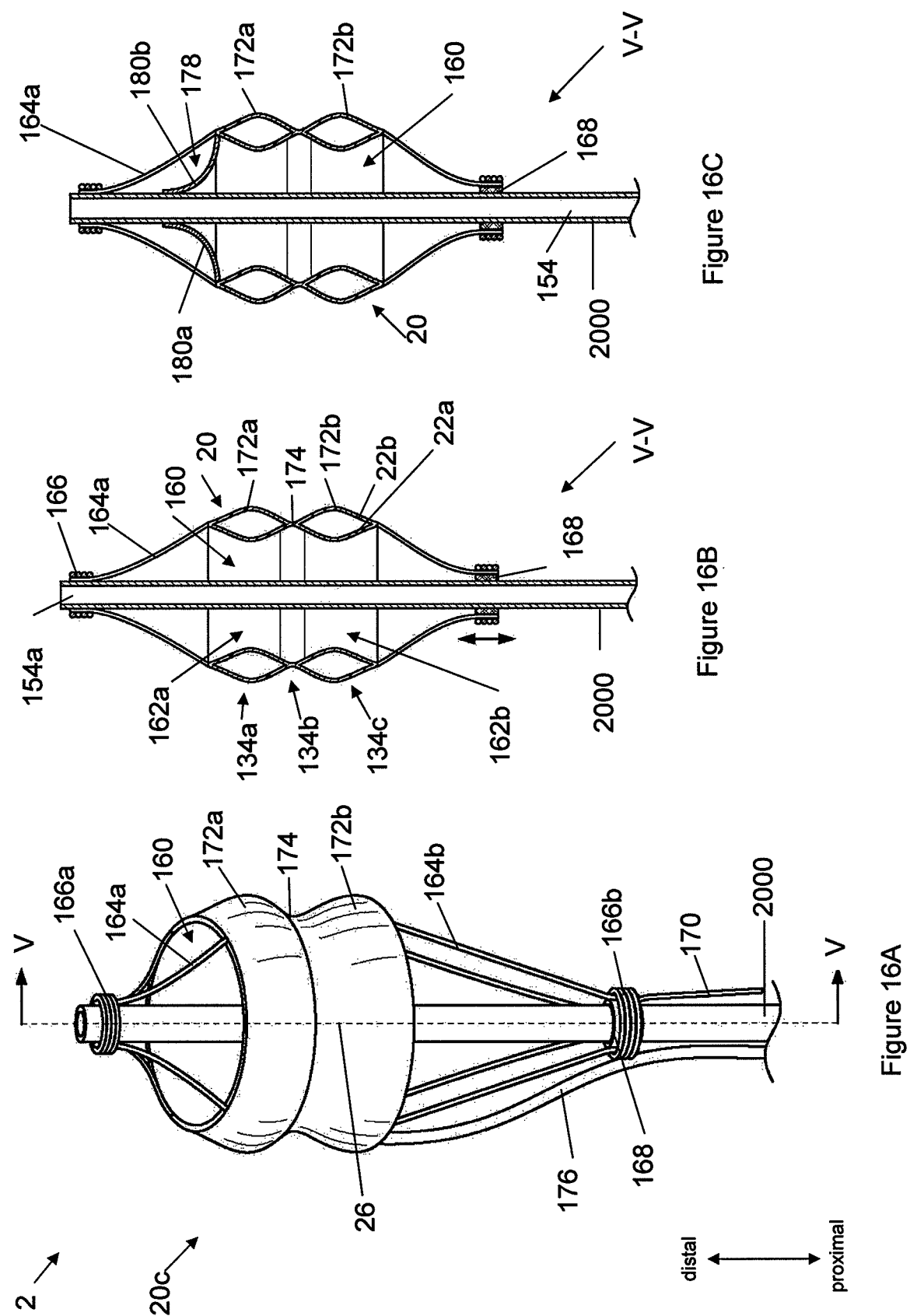

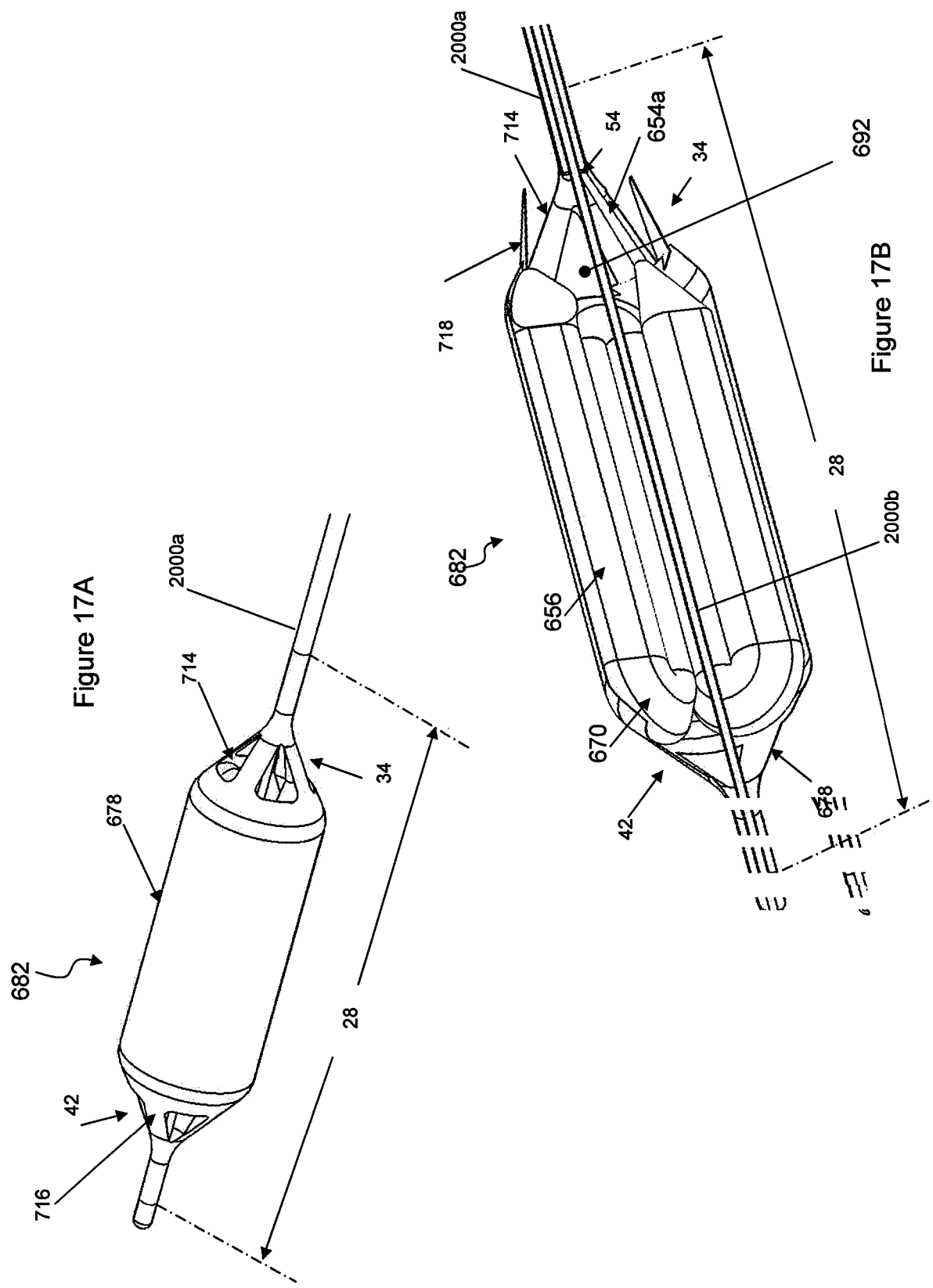

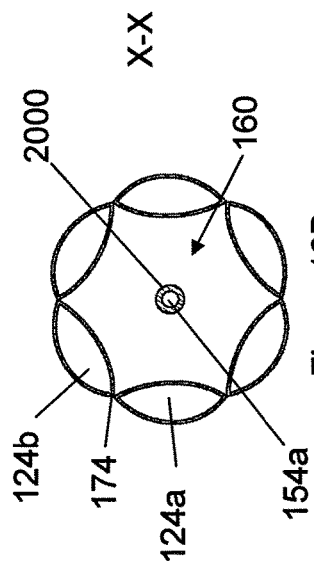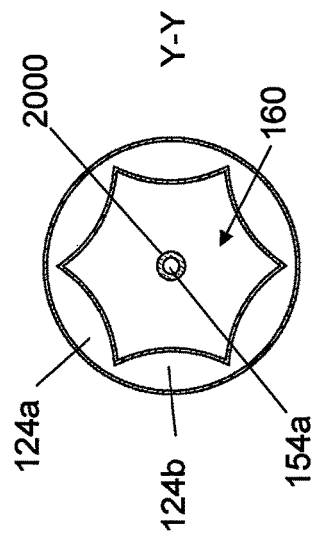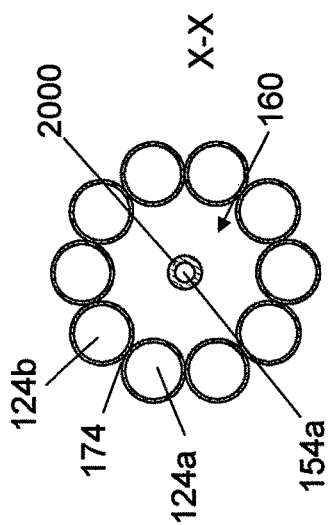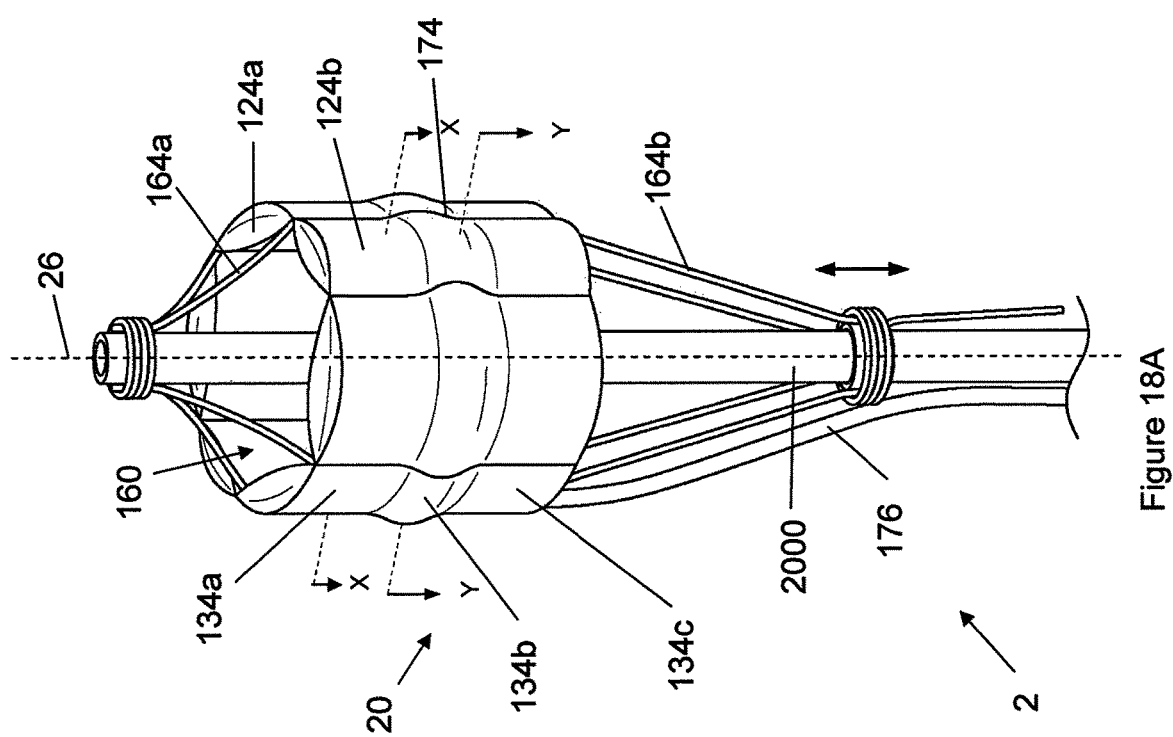

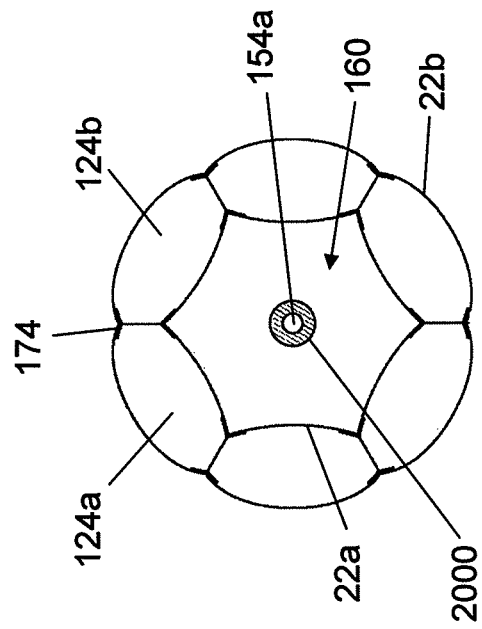
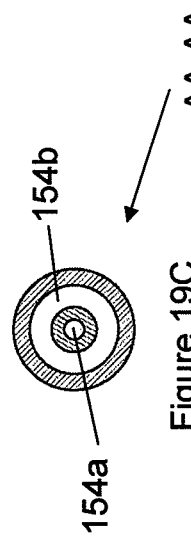
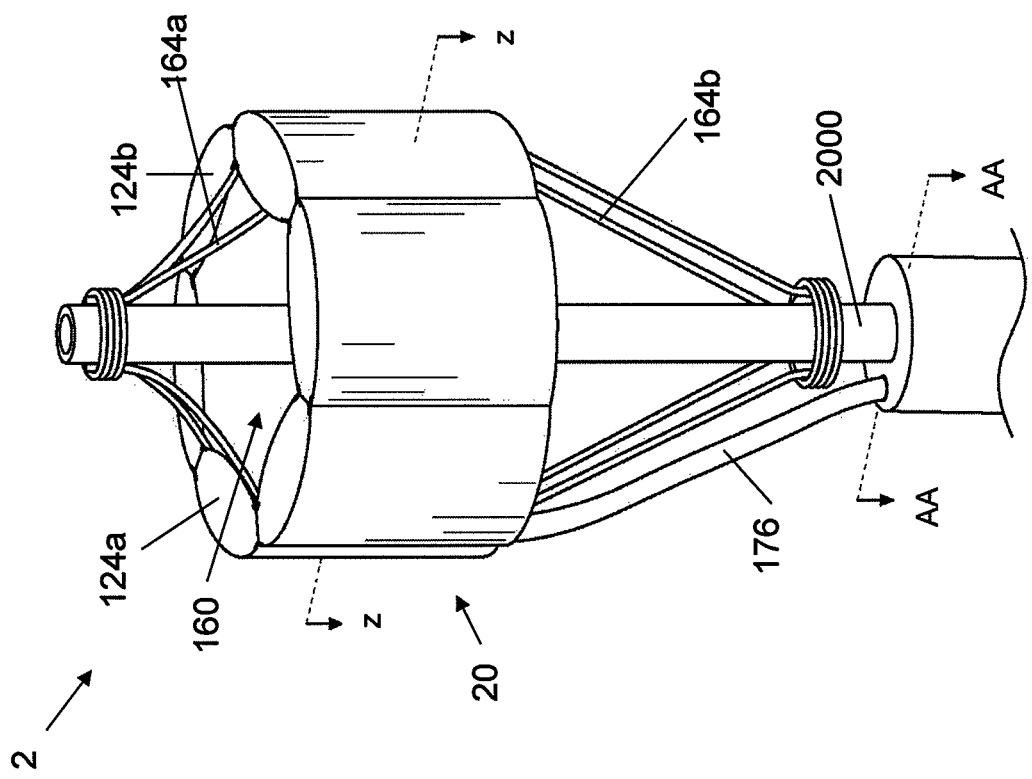

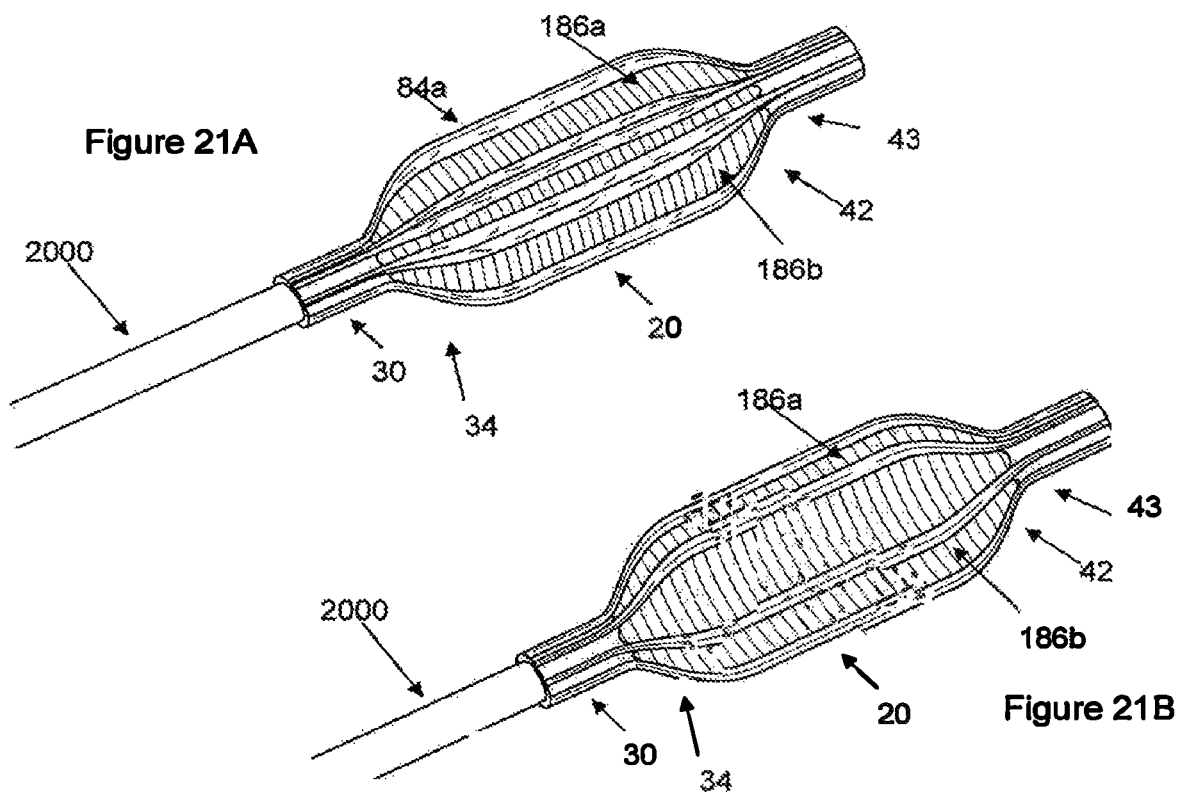
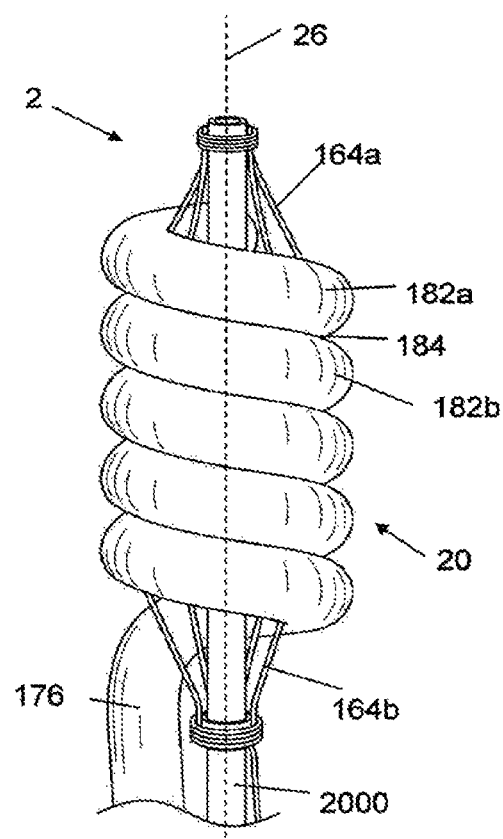

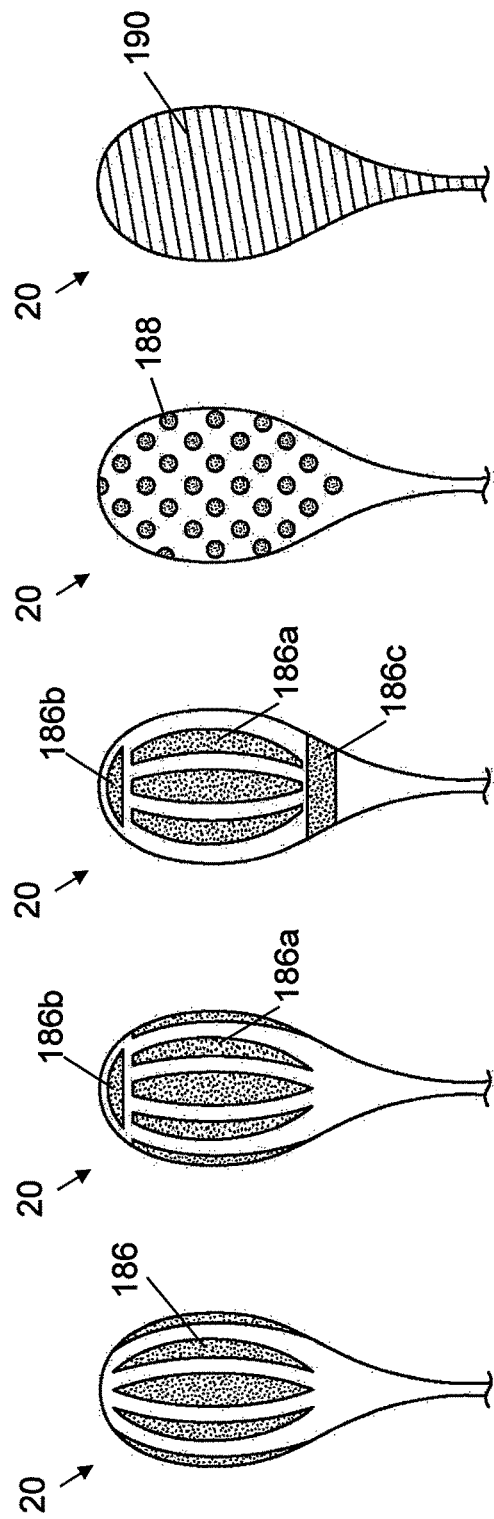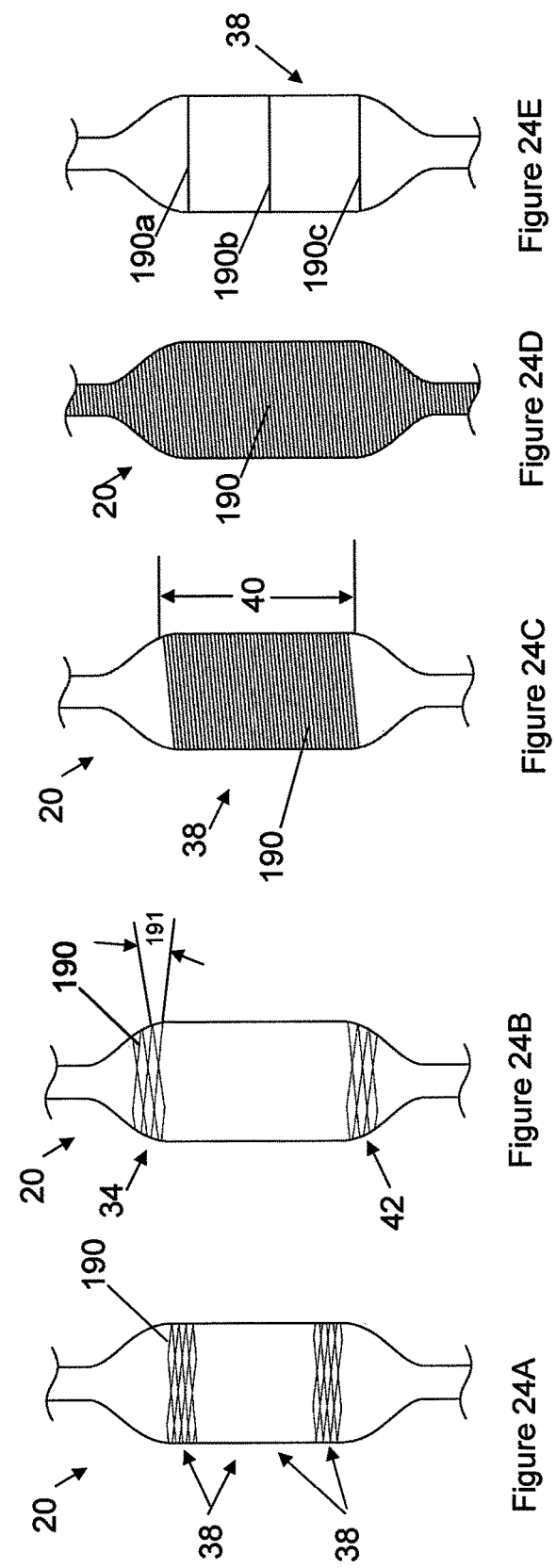

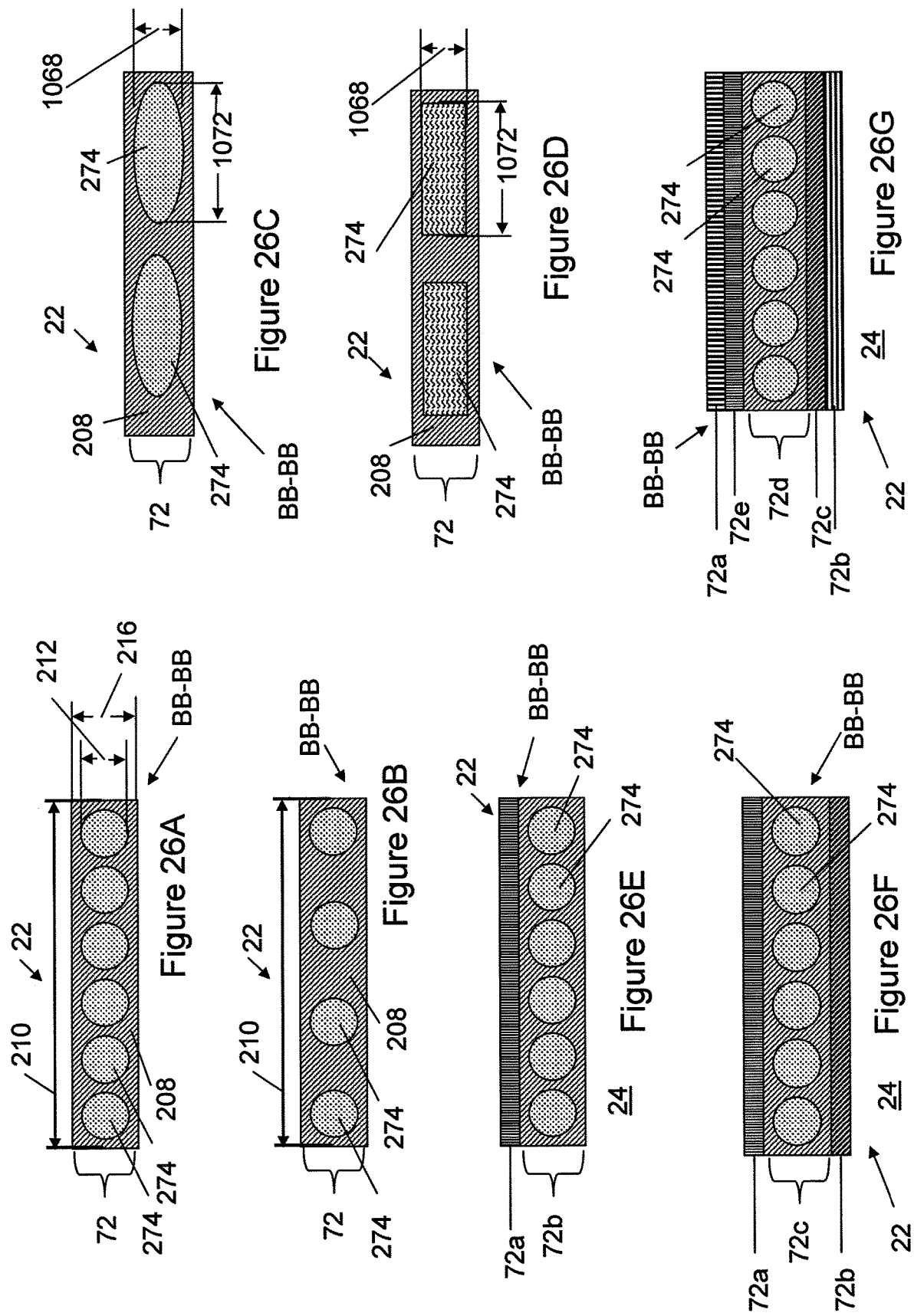

Film Materials

| Type | Sample Manufacturer or Supplier |
|---|---|
| Co-Polyamide | Deerfield Urethane, USA |
| Co-Polyester | Deerfield Urethane, USA |
| ECTFE | Saint-Gobain, France |
| FEP (Fluoroethylene-propylene) | DuPont, USA |
| Kapton | DuPont, USA |
| HDPE | Dow Chemical, USA |
| LDPE | Lyondell Chemical, USA |
| Mylar / PET (Polyethylene Terephthalate) / Polyester | DuPont, USA |
| Nylon | Honeywell, USA |
| PEEK | Victrex, UK |
| PEN (Polyethylene Naphthalate) | DuPont, USA |
| Tedlar (PVF) | DuPont, USA |
| Thermoplastic Polyurethane (TPU) | Deerfield Urethane, USA |
| Vectran (LCP (Liquid Crystal Polymer)) | Hoechst-Celanese, USA |
| Solef | Solvay, Italy |
| Parylene | Para Tech Coating, USA |

Figure 27

Reinforcement material

| Type | Sample Manufacturer or Supplier |
|---|---|
| Vectran | Hoechst-Celanese, USA |
| PBO | Toyobo, Japan |
| Spectra | Allied Signal, USA |
| Conex | Teijin, Japan |
| Dyneema | DSM, Netherlands |
| Technora | Teijin, Japan |
| Dacron | DuPont, USA |
| Polyester | Hoechst-Celanese, USA |
| Compet | Allied Signal, USA |
| Nylon | DuPont, USA |
| PEEK | ICI-Fiberite, USA |
| PPS | Phillips Petroleum, USA |
| Boron Fiber | AVCO-Textron, USA |
| Ceramic Fiber | AVCO-Textron, USA |
| Kevlar | DuPont, USA |
| Inorganic Carbon/Carbon Fiber | Hercules Inc., USA |
| Inorganic Silicon/high strength fiberglass | Owens Corning Fiber, USA |
| Organic Polymer/Aramid | DuPont, USA |
| Twaron | Teijin, Japan |
| Tungsten and and its alloys | California Fine Wire, USA |
| Molybdenumand and its alloys | California Fine Wire, USA |
| Stainless Steel(302, 304, 316, 316L and other alloys) | California Fine Wire, USA |
| Nickel/cobalt alloys | California Fine Wire, USA |
| Titanium and its alloys | California Fine Wire, USA |
| Nitinol alloys | NDC, USA |

Figure 28

Adhesive and Matrix Materials

| Type | Sample Manufacturer or Supplier |
|---|---|
| Urethanes | Hysol, USA |
| Polyesters | Thiokol, USA |
| Silicones | Dow Chemical, USA |
| Polypropylene | Honam Petrochemical, South Korea |
| Polyolefins | INEOS, UK |
| ULDPE, VLDPE, LDPE | ExxonMobil, USA |
| Nylon | Ashley Polymers, USA |
| Epoxies | Hysol, USA |
| Pebax | Arkema, USA |
| Tefzel | Dupont, USA |
| EVA | Dupont, USA |
| Solef | Solvay, Italy |
| Parylene | Para Tech Coating, USA |

Figure 29

| Properties | Eutectics | | | | | | Non-Eutectics | | | |
|---|---|---|---|---|---|---|---|---|---|---|
| | Low | Low | Low | Low | Low | Low | Low | Low | Low | Low |
| Melting Temperature (°F) | 117 | 136 | 158 | 255 | 281 | 158-190 | 217-440 | 281-338 |
| Range °F | 117-117 | 136 | 158-158 | 255-255 | 281-281 | 158-190 | 217-440 | 281-338 |
| Yield Temp °F | 117 | 136 | 158 | 255 | 281 | 162.5 | 240 | 302 |
| Range °C | 47-47 | 58-58 | 70-70 | 124-124 | 138-138 | 70-88 | 103-227 | 138-170 |
| Yield Temp °C | 47 | 58 | 70 | 124 | 138 | 72 | 116 | 150 |
| Tensile Strength Lbs/In² | 5400 | 6300 | 5990 | 6400 | 8000 | 5400 | 13000 | 8000 |
| %Elongation in slow Loading | 1.5 | 50 | 200 | 60-70 | 200 | 220 | <1% | 200 |
| Brinell Hardness No. | 12 | 14 | 9.2 | 10.2 | 22 | 9 | 19 | 22 |

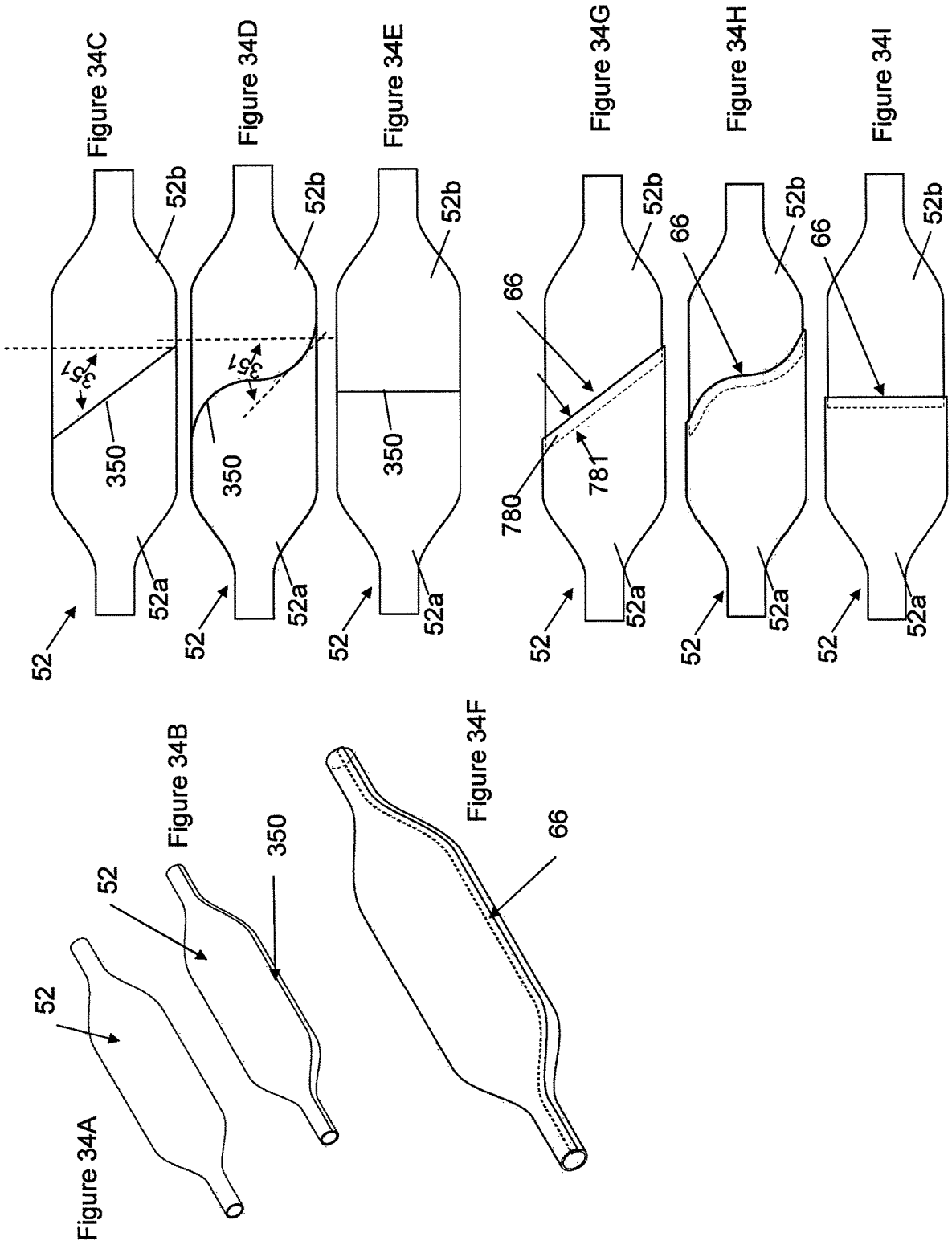

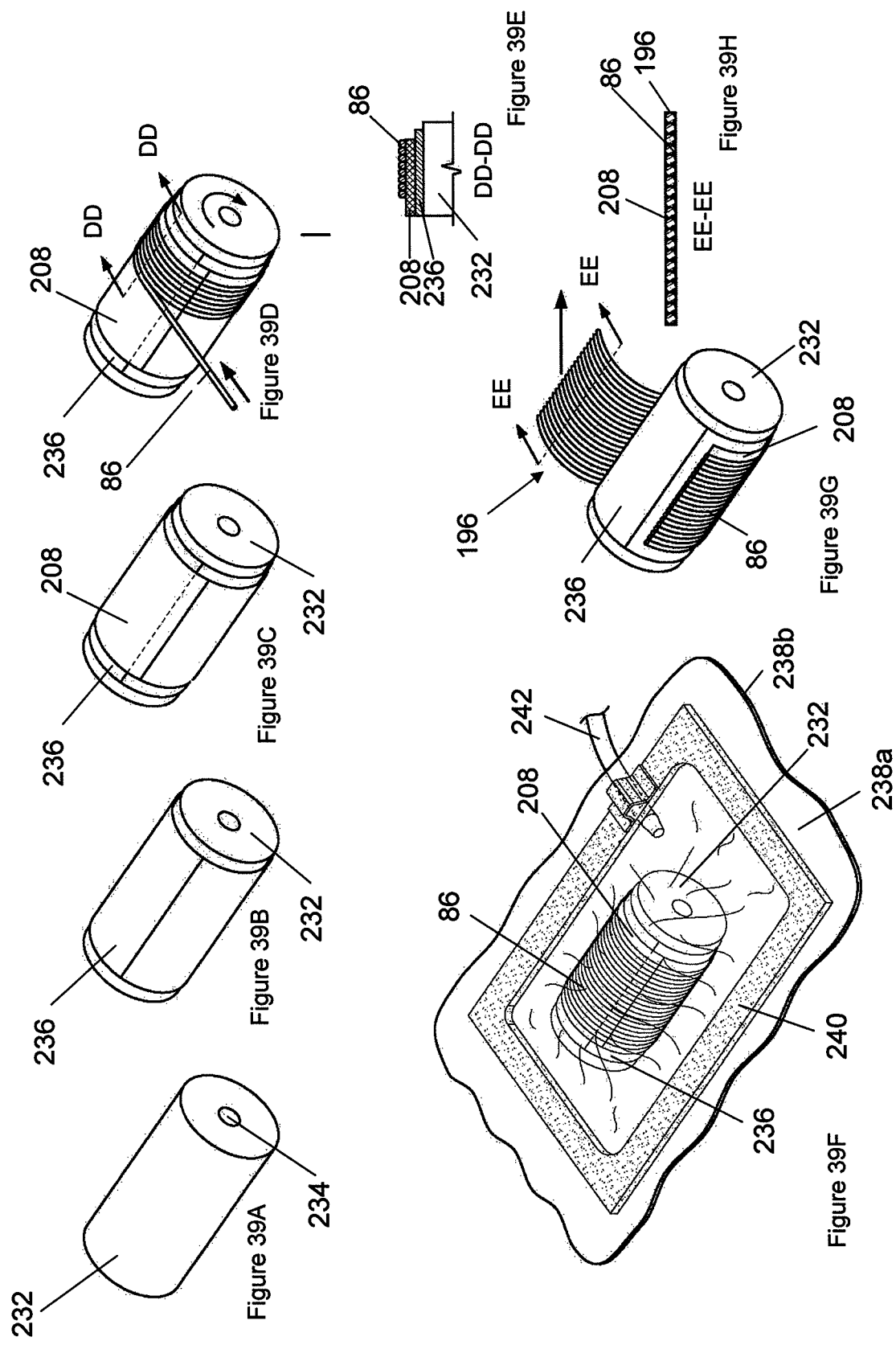

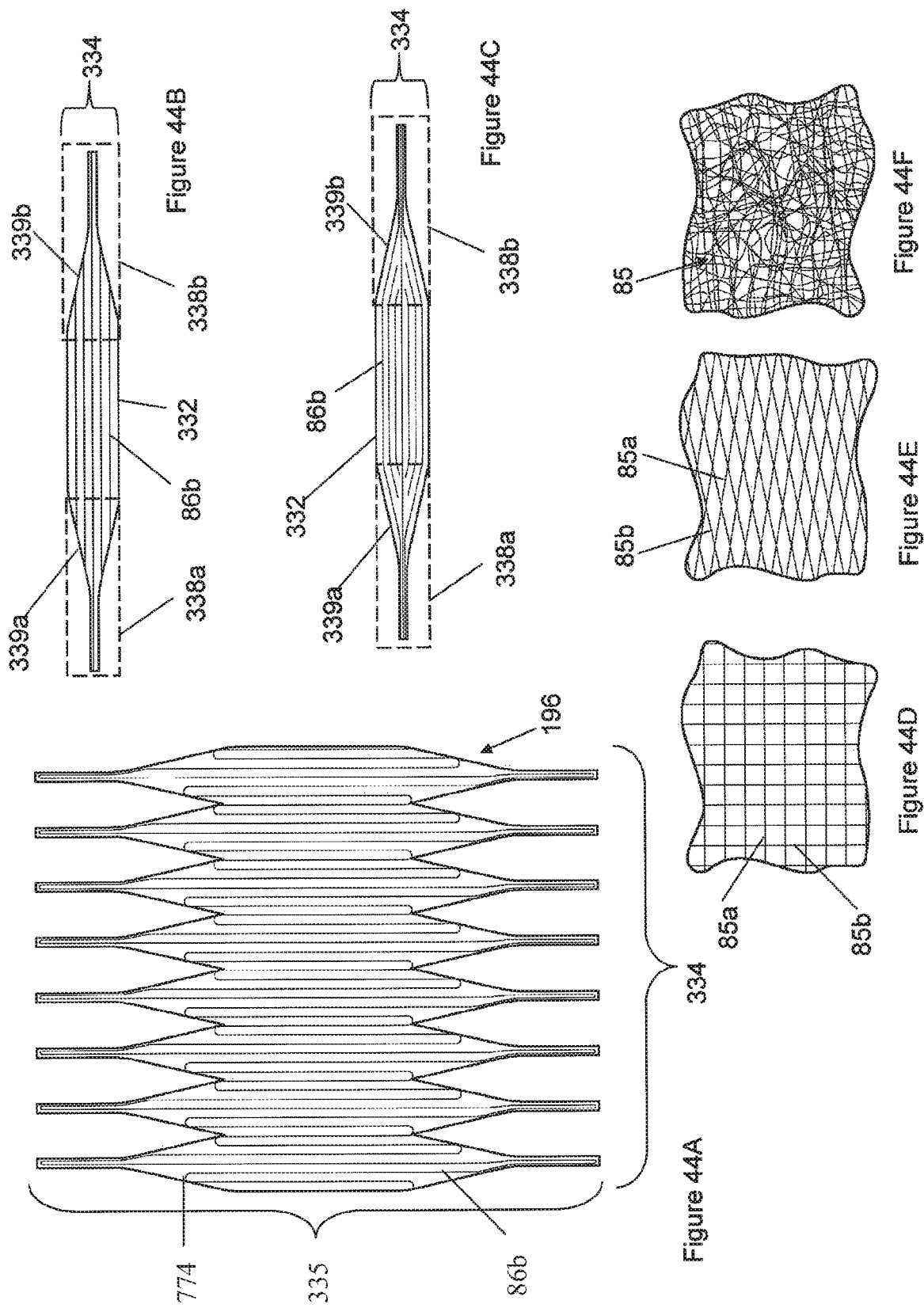

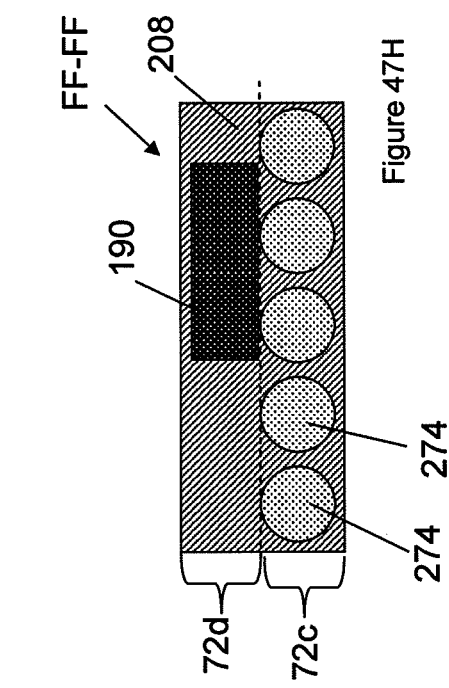
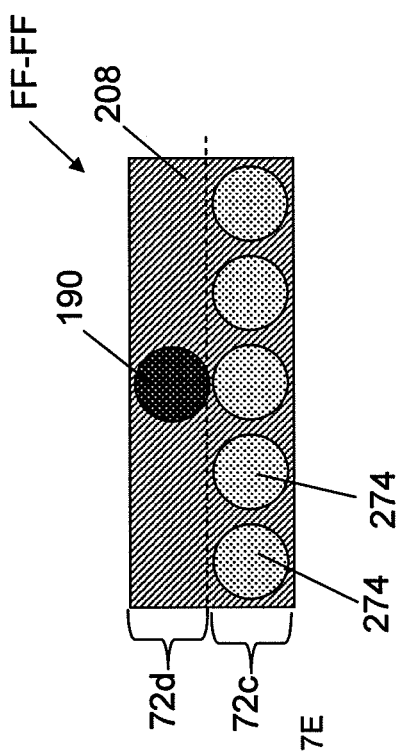
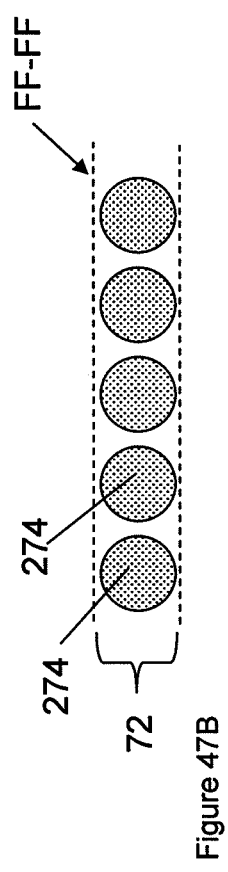
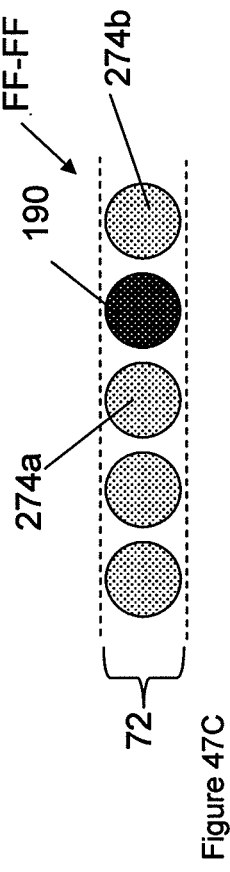
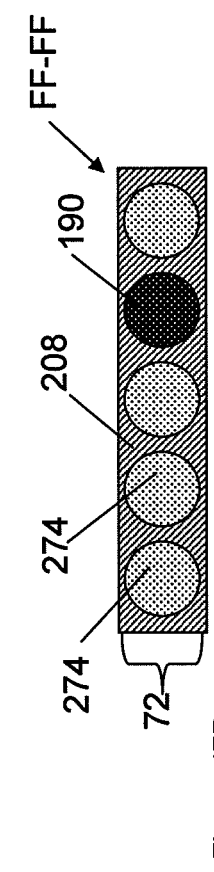
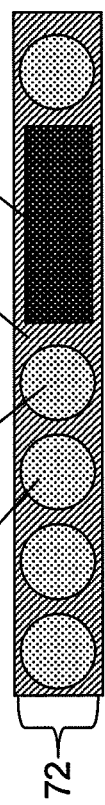

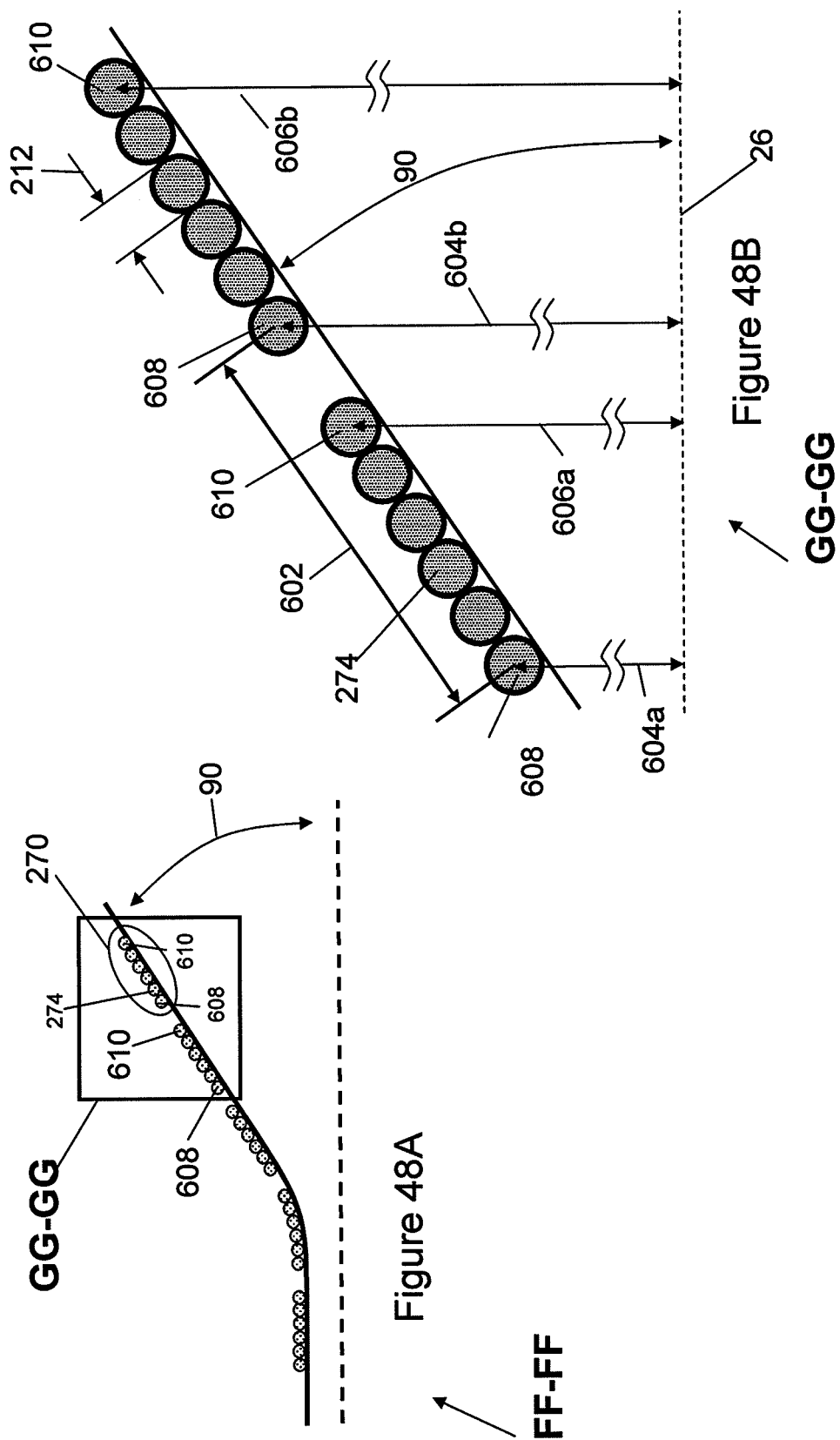

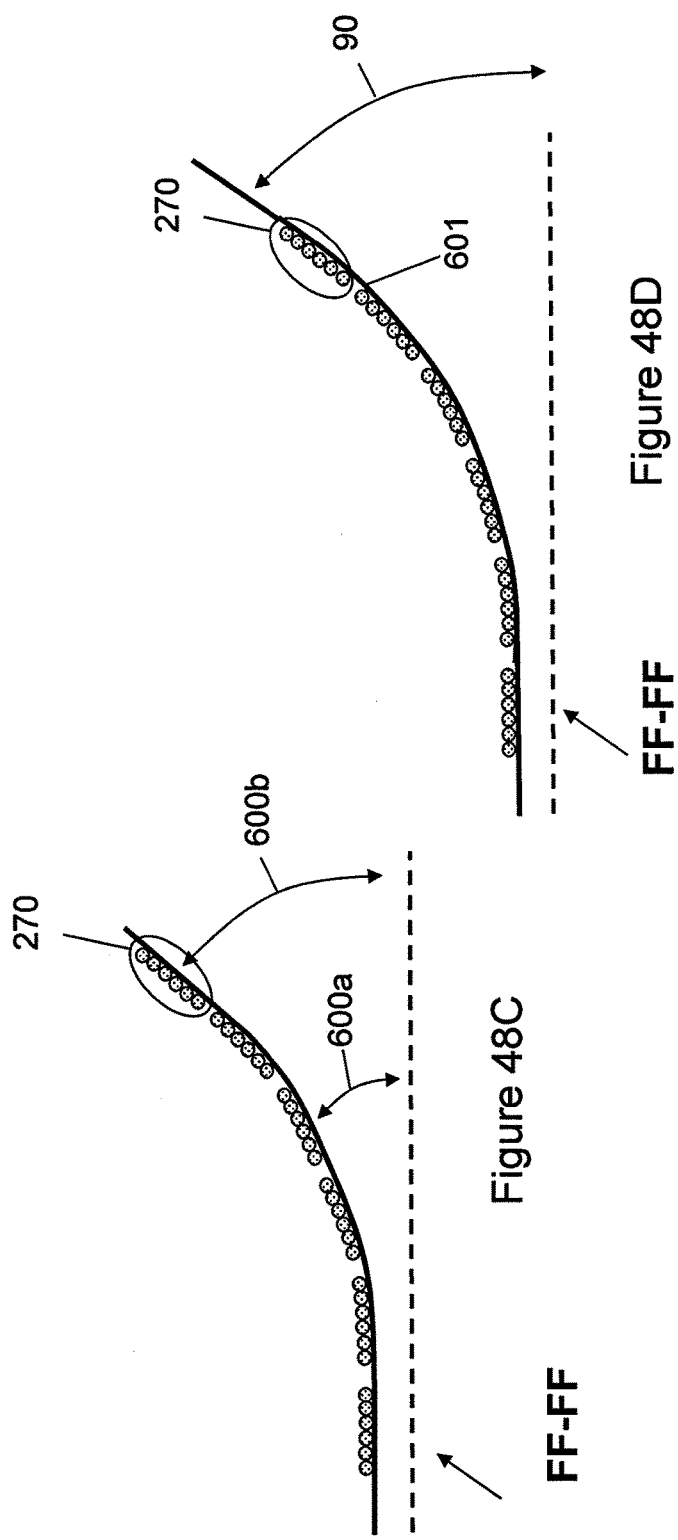
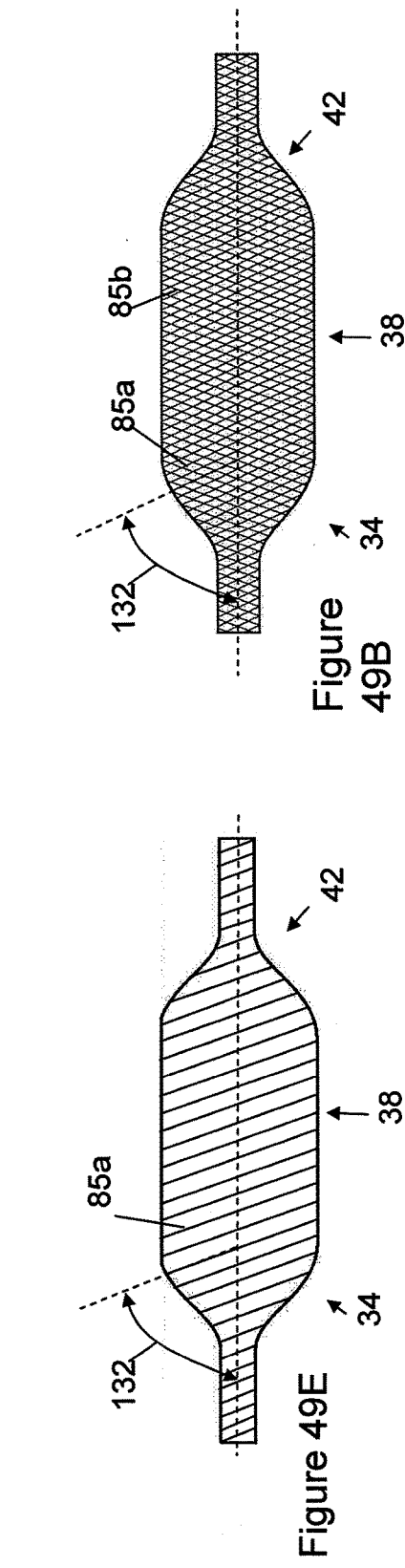

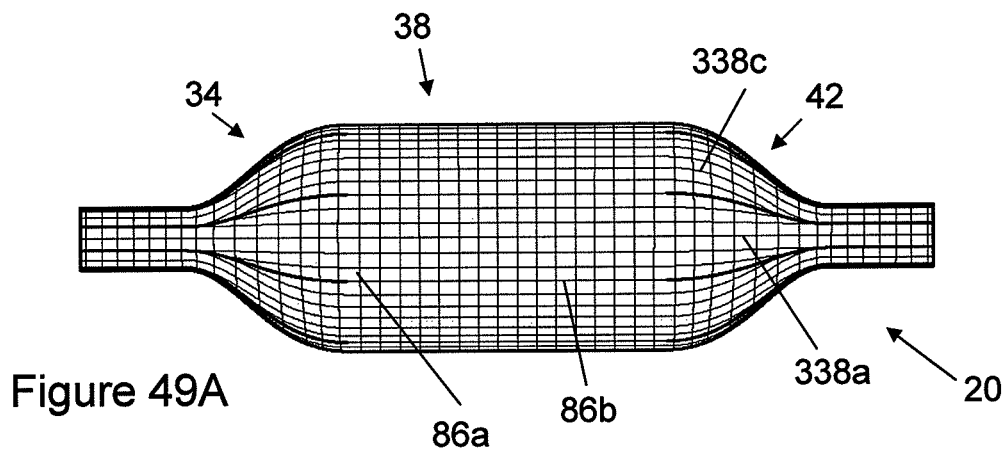
Figure 49A
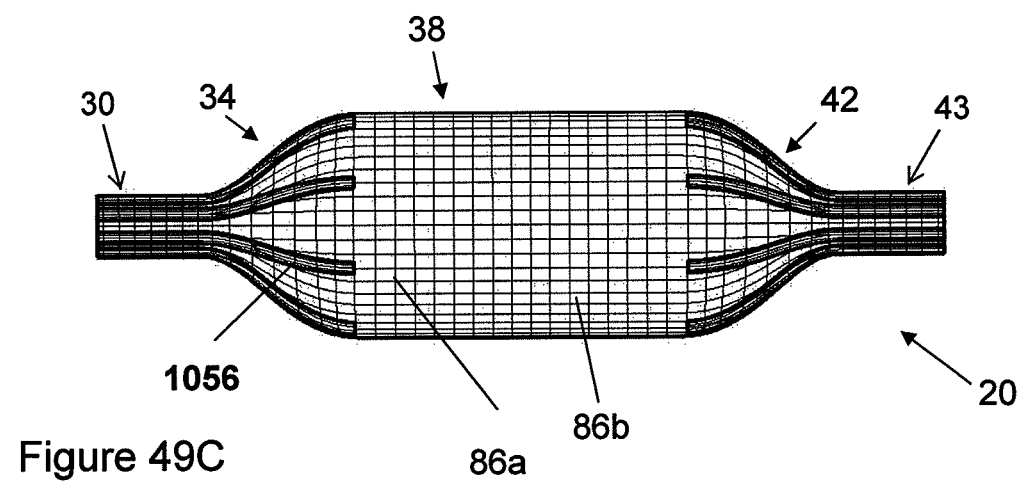
Figure 49C
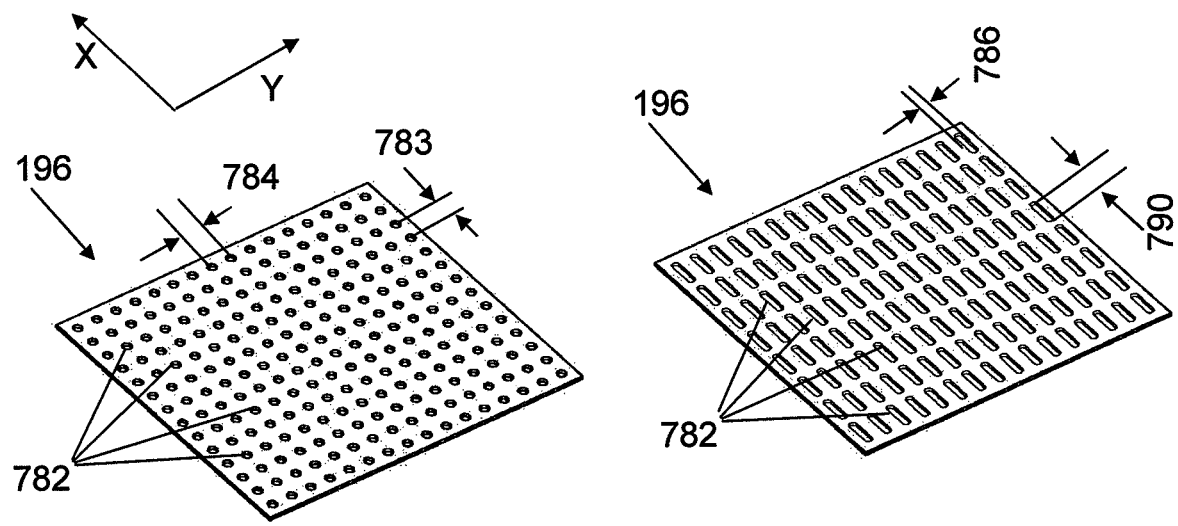
Figure 50A
Figure 50B

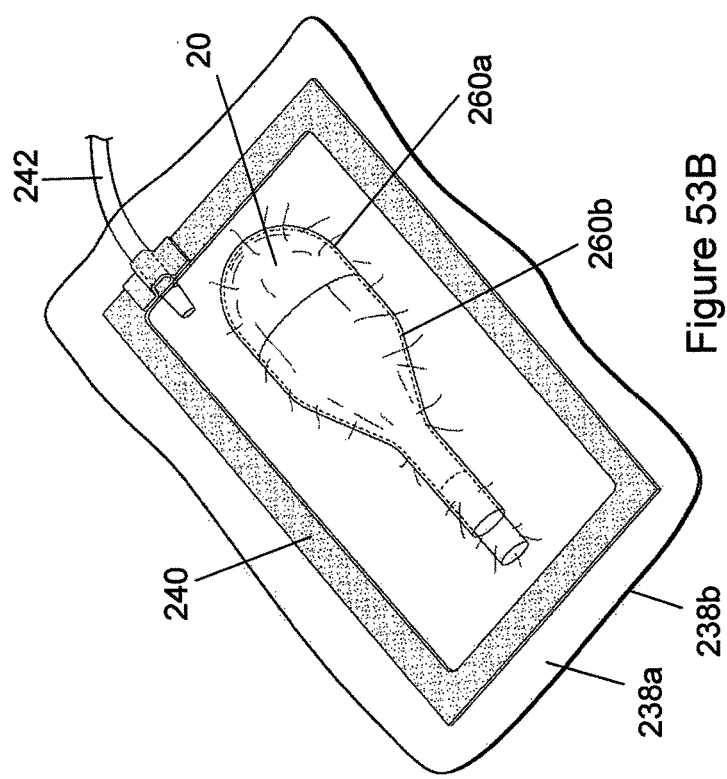
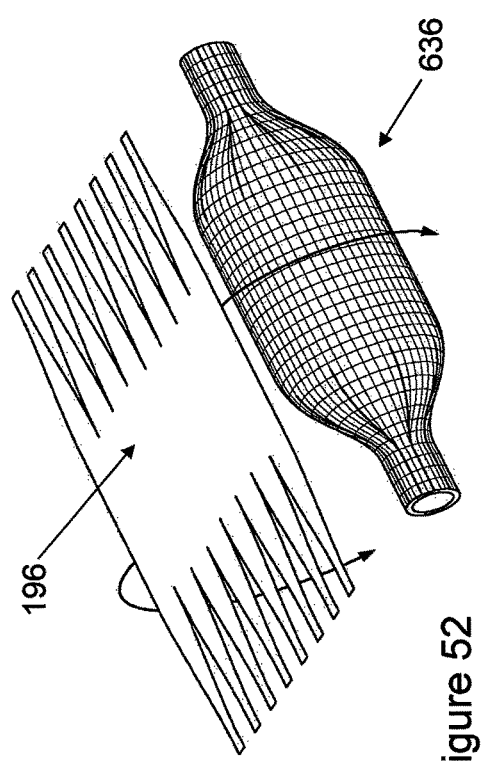
Figure 52
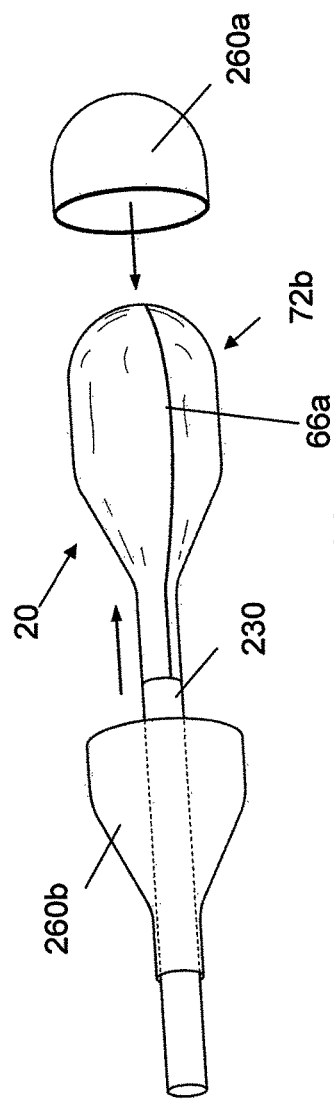
Figure 53A
Figure 53B

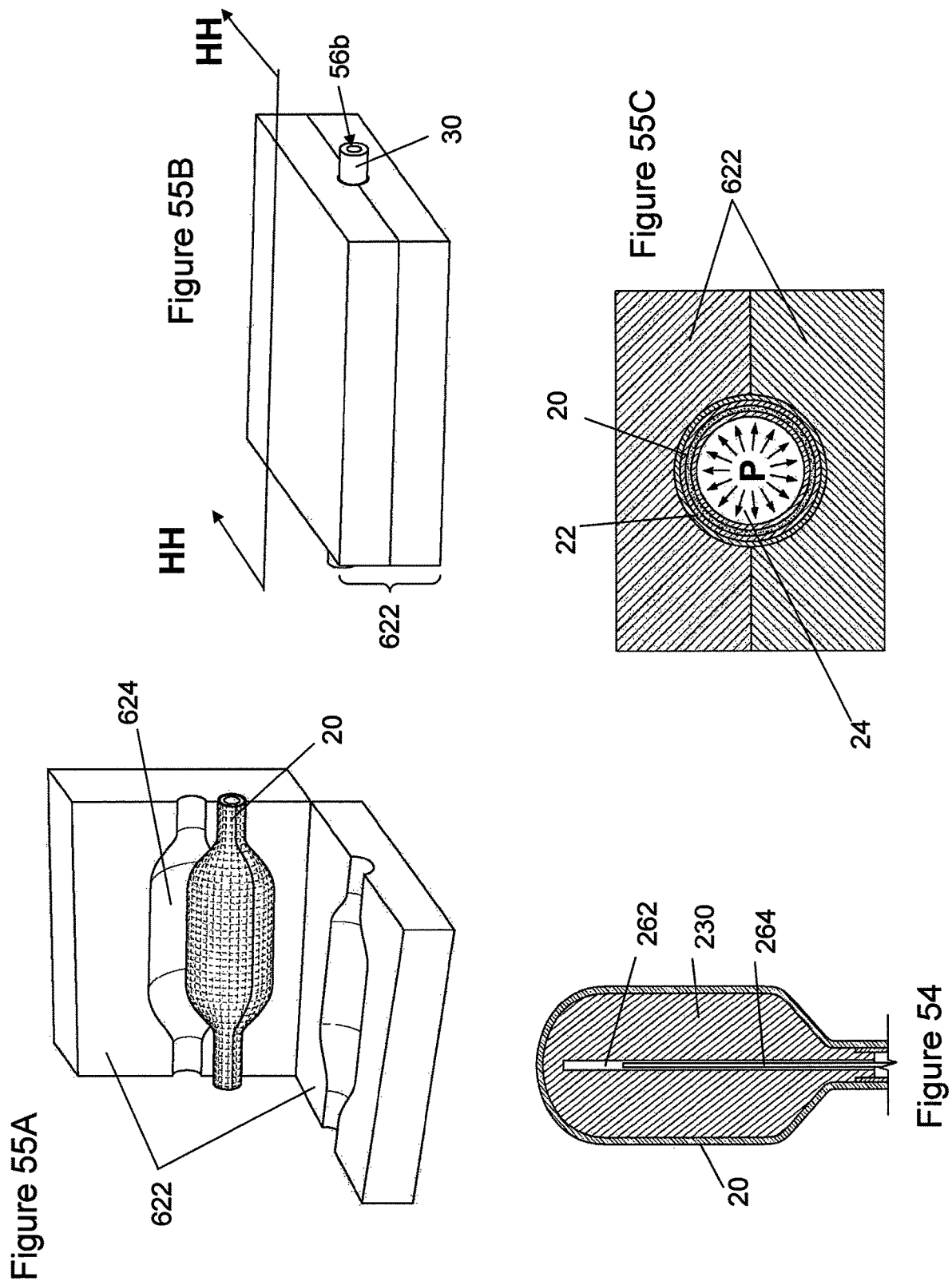

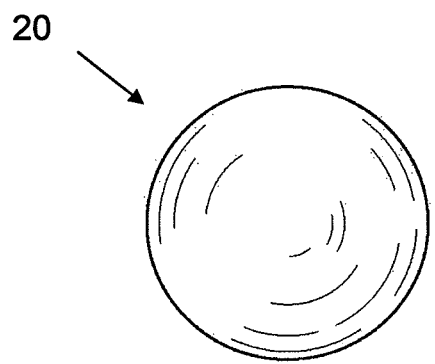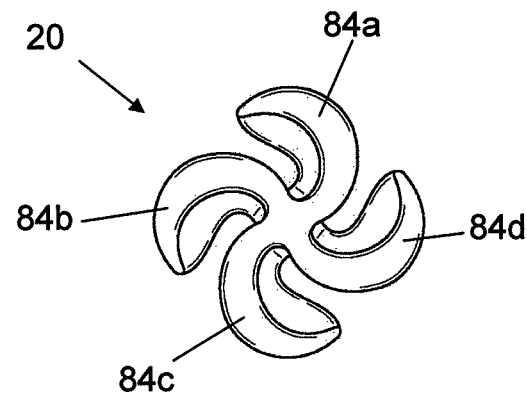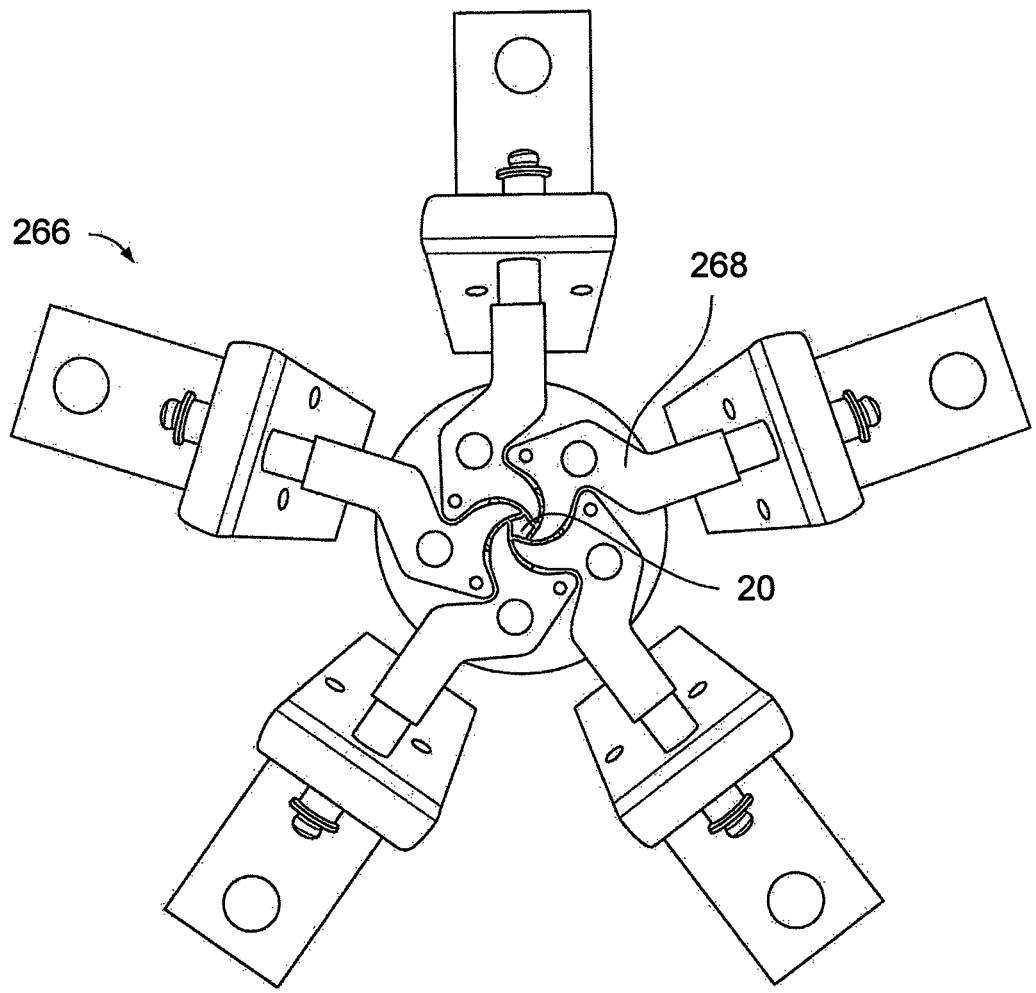
Figure 56A
Figure 56C
Figure 56B

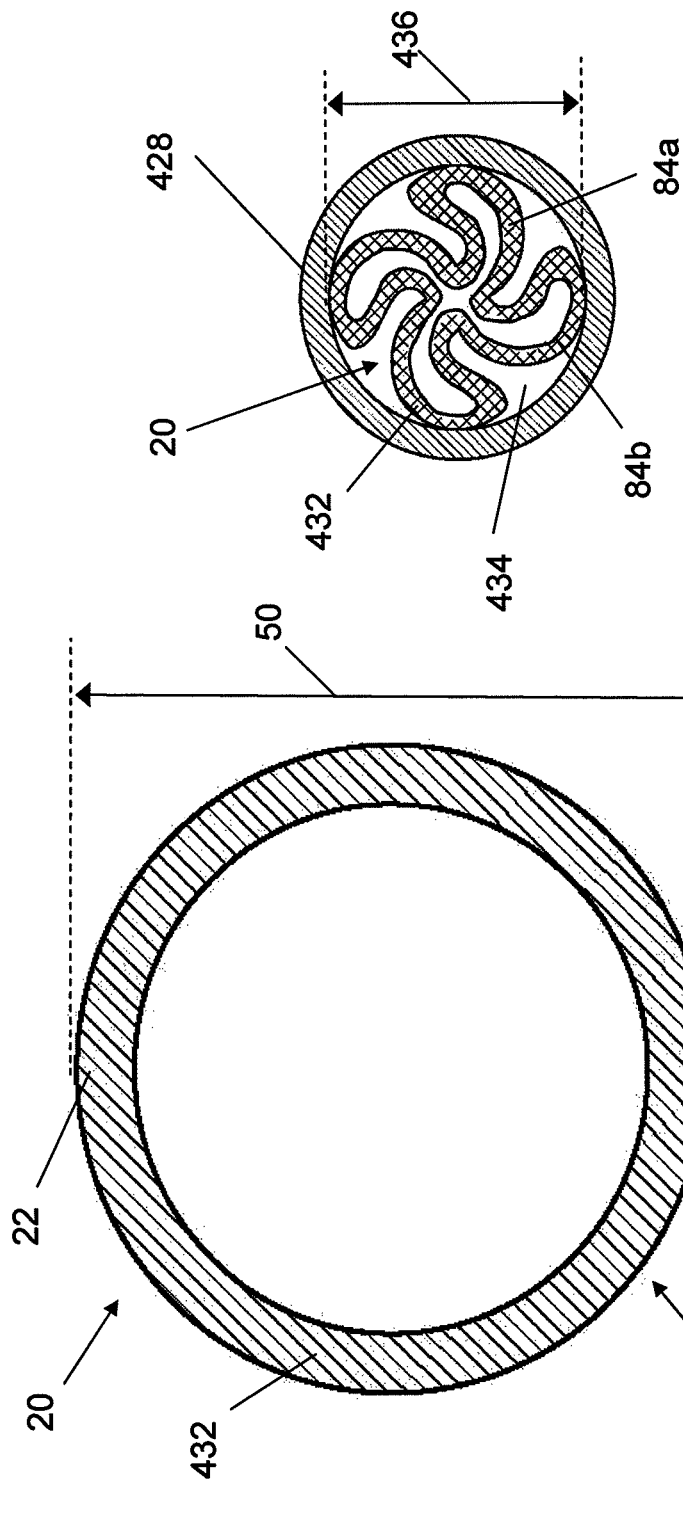

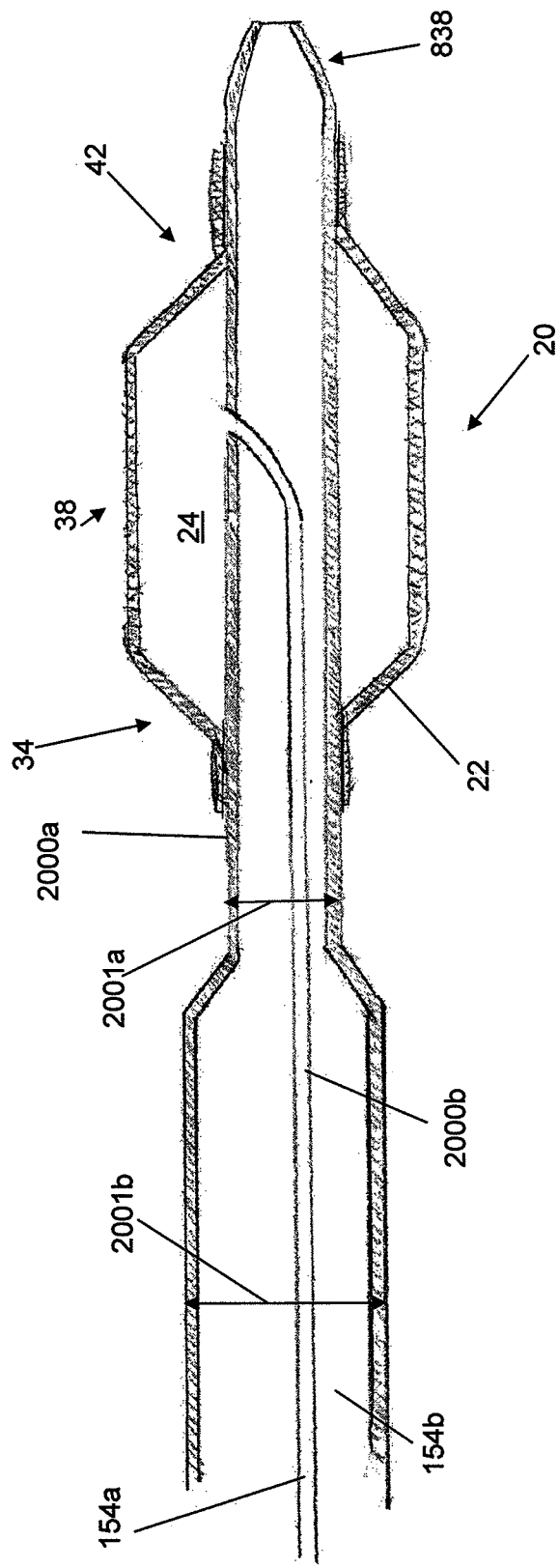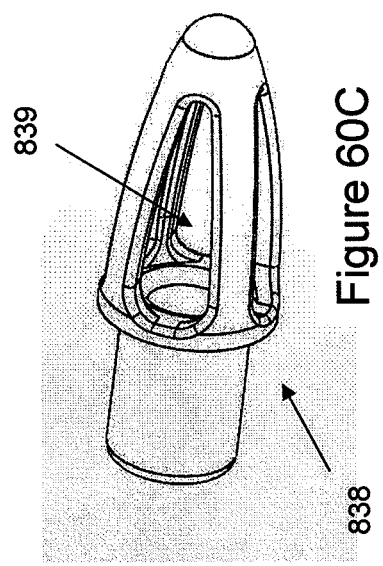
Figure 60B
Figure 60C

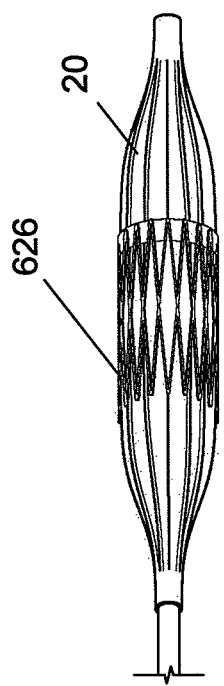
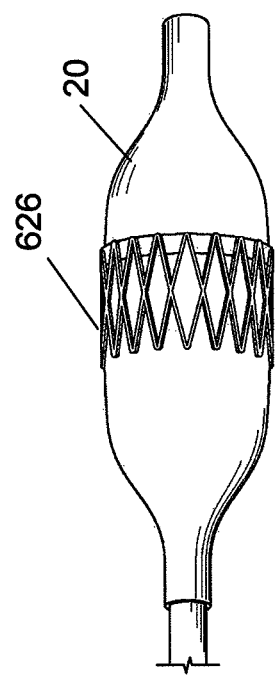
Figure 62A
Figure 62B
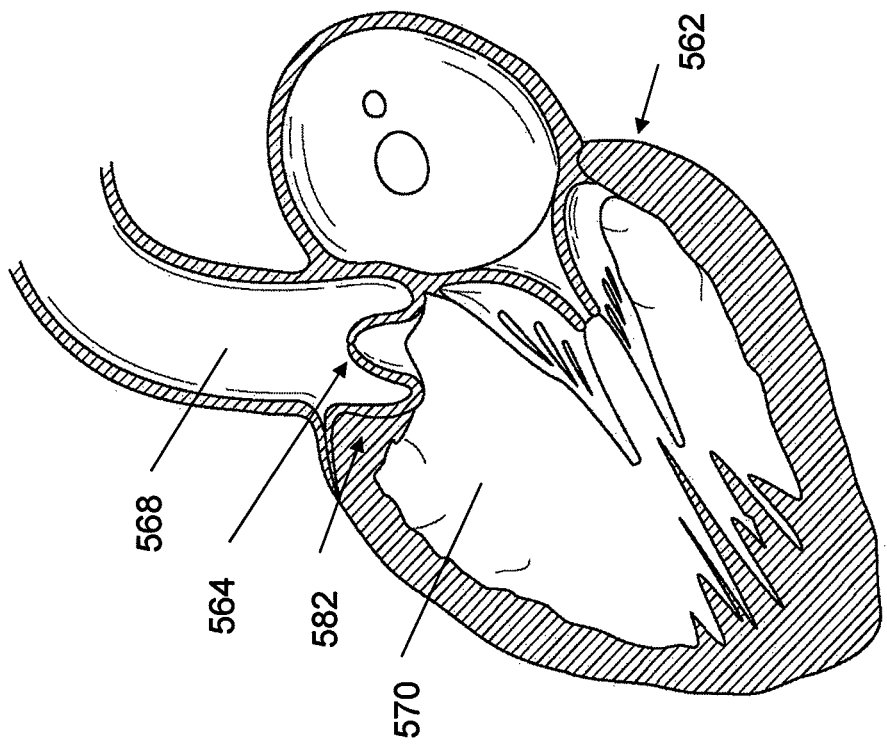
Figure 61

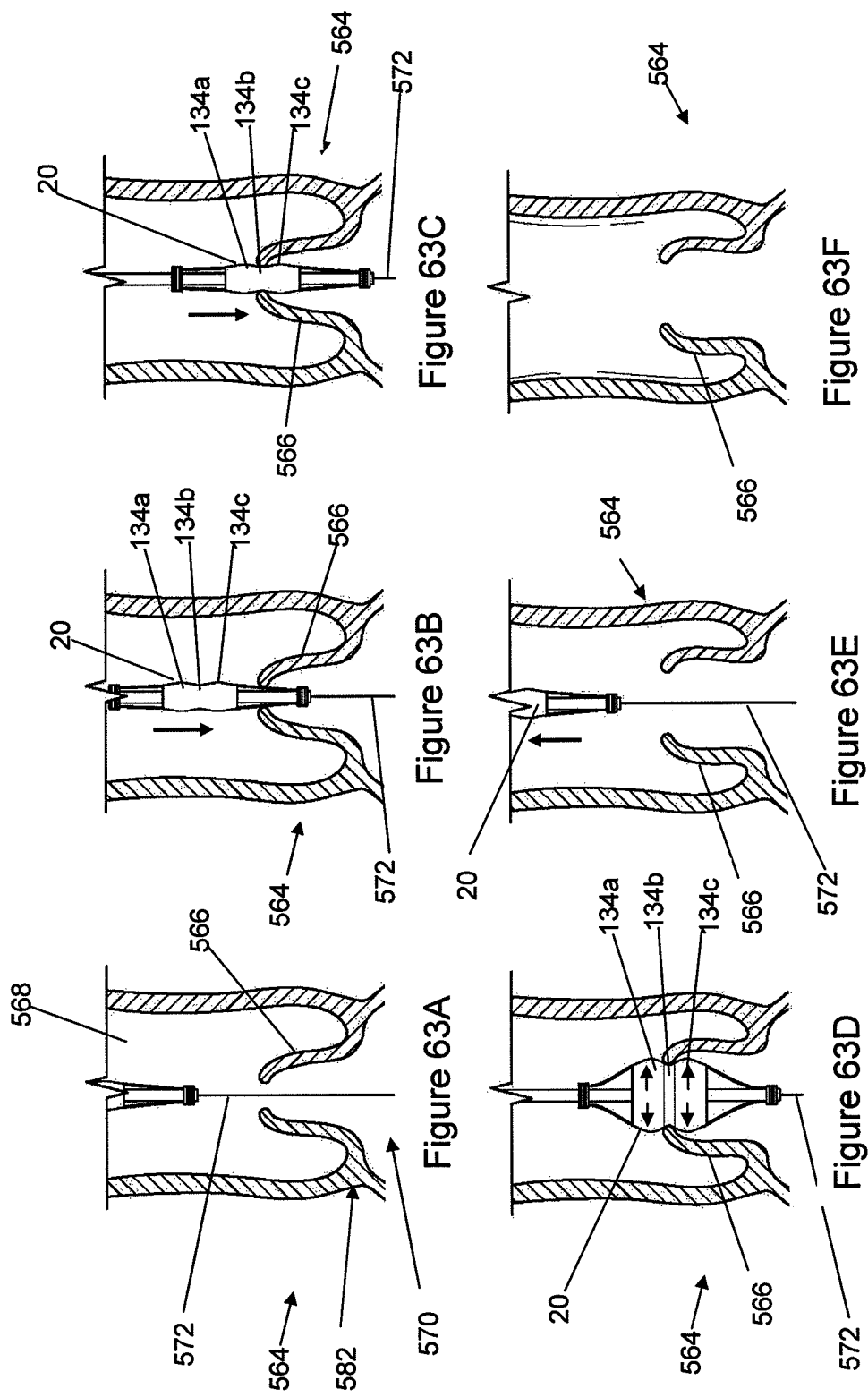

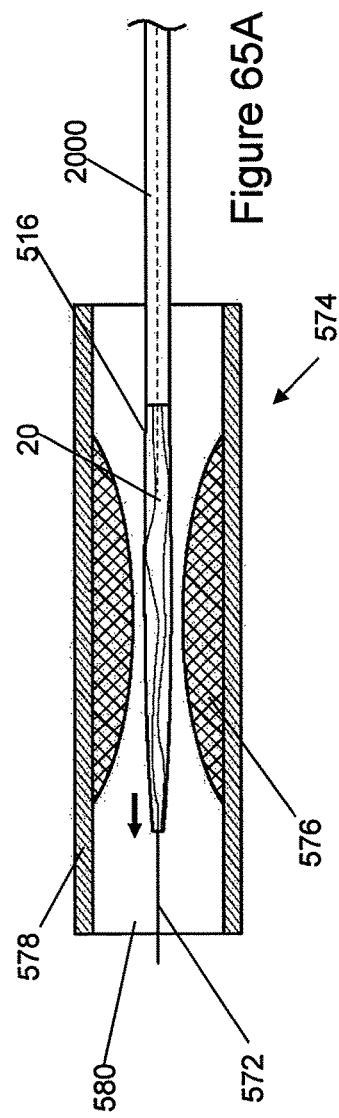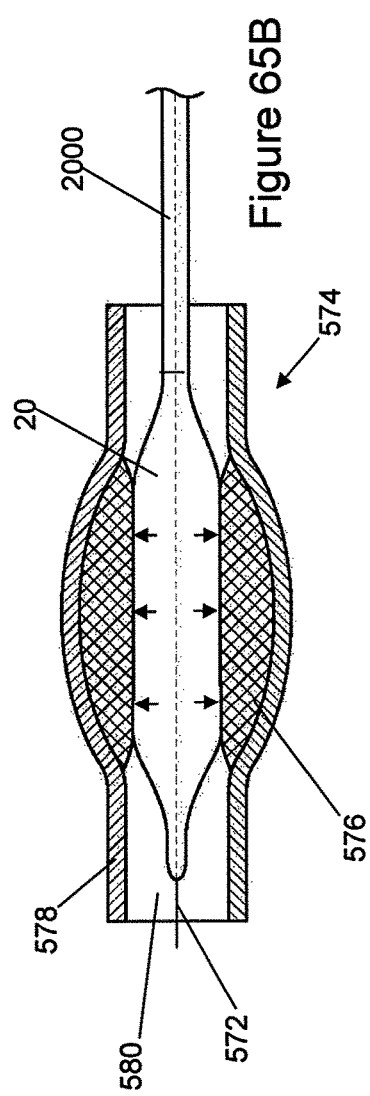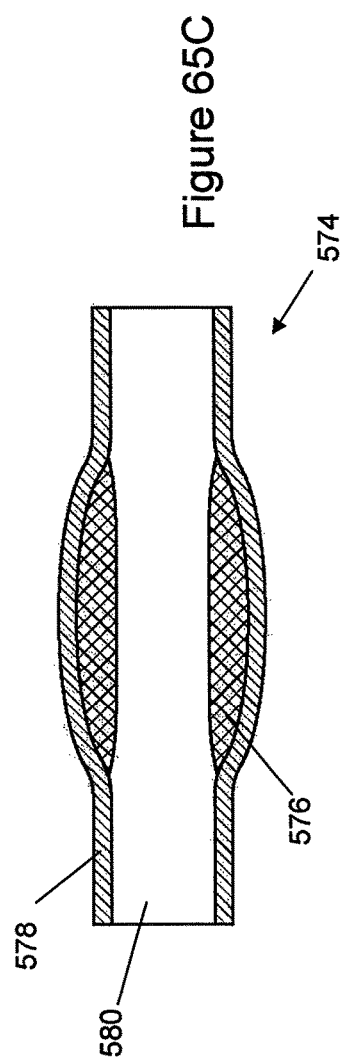

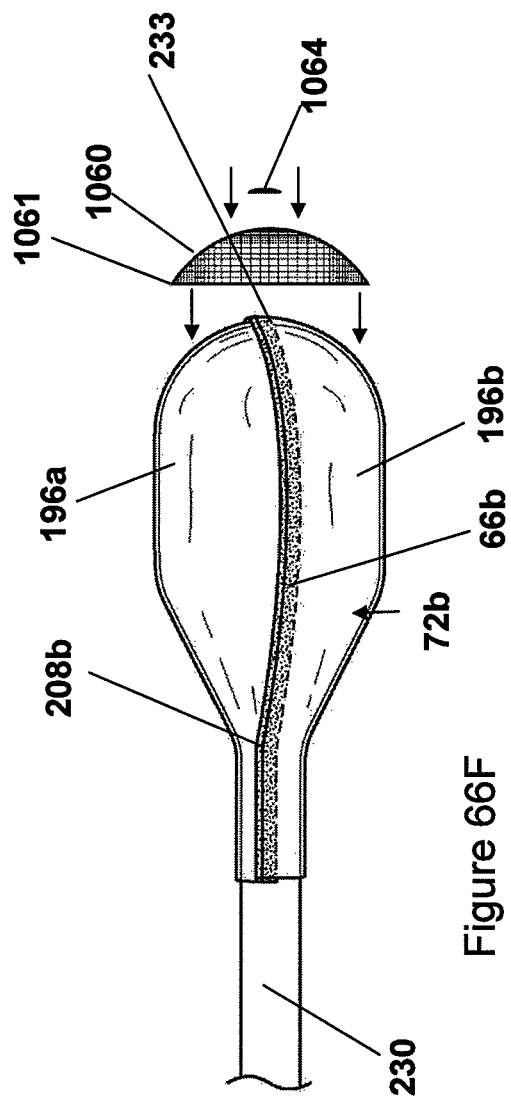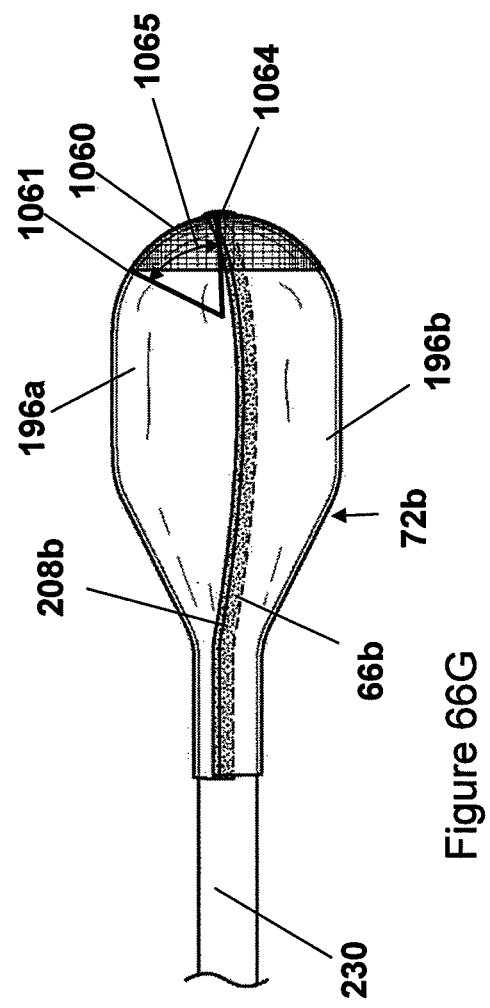
Figure 66F
Figure 66G

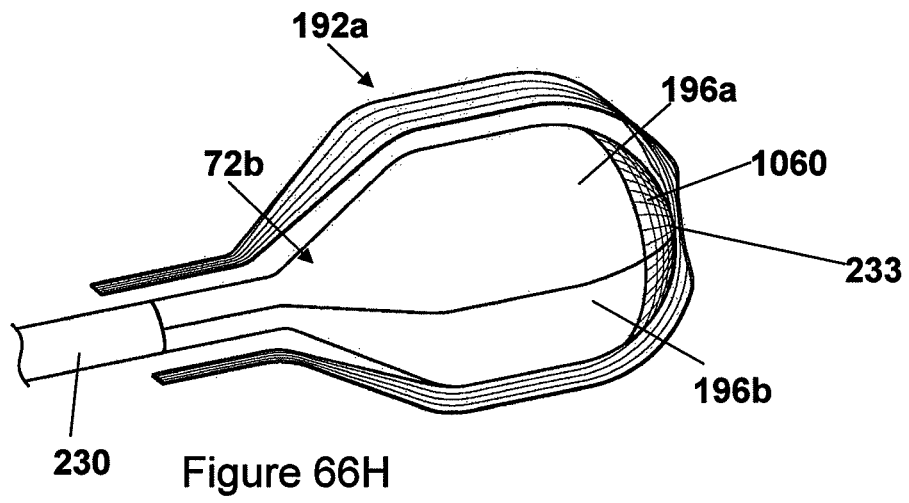
Figure 66H
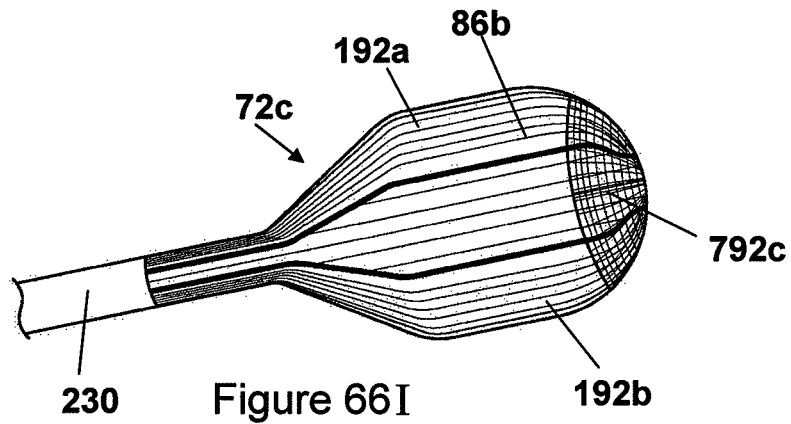
Figure 66I
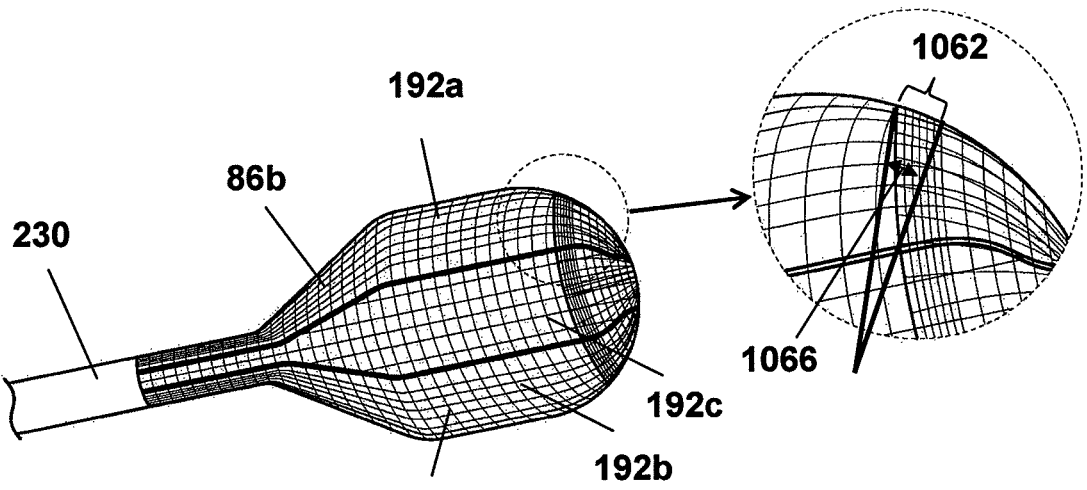
Figure 66J
Figure 66K

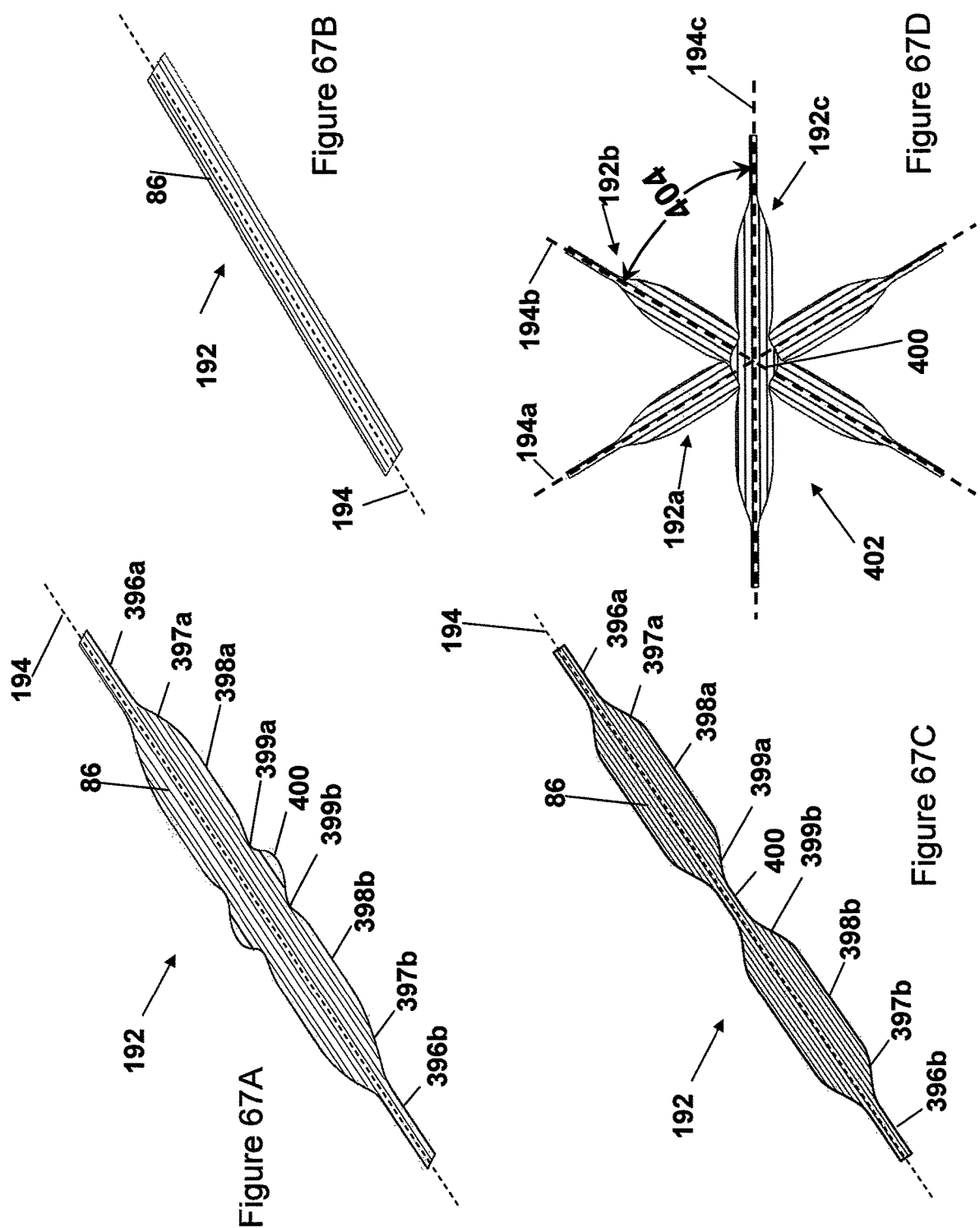

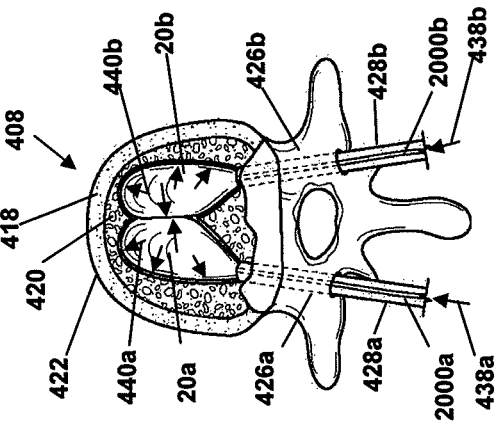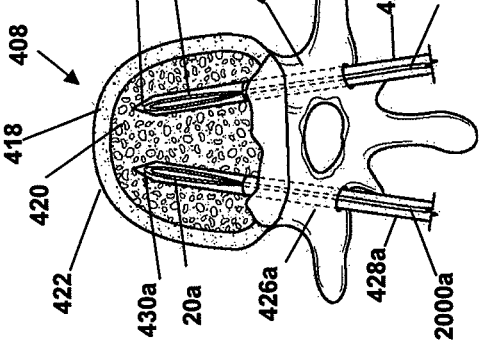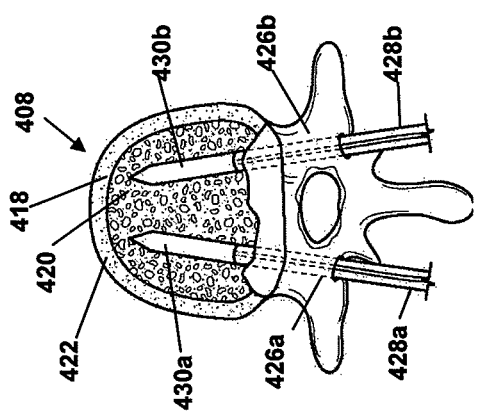

INFLATABLE MEDICAL DEVICES

CROSS REFERENCE TO RELATED APPLICATION

This application claims priority to U.S. Provisional Patent Application No. 61/656,404, PCT/US2013/044561 and U.S. application Ser. No. 14/406,311 all of which are incorporated by reference.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Inflatable structures, such as balloons, are widely used in medical procedures. A balloon is inserted, typically on the end of a catheter, until the balloon reaches the area of interest. Adding pressure to the balloon causes the balloon to inflate. In one variation of use, the balloon creates a space inside the body when the balloon inflates.

Balloons may be used in the heart valves, including during Balloon Aortic Valvuloplasty (BAV) and Transcatheter Aortic Valve Implantation (TAVI). The balloons can be used to open a stenosed aortic valve. A stenosed valve may have hard calcific lesions which may tend to tear or puncture a balloon. Additionally, a precise inflated balloon diameter may be desired for increased safety and control.

Balloons may be used to move plaque away from the center of a vascular lumen toward the vasculature walls, such as during an angioplasty or a peripheral vasculature procedure. During this procedure, a balloon tipped catheter is placed in a vascular obstruction. As the balloon is inflated, the vessel constriction is dilated, resulting in improved blood flow.

Two basic types of balloons are utilized: One is a high pressure, low-compliance balloon. The other is a lower pressure, high-compliance balloon.

High-compliance medical balloons are often composed of urethane, latex, silicone, PVC, Pebax, and other elastomers. As the pressure in a high-compliant balloon is increased, the balloon dimensions expand. Once the pressure is reduced, the high-compliance medical balloon may return to its original shape, or near its original shape. High-compliance medical balloons can easily expand several times in volume between zero inflation pressure and burst.

Traditional high-compliance medical balloons can be inadequate for many reasons. High-compliance, or highly elastic medical balloons typically cannot reach high pressures because their walls have a low tensile strength and their walls thin out as the balloon expands. In some instances, high-compliance medical balloons provide insufficient force to complete a procedure. Exceeding the rated pressure of a high-compliance medical balloon creates an excessive risk of balloon failure which can lead to serious complications for the patient.

High-compliance medical balloons also have poor shape control. As a high-compliance medical balloon expands, it may assume a shape dictated mostly by the particulars of the environment inside the patient rather than the clinical goals. In some cases, this can be contrary to what the medical practitioner desires. Many medical procedures are predicated on forming a particular balloon shape reliably.

High-compliance medical balloons often suffer from poor puncture and tear resistance.

Low-compliance, high pressure medical balloons substantially retain their shape under comparatively high pressures. PET (polyethylene terephthalate) is the most common material for use in high pressure low-compliance balloons. PET is commonly used for high-performance angioplasty balloons. PET is stronger than other polymers, can be molded into a variety of shapes and can be made very thin (e.g., 5 μm to 50 μm (0.0002 in. to 0.002 in.)), thus giving these balloons a low profile.

Balloons made from PET walls are fragile and prone to tears. When pressed against a hard or sharp surface in the body, such as stenosis, PET balloons have poor puncture resistance. PET is very stiff so balloons made from PET may be difficult to pack or fold into a small diameter and may have poor trackability (i.e., the ability to slide and bend over a guidewire deployed through a tortuous vessel).

Balloons made from PET, while stronger than most other balloons made from homogenous polymers, may still not be strong enough to hold pressures sufficient to complete certain medical procedures. Additionally, with a large balloon diameter (For example, 20 mm or greater), a PET balloon still has excessive compliance for procedures such as BAV and TAVI.

PET, like most low compliance balloons, is usually blow-molded. The blow molding process makes it difficult or impossible to create certain shapes. Blow molding can result in wall thicknesses in the balloon that do not match the material thicknesses to the expected load.

Nylon balloons are an alternative material for low-compliance, high pressure balloons. These balloons are typically weaker than PET balloons and so can contain less pressure. Nylon readily absorbs water, which can have an adverse effect on Nylon's material properties in some circumstances. Nylon has improved puncture resistance over PET and is more flexible than PET.

A balloon is desired that can sustain high pressures, provide precise shape control and be highly resistant to tear and puncture.

SUMMARY OF THE DISCLOSURE

Inflatable balloons are described herein.

In general, in one embodiment, an inflatable balloon includes a base balloon having a cylindrical section and a conical section and at least one circumferential fiber extending circumferentially around the conical section. The inflatable balloon includes a plurality of reinforcing strips in the conical section over the at least one circumferential fiber. Each reinforcing strip includes a plurality of fibers extending at an angle relative to the at least one fiber. Each reinforcing strip is positioned a set circumferential distance away from a neighboring reinforcing strip.

This and other embodiments can include one or more of the following features. The angle between the plurality of fibers of the reinforcing strip and the at least one circumferential fiber can be approximately 90 degrees. The plurality of fibers of the reinforcing strip can extend substantially parallel to a longitudinal axis of the balloon. The inflatable balloon can include a plurality of longitudinal fibers extending at an angle to the at least one fiber, and the at least one fiber can extend over the plurality of longitudinal fibers. The angle between the plurality of longitudinal fibers and the at least one circumferential fiber can be approximately 90 degrees. The plurality of longitudinal fibers can extend substantially parallel to the longitudinal axis of the balloon. Each of the reinforcing strips can include a fiber tape. The reinforcing strips can be arranged to radiate from an end of the balloon towards the central portion. The balloon can include only between 3 and 32 reinforcing strips. Each reinforcing strip can include only a single layer of fiber monofilaments in a radial direction. Each reinforcing strip can include a tapered region. The balloon can include a cylindrical end section, the conical section can be located between the cylindrical end section and the cylindrical section. The reinforcing strips can overlap within the cylindrical end section. The plurality of reinforcing strips can be connected together within the cylindrical end section. The reinforcing strips can extend part way into the cylindrical section and end within the cylindrical section.

In general, in one aspect, a latitudinal reinforcement fiber can be applied to an inflatable balloon in a wavy pattern. When inflated, the latitudinal fiber can straighten out.

In general, in one aspect, the pitch of fibers around an inflatable balloon can vary along the length of the taper to help prevent everting of the balloon.

In general, in one aspect, a layer of an inflatable balloon is formed by vapor deposition. Parylene can be vapor deposited and treated to enhanced its bondability.

In general, in one aspect, an inflatable medical balloon includes a spherical reinforcement cap on the distal end thereof. The spherical reinforcement cap can include a plurality of layers, each layer having fibers extending therein, the fibers oriented at an angle relative to a neighboring layer.

In general, in one aspect, one or more layers of an inflatable balloon can be formed of strips of fiber that, when put over the balloon, cover substantially the entire surface.

In general, in one aspect, a distal end of a balloon catheter can include two hollow shafts therethrough. One hollow shaft can be used as an inflation lumen while another lumen can allow blood to flow therethrough for perfusion.

In general, in one aspect, a panel can be applied over a mandrel such that at least portions of the panel yield, stretch, or deform to cover the surface of the mandrel. The mandrel can be, for example, a compound curved surface and/or a double curved surface.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 2A illustrates a variation of the device.
FIG. 2B illustrates a variation of cross section QQ-QQ of FIG. 2A.
FIGS. 3A, 3B, 3C, and 3D are cross-sectional views of a length of variations of the device.
FIG. 6A illustrates a variation of the device.
FIGS. 6B and 6C are variations of cross-section D-D of FIG. 5A.
FIG. 8A illustrates a variation of the device.
FIG. 8B is a variation of cross section E-E of the device of FIG. 8A.
FIG. 8C is a variation of cross section F-F of the device of FIG. 8A.
FIG. 8D is a variation of cross section G-G of the device of FIG. 8A.
FIGS. 8E and 8F illustrate variations of the device.
FIG. 11A illustrates a variation of the device.
FIG. 11B is a variation of cross section R-R of the device of FIG. 11A.
FIG. 12A illustrates a variation of the device.
FIG. 12B is a variation of cross section S-S of the device of FIG. 12A.
FIG. 13A illustrates a variation of the device.
FIGS. 13B and 13C are variations of cross section T-T of the device of FIG. 13A.
FIG. 14A illustrates a variation of the device.
FIG. 14B is a variation of cross section i-i of the device of FIG. 14A.
FIGS. 15A and 15B are variations of the device
FIG. 16A illustrates a variation of the device.
FIGS. 16B and 16C are variations of cross section V-V of the device of FIG. 16A.
FIG. 17A illustrates a variation of the device.
FIG. 17B is a variation of a cross section of the device of FIG. 17A
FIG. 18A illustrates a variation of the device.
FIGS. 18B, 18C and 18D are variations of cross-section X-X and Y-Y of FIG. 18A.
FIG. 19A illustrates a variation of the device.
FIGS. 19B, 19C are variations of cross-section Z-Z and AA-AA respectively of FIG. 19A.
FIG. 20 illustrates a variation of the device.
FIGS. 21A and 21B illustrate a variation of the device in deflated and inflated configurations, respectively.
FIGS. 23A-23E are partial see-through views of variations of the device.
FIGS. 24A, 24B, 24C, 24D and 24E illustrate variations of the device.
FIGS. 27 through 29 are tables listing film materials, reinforcement materials, and adhesive and matrix materials, respectively.

FIGS. 34A through 34I illustrate a method for manufacturing the device.

FIGS. 39A through 39H illustrate a method of making a panel.

FIGS. 47B, 47C, 47D, 47F, and 47G are cross-sectional views of variations of a layer.

FIGS. 47E and 47H are cross-sectional views of variations of multiple layers.

FIGS. 48A through 48D illustrate details of the manufacturing process in FIG. 47A FIGS. 49A and 49B illustrate a method for manufacturing the device.

FIG. 49C shows a balloon having reinforcing strips.

FIG. 49E shows a balloon having fiber wrapped at an angle to the longitudinal axis.

FIGS. 50A and 50B illustrate variations of a panel.

FIG. 52 illustrates a method for manufacturing the device.

FIGS. 53A and 53B illustrate a method for manufacturing the device

FIG. 54 illustrates a variation of a method for removing the mandrel.

FIGS. 55A through 55C illustrate a method for manufacturing the device

FIG. 56A illustrates a variation of the device in an inflated state before being pleated.

FIG. 56B illustrates a method of adding pleats or folds to a variation of the device.

FIG. 56C illustrates a variation of the device in a deflated, pleated state.

FIG. 57A illustrates a cross-section of a variation of the balloon wall.

FIG. 57B illustrates a cross-section of a variation of the balloon contracted inside of a delivery tube.

FIG. 60B shows a cutaway of an alternate embodiment of the distal end of a balloon catheter.

FIG. 60C shows a close-up of the distal end of the balloon catheter of FIG. 60B.

FIG. 61 illustrates a cross section of a human heart.

FIGS. 62A and 62B illustrate a variation of the device in deflated and inflated configurations, respectively.

FIGS. 63A through 63F illustrate a variation of a method for using the device.

FIGS. 65A through 65C illustrate a variation of a method for using the device.

FIGS. 67A-67D illustrate various embodiments of strips that can be used to form a layer of a balloon.

FIGS. 69A through 69I illustrate an exemplary method for deploying balloons bilaterally.

DETAILED DESCRIPTION

Figure 1A:
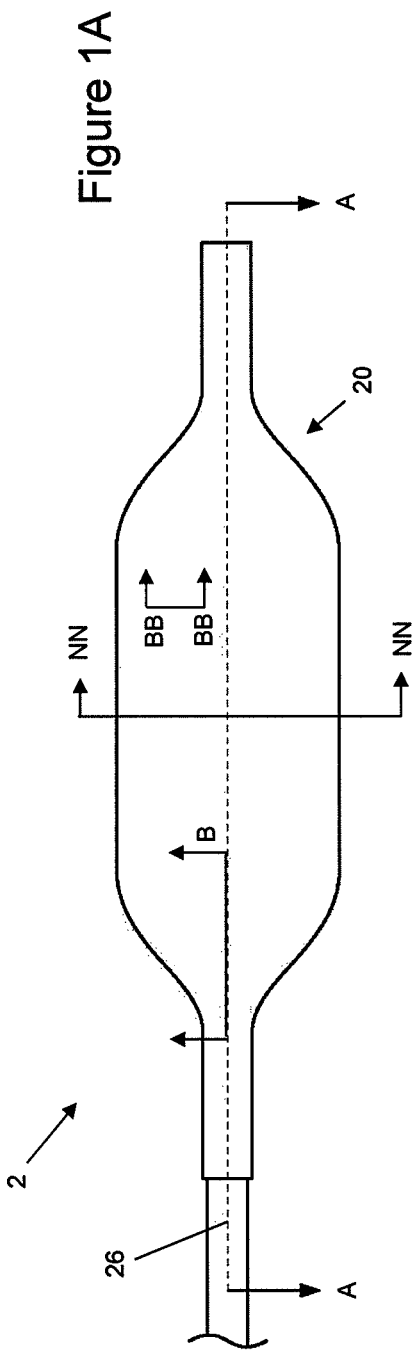
FIG. 1A illustrates a variation of the device.
Figure 1B:
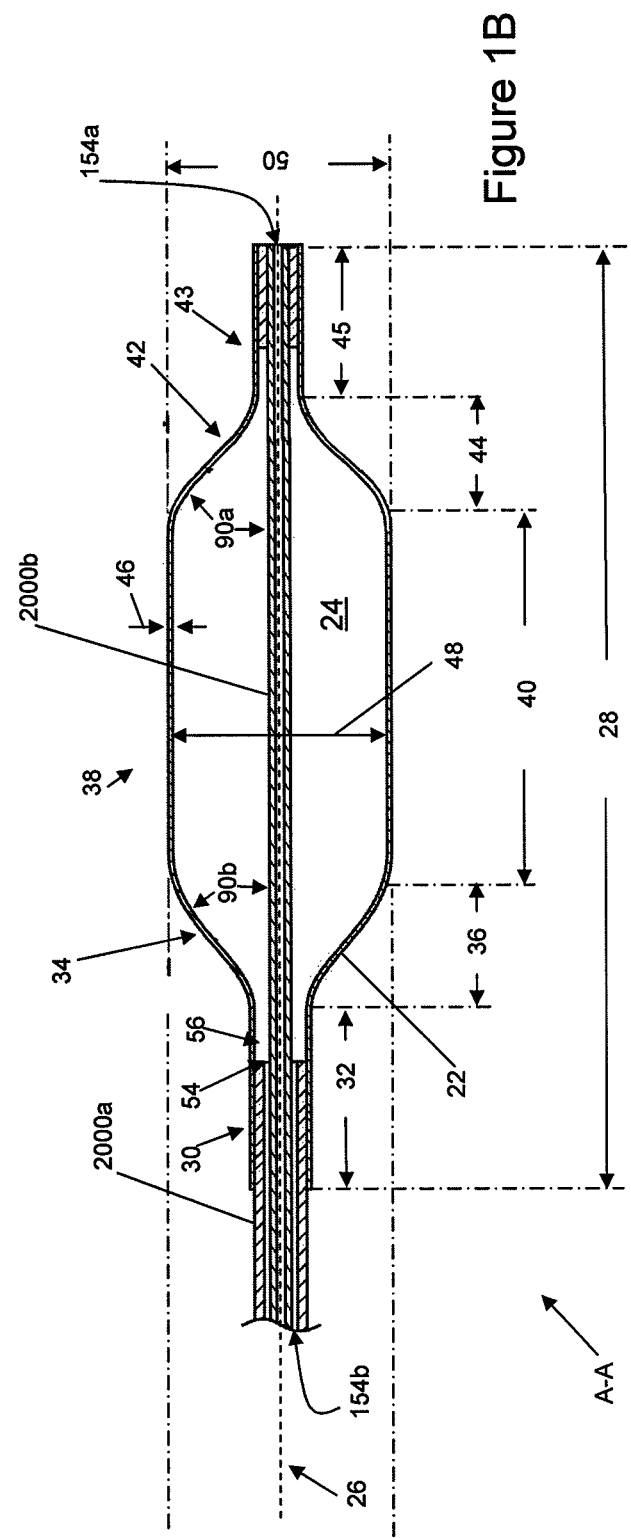
FIG. 1B illustrates a variation of cross section A-A of FIG. 1A.

FIGS. 1A and 1B illustrate that a medical inflatable device 2 can have a balloon 20 and a hollow shaft 2000. An inflation system (shown herein) can be attached to the hollow shaft to deliver a fluid pressure through the hollow shaft 2000 and to the balloon 20. The balloon 20 can be resilient (i.e., elastic) or non-compliant (i.e., inelastic). The balloon 20 can have a balloon longitudinal axis 26. The balloon 20 can have a balloon wall 22. The balloon wall 22 can define a cavity having a balloon volume 24. The balloon 20 can be a tube or a sheath. The tube or sheath can be a tubular structure that can be positioned over a medical device, such as an endoscope, vasculoscope, colonoscope, arthroscope, or combinations thereof. A tube can be a cylinder with a roughly equal inside and outside diameter. The balloon 20 can have a closed end (as shown in FIG. 2). The balloon 20 can have openings on either end (as shown in FIG. 1).

FIG. 1B illustrates that the balloon 20 can have a balloon length 28. The balloon length 28 can be from about 1.0 meter (39 in.) to about 5 mm (0.2 in.), more narrowly from about 200 mm (7.87 in.) to about 10 mm (0.4 in.), yet more narrowly from about 120 mm (4.72 in.) to about 50 mm (1.97 in) The balloon 20 can have a balloon proximal stem 30 having a balloon proximal stem length 32. The proximal stem length 32 can be from about 3.0 mm (0.12 in.) to about 15 mm (0.60 in.), for example about 10 mm (0.40 in.). The balloon 20 can have a balloon proximal taper 34 having a balloon proximal taper length 36. The balloon proximal taper length 36 can be from about 0 mm (0 in.) to about 25 mm (0.98 in.), more narrowly from about 10 mm (0.40 in.) to about 22 mm (0.87 in.), yet more narrowly from about 16 mm (0.63 in.) to about 20 mm (0.79 in.).

The balloon 20 can have a constant-diameter section 38 having a constant-diameter section length 40. The constant-diameter section 38 can be the length between the balloon proximal taper 34 and a balloon distal taper 42. The constant-diameter section length 40 can be from about 0 mm (0 in) to about 55 mm (2.17 in), more narrowly from about 30 mm (1.18 in) to about 50 mm (1.97 in). The constant-diameter section 38 is referred to herein as "constant-diameter" for illustrative purposes, and the constant-diameter section 38 can have a constant or variable diameter along the length of the constant-diameter section 38. In the case of a substantially variable diameter along the constant-diameter section, the constant-diameter section 38 is defined as the portion of the balloon between the cross sections of maximum balloon diameter.

The balloon 20 can have a balloon distal taper 42 having a balloon distal taper length 44. The balloon distal taper length 44 can be from about 0 mm (0 in) to about 25 mm (0.98 in), more narrowly from about 10 mm (0.4 in) to about 22 mm (0.87 mm), yet more narrowly from about 16 mm (0.63 in) to about 20 mm (0.79 in). The balloon 20 can have a balloon distal stem 43 having a balloon distal stem length 45. The distal stem length 45 can be from about 3 mm (0.12 in) to about 15 mm (0.6 in), more narrowly about 10 mm (0.4 in).

The balloon 20 can have an inner lumen 154a and an outer lumen 154b. Inner lumen 154a may be formed by second hollow shaft 2000b. Inner lumen 154a may provide a lumen thru the entire balloon 20. Inner lumen 154a may allow a guidewire to pass thru the interior of the balloon. Outer lumen 154b may connect to balloon volume 24 and allow fluid into the balloon volume 24. Placing fluid into balloon volume 24 may cause the balloon to inflate. Outer lumen 154b may be formed between the inner wall of first hollow shaft 2000a and the outer wall of second hollow shaft 2000b.

The proximal taper angle 90b and the distal taper angle 90a can be from about 0 to about 90°, more narrowly about 50° to about 20°, yet more narrowly about 45° to about 30°, for example about 40° or about 35° or about 30° or about 25° or about 20°. The proximal taper angle 90b and the distal taper angle 90a do not need to be substantially the same.

The balloon 20 can have one or more balloon fluid ports 56. The first hollow shaft 2000a can have a hollow shaft distal port 54. One of the balloon fluid ports 56 can attach to the hollow shaft distal port 54.

The balloon 20 can have a wall thickness 46. The wall thickness 46 can be less than about 25 μm (1 mil). The wall thickness 46 can be from about 25 μm (0.98 mil) to about 250 μm (9.8 mil), more narrowly from about 50 μm (2 mil) to about 150 μm (5.9 mil), more narrowly from about 35 μm (1.4 mil) to about 75 μm (3 mil), for example about 50 μm (2 mil), about 65 μm (2.6 mil), about 75 μm (3 mil), or about 100 μm (4 mil).

The balloon 20 can have a balloon inner diameter 48 and a balloon outer diameter 50. The balloon outer diameter 50 can be measured perpendicular to the balloon longitudinal axis 26 at the widest point along the length of the balloon 20. The balloon outer diameter 50 can be from about 2 mm (0.08 in) to about 50 mm (2 in.) for example about 3 mm (0.12 in.), about 6 mm (0.24 in.), about 10 mm (0.4 in), about 17 mm (0.67 in.), about 20 mm (0.79 in), about 22 mm (0.87 in), about 26 mm (1.02 in), or about 30 mm (1.18 in).

The balloon proximal stem 30 may have a diameter of 2 mm (0.08 in) to about 50 mm (2 in.), more narrowly 2 mm (0.08 in) to about 5 mm (0.20 in), for example about 2 mm (0.08 in), about 3 mm (0.12 in) or about 4 mm (0.16 in).

The balloon 20 can have an unsupported burst pressure. The unsupported burst pressure is the pressure at which the balloon ruptures when inflated without any external constraint on the walls at about 1 atm external pressure and about 20° C. temperature. The unsupported burst pressure can be greater than about 150 psi (1,034 kPa). For example, the unsupported burst pressure can be from about 200 psi (1,379 kPa) to about 1,500 psi (10,343 kPa). More narrowly, the burst pressure can be from about 200 psi (1,379 kPa) to about 500 psi (3,448 kPa). For example, the burst pressure can be about 200 psi (1,379 kPa), 250 psi (1,724 kPa), about 300 psi (2,069 kPa), about 350 psi (2,413 kPa) about 400 psi (2,758 kPa), or about 500 psi (3,448 kPa).

FIGS. 2A and 2B illustrate that the balloon 20 can have balloon length 28. The balloon 20 can have a balloon proximal stem 30 having a balloon proximal stem length 32. The proximal stem length 32 can be from about 5 mm (0.20 in) to about 15 mm (0.59 in). The balloon can have a balloon proximal taper 34 having a balloon proximal taper length 36. The balloon proximal taper length 36 can be from about 0 mm (0 in) to about 20 mm (0.79 in), more narrowly from about 0 mm (0 in) to about 15 mm (0.59 in), yet more narrowly from about 5 mm (0.20 in) to about 10 mm (0.39 in). The balloon 20 can have a constant-diameter section 38 having a constant-diameter section length 40. The constant-diameter section length 40 can be from about 0 mm (0 in) to about 15 mm (0.59 in), more narrowly from about 0 mm (0 in) to about 10 mm (0.39 in). The balloon 20 can have a balloon distal taper 42 at the terminal distal end 68 or tip of the balloon 20. The distal taper 42 can have a distal taper length 44. The distal taper length 44 can be from about 0 mm (0 in) to about 14 mm (0.55 in), more narrowly from about 2 mm (0.08 in) to about 9 mm (0.35 in).

The proximal and/or distal tapers 34 and/or 42 can be concave, convex and/or s-curves. For example, the proximal and/or distal tapers 34 and/or 42 can have continuously varying angles with respect to the balloon longitudinal axis 26.

The balloon 20 can have one, two, three or more balloon fluid ports 56. The balloon 20 can have no through lumen. For example, the balloon 20 can have no longitudinal through-lumen extending through the proximal terminal end 70 nor through the distal terminal end 68.

The balloon 20 can have a balloon inner diameter 48 and a balloon outer diameter 50. The balloon outer diameter 50 can be measured perpendicular to the balloon longitudinal axis 26 at the widest point along the length of the balloon 20.

The balloon 20 can have a radius (i.e., half the diameter), for example about 8.5 mm (0.33 in), and a distal taper length, for example about 8.5 mm (0.33 in). The ratio of the distal end length to the radius can be from about 2:1 to about 0:1, more narrowly about 1:1 to about 0.25:1.

The balloon 20 can have an unsupported burst pressure. The unsupported burst pressure is the pressure at which the balloon ruptures when inflated without any external constraint on the walls at about 1 atm external pressure and about 20° C. temperature. The unsupported burst pressure can be greater than about 150 psi. For example, the unsupported burst pressure can be from about 1,400 kPa (200 psi) to about 10,000 MPa (1,500 psi). More narrowly, the burst pressure can be from about 3,500 kPa (500 psi) to about 6,000 kPa (900 psi). For example, the burst pressure can be about 3,500 kPa (500 psi), about 5,200 kPa (750 psi), about 7,000 (1,000 psi), about 10,000 kPa (1,500 psi), or higher than 10,000 kPa (1500 psi).

The balloon 20 can be non-compliant or inelastic. The balloon 20 can have a failure strain of less than about 0.30, more narrowly less than about 0.20, more narrowly less than about 0.10, yet more narrowly less than about 0.05. A non-compliant balloon can have a failure strain of less than about 0.30.

The failure strain of the balloon 20 is the difference between the balloon outer diameter 50 when the balloon 20 is inflated to 100% of the burst pressure and the balloon outer diameter 50 when the balloon 20 is inflated to 5% of the burst pressure (i.e., to expand from a deflated state without stretching the wall material) divided by the 100% pressure diameter.

For example, the burst pressure of the balloon 20 can be greater than about 3,500 kPa (500 psi) and have an outer diameter 50 of about 17 mm and a wall thickness 46 of less than about 100 μm with a failure strain of less than about 0.10, for example less than about 0.05.

Also for example, the burst pressure of the balloon 20 can be greater than about 200 psi (1,379 kPa) and have an outer diameter 50 of about 24 mm and a wall thickness 46 of less than about 75 μm with a failure strain of less than about 0.10, for example less than about 0.05.

The reinforced balloon wall 22 may have a high tear strength as compared to traditional polymers. Tear strength can correlate to puncture strength and toughness. For example, in a Mod Mil-C-21189 10.2.4 tear test, a specimen is created. That specimen has a width, a height, and thickness. A slit is made in the sample parallel to the width, mid-way along its height. The slit is then pulled to initiate tear at the corners of the slit. The Mod Mil-C-21189 10.2.4 tear test gives resultant data in tensile pounds force (lbf). For the test to be meaningful as a comparison between two material samples, the tear test should be done on a thickness-comparable basis. A nylon 12 balloon material at about 0.0055 in (140 μm) thickness failed the tear test at a mean tensile load of 25 lbf (111 newtons). A variation of the balloon wall 22 of about 0005 in. (127 μm) wall thickness 46 can fail the same tear test performed on the nylon 12 balloon at a mean tensile value of 134 lbf (596 newtons).

In an ASTM D-3039 tensile test, a nylon 12 material at 0.0055 in. (140 μm) thickness, failed at a mean tensile load of 22 lbf (98 newtons). The balloon wall 22 of about 0.005 in. (127 μm) wall thickness 46 can fail the same tensile test performed on the nylon 12 material at a mean tensile value of 222 lbf (988 newtons).

The balloon wall 22 can have a high puncture strength. For example, when a balloon 20 is inflated to about 60 psi (414 kPa) and a 1 mm (0.040 in) gauge pin is driven into the balloon 20 at about 1 mm/sec (0.04 in/sec), the pin may need to exert more than 6 lbf (27 newtons) to puncture the balloon wall 22. A typical non-compliant polymer medical balloon may fail at about 3 lbf (13 newtons).

FIG. 3A illustrates that the balloon 20 can have a constant wall thicknesses 46 along the length of the balloon 20. A wall proximal stem thickness 46a can be substantially equal to a wall constant-diameter section thickness 46c and the wall proximal taper thickness 46b.

FIG. 3B illustrates that the balloon 20 can have a varying, such as increasing and/or decreasing, wall thicknesses 46 along the length of the balloon 20. FIG. 3B illustrates that the wall constant-diameter section thickness 46c can be substantially greater than the wall proximal stem thickness 46a. The wall proximal taper thickness 46b can be less than the wall constant-diameter section thickness 46c and greater than the wall proximal stem thickness 46a.

FIG. 3C illustrates that the wall proximal stem thickness 46a can substantially greater than the wall constant-diameter section thickness 46c. The wall proximal taper thickness 46b can be less than the wall proximal stem thickness 46a and greater than the wall constant-diameter section thickness 46c.

FIG. 3D illustrates that balloon 20 may terminate at the proximal end of the proximal taper 34. The balloon 20 may have no proximal stem 30. First hollow shaft 2000a may have a flare 2004 that attaches to inner wall of proximal taper 34.

Figure 4B:
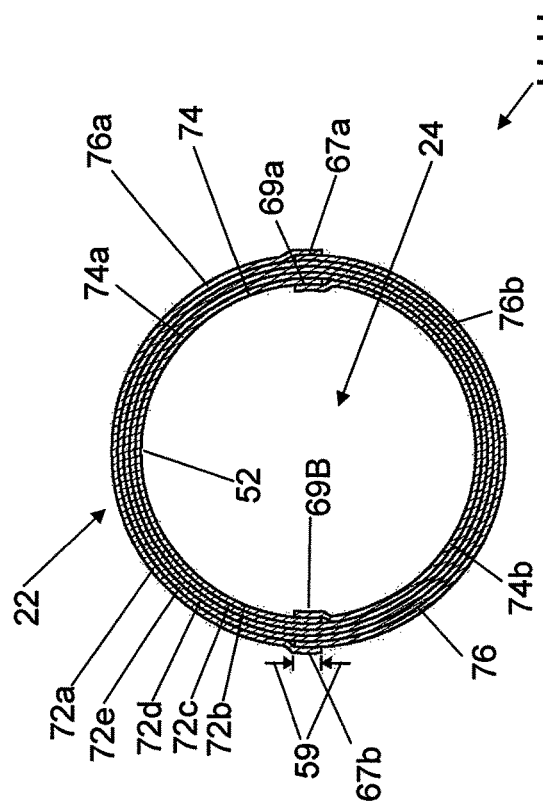
FIGS. 4B and 4C are variations of cross-section H-H of FIG. 4A.
Figure 4C:
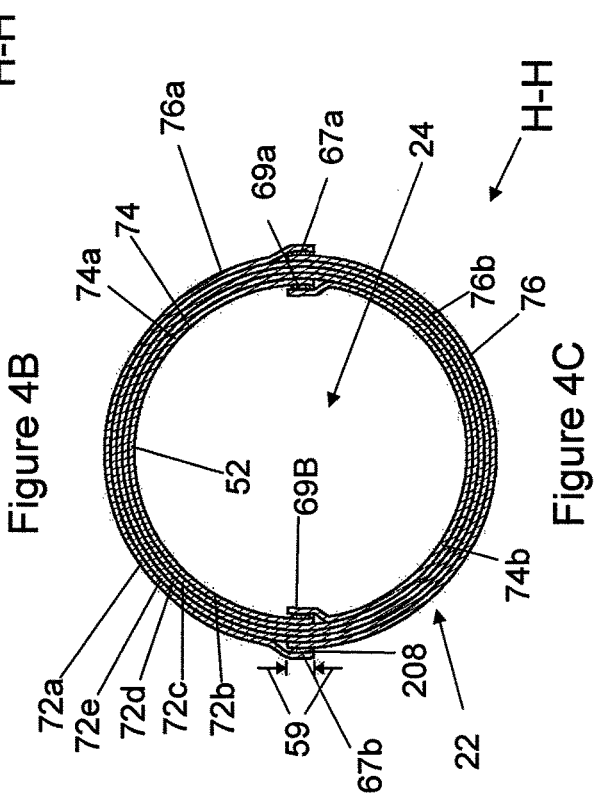
Figure 4A:
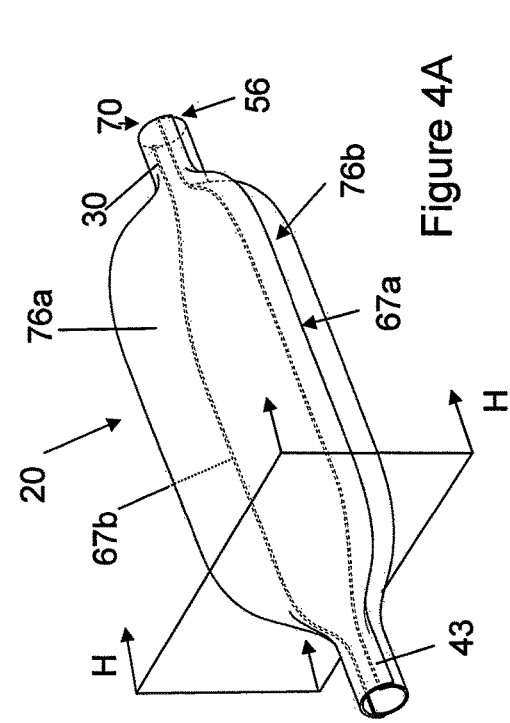
FIG. 4A illustrates a variation of the device.

FIG. 4A illustrates that the balloon 20 can have a first balloon external seam 67a and a second balloon external seam 67b. Any or all seams 67 can extend partially, completely, not at all, or a combination thereof, through the depth of the wall thickness 46. The balloon external seams 67a and 67b can be longitudinal seams (i.e., oriented in a longitudinal direction with respect to the balloon 20, parallel or at an angle to the longitudinal axis 26 of the balloon 20). The balloon external seams 67a and 67b can extend from a first lateral side of the balloon 20 at the proximal terminal end 70 of the balloon 20, along the first lateral side of the balloon to the balloon distal stem 43. A balloon seam may be between 75% and 150% as long as the balloon length 28, more narrowly between 85% and 125% as long as the balloon length 28. A balloon seam may be between 180% and 300% as long as the balloon length 28, more narrowly between 190% and 260%.

FIGS. 4B and 4C illustrate that the balloon wall 22 can have one or more layers 72. Each layer 72 can be a homogenous or heterogeneous discrete element distinguished from other layers by radial distance along the thickness of the balloon wall 22. A layer 72 may comprise film, reinforcement material or adhesive or combinations thereof, for example, the materials listed in FIGS. 27, 28 and 29. The balloon 20 can have a leak-proof bladder 52. The bladder 52 can be defined by one or more leak-proof layers within the balloon wall 22. The bladder 52 can be fluid-tight, such as air-tight or saline tight, or can be a fluid-porous bladder. The bladder 52 can be made of a urethane, a nylon, any material listed infra (eg. the materials listed in FIG. 29), or combinations thereof. The bladder 52 can be made from the radial inner-most layer 72b (as shown in FIGS. 4B and 4C) of the balloon wall 22. A bladder 52 may comprise film, reinforcement material or adhesive or combinations thereof (for example, the materials listed in FIGS. 27, 28 and 29).

The bladder 52 can be fixedly or removably attached to the hollow shaft 2000, for example at the inside and/or outside diameter of hollow shaft 2000. The hollow shaft 2000 can be a flexible or rigid catheter. The hollow shaft 2000 can deliver pressurized fluid to the balloon volume 24.

The balloon wall 22 can be made from panels 76. The panels 76 can, for example, be cut or formed pieces of film and/or resin with or without other materials such as fibers. The layers 72 can each be made from one or more panels 76. The panels 76 can each contain one or more layers 72, or multiple panels 76 (e.g., of the same material) can be formed into a single layer 72, for example by melting panels 76 of the same material into an indiscrete, integral homogenous layer during the method of making the device. A panel 76 or a panel 74 or a panel 196 may comprise film, reinforcement material or adhesive or combinations thereof (for example, the materials listed in FIGS. 27, 28 and 29).

The outer layer 72a of the balloon wall 22 can have an outer layer first panel 76a and an outer layer second panel 76b. The outer layer first panel 76a can cover from about 90° to about 270° of the balloon, as measured in a transverse plane from the balloon longitudinal axis 26, for example about 185° of the balloon 20. The outer layer second panel 76b can cover from about 90° to about 270°, as measured along the balloon longitudinal axis 26, for example about 185°.

The balloon wall 22 can have one or more seams 66 and/or 67 and/or 69 attaching panels 76 to other panels 76 in the same layers or to itself. The seams 66 and/or 67 and/or 69 can be an abutment or overlap of one or two panels 76 and/or panels 196 and/or panels 74. The seams 66 and/or 67 and/or 69 can be linear, curved, circular, equatorial or combinations thereof.

FIG. 4B illustrates that the balloon external seams 67a and 67b can be overlaid seams, lap joints, or combinations thereof. The balloon external seams 67a and 67b can be flush against the side (i.e., having a substantially constant radius with respect to the balloon longitudinal axis 26) of the outer layer first panel 76a or outer layer second panel 76b. The outer layer first panel 76a can be radially outside of the outer layer second panel 76b where the outer layer first panel 76a overlaps the layer second panel 76b. The outer panels 76 may have an overlap length 59. The overlap length 59 can be from about 0 mm (0 in.) (e.g., an abutment seam) to about 3 mm (0.12 in.), more narrowly from about 1 mm (0.04 in.) to about 2 mm (0.08 in.). The outer layer first panel 76a can be bonded or adhered (e.g., with an adhesive) to the outer layer second panel 76b. The adhesive can be an epoxy or a thermally weldable material, such as a thermoplastic urethane.

The inner layer 72b can have balloon internal seams 69a and 69b. The balloon inner seams 69a and 69b can join an inner layer first panel 74a and an inner layer second panel 74b. The inner seams 69a and 69b can have a similar structure to those described here for the balloon outer seams 67a and 67b.

FIG. 4C illustrates that the outer layer first panel 76a can be fused, solvated to, glued, adhered to, welded to, or a combination thereof, with the outer layer second panel 76b at the outer seams 67A and 67B. An adhesive 208 may be placed between the first panel 76a and the second panel 76b at the inner seams 69a and 69b and the outer seams 67a and 67b.

Figure 5:
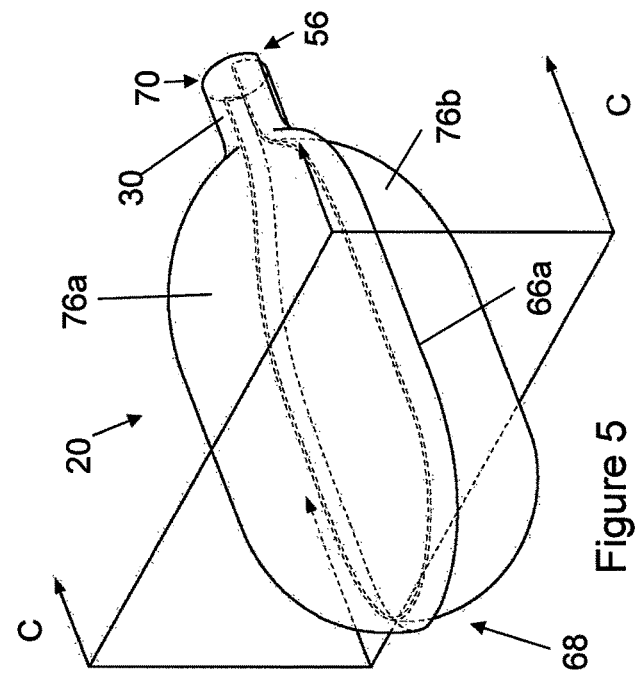
FIG. 5 illustrates a variation of the device.

FIG. 5 illustrates that the balloon 20 can have a single balloon external seam 66a. The seam 66a can extend partially, completely, or not at all through the depth of the wall thickness 46. The balloon external seam 66a can be a longitudinal seam. The balloon external seam 66a can extend from a first lateral side of the balloon 20 at the proximal terminal end 70 of the balloon 20, along the first lateral side of the balloon to the balloon distal terminal end 68. The balloon external seam 66a can wrap around the balloon distal terminal end 68a, extending around the distal end of the balloon 20 and returning on the second lateral side of the balloon 20.

The inner layer 72b can have a balloon inner seam 66b. The balloon inner seam 66b can join an inner layer first panel 74a and an inner layer second panel 74b. The inner seam 66b can have a similar structure to those described here for the balloon outer seam 66a.

Sections C-C can be identical to variations of Sections H-H, except the outer seams 67 would be the single balloon external seam 66a and the inner seams 69 would be the inner seam 66b.

FIG. 6A illustrates that the balloon external seam 66a can be a flange joint. The outer layer first panel 76a can have a seam first flange 80a around the perimeter of the outer layer first panel 76a. The outer layer second panel 76b can have a seam second flange 80b around the perimeter of the outer layer second panel 76b. The seam first flange 80a can attach to the seam second flange 80b at the balloon external seam 66a. The flange 80 can extend radially away from the balloon longitudinal axis 26. The balloon external seam 66a can be reinforced, for example with a metal foil, a wire or a polymer or combinations thereof. The balloon external seam 66a can be used to cut tissue during use in a biological target site or through tissue during delivery to the target site.

FIG. 6B illustrates that the seam first flange 80a can be bonded or adhered to the seam second flange 80b in the flange joint. FIG. 6C illustrates that the layer first panel 76a can be fused, solvated to, glued, adhered to, welded to, or a combination thereof, with the layer second panel 76b in the flange joint. An adhesive 208 may be placed between the first panel 76a and the second panel 76b at the seams inner seam 66b and the outer seam 66a.

Figure 7A:
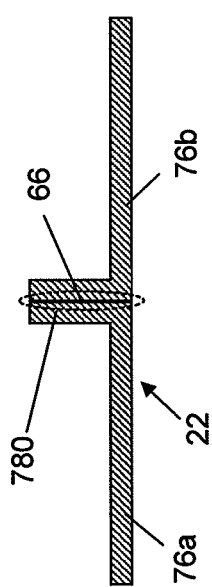
FIGS. 7A, 7B and 7C show close-up cross section views of variations of the seam.

FIG. 7A illustrates that the balloon wall 22 can have a flange seam 66. The panels 76a and 76b can have seam areas 780. The seam areas 780 can be located at the terminal edges and/or areas near the terminal edges of panels 76a and 76b in a plane in which the panels 76a and 76b lie. The seams 66 and/or 67 and/or 69 can join seam areas 780 of first panels 76 to seam areas of adjacent second panels 76 in the same layer or adjacent layers to the first panels 76a.

Figure 7B:
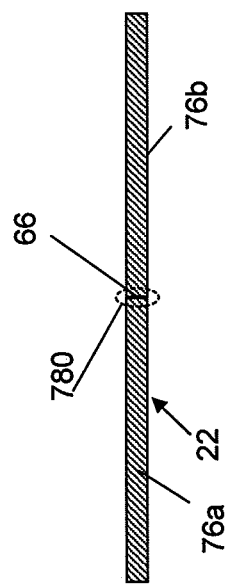

FIG. 7B illustrates that the balloon wall can have an abutment seam 66. The seam areas 780 can be perpendicular to the plane of the panels 76a and 76b.

Figure 7C:
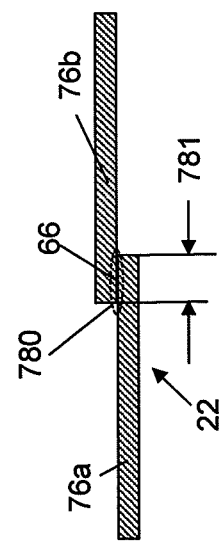

FIG. 7C illustrates that the balloon wall can have a lap joint or overlap seam 66. The seam areas 780 can be parallel to the plane of the panels 76a and 76b.

FIG. 8A illustrates that the balloon external seam 66a can be a lateral or latitudinal seam. The balloon external seam 66a can be in a plane perpendicular or substantially perpendicular to the balloon longitudinal axis 26. The balloon 20 can have one or more balloon external seams 66a and/or 67.

The outer layer first panel 76a can be at the distal end of the balloon 20. The outer layer second panel 76b can be at the proximal end of the balloon 20. The outer layer second panel 76b can overlay the outer layer first panel 76a at the balloon external seam 66a.

FIG. 8B illustrates that the outer layer first panel 76a can overlay the outer layer second panel 76b at the balloon external seam 66a.

FIG. 8C illustrates that the balloon wall 22 at a first length along the balloon 20 can have a first layer and a second layer. The first layer can be a radially inner layer 72b, as measured from the balloon longitudinal axis 26. The second layer can be a radially outer layer 72a. Any of the layers 72 can have a laminate of fiber and resin (e.g., that can be elements of one or more panels 76 in the respective layers 72). The resin can be an adhesive. The fiber and resin laminate can be a matrix of the fiber in the resin.

FIG. 8D illustrates that the balloon wall 22 at a second length along the balloon 20 can have first, second and third layers. The second layer can be a first middle layer 72c between the inner and outer layers 72b and 72a, respectively. Any combination of the layers can be leak-proof, reinforced with one or more fibers, resistant and releasable from MMA, or combinations thereof. The first middle layer 72c can be reinforced with a fiber. The outer layer 72a can be MMA-resistant and/or MMA-releasing.

An MMA-resistant material can substantially maintain material strength and thickness when exposed to MMA bone cement in any stage of the MMA bone cement from mixing to curing. An MMA-releasable material can form no substantial bond with MMA.

FIG. 8E illustrates that the balloon external seam 66A can be positioned at the proximal taper 34 of the balloon 20. The balloon external seams 66a and/or 67 can be in the constant-diameter section 38, the distal taper 42, the proximal taper 34, the proximal stem 30, or combinations thereof.

FIG. 8F illustrates that balloon external seam 66a can lie in a plane at a non-perpendicular angle to the balloon longitudinal axis 26. The plane in which the balloon external seam 66a lies can form a seam angle 82 with the balloon longitudinal axis 26. The seam angle 82 can be from about 0° (i.e., a longitudinal seam) to about 90° (i.e., a latitudinal seam). More narrowly, the seam angle 82 can be from about 30° to about 60°. For example, the seam angle 82 can be about 0°, about 30°, about 45°, about 60°, or about 90°.

Figure 9A:
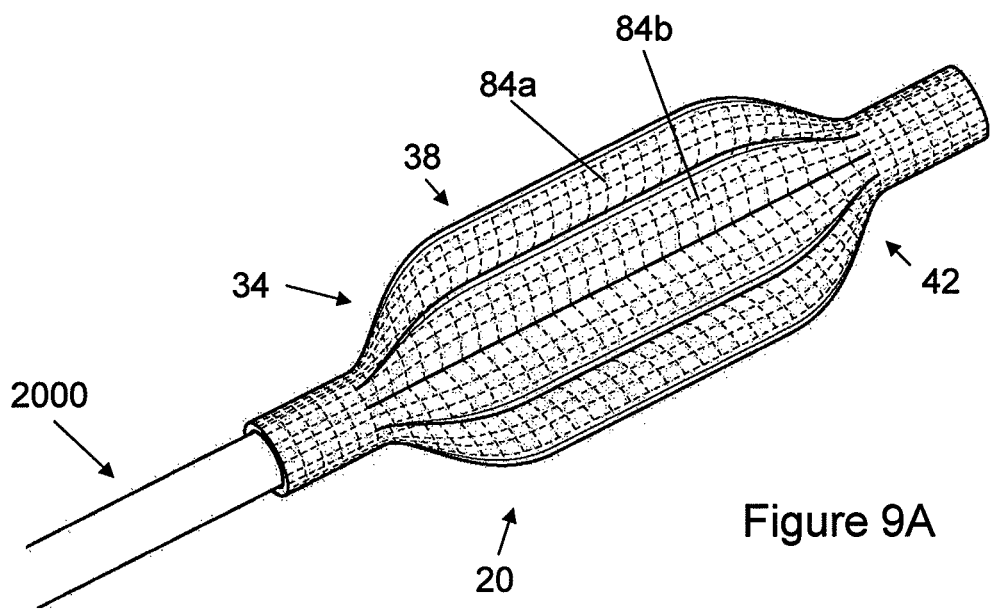
FIG. 9A illustrates a variation of the device in a deflated state.

FIG. 9A illustrates that the balloon 20 can be pleated to form flutes 84, for example four, five or six flutes 84, such as first flute 84a and second flute 84b. The flutes 84 can be made from accordion pleats, box pleats, cartridge pleats, fluted pleats, honeycomb pleats, knife pleats, rolled pleats, or combinations thereof. The pleating can be heat and/or pressure formed and/or the reinforcement fibers and/or panels can be oriented to form the flutes 84. The balloon 20 can be in a deflated configuration when the flutes 84 are shown.

Figure 9B:
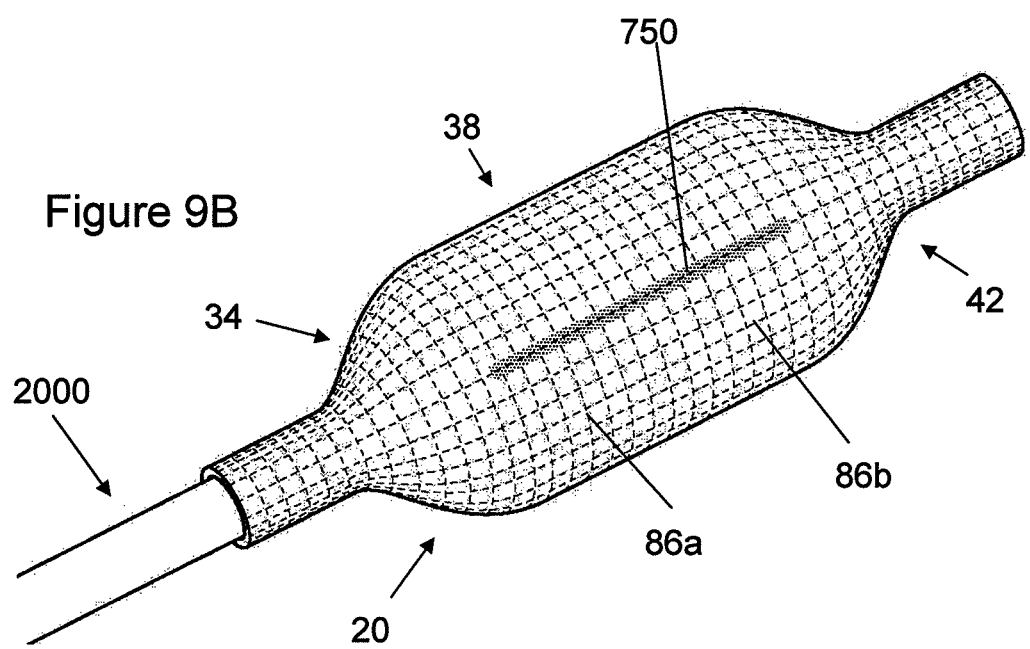
FIG. 9B illustrates a variation of the device in an inflated state.

FIG. 9B illustrates that the balloon 20 in an inflated configuration can push the pleated flutes 84 radially outward to form a substantially smooth outer surface of the balloon wall 22. The balloon 20 can have reinforcement fibers 86. Longitudinal reinforcement fibers 86b can be substantially parallel with the balloon longitudinal axis 26. Latitudinal reinforcement fibers 86a can be substantially perpendicular to the balloon longitudinal axis 26. Latitudinal reinforcement fibers 86a can be multiple fibers or a continuously wound single fiber. The balloon 20 may have a load path 750.

The angle between fibers 86a and 86b may be approximately perpendicular and may not change between inflation and deflation.

Figure 9C:
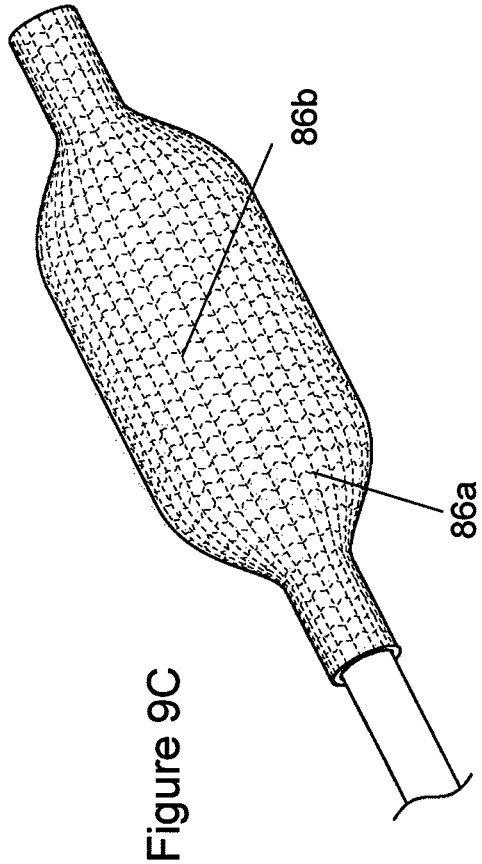
FIGS. 9C, 9D, 9E, 9F, 9G, and 9H illustrate variations of the device.

FIG. 9C illustrates that latitudinal reinforcement fibers 86a can be applied in a wavy or curvy pattern (e.g., a sinusoidal configuration). FIG. 9M shows a close-up of the latitudinal reinforcement fiber 86a of FIG. 9C applied in a wavy or curvy pattern. The wavy pattern can have a first wave amplitude width 754 of less than about 10 mm (0.39 in), more narrowly less than about 5 mm (0.20 in), more narrowly less than about 2 mm (0.08 in). The wave pattern may have wave period width 758 of less than about 10 mm (0.39 in), more narrowly less than about 5 mm (0.20 in), more narrowly less than about 2 mm (0.08 in). When pressure is applied to the balloon 20 of FIG. 9C, the fibers 86a can straighten to resemble the configuration of the fibers 86a in FIG. 9B.

During heating and consolidation of the balloon 20 during manufacture (for example, the process shown in FIGS. 55A, 55B and 55C), the fibers 86a may transform to a straighter configuration (e.g., the wave period width 758 may increase and the first wave amplitude width 754 may decrease). The balloon 20 can expand in the hoop direction without placing the fibers 86a in significant stress, for example, stress in excess of 10% of the yield stress.

Figure 9D:
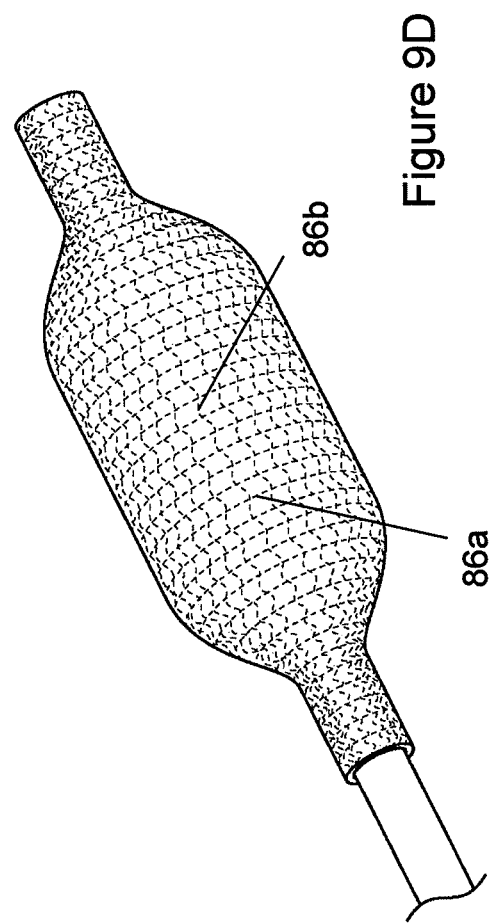
Figure 9M:
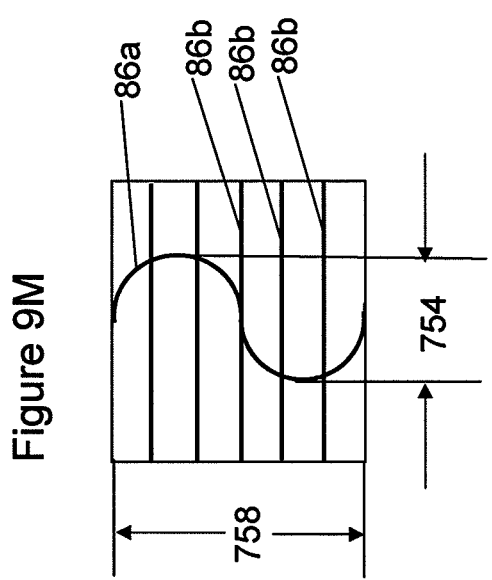
FIG. 9M shows a close-up of a fiber of FIG. 9C.

FIG. 9D illustrates that longitudinal reinforcement fibers 86b can be applied to the balloon 20 in a wavy or curvy pattern similar to the pattern of fiber 86A shown in FIGS. 9C and 9M. Similarly, as described supra, during heating and consolidation of the balloon 20 during manufacture, the fibers 86b may transform to a straighter configuration.

The latitudinal and longitudinal reinforcement fibers 86a and 86b on a single balloon 20 can both have wavy configurations.

When inflated, the balloon 20 may have a biphasic compliance: a first compliance curve and a second compliance curve. The first compliance curve may be generated as the balloon 20 is first pressurized and be the result of the straightening of fibers 86a and/or 86b in the balloon wall 22. The second compliance curve may be generated by the straining under tension of fibers 86a and/or 86b which are then in a substantially straight (e.g., not curvy) configuration.

For example, when the balloon volume 24 is initially inflated to a transition pressure of, for example, about 90 psi (610 kPa), the diametrical compliance of the balloon may average a first compliance of about 0.1% strain per psi (0.1% per 6.9 kPa). Therefore, when the balloon volume 24 is inflated to a transition pressure of 90 psi (610 kPa), the balloon outer diameter 50 may have grown 9%. At pressures beyond the transition pressure of 90 psi (610 kPa), the compliance of the balloon may average a second compliance of about 0.015% per psi (0.015% per 6.9 kPa). Therefore, when the balloon volume 24 is inflated to, for example, about 180 psi (1220 kPa), the balloon outer diameter 50 may have grown 1.35% between about 90 psi (610 kPa) and about 180 psi (1220 kPa).

The transition pressure can be from about 15 psi (101 kPa) to about 1000 psi (6890 kPa), more narrowly from about 15 psi (101 kPa) to about 250 psi (1723 kPa), still more narrowly from about 15 psi (101 kPa) to about 90 psi (610 kPa). The first compliance can be from about 0.025% per psi (0.025% per 6.9 kPa) to about 1% per psi (1% per 6.9 kPa), more narrowly from about 0.05% per psi (0.05% per 6.9 kPa) to about 0.3% per psi (0.3% per 6.9 kPa). The second compliance can be from about 0.005% per psi (0.005% per 6.9 kPa) to about 0.05% (0.05% per 6.9 kPa), more narrowly from 0.01% per psi (0.01% per 6.9 kPa) to about 0.025% per psi (0.025% per 6.9 kPa).

The balloon 20 can have uniphasic compliance. For example, the balloon 20 may have no first compliance. The balloon 20 may have no second compliance. The balloon 20 may have no transition pressure.

Figure 9E:
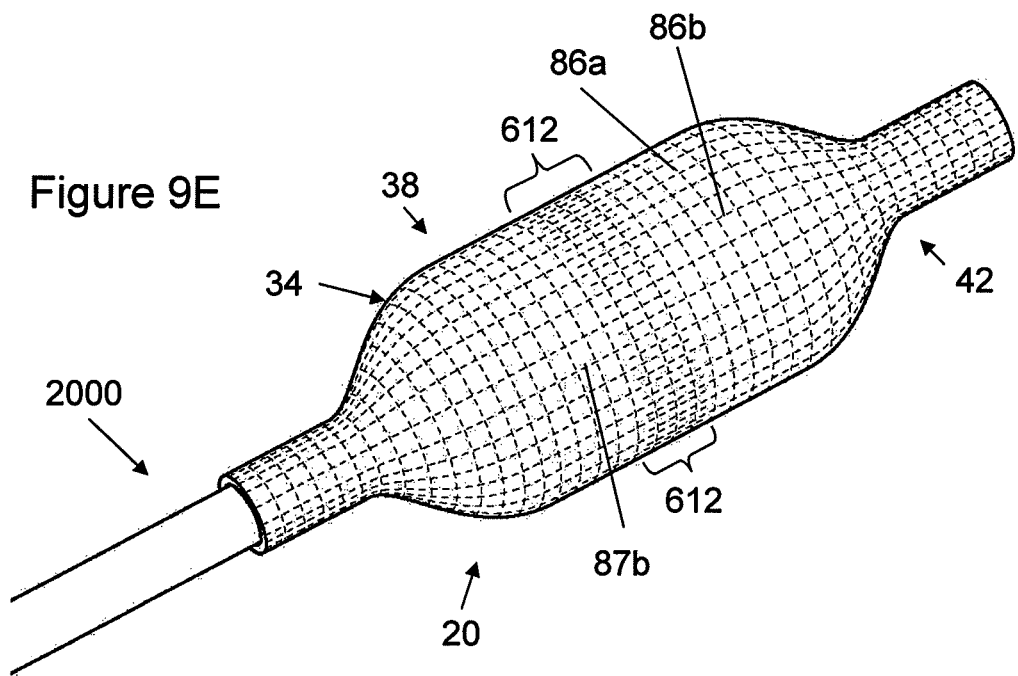

FIG. 9E illustrates that first and second longitudinal reinforcement fibers 86b and 87b, respectively, can be substantially parallel with the balloon longitudinal axis 26. The longitudinal reinforcement fibers 86b and 87b can longitudinally overlap (i.e., have concurrent longitudinal locations along the balloon 20) in reinforcement fiber overlap area 612. The reinforcement fiber overlap area 612 may form a hoop-shaped area that partially or completely encircles the constant-diameter section 38. The fibers 86B and 87B may have fiber lengths less than about 80% of the balloon length 28 more narrowly less than about 75% as long, more narrowly less than about 70% as long, still more narrowly less than about 65% as long, still more narrowly less than about 60% as long as the balloon length 28. Second or latitudinal reinforcement fibers 86a can be substantially perpendicular to the balloon longitudinal axis 26.

Figure 9F:
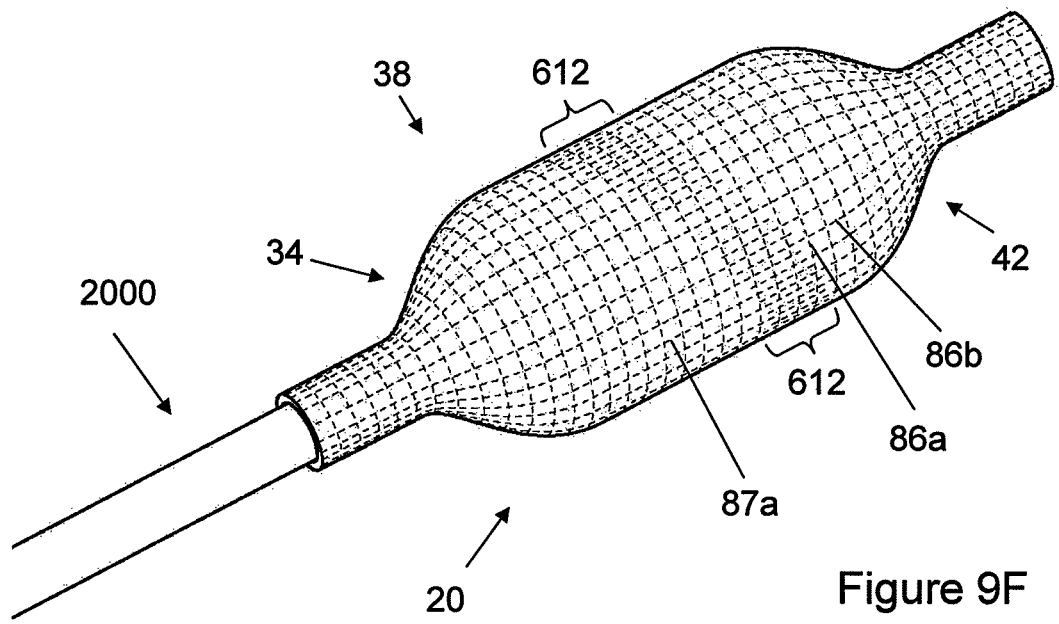

FIG. 9F illustrates that the reinforcement fiber overlap area 612 may form a spiral or helical-shaped area that partially or completely encircles the constant-diameter section 38.

Figure 9G:
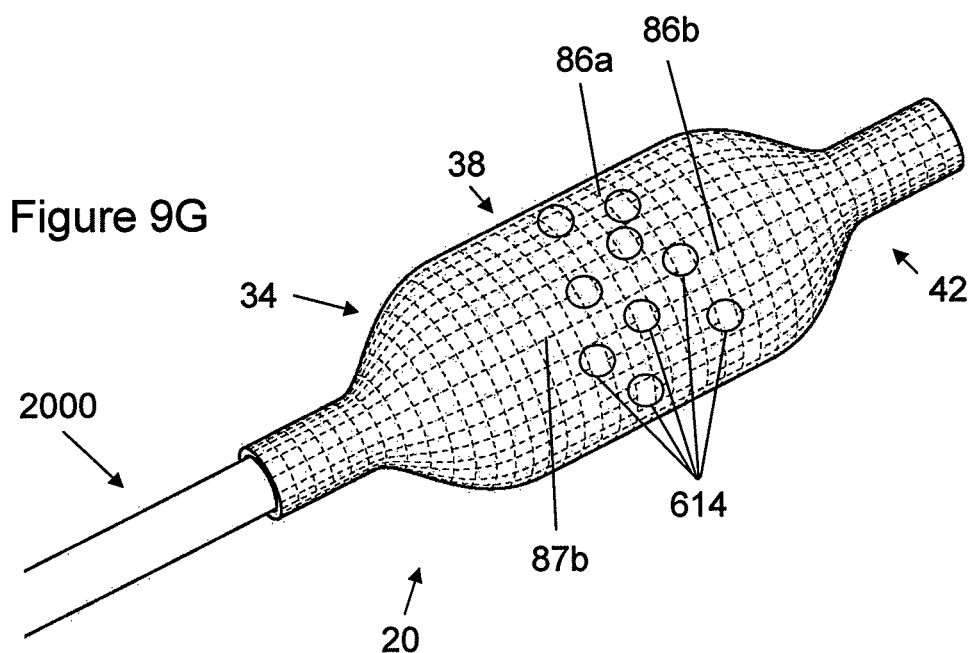
Figure 40:
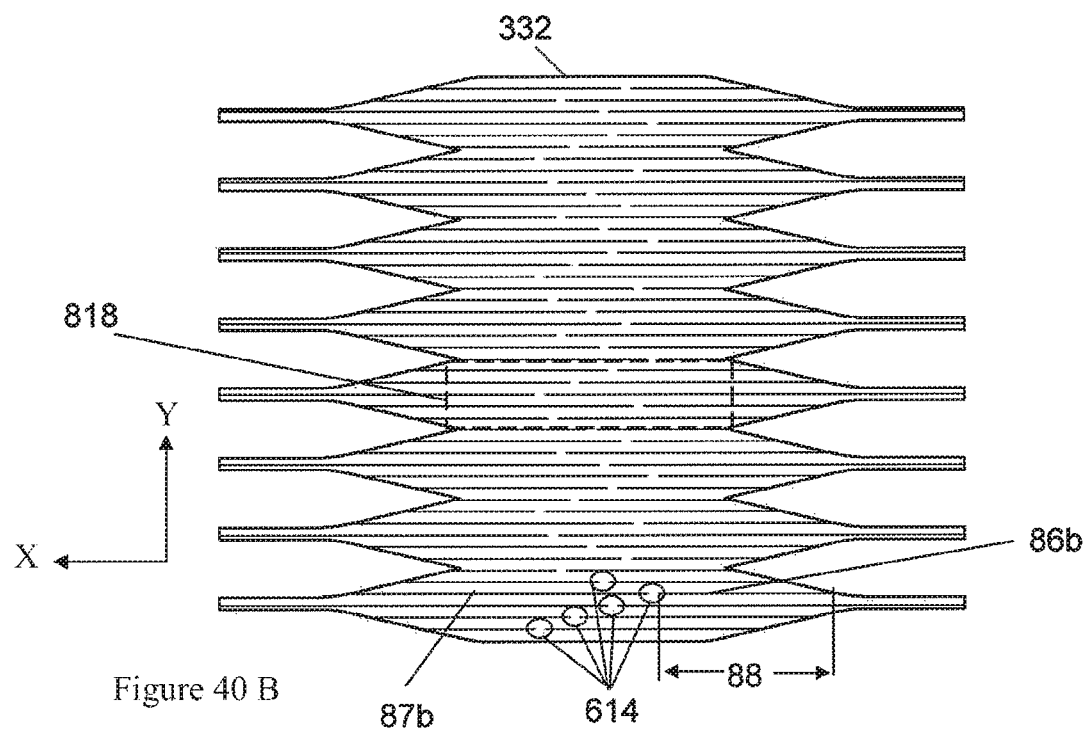
FIGS. 40 through 44 illustrate variations of a panel.

FIG. 9G illustrates that the fibers 86b and 87b can be separated by fiber separation areas 614. Fiber separation areas 614 may be substantially rectangular and may have a fiber separation width 613 and fiber separation length 611. The fiber separation area 614 may separate fibers 86b and 87b by a fiber separation length 611 of about 2 mm (0.079 in.), more narrowly less than about 1 mm (0.039 in.), still more narrowly less than about 0.25 mm (0.01 in.). The fiber separation areas 614 may be distributed on the balloon surface such that no area 614 longitudinally substantially overlaps any other area on the balloon 20. The fiber separation areas 614 may be distributed such that latitudinally adjacent fiber separation areas 614 do not have any longitudinal overlap. The fiber separations 614 may be positioned along the length of the balloon 20 in a pattern sufficient to prevent any fiber from reaching from a first terminal longitudinal end of the balloon 20 to a second terminal longitudinal end of the balloon 20. As shown in FIG. 9G, the balloon 20 may have the panel 196 shown in FIG. 40B, 40C or 41B. Fibers 86$b$ and 87$b$ may have fiber lengths 88 less than about 80% as long as the balloon length 28, more narrowly less than about 75% as long, more narrowly less than about 70% as long, still more narrowly less than about 65% as long, still more narrowly less than about 60% as long as the balloon length 28.

Figure 9H:
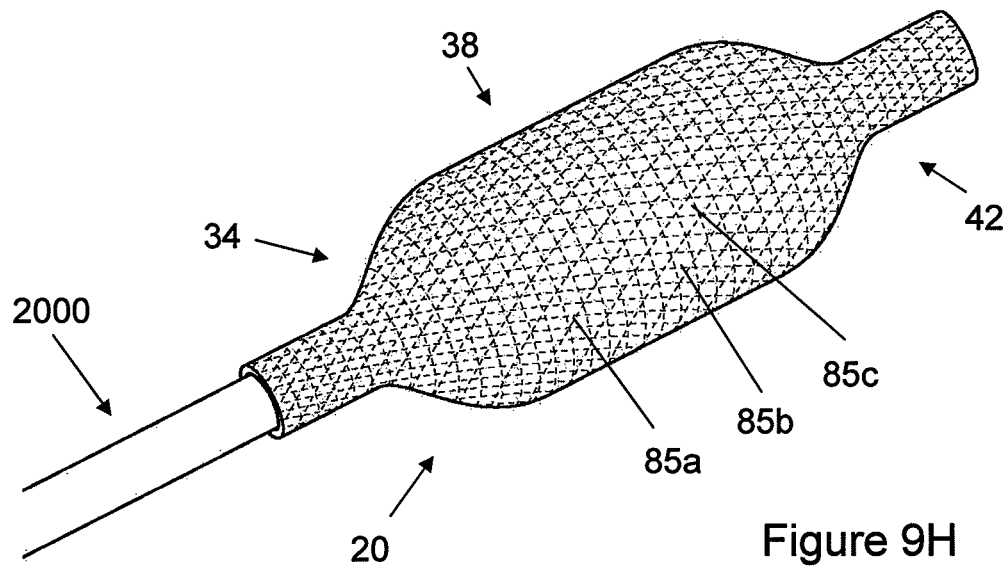

FIG. 9H illustrates that the balloon 20 can have angled reinforcement fibers 85$a$ and 85$b$. First angled reinforcement fiber 85$a$ and/or second angled reinforcement fiber 85$b$ can be at an angle with respect to the balloon longitudinal axis 26. For instance, first angled reinforcement fiber 85$a$ and/or second angled reinforcement fiber 85$b$ can be from about 10° to about 60°. For instance, the fiber 85$a$ and/or 85$b$ can be at about 10°, about 15°, about 20° or about 25° to the balloon longitudinal axis 26. The fiber 85$a$ can be at about 50°, about 55° or about 60° with respect to the balloon longitudinal axis 26. Fiber 85$b$ can have an equal but opposite angle to fiber 85$a$. For example, fiber 85$a$ can be at +20 degrees and fiber 85$b$ can be at about −20° to the balloon longitudinal axis 26. The balloon 20 can have one or more latitudinal reinforcement fibers 85$c$ and/or longitudinal reinforcement fibers (e.g., 86$b$ and/or 87$b$, not shown in FIG. 9H) with one or more angled reinforcement fibers 85.

When inflated, the balloon 20 shown in FIG. 9H may have a biphasic diametrical compliance: a first compliance curve and a second compliance curve. For example, the balloon 20 may have a first angled reinforcement fiber 85$a$ that forms an angle of about 20° with the balloon longitudinal axis 26 and a second angled reinforcement fiber 85$b$ that forms an angle of about −20° with the balloon longitudinal axis 26. The first diametrical compliance curve may be generated as the balloon 20 is first pressurized and be the result of the absolute value of the angle that the fibers 85 make with the balloon longitudinal axis 26 increasing. For instance the angles may change from about 20° to about 39°, or from about −20° to about −39°. The balloon length 26 may decrease and the balloon outer diameter 50 may increase, both in proportion to the pressure contained in balloon volume 24. The second diametrical compliance curve may be generated by the straining under tension of fibers 85$a$ and/or 85$b$ as the pressure in balloon volume 24 is further increased. The first diametrical compliance curve may be more compliant than the second diametrical compliance curve.

Figure 9I:
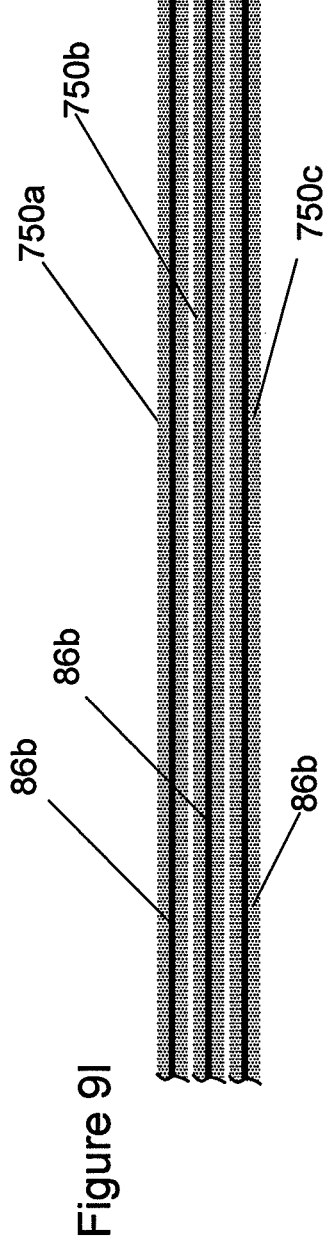
FIGS. 9I and 9J are cross-sectional views of a portion of the wall of variations of the device.
Figure 9J:
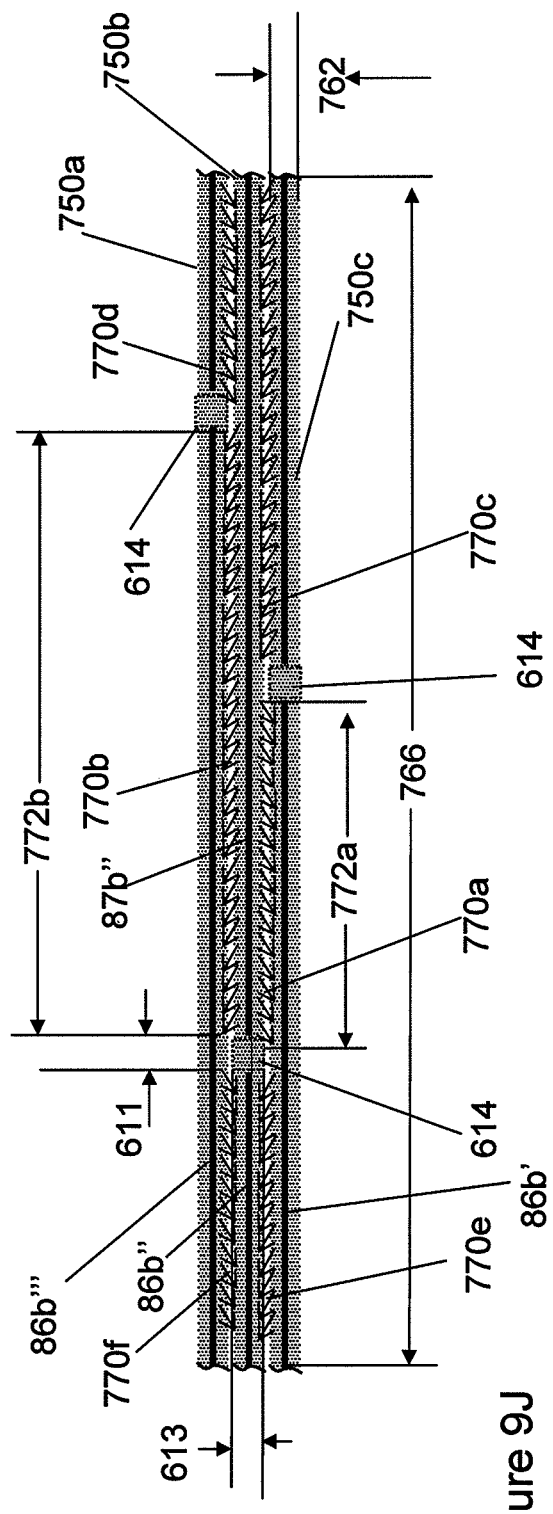

FIGS. 9I and 9J illustrate that the balloon wall 22 can have a first load path 750$a$, second load path 750$b$ a third load path 750$c$, or combinations thereof. The load path 750 may be a portion of the balloon wall 22. The load path 750 can have a load path width 762 and a load path length 766. For instance, the load path 750 may be bounded by the thickness of a layer of longitudinal fiber 86$b$, have a load path length 766 about as long as the constant-diameter length 40 and have a load path width 762 that encompasses one or a plurality of filaments 274 or reinforcement fibers 86 or combinations thereof. The load path length 766 may be about parallel with the longitudinal axis 26 of the balloon 20. A load path 750 may have one or more continuous fibers, one or more cut or separated fibers, or combinations thereof. Load path width 762 may be about equal to fiber separation width 613

FIG. 9I shows that load paths 750$a$, 750$b$ and 750$c$ may each contain a continuous fiber 86$b$. When balloon 20 is inflated, the fibers 86$b$ in the load paths 750 may carry a tensile load along the longitudinal axis 26.

FIG. 9J shows that load paths 750$a$, 750$b$ and 750$c$ may each contain a first longitudinal reinforcement fiber 86$b$ and a second longitudinal reinforcement 87$b$. The first longitudinal reinforcement fiber 86$b$ can be separated by the fiber separation area 614 from the second longitudinal reinforcement 87$b$ in the same load path 750. The tensile load in the respective load path 750 can be transferred by shear loading, as shown by arrows 770, from one load path to one or more adjacent load paths, for example, from the second load path 750$b$ to the adjacent first and/or third load paths 750$a$ and/or 750$c$, respectively; also for example from the first and/or third load paths 750$a$ and/or 750$c$, respectively, to the second load path 750$b$.

When the balloon 20 is inflated, the reinforcement fibers 86$b$ and 87$b$ in the load paths may not carry a tensile load to between the two fibers 86$b$ and 87$b$, for example, because the fiber separation area 614 is in the respective load path 750. The reinforcement fiber 86$b$ or 87$b$ may transfer the respective fiber's tensile load via one or more shear loads 770 to adjacent "receiving" reinforcement fibers 86$b$ and 87$b$ in adjacent load paths 750. The shear transferring of the tensile load can tension the adjacent receiving reinforcement fibers 86$b$ and 87$b$. For instance, first shear load 770A may transfer tension from reinforcement fiber 87$b$" to reinforcement fiber 86$b$' over shear load length 772$a$. Similarly, second shear load 770$b$ may transfer tension from reinforcement fiber 87$b$" to reinforcement fiber 86$b$''' over shear load length 772$b$.

About 20% or more of the longitudinal reinforcement fibers 86$b$ may transmit their tensile loads as shear loads 770, more narrowly about 40% or more, still more narrowly about 60% or more, still more narrowly about 80% or more.

Figure 9K:
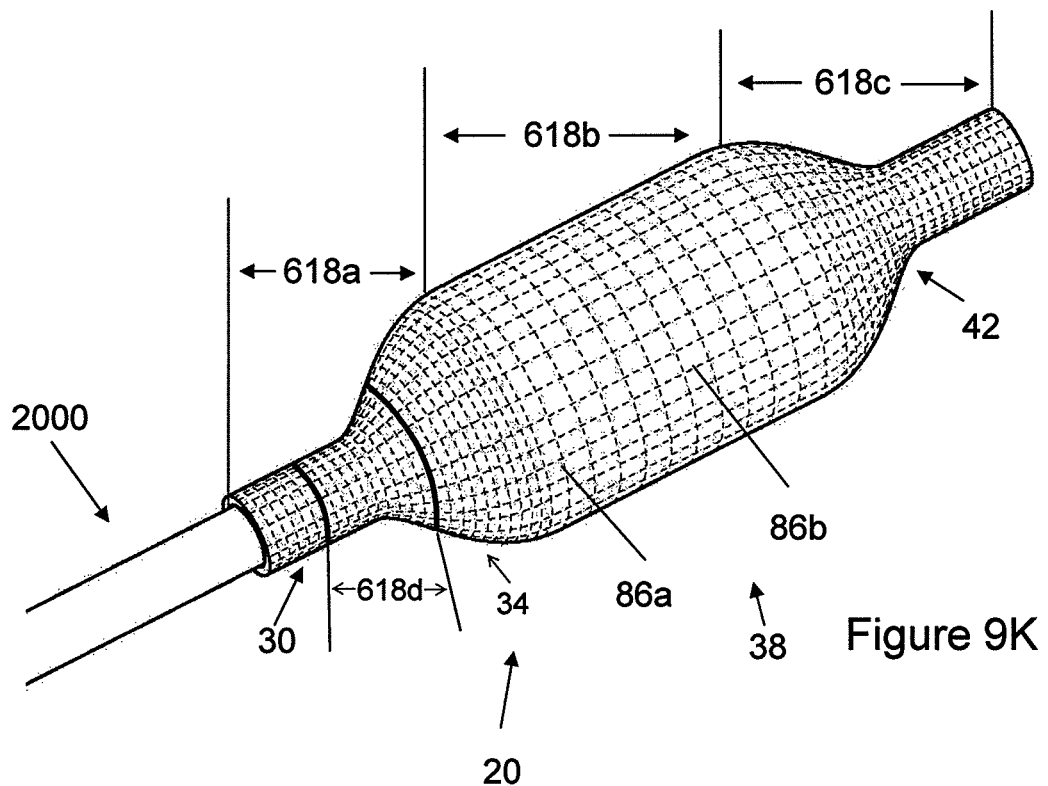
FIGS. 9K and 9L illustrate variations of the device.

FIG. 9K illustrates that the reinforcement fiber 86 can be a single continuous fiber wound (e.g., in a hoop wind) around the balloon 20. The reinforcement fibers 86 can have a fiber density of about 100 winds per inch (i.e., the pitch of the wind). The pitch can vary across the length of the balloon 20. The balloon 20 can have a proximal pitch zone 618$a$, a middle pitch zone 618$b$, a distal pitch zone 618$c$, or combinations thereof. The fiber pitch may be constant in each pitch zone 618. The reinforcement fiber(s) 86 in the pitch zones 618$a$, 618$b$, and 618$c$ can have the same or different pitches. For instance, the pitch of the fiber 86 in zone 618$b$ may be less than the pitches in zones 618$a$ and 618$c$. The pitches in zones 618$a$ and 618$c$ may be substantially equivalent. For example, the pitch in zones 618$a$ and 618$c$ may be about 128 winds per inch, while the pitch in zone 618$b$ may be about 100 winds per inch A lower pitch in one zone, such as middle zone 618$b$ with respect to the other zones, such as the proximal and distal zones 618$a$ and 618$b$, may force the balloon wall 22 to fail (if failure of the balloon wall occurs 22 at all) in the respective zone 618$b$ before failure of the balloon wall 22 were to occur in the other zones 618$a$ and 618$c$. In the example above, zone 618$b$ may burst during failure of the balloon 20 before zones 618$a$ and 618$c$ burst. The pitch zones with a lower pitch, such as middle zone 618$b$, may be more compliant than zones with a higher pitch, such as the proximal and distal pitch zones 618$a$ and 618$b$. The balloon 20 can inflate more in the zone with the lower pitch, such as middle pitch zone 618$b$, relative to the zones with the higher pitch, such as the proximal and distal pitch zones 618$a$ and 618$b$. One pitch zone (e.g., pitch zone 618$b$) may have a 10% lower pitch than the remainder of the balloon wall 22 (e.g., pitch zones 618$a$ and 618$c$), more narrowly a 20% lower pitch.

A pitch zone may cover a portion of balloon proximal stem 30 and an adjoining portion of balloon proximal taper 34. For instance, as shown in FIG. 9K, a pitch zone 618*d* may have a higher pitch than the pitch zones immediately adjacent along the longitudinal axis of the balloon. The pitch zones described herein may give a portion of the balloon wall a significantly higher bending stiffness than other parts of the balloon wall. A balloon wall portion with higher bending stiffness, such as pitch zone 618*d*, may prevent folding or "everting" of the balloon.

Figure 9L:
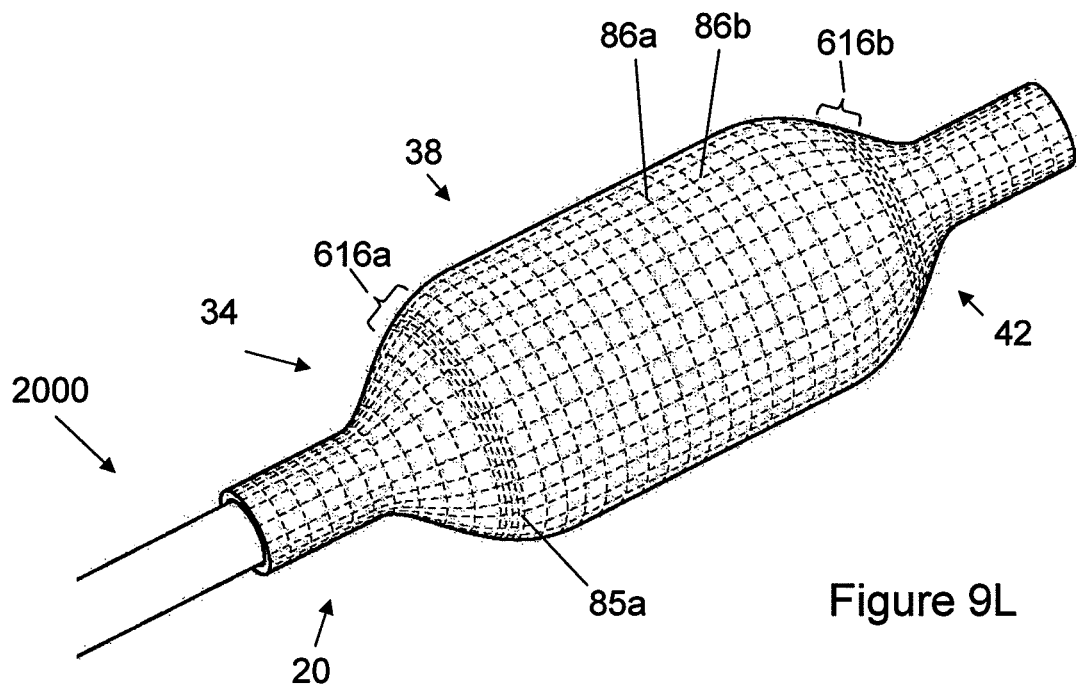

FIG. 9L illustrates that the balloon 20 can have a proximal latitudinal reinforcement band 616*a* and a distal latitudinal reinforcement band 616*b*. The pitch in the latitudinal reinforcement bands 616 may be higher or lower than the pitch of the latitudinal reinforcement fiber 86*a* in the remainder of the balloon. For instance, the pitch in the bands 616 may be at least 10% higher than the pitch in the remainder of the balloon, more narrowly 20% higher. Proximal latitudinal reinforcement band 616*a* may begin at the proximal end of the constant-diameter section 38 and end in the balloon proximal taper 34. For instance, band 616*a* may cover 50% or 25% or 10% of taper 34. Similarly, distal latitudinal reinforcement band 616*b* may begin at the distal end of the constant-diameter section 38 and end in the balloon distal taper 42. For instance, band 616*b* may cover 50% or 25% or 10% of taper 42. The hoop strength of the balloon wall 22 in bands 616 may be increased over the hoop strength in the remainder of the balloon wall 22. The additional strength may minimize or stop balloon rupture propagation. For instance, if the balloon 20 were inflated and subsequently suffered a break in constant-diameter section 38 in latitudinal reinforcement fiber 86*a*, a rupture might form that was substantially parallel to the longitudinal axis. The resulting rupture may propagate into balloon proximal taper 34 or balloon distal taper 42. However, bands 616 may server to stop the propagation of the rupture because of their increased strength in the hoop or latitudinal direction.

A balloon 20 may be designed to burst in a certain mode. For instance, hoop fiber pitch may be chosen such that as pressure in increased in balloon volume 24, the balloon 20 will break fibers 86*a* before breaking fibers 86*b*.

Figure 10A:
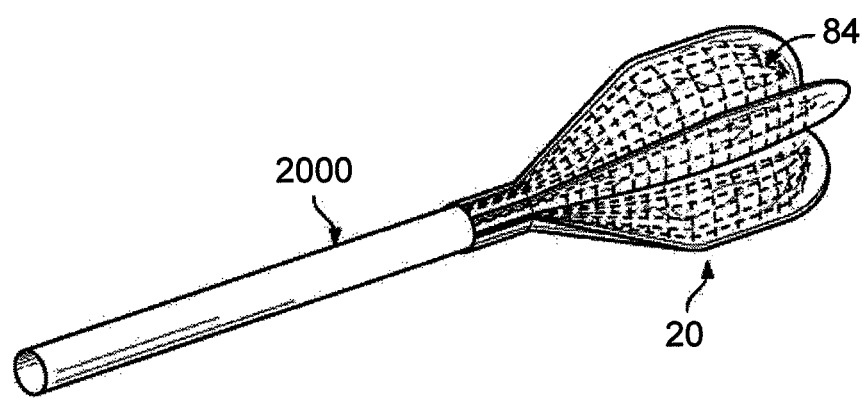
FIG. 10A illustrates a variation of the device in a deflated state.

FIG. 10A illustrates that the balloon 10 can be pleated to form flutes 84, for example four, five or six flutes 84, such as first flute 84*a*, second flute 84*b*. The flutes 84 can be made from accordion pleats, box pleats, cartridge pleats, fluted pleats, honeycomb pleats, knife pleats, rolled pleats, or combinations thereof. The pleating can be heat and/or pressure formed and/or the reinforcement fibers and/or panels can be oriented to form the flutes 84. The balloon 20 can be in a deflated configuration when the flutes 84 are shown.

Figure 10B:
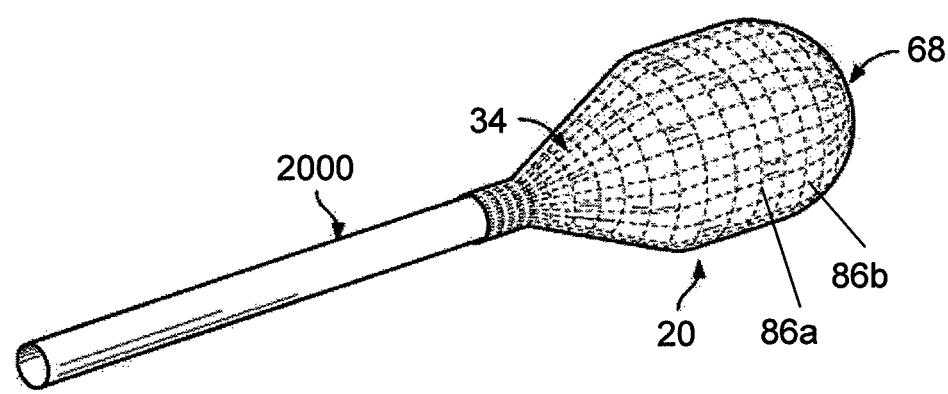
FIG. 10B illustrates a variation of the device in an inflated state.

FIG. 10B illustrates that the balloon 20 in an inflated configuration can push the pleated flutes out to form a substantially smooth outer surface of the balloon wall 22. The balloon 20 can have reinforcement fibers 86. Longitudinal reinforcement fibers 86*b* can be parallel with the balloon longitudinal axis 26. Latitudinal reinforcement fibers 86*a* can be perpendicular to the balloon longitudinal axis 26. FIGS. 10A and 10B do not show spherical reinforcement cap 1060 or longitudinal reinforcing strip 1056, though either or both could be included, as described further below.

FIGS. 11A and 11B illustrates the distal end of the balloon outer wall 22*b* can folded around ("everted") and attached to the outside of the second hollow shaft 2000*b*. The proximal end of the balloon outer wall 22*b* can folded around ("everted") and attached to the outside of the first hollow shaft 2000*a*.

FIGS. 12A and 12B illustrate that from the proximal end to the distal end, the balloon 20 can have a proximal taper 34, a first step 134*a*, a second step 134*b*, a third step 134*c*, and a distal taper 42, or combinations thereof. The first step 134*a* can have a first step outer radius 136*a*. The second step 134*b* can have a second step outer radius 136*b*. The third step 134*c* can have a third step outer radius 136*c*. The first step outer radius 136*a* can be greater than or less than (as shown) the second step outer radius 136*b*. The second step outer radius 136*b* can be greater than or less than (as shown) the third step outer radius 136*c*. The first step outer radius 136*a* can be greater than or less than (as shown) the third step outer radius 136*c*.

During use, the increasing radii steps 134 can be used to measure the target site. The steps 136 may also be used to dilate a target site in a patient. The dilation may be done in succession, first using a step 134 (for example, 134*a*), next using a step 134 with a larger radius (for example, 134*b*). For example, the balloon can sequentially dilate a stenotic vessel or valve with increasing known radii (e.g., instead of purely by feel) of dilation.

FIGS. 13A and 13B illustrate that the first step radius 136*a* and the third step radius 136*c* can be substantially equal. The second step radius 136*b* can be less than the first step radius and the third step radius.

FIG. 13C illustrates that a radially expandable implant 156 can be removably attached to the balloon wall 22. For example, a stent, a percutaneous aortic heart valve, a replacement heart valve annulus, or combinations thereof, can be balloon-expandable and deformed into the second step before insertion of the balloon into the target site.

FIGS. 14A and 14B illustrate that the balloon 20 can have a peanut configuration with a smaller diameter step 134*b* between two larger steps 134*a* and 134*c*.

FIG. 15A illustrates that the balloon proximal stem 30, proximal taper 34, constant-diameter section 38, distal taper 42, or combinations thereof can be curved. The balloon longitudinal axis can be straight or have a balloon radius of curvature 102. The balloon radius of curvature 102 can be from about 2 mm (0.08 in) to about 50 mm (1.97 in), for example about 5 mm (0.20 in), about 8 mm (0.31 in), about 15 mm (0.59 in) or about 30 mm (1.18 in).

FIG. 15B illustrates that the balloon can have a C-shaped configuration. The balloon 20 can trace out an arc (e.g., a portion of a circle). The arc can form an angle of 180 degrees or less, more narrowly 30-120 degrees. The arc can form an angle of 30 degrees, 45 degrees, 60 degrees, 90 degrees or 120 degrees.

FIGS. 16A and 16B illustrate that the balloon 20 can have a toroidal or annular shape. A fluid conduit 176 can extend from the hollow shaft 2000 to the balloon 20. The fluid conduit 176 can delivery fluid pressure to inflate and deflate the balloon 20. The balloon 20 can have an inner wall 22*a* and an outer wall 22*b*. The inner wall 22*a* can be radially inside the outer wall 22*b*. The inner wall 22*a* and/or the outer wall 22*b* can comprise a fiber 86 and/or a panel 196. The balloon 20 can have an annular lumen 160 passing through the radial center of the balloon 20. The annular lumen 160 can open to an annular lumen distal port 162*a* and an annular lumen proximal port 162*b*.

The distal end of the annular lumen 160 can be attached to one or more distal tensioners 164*a*. The distal tensioners 164*a* can be elastic or inelastic wires, fibers or threads. The distal tensioners 164*a* can be fixed at distal tensioner first ends evenly or unevenly angularly distributed around the distal end of the balloon 20. The distal tensioners 164*a* can attach at distal tensioner second ends to a distal tension anchoring wrap 166a. The distal tension anchoring wrap 166a can be fixed to the hollow shaft 2000.

The proximal end of the annular lumen 160 can be attached to one or more proximal tensioners 164b. The proximal tensioners 164b can be elastic or inelastic wires, fibers or threads. The proximal tensioners 164b can be fixed at proximal tensioner first ends evenly or unevenly angularly distributed around the proximal end of the balloon. The proximal tensioners 164b can attach at proximal tensioner second ends to a proximal tension anchoring wrap 166b. The proximal tension anchoring wrap 166b can be fixed to a tensioning collar 168.

The second step can form a waist. The waist can have additional hoop wrapped fibers. The waist can be substantially non-compliant. The waist can be from about 0 mm (0 in) to about 12 mm in the balloon longitudinal direction, more narrowly from about 3 mm to about 9 mm. The waist diameter can be from about 2 mm (0.08 in) to about 35 mm, for example about 3 mm, about 6 mm, about 20 mm, or about 23 mm.

The tensioning collar 168 can be slidably attached to the hollow shaft 2000. The tensioning collar 168 can translate longitudinally, as shown by arrows in FIG. 16B, along the shaft. The tensioning collar can be pulled and/or pushed by a control line 170 or rod. Before deployment of the inflatable device and after deployment but before removal of the inflatable device, the balloon can be deflated and contracted against the hollow shaft. For example, the control line can be pulled to retract the proximal end of the balloon. For example, the balloon can fold and contract against the hollow shaft. The balloon may be pleated such that, when the tensioning collar is pulled or when a vacuum is applied to the inflatable device, the balloon contracts into a small, packed form (not shown).

The balloon can have a distal segment 172a and a proximal segment 172b. The distal segment 172a and the proximal segment 172b can be annular or toroidal. The annular or toroidal planes can be perpendicular to the balloon longitudinal axis 26. The distal segment 172a can be longitudinally adjacent to the proximal segment 172b. The distal segment 172a can be directly bonded to the proximal segment 172b or joined to the proximal segment 172b by a segment joint 174. The segment joint 174 can be open and allow fluid communication between the proximal segment 172b and the distal segment 172a (not shown) or can be closed to isolate the fluid volume or the proximal segment 172b from the fluid volume of the distal segment 172a.

The distal segment and/or the proximal segment may be inflated by a tube. The tube may be attached to the hollow shaft.

The outer wall, the inner wall, or both walls, may contain a radiopaque material as described herein.

The outer wall of the distal segment can form the first step. The segment joint can form the second step. The outer wall of the proximal segment can form the third step. The second step can be radially smaller than the first step and the second step. A device, such as a minimally invasive replacement heart valve can be attached to the outside of the balloon.

FIG. 16C illustrates that the balloon 20 can have a valve 178. The valve 178 can have a first leaflet 180a, a second leaflet 180b, a third leaflet (not shown), or more. The leaflets 180 can be thin and flexible. The leaflets 180 can collapse inside the annular lumen 160 when the balloon is in a contracted configuration. The valve can allow flow through the annular lumen 160 in the distal direction and prevent flow through the annular lumen 160 in the proximal direction. The valve 178 can be fixed to the distal end of the distal segment of the balloon. The leaflets 180 can be oriented to allow flow distally through the annular lumen and impede or prevent flow proximally through the annular lumen. The leaflets 180 can be oriented to allow flow proximally through the annular lumen and impede or prevent flow distally through the annular lumen.

FIG. 17A illustrates that a shell 678 can have apertures 714. The apertures may be located in the proximal taper 34 and/or the distal taper 42. There may be an equal number of apertures on the each taper. The balloon could have 1, 2, 3, 4, 5, 6, 7, 8, 9, 10 or more apertures on each taper. The apertures may be aligned to fall between flutes or pleats. Apertures 714 may allow fluid, such as blood, to flow thru the inside of the shell. Apertures 714 may make the shell incapable of sustaining static pressure. Shell aperture flaps 718 may be made so that they will close apertures 714 when there is no flow through the balloon. When flow proceeds from left to right in FIG. 17A with sufficient pressure, flaps 718 may open to allow flow through apertures 714. When the pressure relaxes, flaps 718 may shut to restrict flow from right to left in FIG. 17A. In this way, flaps 718 may act as a one way valve. Flaps 718 may be created in situ from shell wall 22 while shell aperture 714 is being cut. For example, flap 718 may be created by cutting a slot in shell wall 22 that creates a hinge point between flap 718 and shell wall 22. Flaps 718 may be attached to the shell after shell aperture 714 is cut.

FIG. 17B shows a cutaway of an inflated annular balloon structure 682. Balloon segments 656 are compressed by shell 678. The annular balloon structure has a central fluid passage 692 and apertures 714. Together, these features may allow fluids, such as blood, to pass through the annular balloon structure even when balloon segments 656 are fully inflated. Second hollow shaft 2000b may provide a lumen thru the center of the balloon. This lumen may be used with a guidewire to locate the balloon during a medical procedure. Second hollow shaft 2000b may have some elasticity or compressibility in the axial direction. First hollow shaft 2000a may allow the provision of pressurized fluid to hollow shaft distal port 54 and balloon inflation/deflation ports 654. Provision of pressurized fluid may cause balloon segments 656 to inflate. Removal of fluids may cause balloon segments 656 to collapse and for the shell to return to a pleated or fluted state.

FIG. 18A illustrates that the balloon can have segments that can be angularly adjacent to each other. For example, the segments and the segment joints can be parallel with the longitudinal axis. The second step can have a larger radius than the first step or the third step. The proximal and distal tensioners can attach to the segments and/or segment joints.

The segments may be inflated by a tube. The tube may be attached to the hollow shaft 2000. The distal and/or proximal tensioners can attach to the balloon at the segment joints and/or at the segments.

The segment walls can have a radiopaque foil and/or a wire, such as a radiopaque marker wire.

FIG. 18B illustrates that the segments can be in fluid isolation from each other at cross section X-X. The segments can have a flattened circle longitudinal cross-sectional configuration. For example, the segments can be almond or eye-shaped.

FIG. 18C illustrates that the segments can be in fluid communication with each other at a length along the balloon shown in FIG. M1.

FIG. 18D illustrates that the segments can have a circular longitudinal cross-sectional configuration. For example, the segments can be cylindrical.

FIGS. 19A and 19B illustrate that the balloon can have a constant outer diameter when measured along the longitudinal axis. For example, the balloon can have a single step. The balloon can have an inner wall 22a, an outer wall 22b and segment joints 174. The segment joints 174 can connect the inner wall to the outer wall. The segment joints 174 can minimize the inward radial collapse of the inner wall during inflation.

FIG. 19C illustrates that the hollow shaft can have an inner lumen 154a and an outer lumen 154b. The fluid conduit can be in fluid communication with the outer lumen and the balloon. The outer lumen can deliver pressure through the fluid conduit and to the balloon. The inner lumen can be a through lumen. The outer lumen can extend through the distal proximal tip.

FIG. 20 illustrates that the balloon can have a spiral or helical configuration. The spiral can have a first winding 182a, a second winding 182b, and more (e.g., five, as shown) windings. The first winding 182a can be joined to the second winding 182b at a winding joint 184. The winding joint 184 can have an adhesive or a weld joint. The winding joint 184 can have a strip of elastic or inelastic material attached to the adjacent windings. The balloon 20 can be formed from a single continuous lumen.

Radiopaque foils, wires and any other radiopaque element or metal element herein can be made from gold, platinum, platinum-iridium alloy, tantalum, palladium, bismuth, barium, tungsten, or combinations thereof. A radiopaque element may be a layer or a panel or a reinforcement element or a film or combinations thereof.

A radiopaque element may be low strength. A low strength material can have a tensile yield strength less than about 100 ksi (690 MPa), more narrowly less than about 50 ksi (345 MPa), still more narrowly less than about 35 ksi (241 Mpa), still more narrowly less than about 25 ksi (172 MPa). The addition of the radiopaque element may increase the burst strength of the balloon no more than an insubstantial amount (e.g., by less than about 15%, more narrowly by less than about 10%, still more narrowly by less than about 5%).

A radiopaque element may be ductile. Ductility can be measured by measuring the reduction in area of a test sample when pulled until the sample is fractured. Ductile materials can have about a 30% or more reduction in area, more narrowly, about a 40% or more reduction in area, still more narrowly about a 50% or more reduction in area, still more narrowly about a 70% or more reduction in area, still more narrowly about an 80% or more reduction in area. Ductile materials, as compared to brittle materials, typically can be bent or folded with less chance of fracturing at the bend.

Any of the balloon layers can have radiopaque dyes or pigments or particles in a compounded media.

Figure 22A:
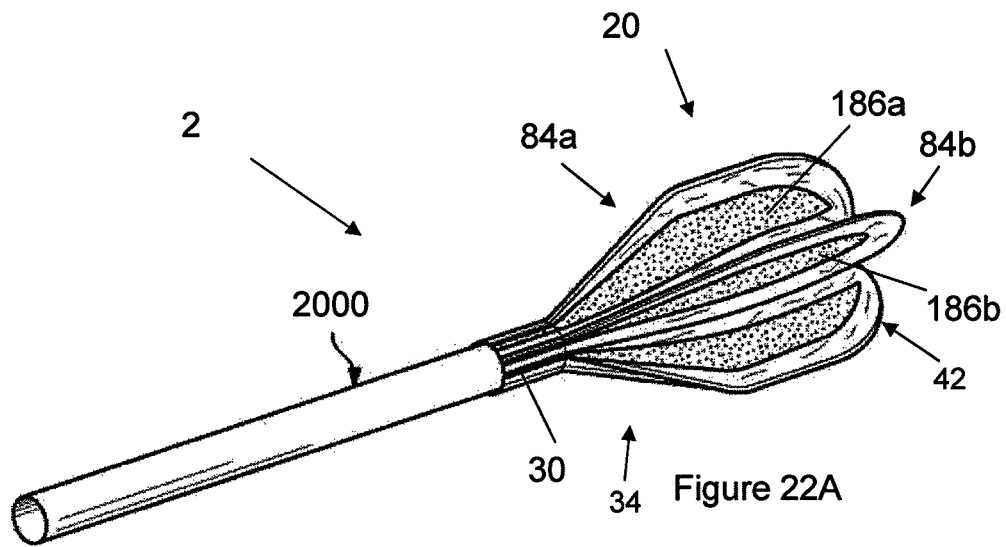
FIGS. 22A and 22B illustrate a variation of the device in deflated and inflated configurations, respectively.
Figure 22B:
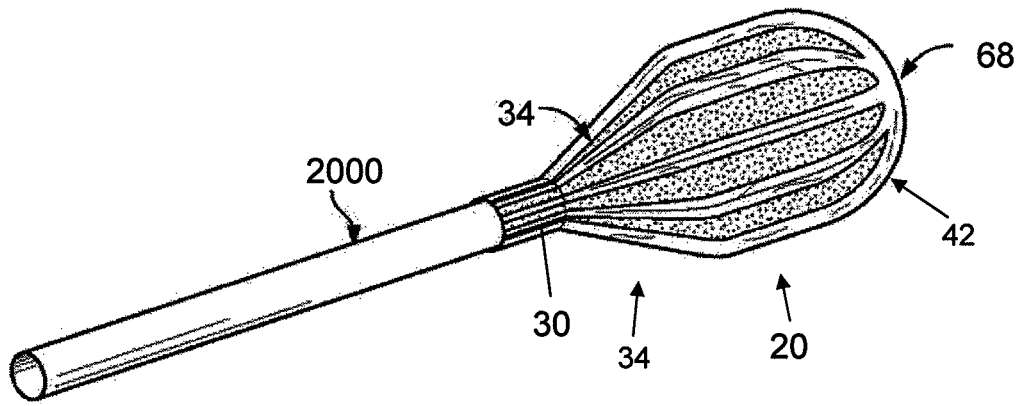

FIGS. 21A and 22A illustrate that the first flute 84A can have a first vane 186a. The second flute can have a second vane 186b. The vanes 186 can be radiopaque elements. The vanes 186 can be panels. The vanes 186 can be embedded within or attached to the inside or outside of the balloon wall 22. All, some, one, or none of the flutes can have vanes. The vanes 186 can be reinforcements. For example, the vanes 186 can be a laminate, foil or wafer. The foil or wafer can be a plastic or metal listed herein, such as tantalum. The vane 186 can be strong enough to cut soft or hard tissue adjacent to the pleat. The vanes 186 can be rigid or flexible. FIGS. 21B and 22B illustrate that in an inflated or expanded configuration, the vanes 186 can lie flat along the wall.

A single radiopaque layer can encompass substantially the entire area of the balloon (as shown in FIG. 1, but with a radiopaque layer congruent with the balloon 20). The radiopaque layer can be a single continuous layer, for example as a deposition or (e.g., radiopaque) foil lining with e.g. a deposition or foil of a metal such as listed herein.

The foil can be less than about 30 μm (0.0012 in) thick, for example less than about 20 μm (0.0008 in) thick, for example about 15 μm (0.0006 in), about 12 μm (0.0005 in), about 10 μm (0.0004 in) or about 8 μm (0.0003 in) thick. Radiopaque foils can be cut or patterned by laser cutting, wire EDM, die cutting or deposition. The foils may be mounted to a removable backing before cutting such that a pattern of foils may be easily applied during the balloon construction process.

The vanes 186 can cover the distal half of the balloon. The vanes 186 can cover the proximal half of the balloon. The vanes 186 can overlap in the longitudinal center of the balloon. A radiopaque foil can strengthen the balloon wall 22.

The balloon 20 can have pleats or flutes between vanes or panels. The vanes or panels can form the pleats or flutes. A panel or vane, such as a radiopaque foil, can minimize leaks from forming between fibers in the balloon during use.

FIG. 23A illustrates that the vanes 186 can be spaced evenly around the balloon longitudinal axis. The vanes can be radiopaque and/or echogenic. The vanes can be rectangular, triangular, circular, oval, or combinations thereof. The vanes can be made of a metal foil. The vanes can be oblong having a major axis and a minor axis. The major axis can be parallel with the balloon longitudinal axis.

FIG. 23B illustrates that the balloon can have first vanes 186a spaced evenly around the balloon longitudinal axis. The balloon can have one or more second vanes 186b at the balloon distal terminal end.

FIG. 23C illustrates that the balloon can have a third vane 186c at the proximal taper. The second and/or third vanes can partially or completely circumferentially envelope the balloon around the balloon longitudinal axis.

FIG. 23D illustrates that the balloon can have marker spots 188 evenly or unevenly distributed around the balloon. The marker spots 188 can be radiopaque and/or echogenic. The marker spots 188 can be circular, oval, square, triangular, rectangular, pentagonal, hexagonal, or combinations thereof. The marker spots 188 can be in a layer of the balloon wall or attached to the inner or outer surface of the balloon wall.

23E illustrates that the balloon can have a marker wire 190 in a helical configuration about the balloon longitudinal axis. The marker wire 190 can be radiopaque and/or echogenic. The wires 190 can be electrically conductive. The wires 190 can carry electrical current, for example for RF delivery, resistive heating, or combinations thereof. The marker wire 190 can be in a layer of the balloon wall or attached to the inner or outer surface of the balloon wall 22.

FIG. 24A shows a pattern for a marker wire 190. Marker wire 190 may be wound around the balloon such that it partially covers the distal and proximal ends of the constant-diameter section 38 of the balloon 20. The constant-diameter section 38 may be the area of the balloon that is responsible for most or all of the expansion done by the balloon 20 in a patient.

FIG. 24B shows a pattern for a marker wire 190. Marker wire 190 may be wound around the balloon on both the distal 42 and proximal tapers 34 of the balloon. The marker wire may be wound up to the distal and proximal borders of the constant-diameter section 38 without any substantial amount of the wire being placed in the constant-diameter section 38. The marker wire may be wound in a helical pattern in both directions on the balloon or be wound in a single direction. The angle 191 between two layers of marker wire may be less than 20 degrees, more narrowly less than 10 degrees, still more narrowly less than 6 degrees.

FIG. 24C illustrates that the balloon 20 can have a marker wire 190 wrapped over approximately the entire length of constant-diameter section 38. The marker wire 190 may be centered on the constant-diameter section 38. The marker wire 190 may cover only a portion of the constant-diameter section 38. For instance, the marker wire 190 may cover more than 70% of the constant-diameter section 38, more narrowly more than 80%, still more narrowly more than 90%. The marker wire 190 may cover a portion of the distal tapers 42 and proximal tapers 34. For example, the marker wire 190 may cover 100% of the distal tapers 42 and proximal tapers 34, more narrowly more than 50%, still more narrowly more than 25%. The marker wire 190 may be a latitudinal reinforcement fiber 86a.

FIG. 24D illustrates that the balloon can have a marker wire 190 wrapped over substantially the whole length of the balloon 20.

FIG. 24E shows that a first marker wire 190a may be placed at the about the proximal end of balloon central section 38, a second marker wire 190b may be placed at about the middle of balloon central section 38 and a third marker wire 190c may be placed at about the distal end of balloon central section 38. Marker wires 190a, 190b and 190c may comprise about a single loop of radiopaque wire.

The pitch of the marker wire 190 may be less than about 150 winds per 1 inch (25.4 mm), more narrowly less than about 75 winds per 1 inch (25.4 mm), still more narrowly less than about 25 winds per 1 inch (25.4 mm), still more narrowly less than about 10 winds per 1 inch (25.4 mm). The pitch of the marker wire 190 may be about 6, 5, 4, 3 or 2 winds per 1 inch (25.4 mm).

The marker wire 190 can be made of any radiopaque material listed supra. The material may be chosen to be highly ductile so that it can form without fracturing as the balloon is folded. The marker wire 190 may be a round or flat wire. For example, the marker wire 190 may be circular and about 6 μm (0.0002 in) to about 25 μm (0.001 in) in diameter. The marker wire 190 may be a flat (or rectangular) wire about 6 μm (0.0002 in) to about 18 μm (0.0007 in) thick and about 12 μm (0.0005 in) to 125 μm (0.005 in) wide. For example, it may be about 12 μm (0.0005 in) thick and 75 μm (0.0015 in) wide.

The marker wire 190 can carry a tensile load. For example, the wire 190 can have a 0.001 in. diameter and maintain a tensile load of 0.3 N without yield or failure. The marker wire 190 can be low strength and/or ductile as defined herein.

The vanes 186, the marker spots 188 and the marker wires 190 can be on the inside of the balloon wall 22, the outside of the balloon wall 22, or within the balloon wall 22.

Figure 25:
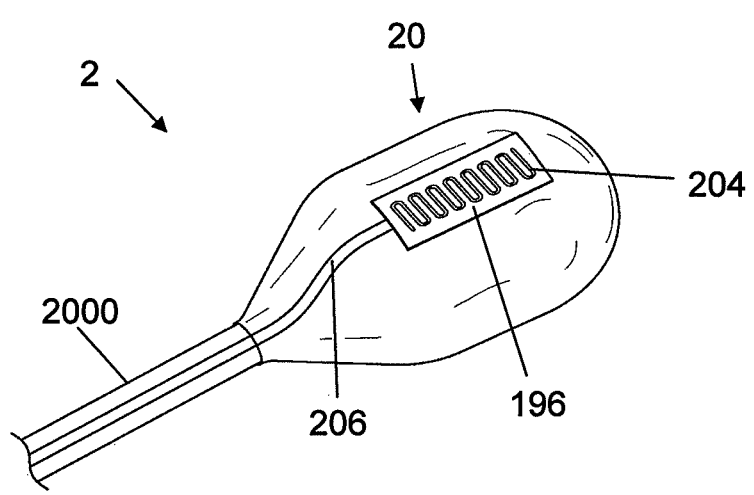
FIG. 25 illustrates a variation of the device.

FIG. 25 illustrates that the balloon can have a resistive heating element 204 in a layer of the balloon wall or on the radial outside or radial inside of the balloon wall. The heating element 204 can have a resistive wire on a panel. The panel can be made from copper or another metal. The heating element 204, such as the resistive wire or panel, can be connected to a heating lead 206. The heating lead 206 can extend proximally along the hollow shaft 2000. The heating lead 206 can be proximally connected to a controller and power source. The system can have a heat control unit for controlling the level of energy delivery to the resistive heating element 204. The heating element 204 can be separated positive and negative electrodes on the balloon wall outer surface and contact the target site tissue directly, within the balloon wall, or on the radial inside of the inside surface of the balloon, or combinations thereof. The heating element 204 can have a dielectric material. Radiofrequency energy can be delivered across the dielectric material of the heating element 204 to create ohmic heating in the tissue. The balloon 20 can be used to heat, cool (e.g., when the panel is a Peltier junction), emit RF power, or combinations thereof.

The heating element 204 can be substituted for or configured in combination with a UV-emitting element, visible light-emitting element, microwave-emitting element, ultrasonic-emitting element, radio frequency emitting element or combinations thereof. The heating element 204 can be replaced or configured with a strain gauge, a peltier junction or a temperature measuring device, or combinations thereof.

The balloon can be used to treat abnormal mucosa in an esophagus, for example by positioning the heating element near or in contact with the abnormal mucosa and delivering heat. The mucosal layer of the esophageal wall, for example the columnar epithelium, can be injured or ablated and made necrotic with the balloon to normalize mucosa in the esophagus.

FIG. 26A illustrates that the balloon wall 22 at section BB-BB or at other sections taken through a single wall of the balloon can have a layer 72 that can have a fiber matrix. The fiber matrix can have one or more monofilaments 274 and one or more resins. The resin can be a flexible adhesive 208. The flexible adhesive can remain flexible when cured or melted to form the medical inflatable device 2.

Monofilament 274 can be a reinforcement fiber 85 a reinforcement fiber 86 or reinforcement fiber 87. A reinforcement fiber can be a tow. A tow may contain one or more monofilaments. A fiber may contain one or more monofilaments. The fiber matrix may have one, two or more monofilaments 86 running substantially parallel to each other and embedded in a flexible adhesive 208. The substantially parallel monofilaments may be positioned within the flexible adhesive such that they are touching each other along their length. The substantially parallel monofilaments may be positioned such that there is flexible adhesive separating each fiber along its length.

FIG. 26A illustrates fiber array layer 72 having a layer width 210 in cross-section. The layer width 210 can include a number of monofilaments 274. The layer 72 can have a linear quantity fiber density measured, for example, as the number of monofilaments 274 per unit of layer width 210. The linear quantity fiber density can be equal to or greater than about 500 monofilaments 274 per inch, more narrowly equal to or greater than about 1000 monofilaments 274 per inch, more narrowly equal to or greater than about 2000 monofilaments 274 per inch, yet more narrowly equal to or greater than about 4000 monofilaments 274 per inch. For example, the liner quantity monofilaments 274 density can be from about 1,000 monofilaments 274 per inch to about 2,000 monofilaments 274 per inch.

The fibers 86 or monofilaments 274 can be high strength and inelastic. The fibers may have a strain to failure of less than 10%, more narrowly less than 5%. The fibers may have an ultimate tensile strength greater than 1.8 GPa (260 ksi), more narrowly greater than 2.4 GPa (350 ksi), still more narrowly greater than 2.9 GPa (420 ksi). The fibers can have a fiber or monofilament diameter 212, for example, from about 1 μm (0.00004 in.) to about 50 μm (0.002 in.), for example less than about 25 μm (0.001 in.), more narrowly less than about 20 μm (0.0008 in.). The high strength fibers may be radiolucent or radiopaque. The unidirectional fiber-reinforced matrix can have the same or different sizes and materials of fibers within the same unidirectional fiber-reinforced matrix.

The fiber matrix layer 72 can have a layer thickness 216 from about 1 μm (0.00004 in.) to about 50 μm (0.002 in.), more narrowly from about 8 μm (0.0003 in.) to about 25 μm (0.001 in.), yet more narrowly from about 10 μm (0.0004 in.) to about 20 μm (0.0008 in.)

FIG. 26B illustrates that the fiber density can be less than the fiber density shown in FIG. 26A. For example, the fiber density can be about 500 fibers per inch.

FIGS. 26C and 26D illustrate that the monofilaments 274 or fibers may have a non-circular cross section. For instance, they may have a rectangular or oval cross-section. The cross section of monofilament 274 may have a fiber maximum height 1068 of, for instance about 5 μm to about 20 μm and a fiber maximum width 1072 of, for instance, about 20 μm to about 500 μm. For example, the fiber or monofilament 274 can be about 8 μm high and 25 μm wide. For example, the fiber or monofilament 274 can be about 12 μm high and 50 μm wide.

FIG. 26E illustrates that the inner layer 72b can have a fiber matrix having monofilament 274 in an adhesive 208. The outer layer 72a can have a polymer film, for example as shown in FIG. 27. The laminate shown can be a part of or the entire balloon wall 22.

FIG. 26F illustrates that the outer layer 72a and the inner layer 72b can be polymer films, for example as shown in FIG. 27. In any variation, the polymer films can be the same or different polymers, or any combination thereof. The first middle layer 72c can be a fiber matrix.

FIG. 26G illustrates the outer layer 72a, inner layer 72b, first middle layer 72c and third middle layer 72e can be polymer films, for example as shown in FIG. 27. The second middle layer 72d can be a fiber matrix.

Part or all of the balloon wall 22 can have a volumetric quantitative density of monofilaments 274 measured, for example, as the number of monofilaments 274 per unit of area. The area quantity monofilaments 274 density can be equal to or greater than about 100,000 monofilaments 274 per square inch, more narrowly equal to or greater than about 250,000 monofilaments 274 per square inch, more narrowly equal to or greater than about 1,000,000 monofilaments 274 per square inch, yet more narrowly equal to or greater than about 4,000,000 monofilaments 274 per square inch. The area quantity of fiber can be about 25% of the area of a wall cross section, more narrowly about 50%, more narrowly about 75%.

The ratio of the volume of the fiber matrix to the volume of the monofilaments 274 can be about equal to or greater than about 15%, more narrowly equal to or greater than about 30%, more narrowly equal to or greater than about 50%, yet more narrowly equal to or greater than about 75%.

Figure 26J:
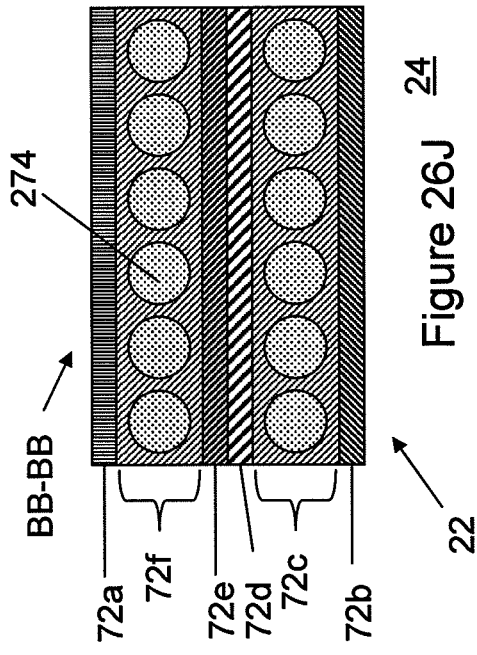
FIGS. 26A through 26O are sectional views through variations of cross section BB-BB of FIG. 1A.
Figure 26K:
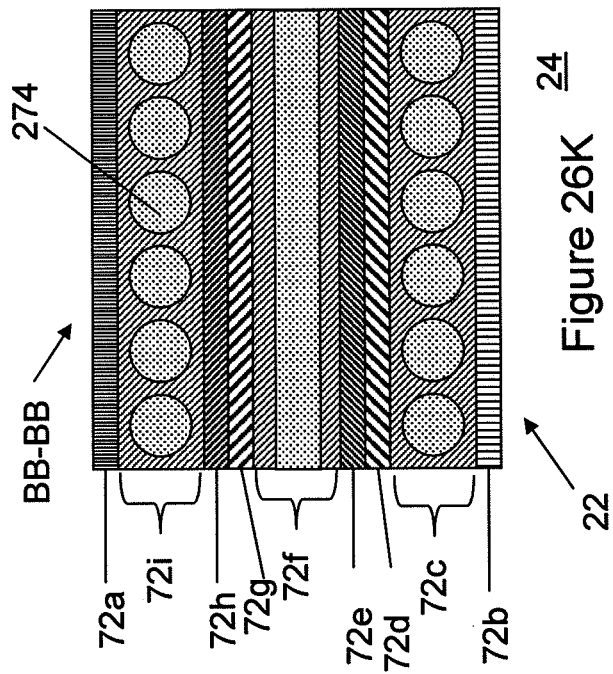
Figure 26H:
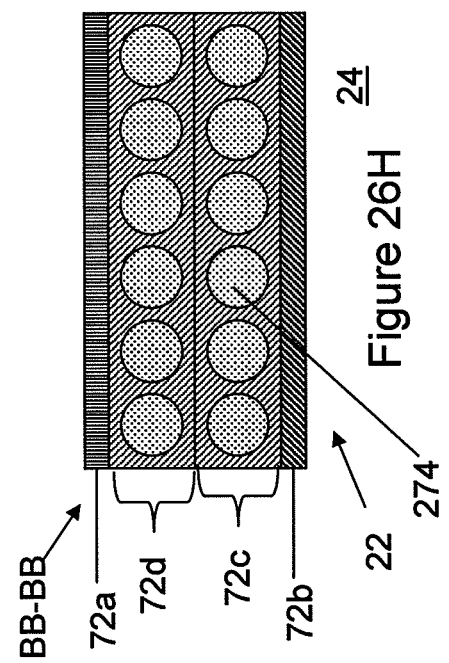

FIG. 26H illustrates that the outer layer 72a, and inner layer 72b can be polymer films. The first middle layer 72c and the second middle layer 72d can be fiber matrices. The first middle layer 72c and the second middle layer 72d can be positioned with the monofilaments 274 substantially parallel to each other (as shown), substantially perpendicular to each other, or at an angle to each other.

Figure 26I:
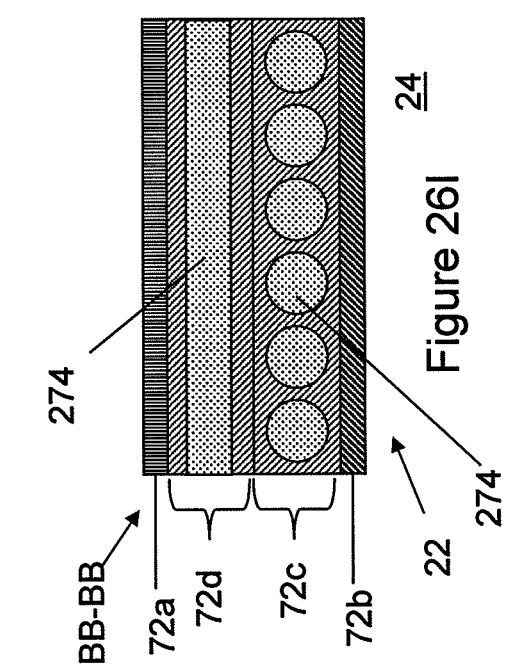

FIG. 26I illustrates FIG. 26H with the monofilaments 274 in second middle layer 72d substantially perpendicular the monofilaments 274 in first middle layer 72c.

FIG. 26J illustrates that the outer layer 72a, inner layer 72b, second middle layer 72d, and third middle layer 72e can be polymer films. The first middle layer 72c and the fourth middle layer 72f can be fiber matrices.

FIG. 26K illustrates that the outer layer 72a, inner layer 72b, second middle layer 72d, third middle layer 72e, fifth middle layer 72g, and sixth middle layer 72h can be polymer films, for example as shown in FIG. 27. The first middle layer 72c, fourth middle layer 72f and seventh middle layer 72i can be fiber matrices.

Figure 26N:
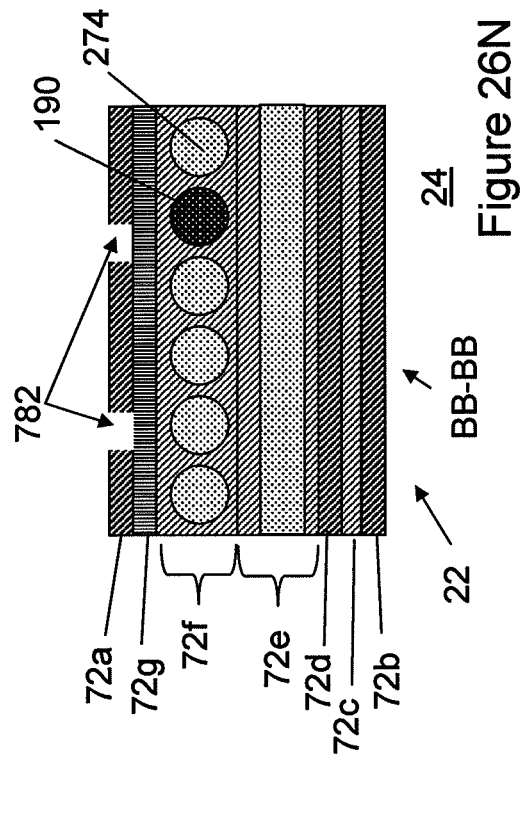
Figure 26O:
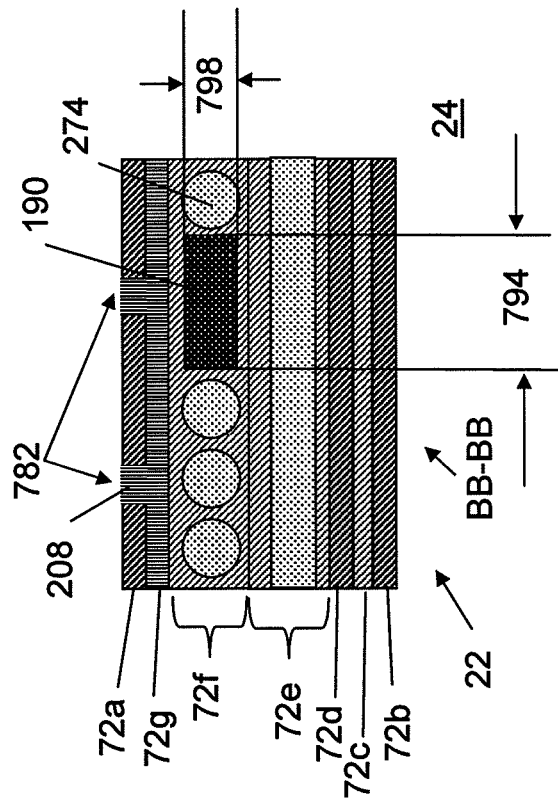
Figure 26L:
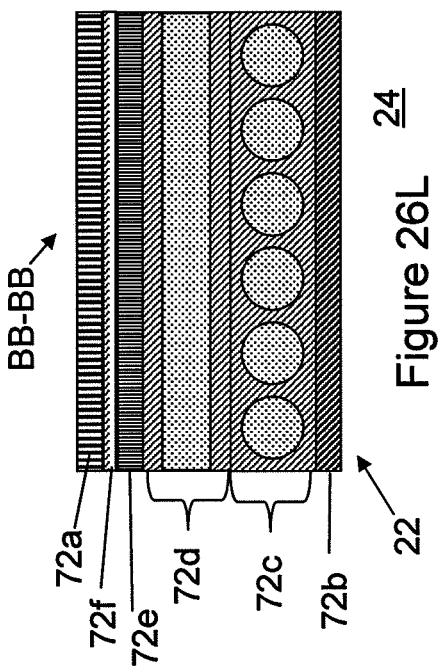

FIG. 26L illustrates that the outer layer 72a can be an MMA-resistant and MMA-releasing polymer film. The inner layer 72b can be a leak proof bladder made from a polymer film, for example as shown in FIG. 27. The first middle layer 72c can be a fiber matrix, for example with the fibers oriented as longitudinal fibers. The second middle layer 72d can be a fiber matrix, for example with the fibers oriented as latitudinal or hoop fibers. The third middle layer 72e can be a resin or adhesive. The fourth middle layer 72f can be a radiopaque layer, such as a metal foil.

Figure 26M:
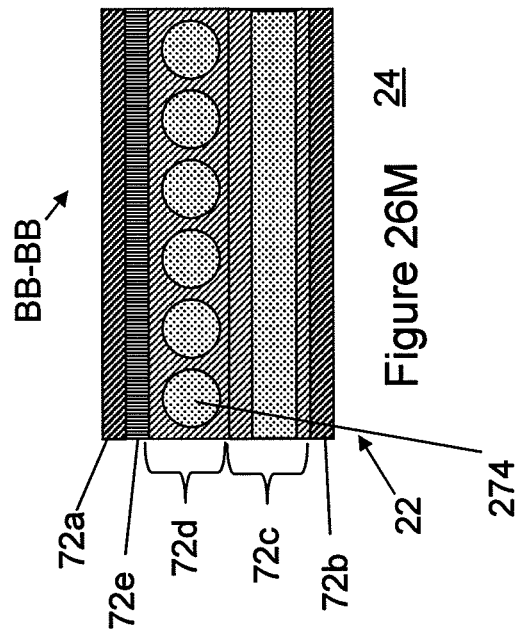

FIG. 26M illustrates that the outer layer 72a can be a polymer film, for example as shown in FIG. 27. The inner layer 72b can be a leak proof bladder made from a polymer film, for example as shown in FIG. 27. The first middle layer 72c can be a fiber matrix, for example with the monofilaments 274 oriented as latitudinal or hoop fibers. The second middle layer 72d can be a fiber matrix, for example with the monofilaments 274 oriented as longitudinal fibers. The third middle layer 72e can be a resin or adhesive. The outer layer 72a may serve to isolate and protect the filaments 274. For example, the filaments may be never get closer than 12 μm, or 10 μm, or 8 μm or 6 μm or 4 μm or 2 μm to the outside surface of the outer layer 72a. The outer layer 72a and/or the inner layer 72b may not melt when adhered to adhesive 208 using processing methods describe herein.

FIG. 26N illustrates that the outer layer 72a can be a polymer film, for example as shown in FIG. 27. Outer layer 72a may have perforations 782 as described infra. The inner layer 72b can be a leak proof bladder made from a polymer film, for example as shown in FIG. 27. The first middle layer 72c can be an adhesive 208. The second middle layer 72d can be a polymer film. The third middle layer 72e can be a fiber matrix, for example with the monofilaments 274 oriented as latitudinal or hoop fibers. The fourth middle layer 72f can be a fiber matrix, for example with the monofilaments 274 oriented as longitudinal fibers and with marker wire 190. The fifth middle layer 72g can be an adhesive 208.

Layers 72 of the balloon may be parylene. For instance, one, two, three, four or more layers of parylene may be deposited.

FIG. 26O illustrates that the adhesive 208 in fifth middle layer 72g may fill in perforations 782 in outer layer 72a. Fourth middle layer 72f may contain a rectangular marker wire 190.

Any of the polymer or fiber matrix layers can be leak proof, water tight, air tight, MMA-resistant, MMA-releasing, or combinations thereof.

Magnetic resonance visualization enhancement materials, such as magnetic contrast agents, can be added to the adhesive, the film or the fiber. The magnetic resonance visualization enhancement materials can enhance the visualization of the balloon during an magnetic resonance imaging (MRI) procedure. For example, the magnetic resonance visualization enhancement material can be gadolium, Omniscan, Optimark, ProHance, Magnevist, Multihance, or combinations thereof.

Any of the layers, for example the outer layer, can be tinted or dyed a visible spectrum color. For example, a pigment, coloring additive, dispersions or other coloring agents, such as an coloring additive from Plasticolors (Ashtabula, Ohio) can be added to the adhesive, laminate or fiber before consolidation. A paint or coating can be added to a layer surface or to the outer surface of the balloon wall.

The color can be selected for branding, market differentiating, as an indication of the type of device, the size of the device, or combinations thereof. For example, devices having a selected diameter, length, pressure rating, clinical indication or efficacy, other common performance metric, or combinations thereof, can be dyed a specific color (e.g., green for a first type of device, red for a second type of device).

The layers can have one or more optical fibers. The fiber optic can be a strain sensor. The strain sensor can monitor the laminate's mechanical status in real time. The fiber optic can guide light delivery into the body. The fiber optic can visualize a target site (e.g., gather light from the body to produce a visual image).

FIG. 27 illustrates polymer films from which panels 196 and/or panels 74 and/or panels 76 and/or layers 72 can be made. The thickness of the polymer films can be from about 2 μm (0.00007 in.) to about 50 μm (0.002 in.), more narrowly from about 2 μm (0.00007 in.) to about 18 μm (0.0007 in.), yet more narrowly from about 4 μm (0.00016 in.) to about 12 μm (0.0005 in.). Films may be metalized or coated to change their surface properties. Metallization or coating may take place before or after a film is formed. Films may be treated chemically or via plasma or via corona treating or by combinations thereof in order to modify their bondability, for example to make them easier to bond too.

FIG. 28 illustrates materials from which the reinforcement fibers 86 or monofilaments 274 can be made. Reinforcement materials may be high strength as described supra. The reinforcement fibers 86 may be a wire or wires. The wire may have chosen with very low strain to failure (for instance, about 2%) or a high strain to failure (for instance, 10% or greater). The wire may be annealed or tempered to adjust its mechanical properties. The wire may have a breaking strength of greater than about 150 ksi, more narrowly greater than 250 ksi, still more narrowly greater than 400 ksi. The wire may be less than 25 μm in diameter. The wire may be substantially rectangular and less than about 25 μm in thickness 1068, more narrowly less than about 15 μm in thickness 1068 when integrated into the wall of the balloon. The ratio of the width 1072 of the wire to the thickness 1069 of the wire may be greater than or equal to about 3, more narrowly greater than or equal to about 5, more narrowly greater than or equal to about 10. The density of the wire may be greater than about 2.4 g/cm^3, more narrowly greater than about 6.9 g/cm^3, more narrowly greater than about 15 g/cm^3.

The reinforcement fiber or wire 86 may be substantially radiopaque when used under a fluoroscope as part of a medical procedure in the human body. The physician may use an inflation medium, such as saline, which is not radiopaque when inflating a balloon 20.

The reinforcement fibers or wires 86 may be coated. The coating may be an adhesive or otherwise increase adhesion of the fibers or wires 86. The coating may be a thermoplastic chosen from one of the materials (or combinations thereof) listed in FIG. 29. The thermoplastic may be melted as part of the process of applying reinforcement fibers 86 to a balloon 20.

FIG. 29 illustrates that the adhesive 208 can be an elastomeric thermoset material, an elastomeric thermoplastic material, an epoxy, a coating or a combination thereof. The adhesive can be selected from any of the materials, or combinations thereof, listed in FIG. 29. The matrix can have a resin and a fiber. The resin can be an adhesive.

Method of Manufacture

Figures 30A, 30B, 31:
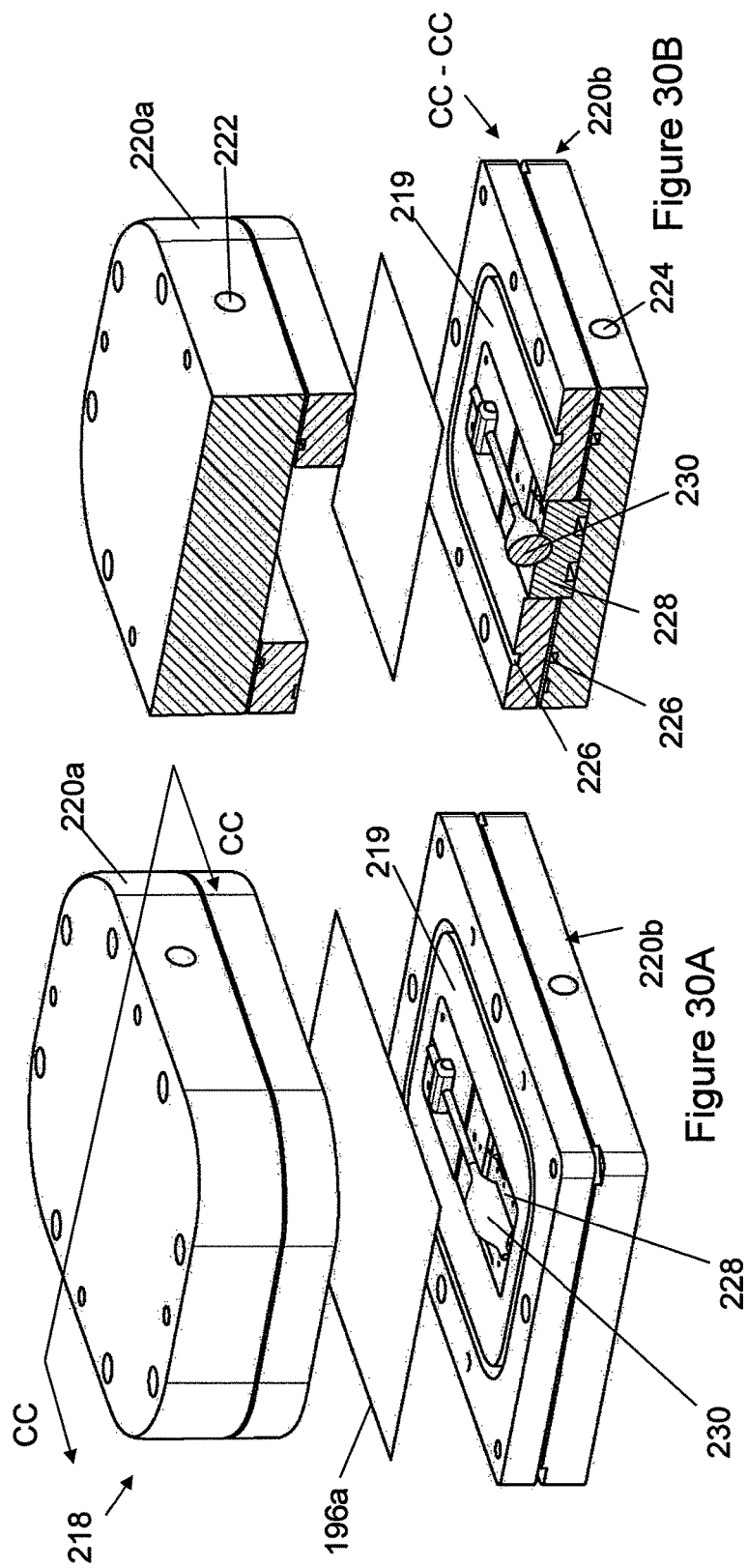
FIG. 30A illustrates a variation of a tool for manufacturing a variation of the inflatable device.
FIG. 30B is a variation of cross-sectional view CC-CC of FIG. 30A.
FIG. 31 is a chart of material characteristics for variations of mandrel materials.

FIGS. 30A and 30B illustrate that the device can be partially or completely manufactured in a pressure chamber 219. The pressure chamber 219 can be in a pressure chamber case 218. The pressure chamber case 218 can have a case top 220a separable from a case bottom 220b. The case top 220a can have a case top port 222. The case bottom 220b can have a case bottom port 224. The case top port 222 can be in fluid communication with the top of the pressure chamber 219. The case bottom port 224 can be in fluid communication with the bottom of the pressure chamber 219.

The case top can screw or otherwise tightly join to the case bottom. The pressure chamber case can have one or more o-rings (not shown) in o-ring seats 226.

The pressure chamber can have a mandrel seat 228. The mandrel seat 228 can be configured to receive a mandrel 230. The mandrel seat 228 can have holes or pores. The holes or pores in the mandrel seat 228 can allow pressure from the case bottom port and the bottom of the pressure chamber to reach the top surface of the mandrel seat around the mandrel and/or directly under the mandrel.

The mandrel 230 can have the inner dimensions of the balloon 20.

The mandrel 230 can be a water soluble mandrel. The mandrel 230 may be made from a low melting point wax or metal, a foam, some collapsing structure or combinations thereof. The mandrel 230 may be an, inflatable bladder. An inflatable bladder may be inflated during part or all of the manufacturing processes described in this application. The mandrel 230 can be made from a eutectic or non-eutectic bismuth alloy and removed by raising the temperature to the melt point of the metal. The mandrel 230 can be made from aluminum, glass, sugar, salt, corn syrup, hydroxypropylcellulose, ambergum, polyvinyl alcohol (PVA, PVAL or PVOH), hydroxypropyl methyl celluslose, polyglycolic acid, a ceramic powder, wax, ballistic gelatin, polylactic acid, polycaprolactone or combinations thereof.

FIG. 31 illustrates characteristics of bismuth alloys from which the mandrel 230 can be made. The characteristics are characterized by melting temperature (as shown in the third row of FIG. 31) of the bismuth alloy.

The mandrel 230 can be transparent or translucent to light and/or an electron beam. The mandrel 230 can be hollow. The outside surface of the mandrel 230 can be coated in a release agent. The mandrel 230 may be molded, machined, cast, injection molded or combinations thereof. The mandrel 230 may be fabricated by blow molding, machining, casting, injection molding, forming, or combinations thereof.

The mandrel 230 can be in the mandrel seat 228 and a first panel 196a to be formed into about half of the inner layer of the balloon wall 22 can be placed between the case top 220a and the case bottom 220b. The case top can then be secured to the case bottom.

Figure 32A:
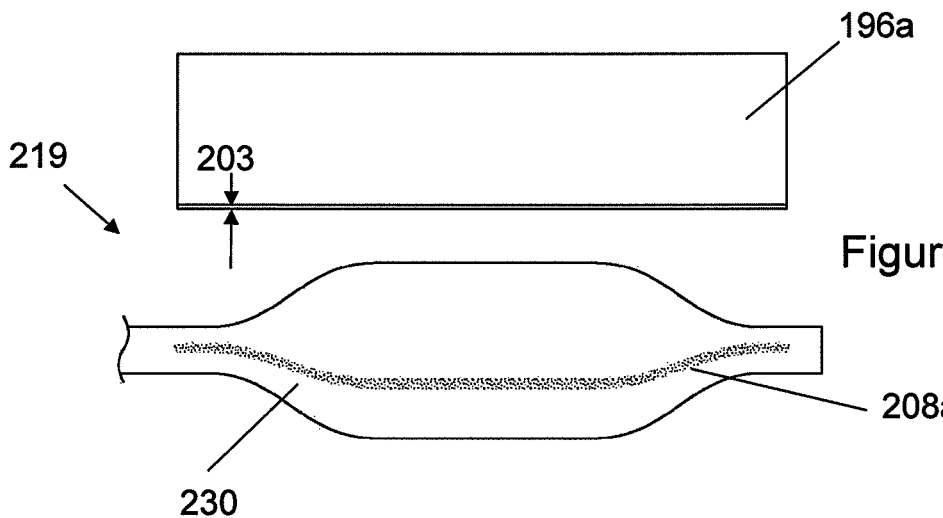
FIGS. 32A through 32E illustrate a variation of a method for manufacturing the device.

FIG. 32A illustrates that the outer surface of the mandrel 230 can have some glue or first adhesive 208a. The first adhesive 208a can be located around the perimeter of the first panel's 196a contact area with the mandrel. The first adhesive 208a can be water soluble. The first adhesive 208a can be a sugar syrup. A panel 196a may be positioned over the mandrel. The panel 196a may be a single layer or multiple layers. For instance, the panel could be a layer of film (for example, taken from FIG. 27) and meltable adhesive (for example, taken from FIG. 29). Panel 196a may have a panel thickness 203. Panel thickness 203 can be about equal across the surface of the panel. The panel 196a can be positioned with film on the side that touches the mandrel and adhesive on the radially outer side. The panel 196A may be perforated as described infra. The panel 196a may not be capable of sustaining pressure between the top and bottom of the panel. Portions or all of the outer surface of mandrel 230 may be a compound curved surface and/or a double curved surface. A compound curved surface and/or a double curved surface may be a surface that is generated by rotating a curved line (the surface generator) about an imaginary straight line wherein the curved line does not cross the straight line.

Figure 32B:
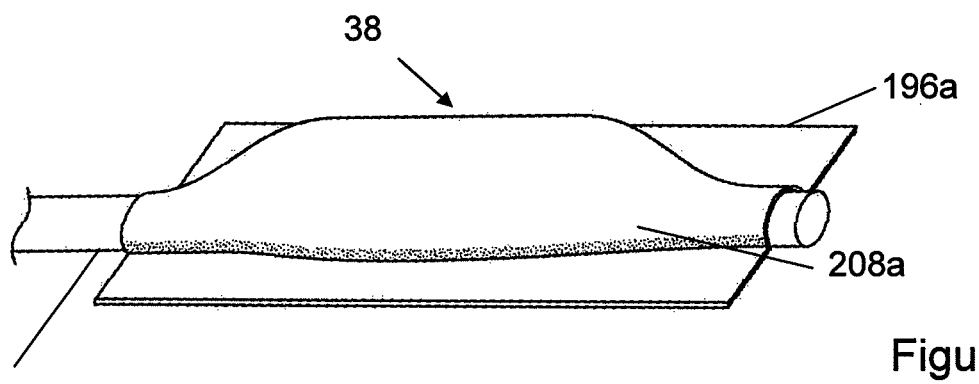

FIG. 32B illustrates that a positive pressure can be applied to the top 220a of the pressure chamber (e.g., through the case top port 222) and/or a negative pressure or differential pressure or suction or vacuum applied to the bottom 220b of the pressure chamber (e.g., through the case bottom port 224). The panel 196A can get sucked and/or pressed down and/or formed onto the mandrel 230. Forming of the panel 196a may cause portions of panel 196a to yield or stretch or deform or become thinner or combinations thereof. For instance, more than about 25% of the panel 196a covering central section 38 may have been significantly yielded and/or stretched during the forming operation. The first panel can be smoothly fitted to the mandrel 230 and adhered to the mandrel at the first adhesive 208A. Heat may be applied to panel 196a before forming onto mandrel 230. Forming of one panel 196a may be done more than once on different sized mandrels before the panel 196a reaches the form shown in FIG. 32B.

Forming of panel 196a may also be accomplished with a mechanical die. The mechanical die may be heated and conform closely to the shape of the mandrel 230. The mechanical die may have a shape similar to the mandrel seat 228. Forming of panel 196a may be accomplished without fluid pressure or dies, by moving the mandrel 230 and panel 196a relative to each other. This can be accomplished by suspending the panel 196a in, for example, a frame.

The mandrel 230 and panel 196a can be mounted into a trimming jig. Any excess portion of the first panel 196a extending from the mandrel 230 can be trimmed with a blade, with a laser, with a water jet cutter, with a die cut tool or combinations thereof. The trimming jig can cover the mandrel 230 and the first panel 196a attached to the mandrel. Several panels 196a and/or layers 72 can be formed over the mandrel 230 and cut. The panels 196a and/or layers 72 may be trimmed at the same time or one at time.

Figure 32H:
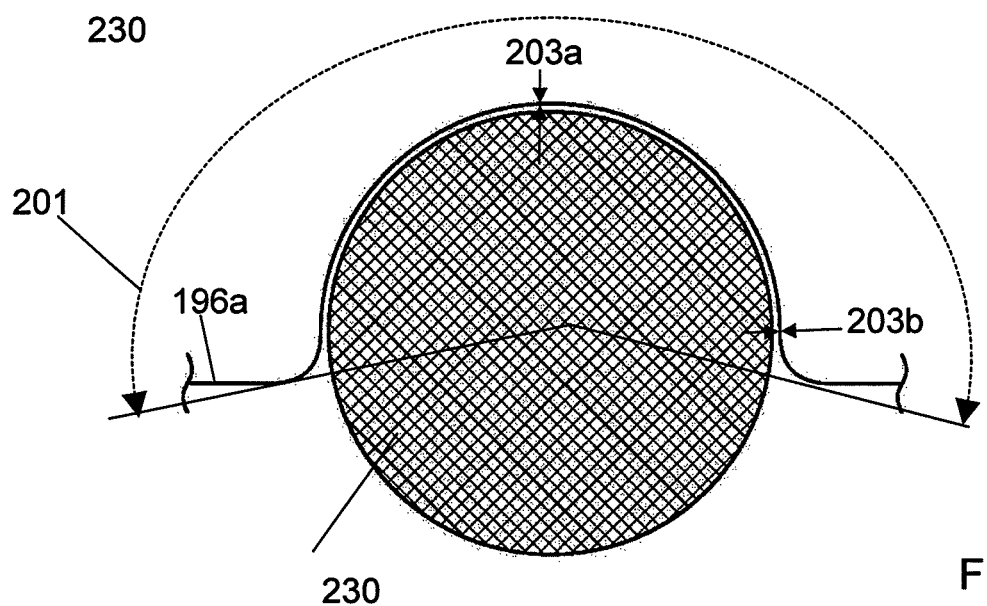
FIG. 32H illustrates a cutaway view of FIG. 32B.

FIG. 32H illustrates a cutaway view of FIG. 32B taken through central section 38. Panel 196a forms a panel forming angle 201. Angle 201 may be from about 0° to about 360°. Angle 201 may be at least 90°, at least 120° or at least 180°. When angle 201 is about 180°, panel 196a may cover about half of the outer surface of the mandrel 230 in central section 38. A first panel thickness 203a may be greater than a second panel thickness 203b. For instance, the ratio of thickness 203b to thickness 203a may be less than about 0.90, more narrowly less than about 0.80, more narrowly still less than about 0.70, more narrowly still less than about 0.60.

Figure 32C:
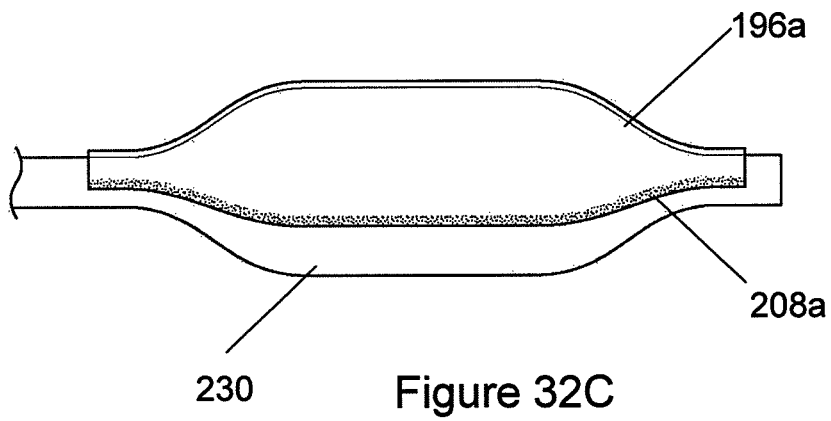

FIG. 32C illustrates that the mandrel can have the excess area of the first panel 196A removed in preparation for attachment of the second panel 196b.

Figure 32D:
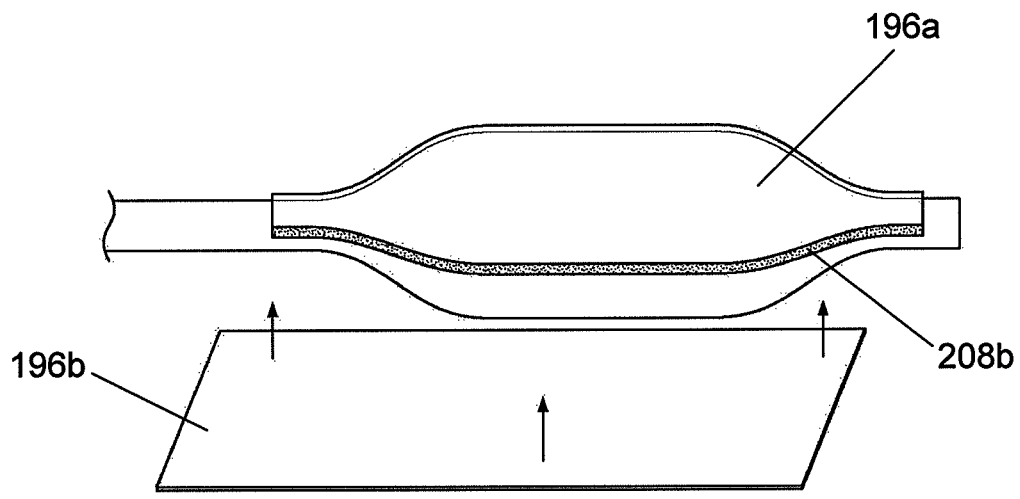

FIG. 32D illustrates that a second adhesive 208b can be applied to the first panel 196a around the perimeter of the second panel's 196b contact area with the first panel 196a. The second adhesive 208b can be an epoxy, urethane, a thermoplastic, a cyanoacrylate, a UV curing adhesive, or combinations thereof. The mandrel 230 can be seated in the mandrel seat 228 with the first panel 196a in the mandrel seat. The second panel 196b can be placed on the mandrel 230 as shown (upside down relative to the FIGS. 30A and 30B for illustrative purposes).

Figure 32E:
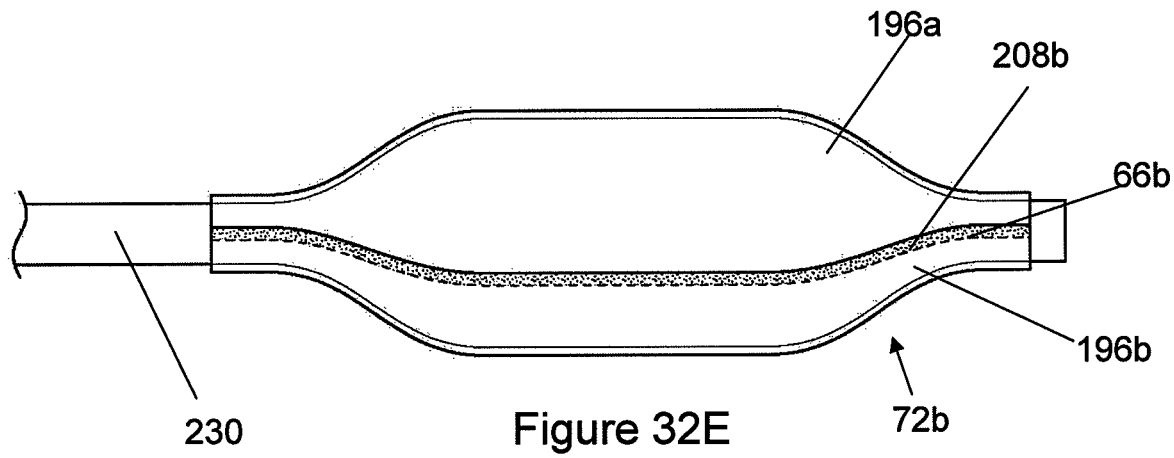

FIG. 32E illustrates that after the case top 220a is secured to the case bottom 220b, the positive and/or negative pressures can be applied to the pressure chamber as described infra. The second panel 196b can be smoothly fitted or pressure formed to or against the mandrel 230 and adhered to the first panel 196a at the second adhesive 208b. Adhesion can be accomplished by the application of heat. The first and second panels (196A and 196B) can form the inner layer 72b or bladder 52 of the balloon wall. The inner layer may be leaktight. The inner layer may be capable of sustaining pressure. Multiple layers can be made by repeating the method described infra. The pressure chamber can be heated, for example, to decrease the viscosity of and decrease the modulus of the panels.

Figure 32G:
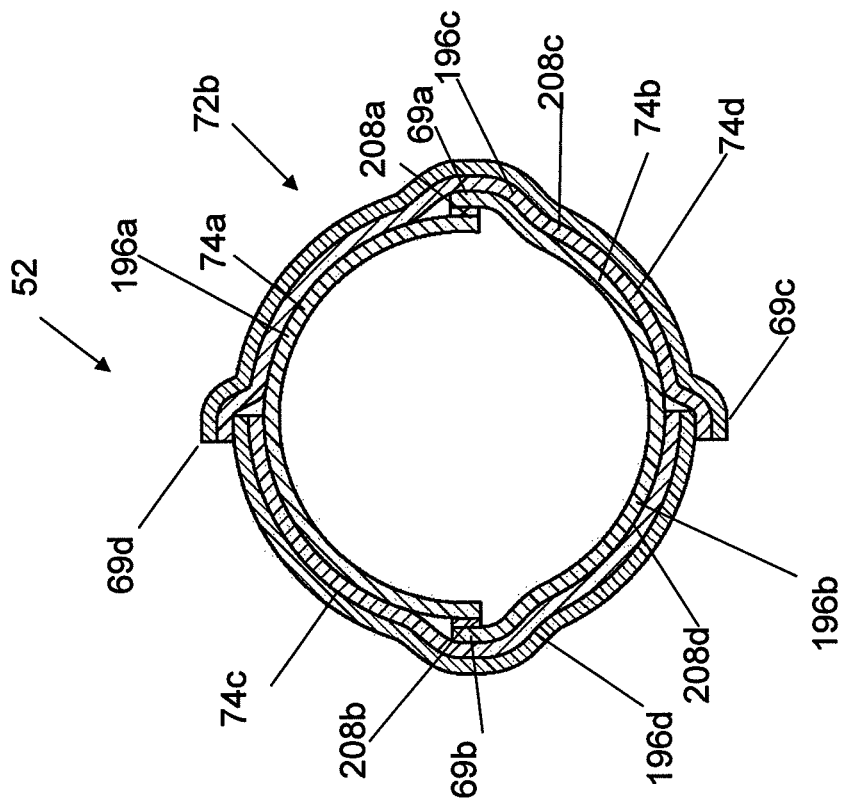
FIGS. 32F and 32G are transverse cross-sectional views of variations of a bladder.
Figure 32F:
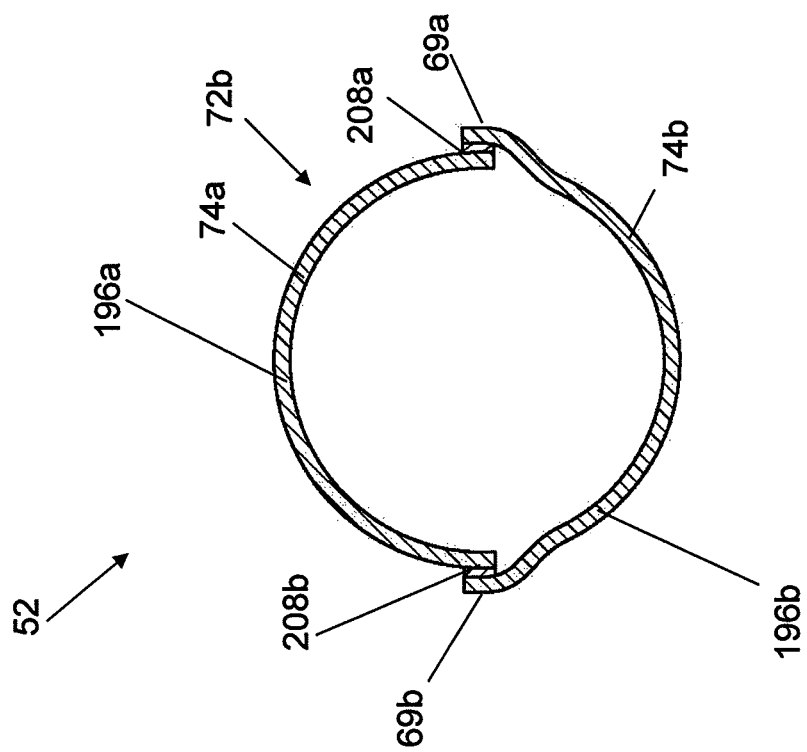

FIG. 32F shows a cross section of 32E with the mandrel 230 omitted. The process in FIGS. 32A thru 32E may be repeated on the part shown in FIGS. 32E and 32F to produce the bladder 52 cross section shown in FIG. 32G. Panels 196c and 196d may be formed. Each panel may have an adhesive 208c and 208d facing radially inward. Balloon third and fourth internal seams 69c and 69d may be oriented about midway between balloons first and second internal seams 69a and 69b. The bladder 52 may be leaktight.

Figure 33C:
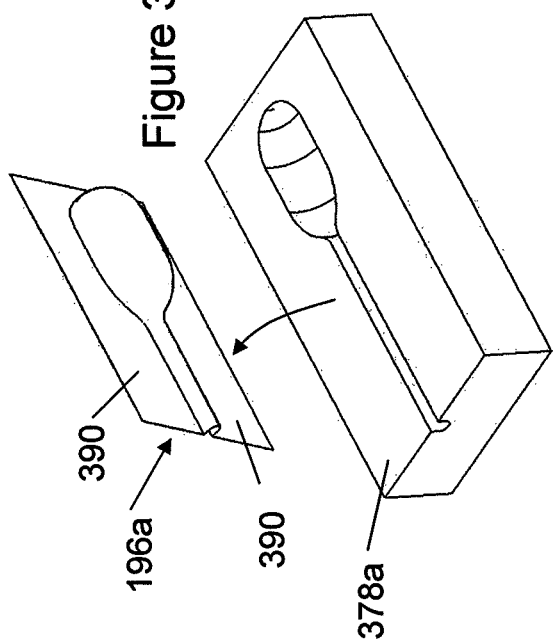
FIGS. 33A through 33D illustrate a method for manufacturing the device.
Figure 33D:
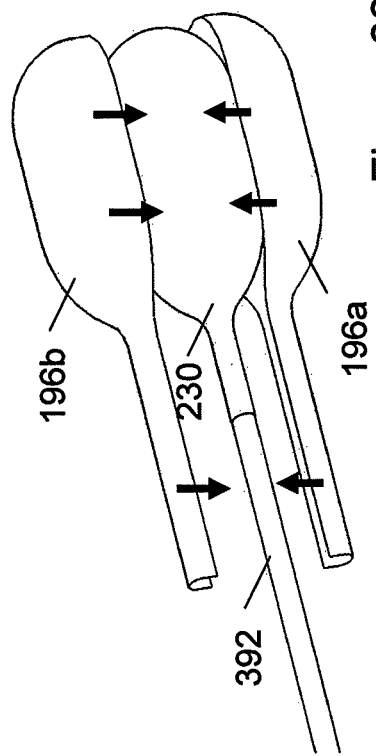
Figure 33A:
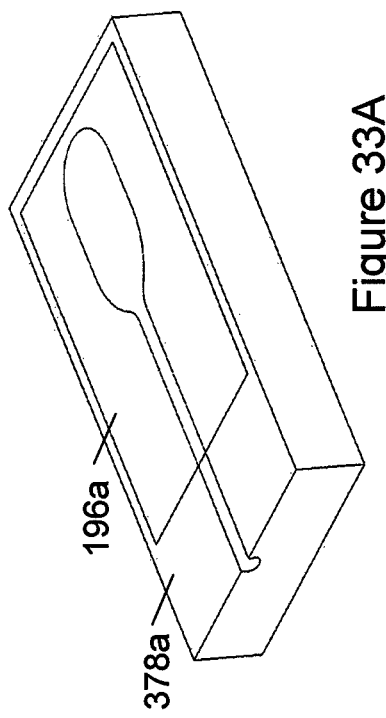

FIG. 33A illustrates that a first panel 196a can rest on top of the female mold half 378a. (The first panel 196a can be a see-through polymer for illustrative purposes. For example, the contours of the mold may be seen.) The first panel 196a can be a polymer, such as a nylon, PET, polycarbonate, urethane or those materials shown in FIG. 27 or any other polymer that can be readily formed or combinations thereof. The first panel can be about 0.002 inches (50 μm) thick, more narrowly about 0.001 inches (25 μm), thick yet more narrowly about 0.0005 inches (12 μm) inches thick.

Figure 33B:
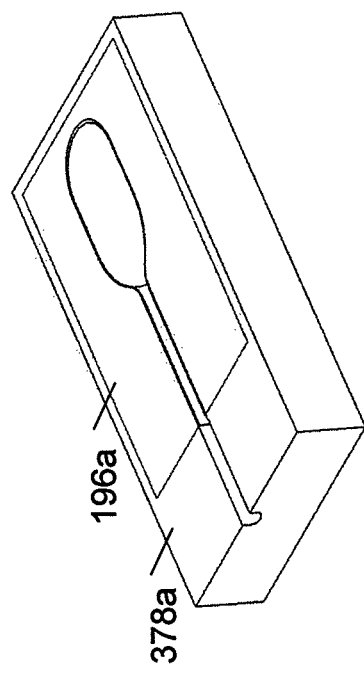

FIG. 33B illustrates that the first panel 196a can be formed to the contours of mold. Molding could be via heat or vacuum or pressure or combinations thereof.

FIG. 33C illustrates that the first panel 196a can be lifted free of the mold half 378a. The first panel 196a can have a panel flat 390 that did not enter the form of the female mold during forming. The panel 196a can be trimmed, for example in a trimming jig.

FIG. 33D illustrates that first and second panels (196a and 196b respectively) can have their flats 390 trimmed. The two panels can be closed tightly around a mandrel 230 and a mandrel shaft 392. The panels can then be bonded to each other at the seam 66b where they overlap. The seam 66b may connect all or some of the material that overlaps. The seam 66b may be leak tight to the passage or air and water. The bonding of the seam 66 and/or 67 and/or 69 may be caused by addition of an adhesive, by the application of heat, by the application of ultrasonic energy, by use of a laser, by the application of radio frequency energy, by the application of pressure or by combinations thereof. A material may be added to the seam, for example to bond the seam. The material may absorb laser light to generate heat in the seam.

FIG. 34A shows a bladder 52. The bladder 52 may be a thin-walled, blow-molded balloon. The bladder 52 may have a wall thickness of less than about 0.001 inches (0.025 mm), more narrowly less than about 0.0005 inches (0.0125 mm).

The bladder 52 may have a constant of variable wall thickness along the length of the bladder 52 and/or around the circumference of the bladder 52. The bladder 52 may form the inner wall of a balloon 20 and be leak-tight.

The inner volume of the bladder 52 may be filled with a mandrel material (types of mandrel material are described herein). The filling may be by injection or by pouring or combinations thereof. The filling may occur after the bladder 52 has been formed. The mandrel material may be chose to match the thermal expansion properties of the fibers 86.

FIG. 34B shows a cut 350 that may be made through the wall of the bladder 52. The cut 350 may be a longitudinal cut running the entire length of the bladder 52. The cut 350 could be made mechanically (i.e., with a knife), with a laser, a water jet cutter, an ultrasonic blade a heated blade or combinations thereof. The cut 350 may allow one side of the bladder 52 to be opened. The cut 350 in FIG. 34F may leave the bladder 52 in one piece. The cut 350 can extend along a portion (e.g., from one terminal end to a mid-point, or from a first mid-point to a second mid-point), or the entire length of the bladder 52.

FIG. 34C shows a cut 350 through the bladder 52 at a cut angle 351. Cut angle 351 may be about 0° to about 70°, more narrowly about 0° to about 50°, still more narrowly about 25° to about 45°. FIG. 34D shows a cut 350 through the bladder 52. Cut angle 350 may vary continuously over the length of the cut from about 90° (at the top of FIG. 34D) to about 0° (at the middle of FIG. 34D) and back to about 90° (at the bottom of FIG. 34D). The cut angle 350 may be a spiral. FIG. 34E shows a cut 350 through the bladder 52 at a cut angle 351 of 0°. The cut 350 may separate the bladder 52 into a first detached bladder portion 52*a* and a second detached bladder portion 52*b*. The first and second detached bladder portions 52*a* and 52*b* can each be half of the bladder 52 or can otherwise together comprise the complete bladder 52. The first bladder portion 52*a* can be symmetric or asymmetric with the second bladder portion 52*b*.

Bladder portions 52 can also be formed separately and then joined as described infra. For instance bladder portions 52 could be formed by thermoforming, injection molding, physical vapor deposition, dip molding or combinations thereof.

FIG. 34F shows the bladder 52 in FIG. 34B after being fit over a mandrel 230 (mandrel 230 is inside bladder 52 and not directly shown in FIG. 34F). The bladder 52 may be made slightly larger in diameter and/or longer in length than the mandrel 230 onto which the bladder 52 is fit. This may allow the bladder 52 to be re-assembled on the mandrel 230 with an internal seam 66 that may be sealed. FIG. 34F shows a longitudinal seam 66 running the length of the bladder 52. The seam 66 may be sealed with adhesive, by fusing, by heating, with a solvent or combinations thereof. The sealed bladder 52 may form the inner layer 72*b* of a balloon 20 and be leak-tight. Seam 66 may be an external seam 66*a* or internal seam 66*b*.

FIG. 34G through 34I illustrate the bladder 52 of FIGS. 34C, 34D, and 34E, respectively, after being fit over a mandrel 230 (mandrel not shown). The first bladder portion 52*a* can overlap at a lap joint or overlap (as shown), abut at an abutment, or flange with the second bladder portion 52*b* at the seam 66. The seam may have a seam area 780 and a seam width 781.

FIG. 34G shows that an angled seam 66 may be formed when the bladder 52 is reassembled on the mandrel 230. FIG. 34H illustrates that a spiral seam 66 may be formed when the bladder is reassembled on the mandrel 230. FIG. 34I shows that a 90 degree seam 66 may be formed when the bladder is reassembled on the mandrel 230. The seam 66 may be sealed as described supra.

Figure 35:
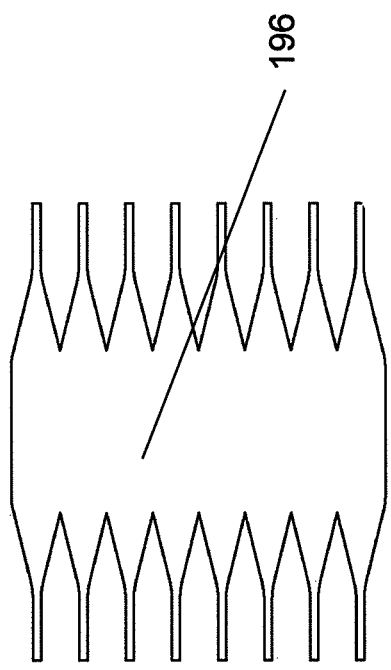
FIG. 35 illustrates a variation of a panel.

FIG. 35 shows a panel 196. Panel 196 may be constructed of a thin film such as those shown in FIG. 27. The thin film may be a thermoplastic with a thickness less than about 20 µm, more narrowly less than about 15 µm, still more narrowly less than about 10 µm, still more narrowly less than about 6 µm. Panel 196 may have a similar outline to the panel described infra in FIG. 40.

Figure 36:
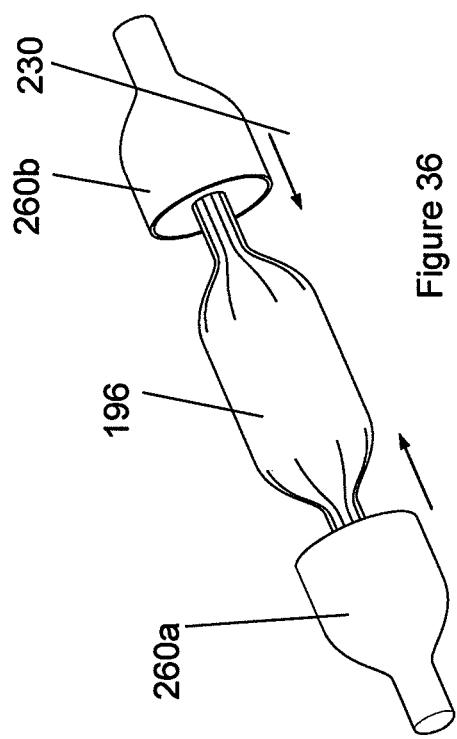
FIG. 36 illustrates a variation of a method for manufacturing the device.

FIG. 36 shows panel 196 applied to mandrel 230 (not shown). Distal caul 260*a* and proximal caul 260*b* may be applied over the panel 196. As demonstrated in FIG. 53 the assembled parts may be placed in a vacuum bag and heated until panel 196 fuses into a leak-tight bladder 52. The cauls 260 may be removed and the remainder of the balloon built on top of the bladder 52 and mandrel 230 as formed. As shown in FIGS. 34A through 34I, the bladder 52 may be cut such that the bladder 52 can be removed from one mandrel 230 and placed on another mandrel 230. A seam 66 may be formed. The bladder 52 may preferentially adhere to the cauls 260 allowing for easier handling and subsequent placement of bladder 52.

Figure 37:
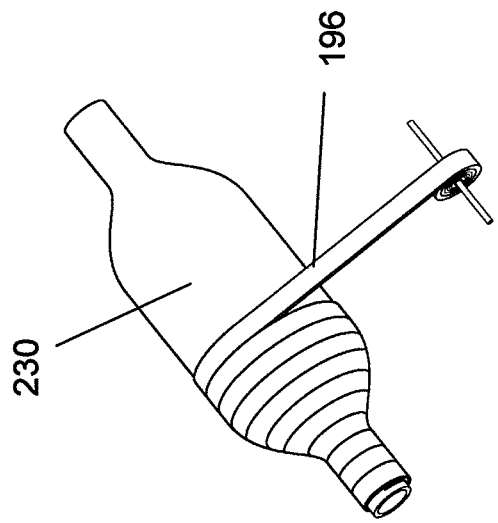
FIG. 37 illustrates a variation of a method for manufacturing the device.

FIG. 37 shows a panel 196 being wrapped onto mandrel 230. The panel 196 may be wrapped onto the mandrel 230 such that each successive wrap slightly overlaps the previous wrap. Cauls 260 (not shown) may be placed over panel 196. The assembled parts may be placed in a vacuum bag, heated and processed into a bladder 52 as described herein.

A bladder 52 may be formed by deposition. For example, a metal such as gold (or other materials listed herein) may be deposited to form a bladder 52. Deposition could be by various techniques such as dipping, coating, spraying or combinations thereof.

A bladder 52 may be formed by vapor deposition, for example by physical vapor deposition or chemical vapor deposition. Parylene may be deposited by vapor deposition to form a bladder 52 or any other layer 72 in the balloon. Parylene may be treated to enhance its ability to bond to other substances, for instance to adhesive 208. For instance, Parylene may be exposed to a plasma or to a chemical in order to increase its ability to bond and/or its surface energy. For example, before a treatment to enhance its ability to bond, Parylene may have a surface energy of less than about 35 dyne/cm. After a treatment to enhance its ability to bond, Parylene may have a surface energy of greater than about 40 dyne/cm.

A bladder 52 may be formed from a heat shrink tube. The tube may be formed in manufacture to fit the mandrel 230, blown out to size, then placed over the mandrel 230 and shrunk to fit the mandrel. Shrinking may be accomplished by the application of heat.

Figure 38A:
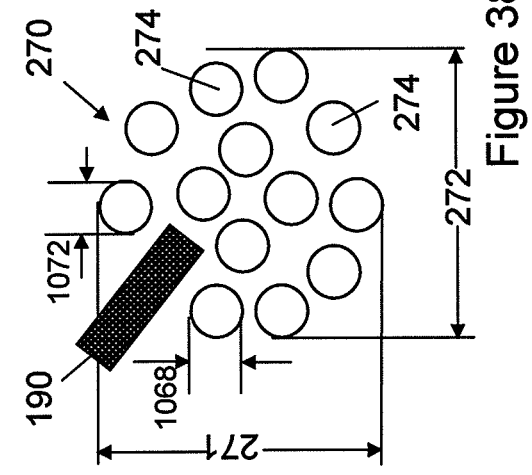
FIGS. 38A through 38E are transverse cross-sections of variations of fiber tows in various configurations during a method of manufacturing.

FIG. 38A shows a cross section of a tow 270. A tow 270 may be or have one or more reinforcement fibers 86. A tow 270 may have one or more monofilaments 274. For example, the tow 270 may contain about 6, 25, 100, 500 or 1500 monofilaments. The tow 270 may have a tow height 271 and a tow width 272. The tow 270 may be approximately circular. For example, the tow height 271 and tow width 272 may be about 0.025 mm (0.001 in) to about 0.150 mm (0.006 in), more narrowly 0.050 mm (0.020 in) to about 0.100 mm (0.040 in), more narrowly 0.075 mm (0.003 in). The tow 270 may be loosely held together by a polymer finish (not shown).

Figure 38B:
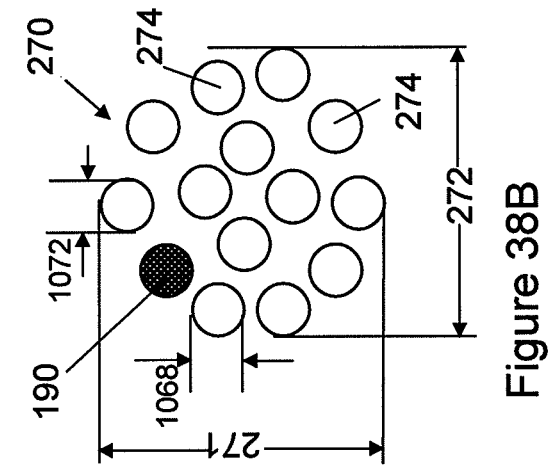
Figure 38C:
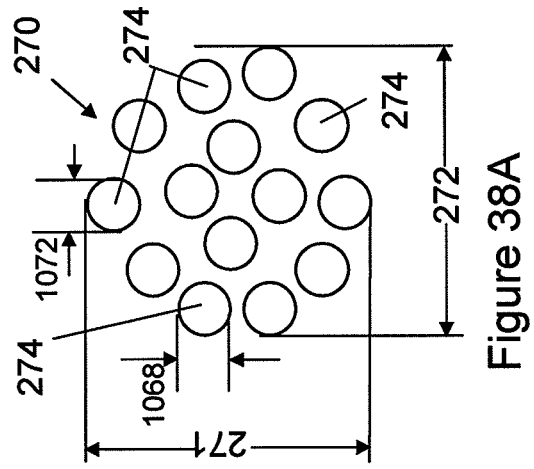

FIG. 38B shows that tow 270 may contain a marker wire 190. Marker wire 190 may be circular, as shown, and radiopaque. FIG. 38C shows that the marker wire 190 in tow 270 may be rectangular with dimensions as described supra.

Figure 38D:
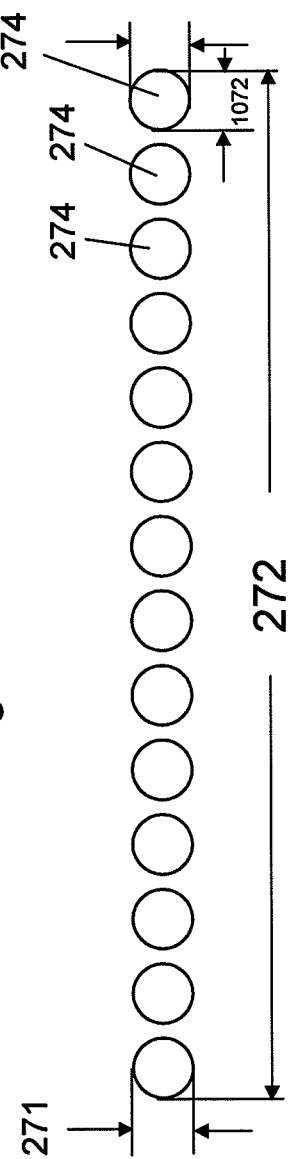

FIG. 38D shows the tow 270 after the tow 270 has been spread. The tow 270 may be flattened or spread by passing the tow 270 through a closely spaced set of rollers that form a narrow pinch gap. The tow 270 may be spread by pulling the tow 270 under tension over a set of rollers or pins. After spreading, the tow 270 may have a tow height 271 less than about twice the fiber height 1068, for example about the same as fiber height 1068. The fiber height 1068 and fiber width 1072 may be substantially unchanged after spreading. For example, the fiber width 1072 and fiber height 1068 may be about 15 µm (0.0006 in), tow width 272 may be about 210 µm (0.008 in) and tow height 271 may be about 15 µm (0.0006 in). The marker wire 190 is not shown in FIG. 38D but may be present after the tow 270 has been spread.

Figure 38E:
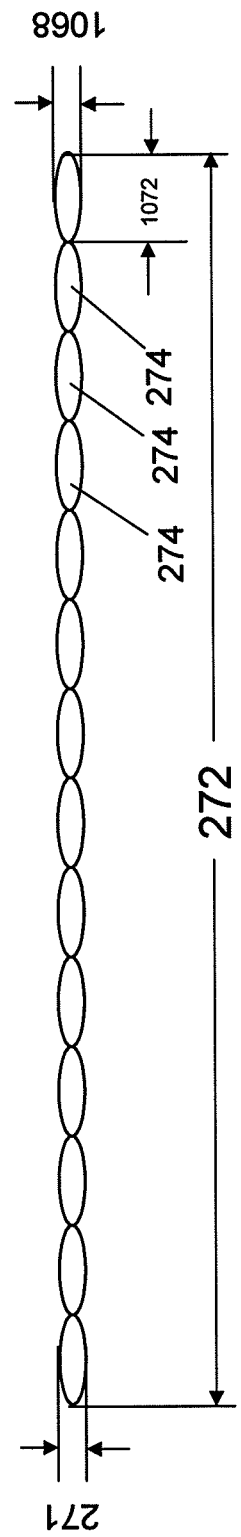

FIG. 38E shows the tow 270 from 38D after the tow 270 has had additional processing to flatten the monofilaments 274. The monofilaments 274 may be flattened by, for example, running the flattened tow 270 as shown in FIG. 38D through a precision rolling mill. The fiber width 1072 may be about 25 µm (0.001 in). The fiber height 1068 may be about 9 µm (0.0004 in). The tow height 271 may be about 9 µm (0.0004 in). The tow width 272 may be about 350 µm (0.0014 in). The marker wire 190 is not shown in FIG. 38E but may be present after the tow 270 has been spread and the fibers flattened.

FIG. 39A illustrates that a layer of fiber matrix can be made on a roller 232. The roller 232 can be configured to rotate about a roller axle 234. The roller 232 may have a diameter from about 100 mm (3.9 in) to about 1,000 mm (39.4 in). The roller 232 may be made or coated with an anti-stick material such as a flouropolymer.

FIG. 39B illustrates that a releaser 236, such as a release layer, can be placed around the circumference of the roller 232. The release layer can be a low friction film or coating. The release layer may be a thin and/or flexible flouropolymer sheet.

FIG. 39C shows that an adhesive 208 can be placed on the releaser or directly onto the roller 232 (e.g., if no releaser 236 is used). The adhesive 208 may be a thermoplastic film. The adhesive 208 may be a thermoset adhesive. The adhesive 208 may be a solvated thermoplastic or thermoset. The adhesive 208 may have a backing film, such as paper.

FIG. 39D shows the application of the reinforcement fiber 86 to the roller 232. The fiber 86 may be unwound from a spool (not shown) and rolled onto the top surface of the adhesive 208. The fiber 86 may contain one or more monofilaments 274. Before winding, the fiber 86 may be infused or coated with an adhesive 208, a solvent, or both. The coating may be a thermoplastic. The fiber 86 may have been previously flattened as detailed supra. The fiber 86 may have a non-circular cross section, such as a rectangle or an ellipse. Any coating or sizing on the fiber may have been removed using a solvent. The fiber 86 may be placed with a gap between each successive fiber wrap. The gap may be less than 200 µm (0.008 in), more narrowly less than 5 µm (0.0002 in). A heat source or a solvent may be used to fix the fiber 86 to the adhesive 208 (i.e., tack the fiber 86 in place on the adhesive 208), to melt or solvate a material onto the release layer 236, to melt or solvate a material on the fiber 86 or combinations thereof. For example, a separate resistive heater, a laser, a source of hot air, or an RF welder may be used. A solvent such as methyl ethyl ketone or tetrahydrofuran may be used. The fiber 86 can be wound with a pitch of 3000 to 30 turns per 1 inch (25.4 mm). The pitch can be chosen based on the total size of the fiber 86 or tow 270 being applied and the chosen gap between each subsequent fiber 86 or tow 270 on the roller 232. Applications of a single monofilament 274, which may be a wire, can have pitches from about 2000 to about 100 turns per 1 inch (25.4 mm).

FIG. 39E shows reinforcement fiber 86 on top of adhesive 208 on top of release layer 236. FIG. 39E may show a cross section after the operation shown in FIG. 39D is performed.

After reinforcement fiber 86 is placed on roller 232, the fiber 86 may be coated, sprayed, dipped or combinations thereof. For instance, the fiber 86 may be coated with parylene using, for example, a physical vapor deposition process. Adhesive 208 may be omitted in FIG. 39E.

FIG. 39F illustrates that the roller can be placed between a vacuum top sheet 238a and a vacuum bottom sheet 238b, for example in a vacuum bag. A vacuum seal tape 240 can surround the roller 232 between the vacuum bottom and top sheets 238b and 238a, respectively. Air can be removed from between the vacuum top and bottom sheets 238a and 238b and within the vacuum seal tape, for example by suction from a suction tube 242. Inside and/or outside of the vacuum bag, the roller 232 can be heated, for example to melt or cure the adhesive 208. Roller 234 can be removed from the vacuum bag, for example after melting or curing of the adhesive is complete.

FIG. 39G shows the removal of the panel 196. For instance, a cut may be made substantially perpendicular to the fiber. The panel 196 may be peeled away from the release layer. The panel 196 may be substantially foldable and/or flexible.

FIG. 39H illustrates that the panel 196 of fiber matrix can be removed from the roller 232. For example, the panel 196 can be peeled off the releaser 236. The panel 196 can be repositioned on the roller 232 at about 90 degrees to the layer's previous angle and additional reinforcement fibers 86 can be applied as shown in FIG. 39D. This may result in a panel 196 with fibers 86 running perpendicular to each other (e.g., a "0-90" panel, so called for the angle the two layers of fiber make with respect to each other). The panel 196 can be cut into a smaller panel. For instance, the panel 196 can be cut with a trimming jig, a laser, a water jet cutter, a die cut tool, or a combination thereof.

Figure 40A:
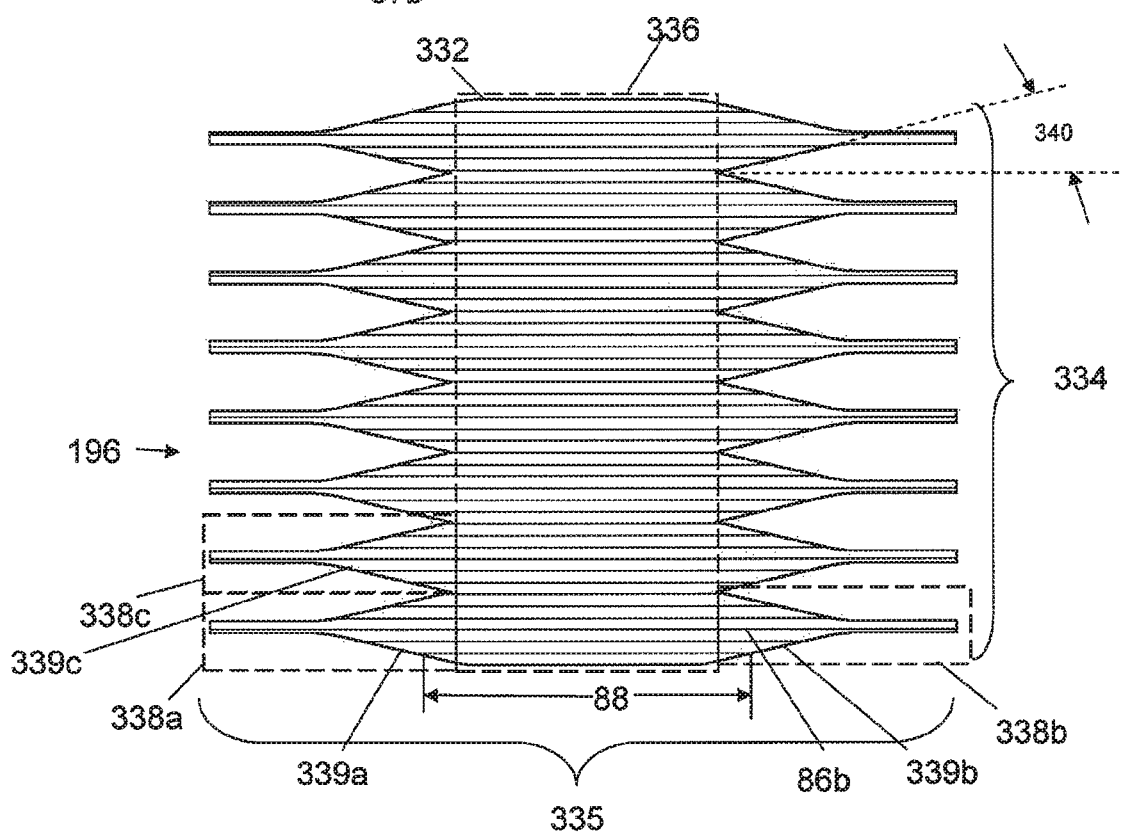

FIG. 40A shows that a panel 196 may have reinforcement fibers 86b oriented substantially parallel to panel longitudinal edge 332. The panel 196 can have a panel width 334. The panel width 334 can be about equal to the circumference of the balloon 20 in the constant-diameter section 38. The panel 196 can have a panel length 335. The panel length 335 can be greater than the balloon length 28. The panel 196 can have a panel rectangular section 336 and one or more panel serrations 338a, 338b and 338c. Each panel serration 338a, 338b and 338c can have a portion of the panel 186 that forms a portion of the stem 30 or 43 and taper 34 or 44. Each serration 338a, 338b and 338c can have a serration edge 339a, 339b and 339c, respectively. The angle between the serration edges 339 and a line parallel to the reinforcement fibers 86b can be a panel serration angle 340. The panel serration angle 340 can be about 30°, about 20°, about 10°, or about 0°. A first panel serration 338a can be substantially in line with a second panel serration 338b. One or more fibers 86b may run from the terminal end of the first serration 338a to the terminal end of the second serration 338b.

FIG. 40B illustrates that longitudinal reinforcement fiber 86b can be parallel with longitudinal edge 332. Second longitudinal reinforcement fiber 87b can be parallel with the fiber 86b. Fibers 86b and 87b can be separated by fiber separation areas 614. The fiber separation areas 614 may separate fibers 86b and 87b by about 2 mm (0.079 in), more narrowly less than about 1 mm (0.039 in), still more narrowly less than about 0.25 mm (0.01 in). The fiber separation areas 614 may be distributed on the panel such that no area 614 substantially overlaps any other area in the X and/or Y direction. The fiber separation areas 614 may be positioned in the X and Y directions on the panel 196 in a pattern sufficient to prevent any fiber from reaching all the way across the panel rectangular section in the X direction. The balloon 20 in FIG. 9G may be built in part with the panel 196 shown in FIG. 40B or 41B. Fibers 86*b* and 87*b* may have fiber lengths 88 less than about 80% of the balloon length 28 more narrowly less than about 75% as long, more narrowly less than about 70% as long, still more narrowly less than about 65% as long, still more narrowly less than about 60% as long as the balloon length 28.

Figure 40C:
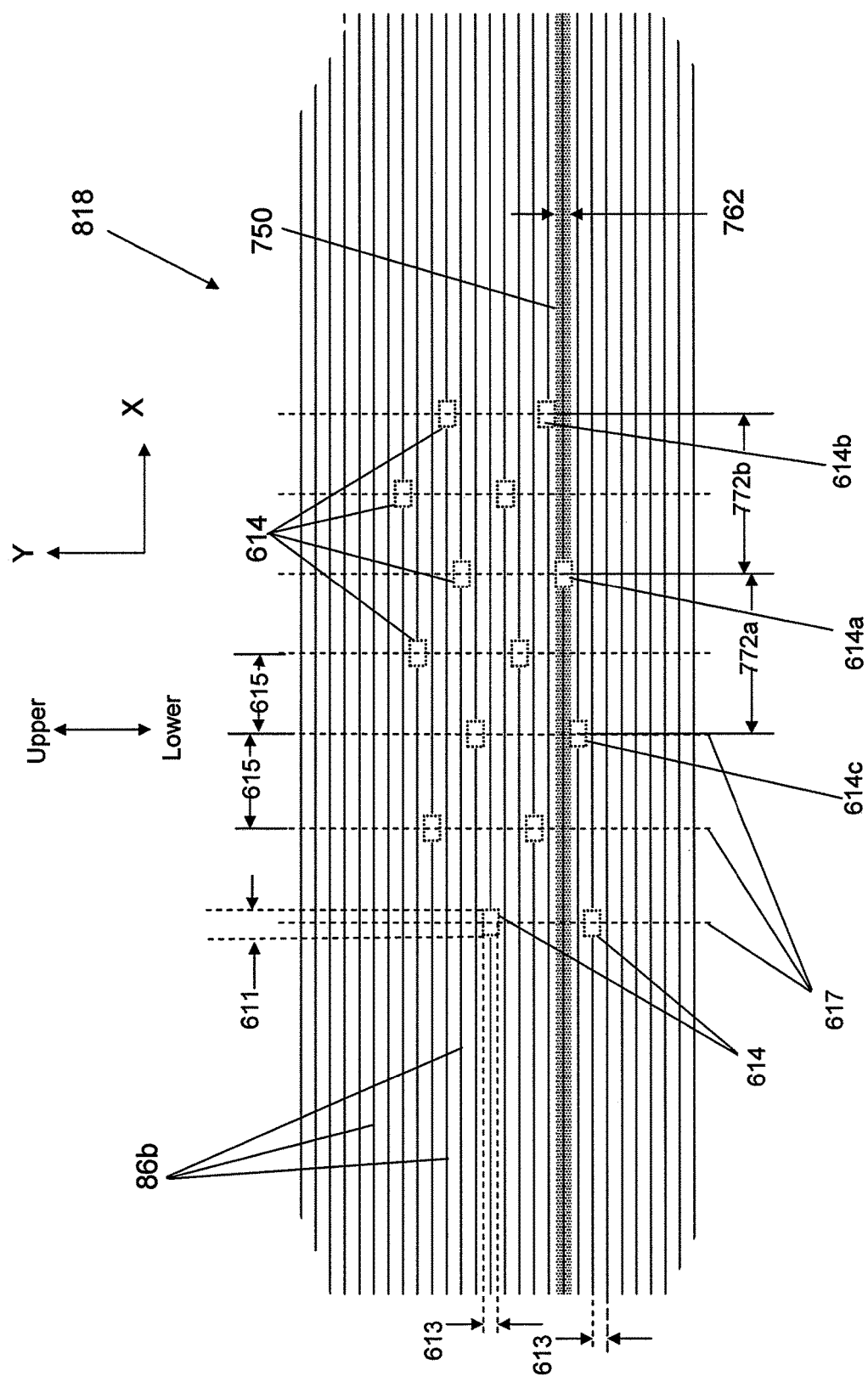

FIG. 40C illustrates a magnified view of panel area of separations 818. Fiber separation areas 614 are located on fiber separation bands 617. Fiber separation bands are arranged parallel to the Y-axis and are separated by fiber separation spacing 615. Each fiber separation areas 614 may be rectangular and have a fiber separation width 613 oriented in the Y-direction and a fiber separation length 611 oriented in the X-direction.

Load path 750 may have a load path width 762. The load path 750 may be substantially aligned with fiber separation width 613 along the X axis. The load path width 762 may be about equal to the fiber separation width 613. The upper edge of separation area 614*a* may be substantially inline with the lower edge of separation area 614*b*. The lower edge of separation area 614*a* may be substantially inline with the upper edge of separation area 614*c*. By substantially inline it is meant that there may be an overlap between areas 614 of 0 mm (0 in.) to about 0.2 mm (0.008 in.).

There may be from 2 to 25 separation bands 617, more narrowly 4 to 12, still more narrowly, 6 to 10. There may be 7 separation bands 617. Fiber separation width 613 may be from about 0.10 mm (0.004 in.) to about 2 mm (0.08 in.), more narrowly from about 0.2 mm (0.008 in.) to about 1.0 mm (0.04 in.), still more narrowly from about 0.3 mm (0.012 in.) to about 0.75 mm (0.03 in.). Fiber separation spacing 615 may be from about 0.50 mm (0.020 in.) to about 12.5 mm (0.5 in.), more narrowly from about 1.0 mm (0.04 in.) to about 6 mm (0.24 in.), still more narrowly from about 2 mm (0.08 in.) to about 4 mm (0.16 in.).

Shear load length 772 between load paths 750 will always be at least about 2 times separation spacing 615. During heating and consolidation of the balloon 20 during manufacture (for example, the process shown in FIGS. 55A, 55B and 55C), Separation areas 614 may allow the balloon 20 to expand in the longitudinal direction without placing the fibers 86*b* in significant stress, for example, stress in excess of 10% of the yield stress.

Figures 41A, 41B:
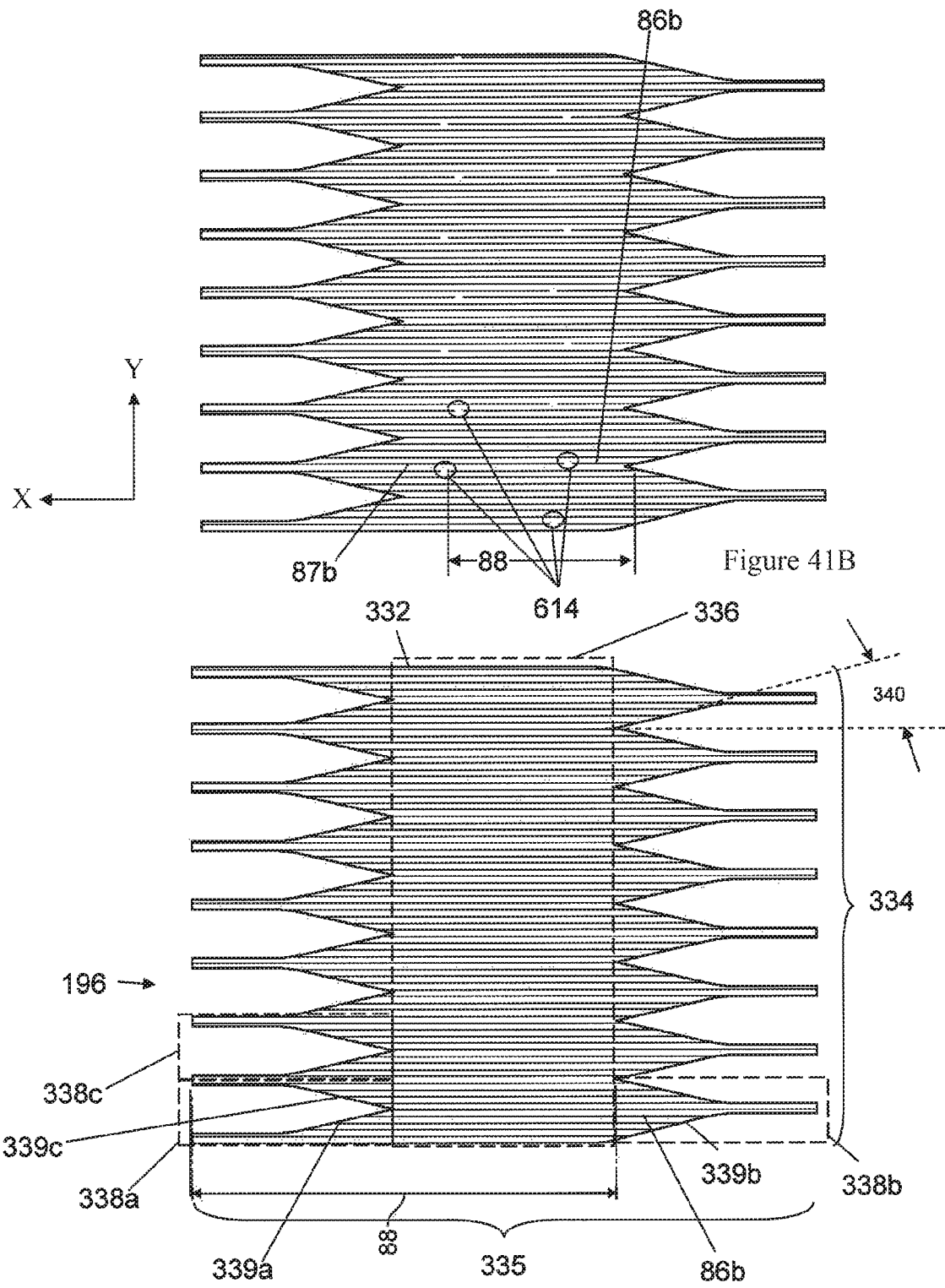

FIG. 41A shows that a panel 196 can have a panel rectangular section 336 and one or more panel serrations 338*a*, 338*b* and 338*c*. Panel serration 338*b* can be oriented in the Y direction substantially midway between panel serrations 338*a* and 338*c*. Panel serration 338*b* can be oriented in the Y direction substantially closer to either panel serrations 338*a* or 338*c*. The longest reinforcement fiber length 88 in panel 196 may be less than 75% of the length of the balloon, more narrowly less than 70% of the length of the balloon.

FIG. 41B illustrates that first longitudinal reinforcement fiber 86*b* can be parallel with longitudinal edge 332. The second longitudinal reinforcement fiber 87*b* can be parallel with first longitudinal fiber 86*b*. The first and second longitudinal fibers 86*b* and 87*b* can be separated by the fiber separation areas 614. The fiber separation areas 614 may be positioned in the X and Y directions on the panel 196 in a pattern so the first and second longitudinal reinforcement fibers 86*b* and/or fiber 87*b* have fiber lengths 88 less than about 80% of the balloon length 28, more narrowly less than about 75%, more narrowly less than about 70%, still more narrowly less than about 65%, still more narrowly less than about 60% of the balloon length 28. A continuous fiber 86 may connect from a first terminal end of the panel 196 to the second terminal end of the panel 196, where the first terminal end of the panel 196 is in the opposite X direction of the second terminal end of the panel 196.

Figure 42B:
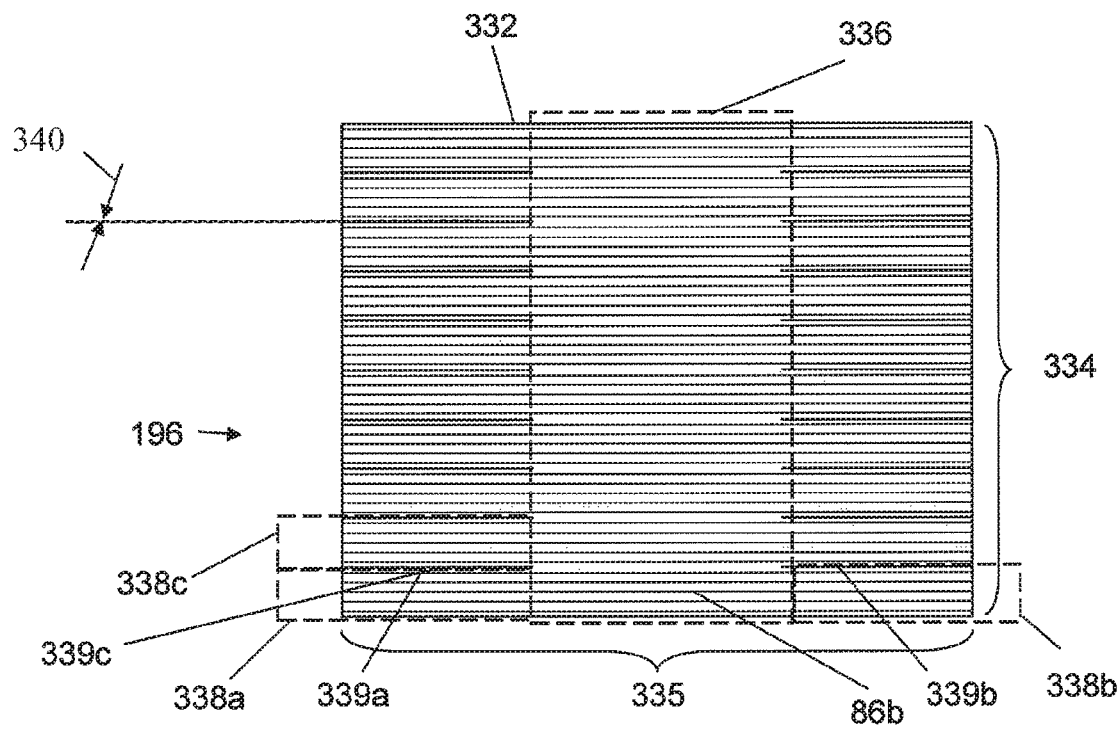
Figure 42A:
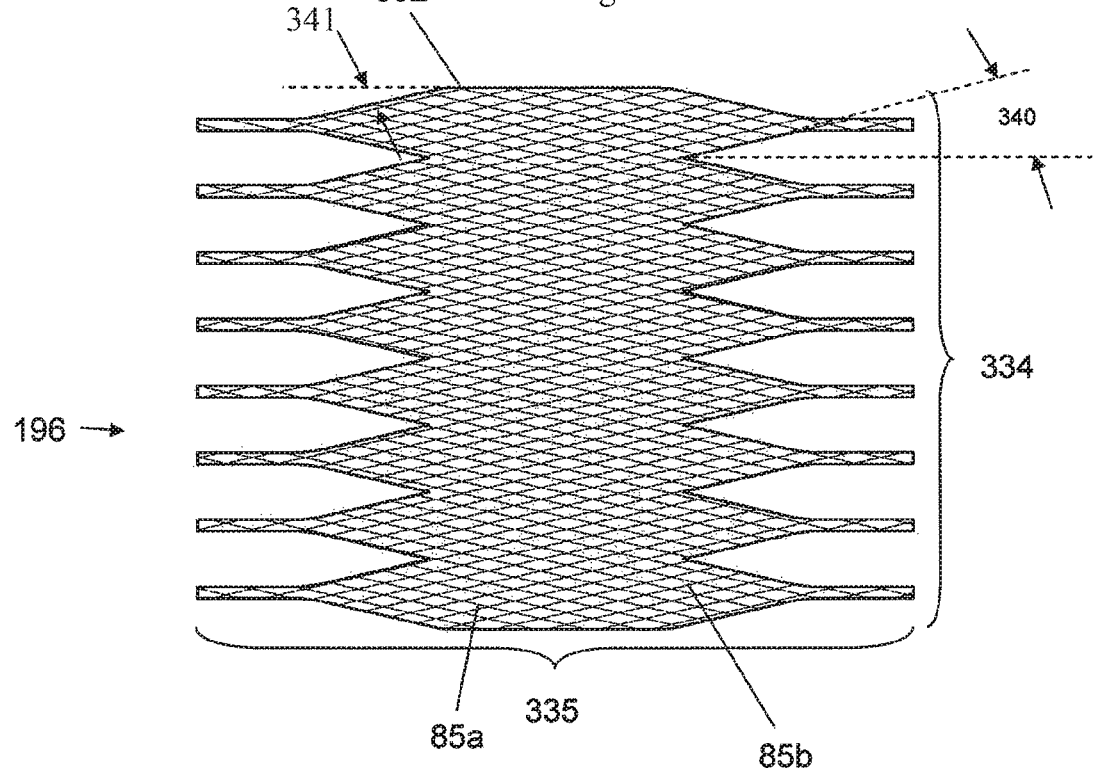

FIG. 42A shows that a panel 196 may have reinforcement fibers 85*a* and 85*b* oriented at equal and opposite angles 341 to panel longitudinal edge 332. Angle 341 may be, for example, about 10°, about 15°, about 20° or about 25° to the panel longitudinal edge 332. Fibers 85*a* and 85*b* can be at about 50°, about 55° or about 60° to the balloon longitudinal axis.

FIG. 42B shows that the panel serration angle 340 can be about 0°.

Figure 43A:
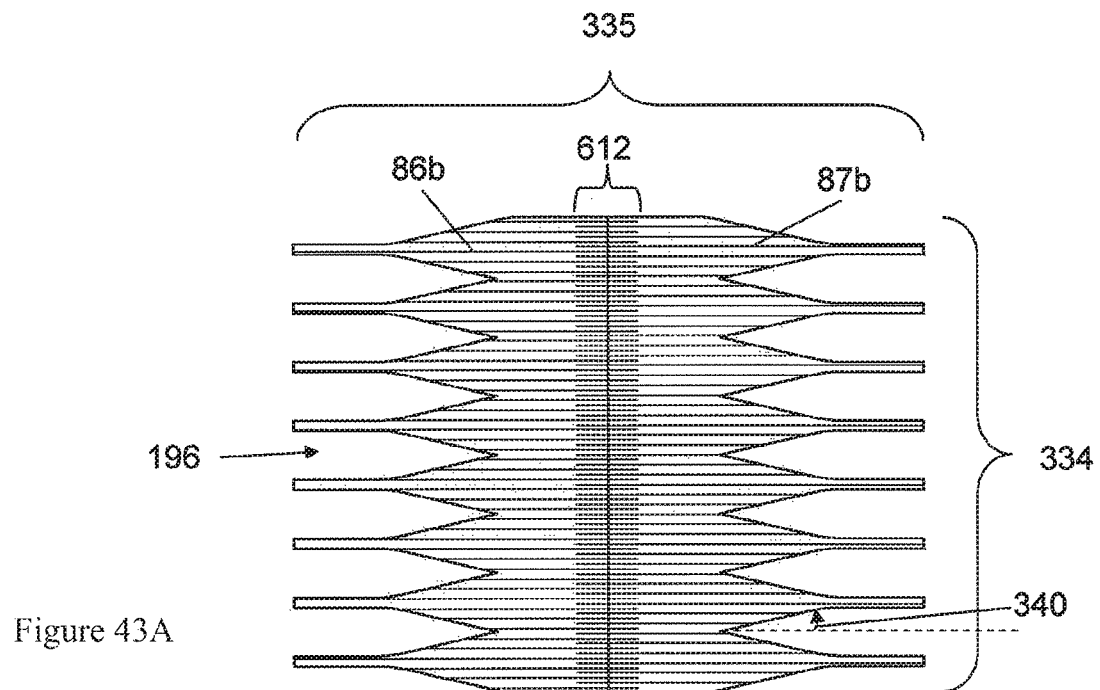
Figure 43B:
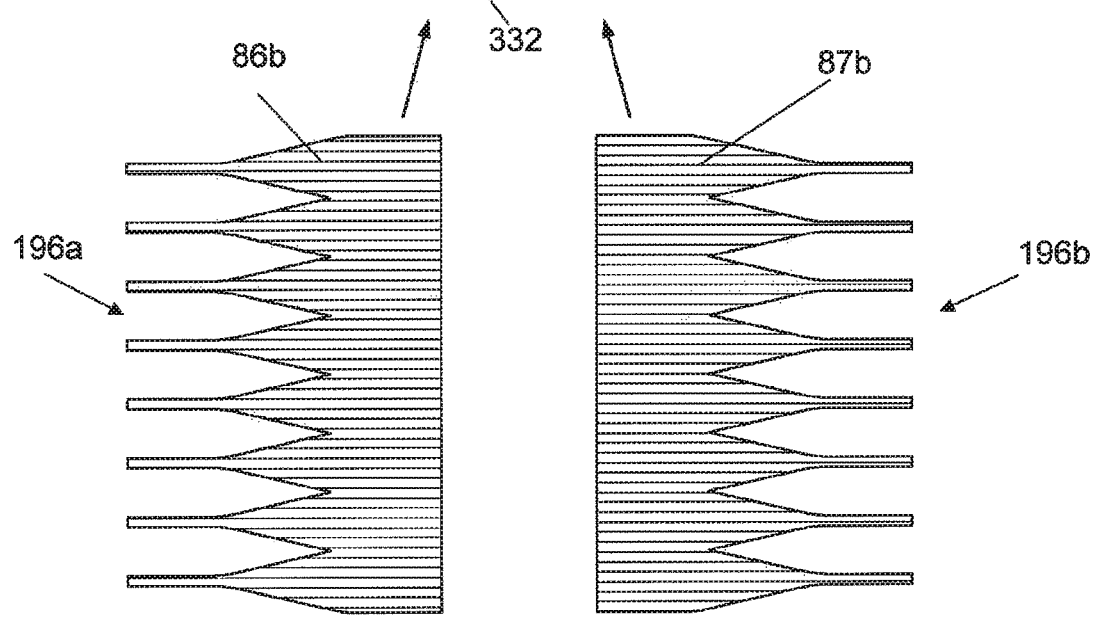

FIGS. 43A and 43B show that a panel 196 can be made from two panels 196*a* and 196*b*. Panels 196*a* and 196*b* can be overlapped in reinforcement fiber overlap area 612. The long axis of overlap area 612 may be substantially perpendicular to the reinforcement fibers 86*b* and 87*b*. The panels can be joined with adhesive or by melting the adhesive in the fiber matrix. The panel 196 in FIG. 43A may be used to make the balloon 20 shown in FIG. 9E

Figures 43C, 43D:
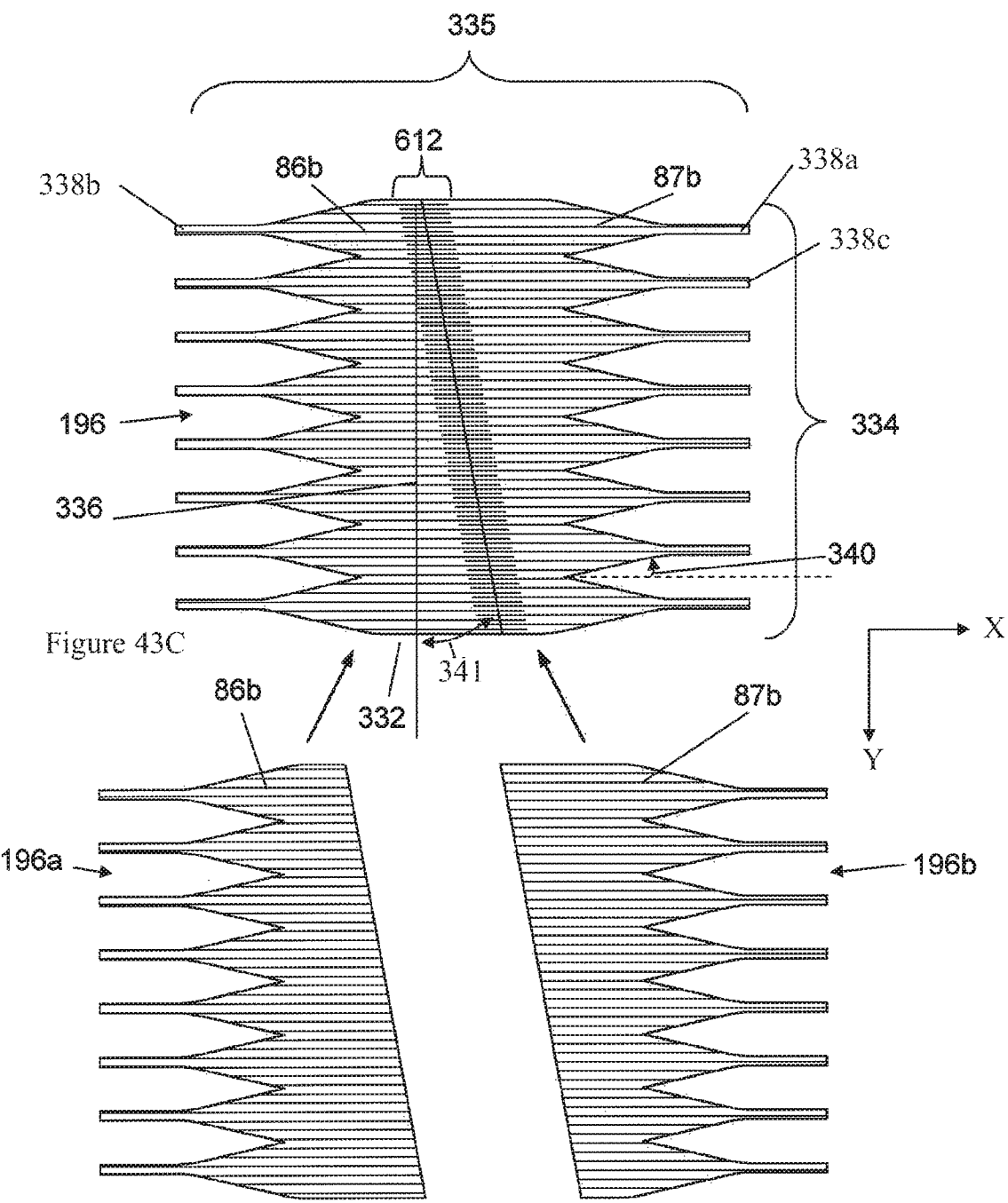

FIGS. 43C and 43D show that the long axis of reinforcement fiber overlap area 612 can be at an angle 341 to the Y axis. For example, overlap area 612 can be at an angle 341 of from about 0° to about 50° to the Y-axis, more narrowly from about 5° to about 45°, still more narrowly from about 15° to about 40° to the Y-axis. The panel 196 in FIG. 44A may be used to make the balloon 20 shown in FIG. 9F.

FIG. 44A shows a panel 196 similar to the panel shown in FIG. 40A. However, reinforcement fiber 86*b* forms reinforcement fiber loop back 774. The reinforcement fiber 86*b* can make about a 180° turn at the loop back 774. Reinforcement fiber 86*b* may be continuous through loop back 774. Reinforcement fiber 86*b* may have a continuous length longer than panel length 335.

FIG. 44B shows that a panel 196 may have a panel width about from about ¼ to about ¹⁄₁₀ the circumference of the balloon 20, more narrowly from about ⅙ to about ⅛ the circumference of the balloon 20. The circumference of the balloon 20 may be balloon outer diameter 50 multiplied by pi. A panel 196 may have a first panel serration 338*a* and second panel serration 338*b*.

FIG. 44C shows a variation of the panel 196 in FIG. 44B. Panel 196 may have fibers 86*b* that are parallel to panel serration edge 339 within the panel serration 338. Fibers 86*b* may end on the centerline of the long axis of panel 196

FIG. 44D shows that panel 196 may contain reinforcement fibers 85*a* and 85*b* arranged in a woven pattern. A woven pattern can have fibers 85*a* and 85*b* that alternately pass over and under each other.

FIG. 44E shows that the panel 196 may contain reinforcement fibers 85 in a braided configuration.

FIG. 44F shows that the panel 196 may contain reinforcement fibers 85 of various lengths in random orientations, sometimes referred to as chopper fiber.

Figure 44H:
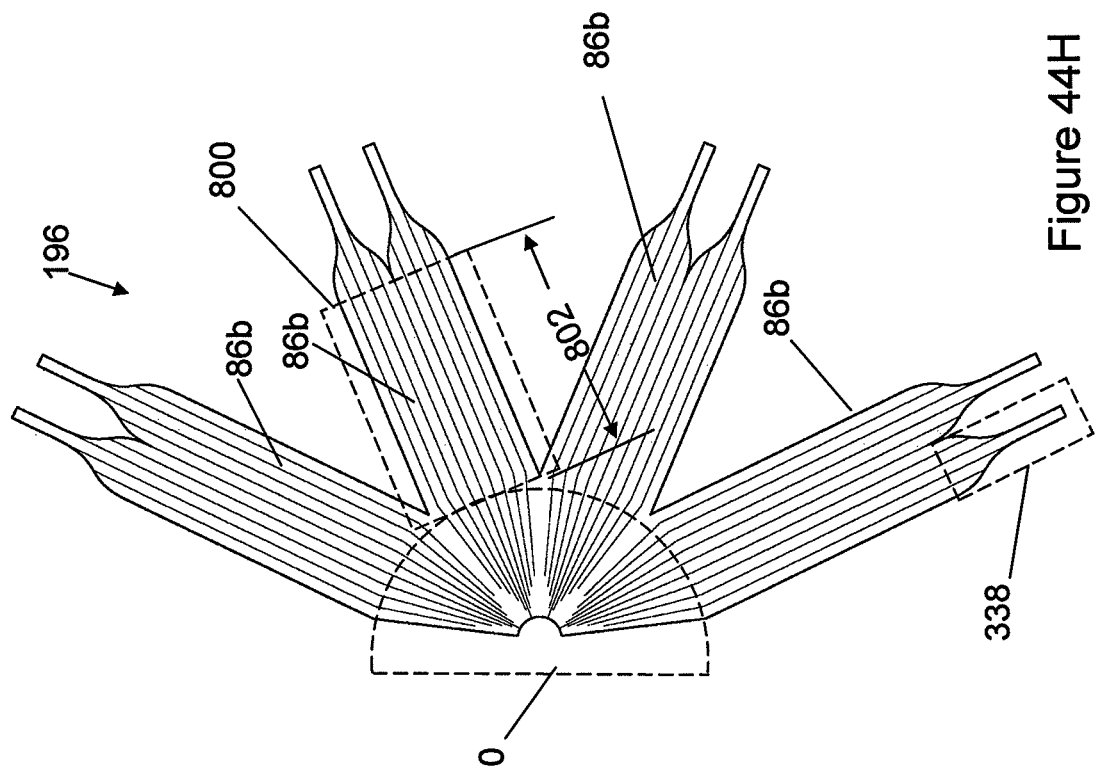
Figure 44G:
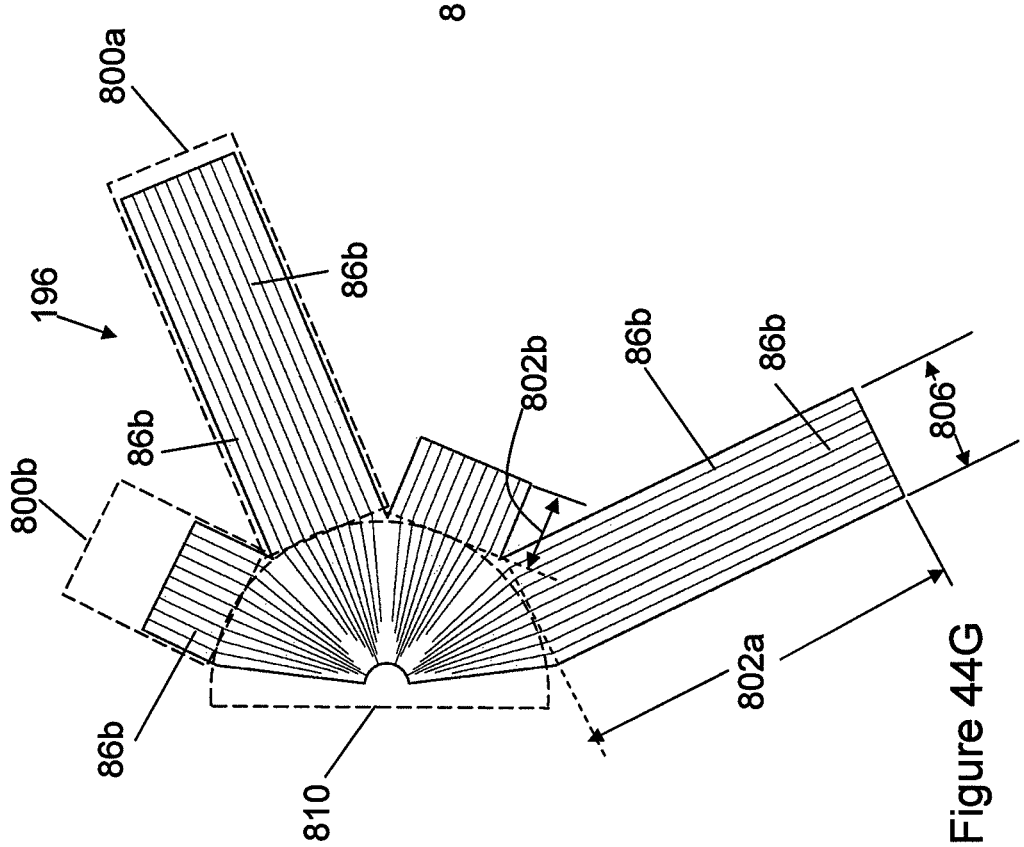

FIG. 44G shows that a panel 196 may contain a panel arc section 810 and panel legs 800. In panel arc section 810, fibers 86*b* may travel on a radius of the arc section 810. In the panel legs 800, fibers 86*b* may travel on a line parallel to the edge of the panel legs. First panel 800*a* may have a panel length 802a from about 50% to about 100% of the constant-diameter section length 40, more narrowly from about 60% to about 80%. Second panel 800b may have a panel length 802b from about 10% to about 50% of the constant-diameter section length 40, more narrowly from about 20% to about 40%. The panel leg width may be about ⅓ to about ⅙ of the balloon outer diameter multiplied by pi, more narrowly, about ¼. The panel 196 shown in FIG. 44G may be applied to a balloon 20. The panel arc section 810 may substantially cover the taper of the balloon. Panel legs 800 may cover a portion of the constant-diameter section 38. A second panel 196 as shown in FIG. 44G may be applied similarly on the opposite taper. The two panels may interleave, substantially covering the balloon outer wall 22b.

FIG. 44H show that panel length 802 may be about 100% of the constant-diameter section length 40. Panel serrations 338 may be appended. Panel serrations may be applied to a balloon taper as described herein. The panel in FIG. 44H may substantially cover the balloon outer wall 22b when applied to a balloon 20.

Panels 196 can be flattened. For instance, a panel 196 may be flattened in an industrial press by applying pressure and, optionally heat. A panel may be passed thru a precision pinch gap roller and flattened. Flattening may comprise changing the shape of monofilaments 274 (as shown in FIG. 38E) and/or redistributing with the panel some or all of adhesive 208.

FIGS. 45A, 45B, 45C and 45D illustrate that a panel 196 may be applied to a mandrel with none, one or more layers 72 on the mandrel 230. The panel 196 may be joined to layers 72 by the application of adhesive or by heat or by combinations thereof. The panel 196, when folded onto the shape of the mandrel 230 may give a substantially complete coverage of the mandrel 230 with minimal or no overlap of the panel 196. Panel rectangular section 336 may cover the balloon constant-diameter section 38. Panel serrations 338 may cover proximal taper 34, distal taper 42, proximal stem 30 and distal stem 43.

Figure 45A:
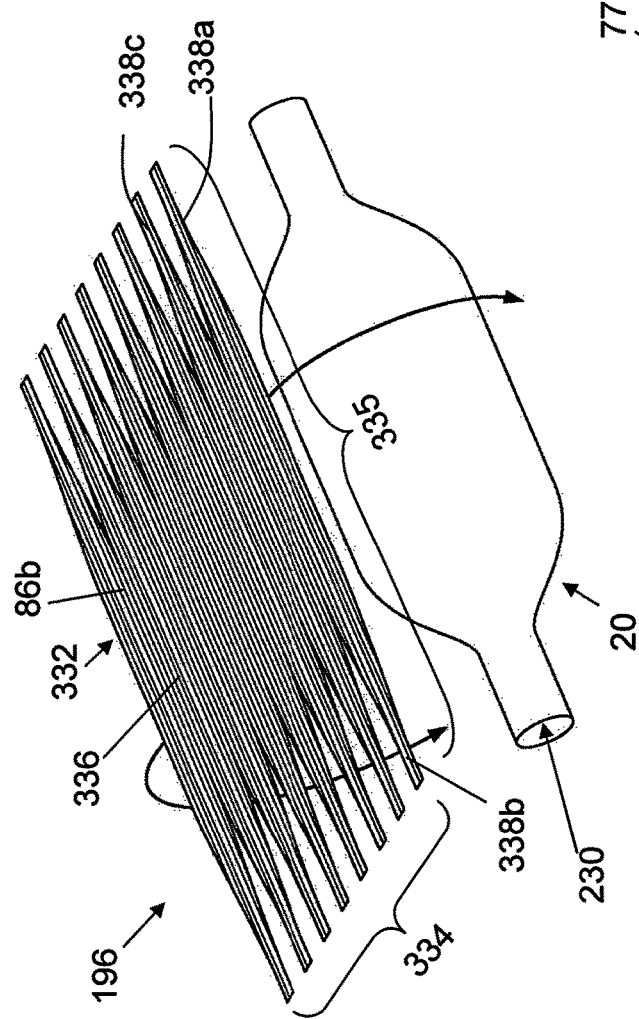
FIGS. 45A through 45D illustrate a method for manufacturing the device
Figure 45B:
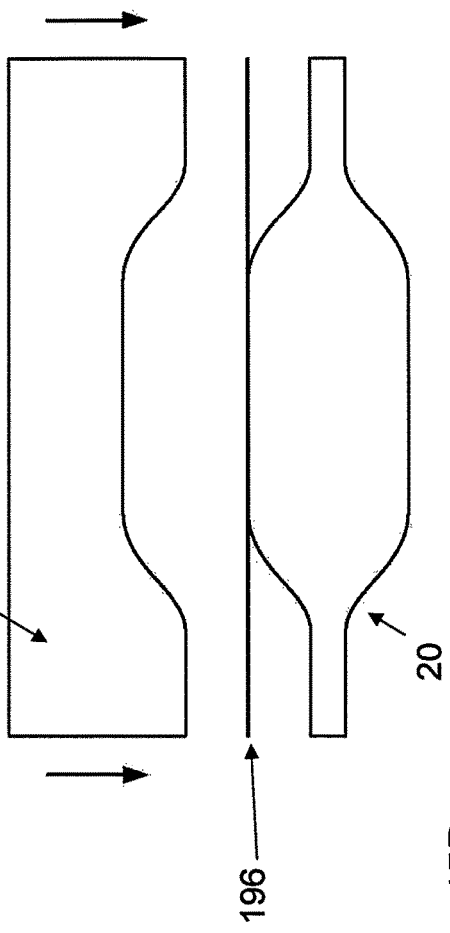
Figure 45D:
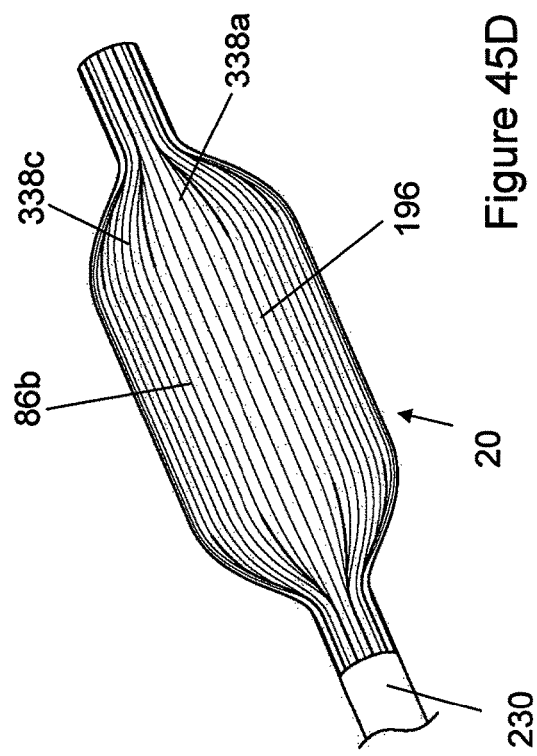
Figure 45C:
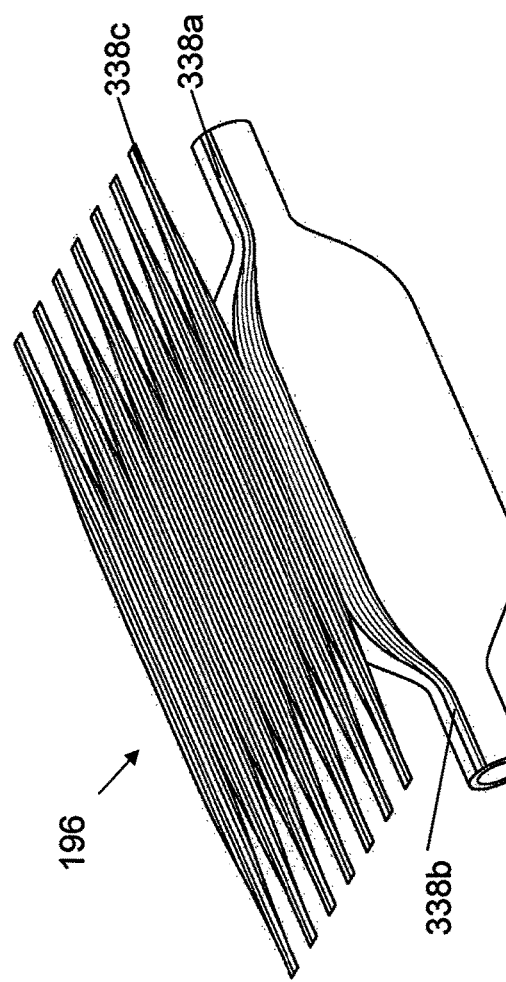

FIGS. 45B and 45C show that a die 778 may be used to press the panel 196 onto the balloon 20. The die 778 may be heated and the panel 196 may contain a thermoplastic. The die 778 may melt the thermoplastic and adhere the panel 196 to the balloon 20. The die may be shaped to match the mandrel 230 shape. After attaching two serrations 338 (one serration at each end of the mandrel 230. See FIG. 45C), the mandrel 230 may be rotated about its longitudinal axis to advance the next set of serrations 338 into place under the die 778. The die 778 may again press two serrations 338 into place on the balloon 20. Subsequent use of the die in this manner may attach substantially the entire panel 196 to balloon 20.

Figure 46:
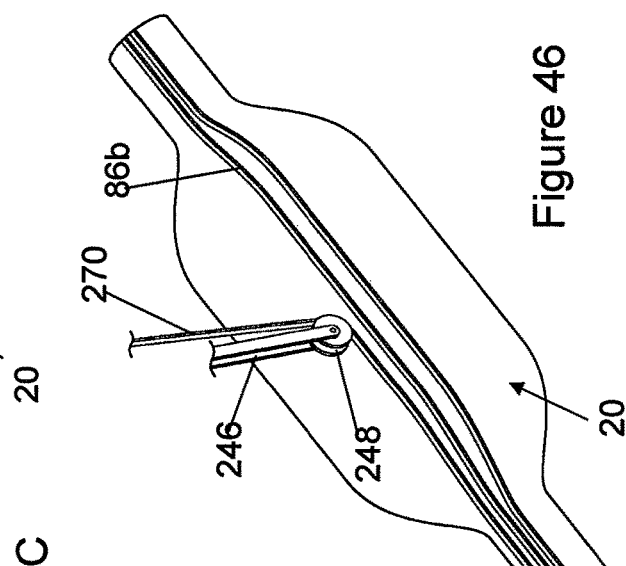
FIG. 46 illustrates a method for manufacturing the device.

FIG. 46 shows a method of attaching longitudinal reinforcement fiber 86b to balloon 20. A tool wheel 248 mounted to a tool arm 246 follows a longitudinal path on balloon 20. As the wheel 248 rolls, it presses into place tow 270. Adhesive (not shown) may be added to tow 270 before application so that tow 270 will stick to balloon 20. The tow may be cut when the tool wheel 248 reaches the end of the mandrel 230, the mandrel 230 may be rotated about its longitudinal axis, and a second track of reinforcement fiber 86B may be applied as shown in FIG. 46.

Figure 47A:
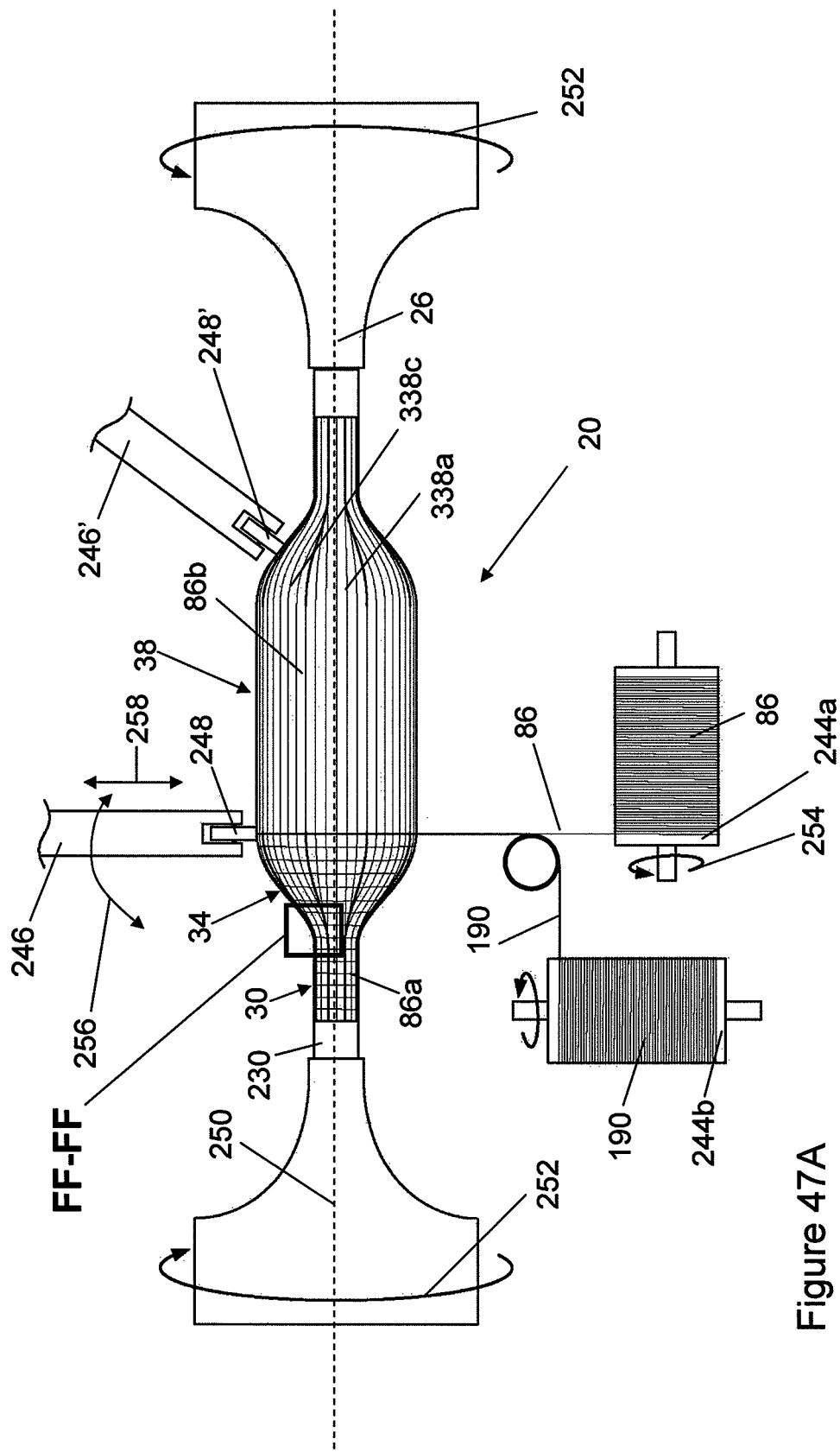
FIG. 47A illustrates a method for manufacturing the device.

FIG. 47A illustrates that fiber 86 can be wound over the mandrel 230 or over balloon 20. The fiber 86 may be continuous or discontinuous. The mandrel can be rotated, as shown by arrow 252, about the mandrel longitudinal axis 250 or balloon longitudinal axis. The first spool 244a can be passively (e.g., freely) or actively rotated, as shown by arrow 254, deploying fiber 86 (shown) or tow 270. Before or during winding, the fiber may be infused or coated with an adhesive, a solvent, or both. The coating may be a thermoplastic. A fiber distal end can fix to the balloon 20 or directly to the mandrel 230.

The fiber 86a may be wound with a gap between each successive fiber wind. The gap can be less than about 200 μm (0.008 in), more narrowly less than about 5 μm (0.0002 in).

The fiber 86 can be wound with a pitch of about 3000 to about 30 winds per 1 inch (25.4 mm). The pitch can be chosen based on the total size of the fiber 86 or tow 270 being applied to the part from first spool 244a and the chosen gap between each subsequent fiber 86 or tow 270 on the part. Applications of a single monofilament, which may be a wire, can have pitches from about 2000 to about 100 turns per inch.

A tool arm 246 can be attached to a rotating tool wheel 248. The tool arm 246 can rotate and translate, as shown by arrows 256 and 258, to position the tool wheel 248 normal to and in contact with the balloon 20. A second tool wheel 248' (attached to tool arm 246') can have a range of motion sufficient to apply pressure normal to the surface of a balloon taper section.

The tool wheel 248 can press the fiber 86 or tow 270 against the balloon 20 and spread the monofilaments 274 as shown in FIG. 47B. The tool wheel 248 may help to adhere the tow 270 to the balloon, for example by applying pressure and following closely the surface of the balloon. The tool wheel 248 can be heated to soften or melt the material on the surface of the balloon 20. Another heat source or a solvent may be used to tack the fiber in place, to melt or solvate a material on the balloon, to melt or solvate a material on the fiber or combinations thereof. A separate resistive heater, a laser, a UV light source, an infrared light source, a source of hot air, or an RF welder may be used with our without the tool wheel 248 to attach the fiber. A solvent such as methyl ethyl ketone or tetrahydrofuran or alcohol or combinations thereof may promote adhesion of the fiber 86 and may be used with our without the tool wheel 248. The tool wheel 248 can be made of or coated with a non-stick material. The tool wheel 248 may not rotate. The tool wheel 248 may comprise a hard surface, for example carbide.

A second spool 244b may deploy marker wire 190 during a winding operation. Second spool 244b may also deploy a reinforcement fiber 85 (not shown). Marker wire 190 (or reinforcement fiber 85) may be applied simultaneously with fiber 86 and/or tow 270 to the balloon. Marker wire 190 may interleave with reinforcement fiber 86 to form a single fiber layer on balloon 20, for example as shown in FIG. 47C. Marker wire 190 may be deposited on top (for example, as shown in FIGS. 47E and 47H) or bellow another existing fiber layer.

The resulting layer deposited in FIG. 47 can have a layer thickness 216 of from about 1 μm (0.00004 in) to about 50 μm (0.002 in), more narrowly from about 8 μm (0.0003 in) to about 25 μm (0.001 in).

FIG. 47B illustrates that a hoop wind can deposit a layer 72 of monofilaments 274 side by side on the balloon 20.

FIGS. 47C and 47F illustrate that a hoop wind can deposit a layer 72 of monofilaments 274 side by side on the balloon 20 and that one of those monofilaments may be a marker wire 190

FIG. 47C shows that a radiopaque marker wire 190 or radiopaque filament may be located between first monofilament 274a and second monofilament 274b. Monofilaments 274a and 274b may be deposited on subsequent winds of one tow. That is, marker wire 190 may be between the successive winds of one tow and occupy the same layer 72 as the monofilaments 274a and 274b.

FIGS. 47D and 47G illustrate that a hoop wind can deposit a layer 72 of monofilaments 274 side by side on the balloon 20 and that one of those monofilaments may be a marker wire 190 and that an adhesive 208 may surround those monofilaments in the layer 72.

FIGS. 47E and 47H illustrate that a hoop wind can deposit a layer 72c of monofilaments 274 side by side on the balloon 20 and may deposit a second hoop wind layer 72d comprising a marker wire 190. Layers 72c and 72d may comprise an adhesive 208.

Panels 196 may also be formed in the cross sectional configuration shown in FIGS. 47B-H.

FIG. 48A shows a close-up cross-sectional view of the fiber application process in FIG. 47. Tow 270 is herein shown to contain 6 monofilaments 274 spread flat and being wound on a balloon taper angle 90. The tow contains a lowest monofilament 608 and a highest monofilament 610. Monofilaments 608 and 610 can be monofilament 274.

FIG. 48B shows a further magnification of the wind cross-section in FIG. 48A. Monofilaments 608 and 610 spiral around the balloon taper. Single turn distance 602 gives the distance between each instance of the fiber in cross section. Lowest monofilament 608 has a lowest monofilament wind radius 604a to the balloon longitudinal axis at a first position and lowest monofilament wind radius 604b at a second position. The first and second groups of fibers shown in cross section may correspond to a single wind around the balloon. Similarly, highest monofilament 610 can have a highest monofilament wind radius 606a at a first position and a highest monofilament wind radius 606b at a second position.

Based on geometry, the radius 604b is equal to radius 604a+sin(angle 90)*(distance 602). The "*" symbol denotes multiplication, the "l" symbol denotes division and the "sin" symbol denotes a sine operation. The average radius between the first position and the second position is therefore 604a+sin(angle 90)*(distance 602/2). Finally, based on average radius, we can calculate an approximate monofilament length from the first to the second position of lowest monofilament 608 of 2*pi*(radius 604a+sin(angle 90)*(distance 602/2)). For example, the monofilament length for lowest monofilament 608 for a radius 604a of about 2.000 mm a distance 602 of about 0.250 mm and angle 90 of about 35.000 degrees is about 13.017 mm If monofilaments are assumed to lay down flat in a single layer (as shown in FIG. 48), radius 606a can be shown to be equal to radius 604a+(sin(angle 90)*(fiber diameter 212*(number of fibers−1))). Similarly, the average radius between radius 606a and radius 606b is therefore about equal to (radius 604a+(sin(angle 90)*(fiber diameter 212*(number of fibers−1))))+(sin(angle 90)*(distance 602/2)). With the average radius we can calculate monofilament length. For example, the monofilament length for highest monofilament 608 for a radius 604a of 2.00 mm, a fiber diameter 212 of 25 μm, 6 fibers, a distance 602 of 0.250 mm and an angle 90 of 35.00 degrees is about 13.47 mm In the previous two examples monofilament length is calculated for the lowest and highest monofilaments in a given tow as 13.017 mm and 13.467 mm, respectively. The highest monofilament would need to be about 3.5% longer than the lowest monofilament. Over long distances, the monofilaments cannot significantly slide longitudinally with respect to one another, the uphill monofilament would need to strain (change its length) about 3.5%. High strength fibers typically have strains to failure of less than about 5%. The lowest fiber can experience no strain. The highest fiber can experience strain near the failure point of the highest fiber. Alternately, the highest fiber can relieve the strain by sliding down the curve. The fiber tow can transform from a flat 1×6 layer of fiber as shown in FIG. 48 to more of a bundle in which the tow 270 is significantly thicker than a single monofilament diameter (for example, the tow 270 shown in FIG. 38A). The difference in strain may cause the tow 270 (or filaments in the tow) to pull away from the balloon and thus have poor adhesion.

At an instantaneous point in the wind of a tapered part wherein the tow is spread to a single monofilament thickness, the difference in strain between the highest monofilament and the lowest monofilament is about:

Strain=(*C/R*)*100%

Where C=(sin(angle 90)*(fiber diameter 212*(number of fibers−1)))
R=radius of lowest monofilament 604a
Note that strain is a function of the sine of the angle, a linear function of the number of fibers, and that for larger R, the strain is far less than for a small R.

The balloon stem 30 may have a small radius. Hoop winding may begin at the stem 30, progress up the proximal taper 34 and continue in the constant-diameter section 38. It may be desirable to minimize balloon proximal taper length 36 while minimizing strain in the tow 270.

FIG. 48C shows that a first angle 600a may be used initially as the wind begins, for instance, at the proximal taper 34. A second angle 600b may be used after the diameter of the balloon has grown larger than the balloon stem 30 diameter. Second angle 600b may be larger than first angle 600a. Additional angles may be used as the balloon diameter at the point of application of the tow 270 increases. These angles may be chosen to keep the difference in strain between the highest and lowest monofilament at or below a certain value, for example less than 4%, or less than 3%, or less than 2% or less than 1%. A curve 601 with a continuously variable radius of curvature, as shown in 48D may be used that holds the difference in strain at or below a certain value, for example less than 4%, or less than 3%, or less than 2% or less than 1%.

The flattened fiber tow width may be the fiber diameter 212 multiplied by the number of fibers. For instance, for a fiber diameter of about 17 μm and 8 fibers, the fiber tow width may be about 136 μm. For instance, for a fiber diameter of about 17 μm and 12 fibers, the fiber tow width may be about 204 μm. For instance, for a fiber diameter of about 23 μm and 5 fibers, the fiber tow width may be about 115 μm. The fiber tow width may be less than 300 μm, more narrowly less than 250 μm, still more narrowly less than 200 μm, still more narrowly less than 160 μm.

FIG. 49A illustrates that a fiber 86a can be helically wrapped around the balloon 20.

FIG. 49C shows that the balloon 20 can have reinforcing strips 1056 along the proximal and/or distal ends of the balloon 20 over the latitudinal fibers 86a. As shown in FIG. 49C, a reinforcing strip 1056 can run the length of substantially all of the taper 42, 34 on which the reinforcement strip is placed. The reinforcing strips 1056 can also partially or fully extend along the length of the balloon stems 30, 43. As shown in FIG. 49C, each reinforcing strip 1056 can end within the cylindrical section 38, thereby partially covering the constant-diameter section. In some embodiments, the reinforcing strips 1056 cover substantially all of the tapers 42, 34 while still ending within the tapers 42, 34.

Figure 49D:
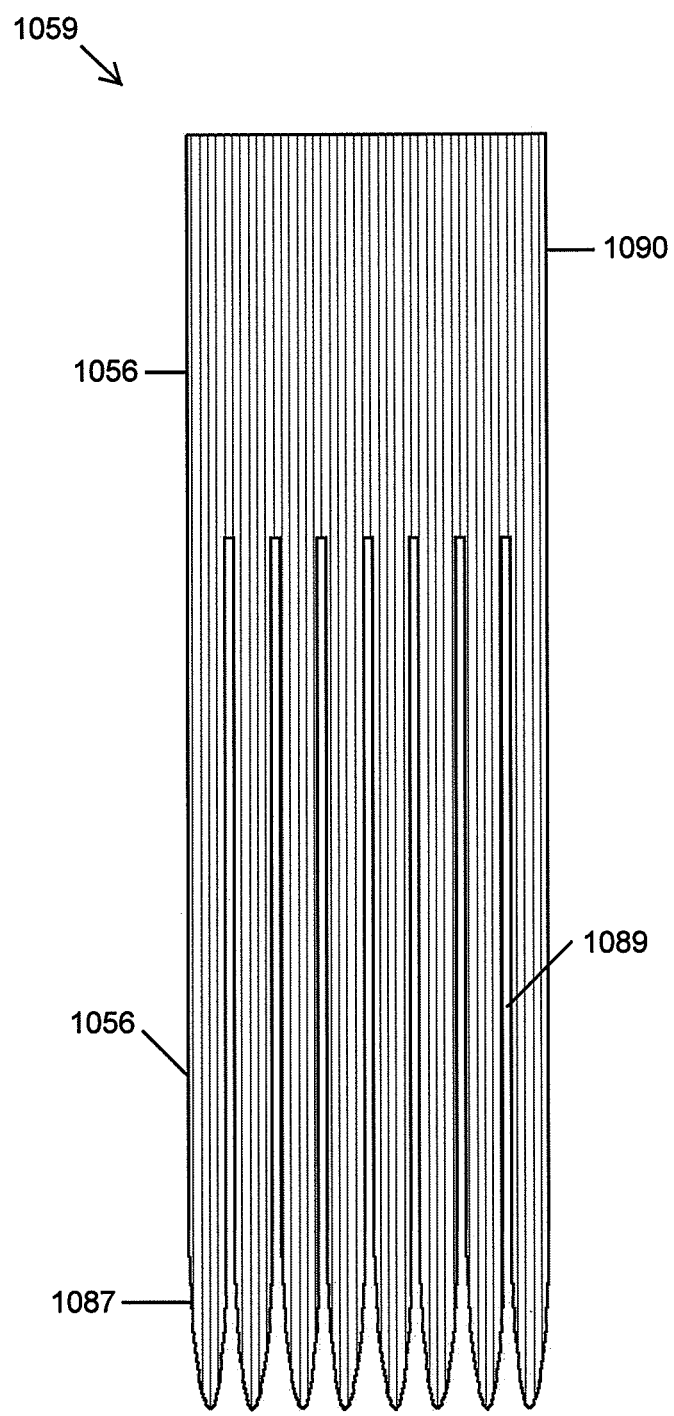
FIG. 49D shows an exemplary sheet that can be used to form reinforcing strips.

Each reinforcing strip 1056 can include fibers 1086 therein, as shown in FIG. 49D. The fibers 1086 can be arranged in a matrix, such as be formed from a fiber tape including fibers in a resin. The fibers 1086 can extend substantially parallel with the longitudinal axis of each strip 1056 and/or extend substantially perpendicular to the latitudinal fibers 86a. The strips 1056 can include a single layer of fiber monofilaments in the radial direction.

Having the reinforcing strips 1056 over the fiber 86a within the tapers 34, 42 advantageously helps keep the latitudinal fiber 86a in the correct position. The latitudinal fiber 86a, when placed on a taper 42, 34 can slump or fall down the taper, particularly with steep taper angles and when the balloon is inflated to high pressures (pressures approaching the rated burst). The reinforcing strips 1056 can minimize this slumping effect. That is, the reinforcing strips 1056 can help latitudinal fiber 86a resist longitudinal shear loads that develop at the interface between strips 192 and latitudinal fiber 86a when balloon 20 is inflated. Because the reinforcing strips 1056 include fibers 1086 extending longitudinally, the reinforcing strips 1056 are resistant to tension. This resistance to tension prevents the fibers 1086 (oriented 90 degrees relative to the fibers 86a) from slumping down the tapers 42, 34.

Moreover, when reinforcing strips 1056 are used in combination with longitudinal fibers 86b, the combination of the fibers 86b from the lower panel and the fibers 1086 in the reinforcing strips 1056 can create a double shear condition on the hoop fibers 86a. This double shear condition provides additional resistance to hoop fiber 86a slumping when the balloon is inflated to high pressures (i.e., in order for the latitudinal fiber 86a to slump, it would have to break bonds with both the fibers 1056 in the reinforcing layer and the underlying longitudinal fibers 86b).

Each strip 1056 can have a substantially elongated shape, such as an elongate rectangular shape. In some embodiments, the strips 1056 can have a tapered portion 1087 at the end (i.e., at the end that is configured to be placed within or near the constant-diameter section 38). The tapered section can advantageously help spread out the loads across the fibers 86a,b, 1056 and help avoid abrupt load drop-off.

There can be between 0 to 20 strips 1056, between 3 and 32 strips, between 4 and 16 strips, or between 8 and 16 strips 1056. Each strip 1056 can be, for example, 0.50 to 0.10 inches wide, such as approximately 0.08 inches wide.

As shown in FIG. 49C, the strips 1056 can be arranged so as to radiate outwards (i.e., be close together towards the end of balloon and spread out as the diameter of the balloon 20 increases along the tapers 34, 42). The distance between neighboring reinforcing strips 1056 can be constant at a given longitudinal position. For example, at the major diameter of the balloon (i.e., at the constant-diameter section), the center-to-center distance from one strip 1056 to a neighboring strip can be 0.1 inches to 0.3 inches, such as approximately 0.2 inches. The radiating formation of the reinforcing strips 1056 can advantageously provide a minimal increase in diameter or wall thickness of the balloon at the major diameter of the balloon. The reinforcing strips 1056 can thus add performance without substantially affecting sheath or French size.

In some embodiments, as shown in FIG. 49D, the reinforcing strips 1056 can be formed from a sheet 1059. The sheet 1059 can include slits 1089 that extend partially into the sheet and that extend parallel to the fibers 1086. The slits 1089 can form the reinforcing strips 1056. In use on the balloon 20, the sheet 1059 can be wrapped such that unslit portion 1090 wraps around the stem 30, 43 while the reinforcing strips 1056 between the slits 1089 extend along the tapers 34, 42. In other embodiments, as shown in FIG. 49C, each reinforcing strip 1056 can be disconnected along the entire length of the balloon. The reinforcing strips 1056, if not part of a single sheet 1059, can be overlapping in some areas, such as within the stems 30, 42, so as to cover the desired amount of the tapers 34,42.

FIG. 49E illustrates that a fiber 85a can be wrapped at an angle 132 to the longitudinal axis. Fibers substantially parallel to the longitudinal axis may be omitted. Angle 132 may be less than about 75°, more narrowly less than about 60°, for example about 55°. Angle 132 may be about 40°, about 35°, about 30°, about 25°, about 20°, or about 15°.

FIG. 49B shows that a second fiber 85b may be wound at an equal and opposite angle to the angle of fiber 85a. Fibers 85a and 85b may be on separate layers. Fiber 85b may be radially outside fiber 85a. Fiber 85a may not cross on top of fiber 85b. Fiber 85a may cross on top of fiber 85b one or more times. Fibers 85a and 86a may be applied to balloon 20 with an adhesive 208.

FIGS. 50A and 50B illustrate that a panel 196 may have perforations 782. A perforation 782 may be defined as a hole or absence in a panel 196 or gap between panels 196. A perforation 782 may be circular, elliptical, rectangular, substantially linear or combinations thereof. A perforation 782 may be formed mechanically (for example with a sharp tool or with a roller covered in spikes that extend radially outward), with a laser, a water jet cutter, via photolithography or combinations thereof. A perforation 782 may be formed by applying two or more panels with a gap.

FIG. 50A shows a panel 196 with substantially circular perforations 782. The perforations 782 may have a diameter of about 0.025 mm (0.001 in.) to about 3.0 mm (0.12 in.), more narrowly about 0.10 mm (0.004 in.) to about 0.50 mm (0.02 in.), still more narrowly from about 0.10 mm (0.004 in.) to about 0.25 mm (0.01 in.). The perforations may be placed on the panel 196 in a pattern. The perforations may separated from each other in the X direction by perforation X-axis gap 783 and perforation Y-axis gap 784. Gaps 783 and 784 may be about 0.10 mm (0.004 in.) to about 12 mm (0.47 in.), more narrowly about 0.5 mm (0.02 in.) to about 6.0 mm (0.24 in.), still more narrowly about 1.0 mm (0.039 in.) to about 4.0 mm (0.16 in.). Gaps 783 and 784 may between columns (A column is line of holes in the Y direction) and rows (A row is a line of holes in the X direction).

FIG. 50B shows a panel 196 with rectangular perforations 782 having perforation width 786 and perforation length 790. Width 786 and length 790 can be from about 0.025 mm (0.001 in.) to about 12 mm (0.47 in.), more narrowly from about 0.025 mm (0.001 in.) to about 6.0 mm (0.24 in.).

Panel 196 may have a perforation density of about 10 to about 1000 perforations 782 per square inch (per 645 square millimeters), more narrowly about 25 to about 500, still more narrowly about 50 to about 250.

Perforations 782 may pass thru one or more panels 196, one or more layers 72 or thru the entire balloon wall 22.

Figure 51A:
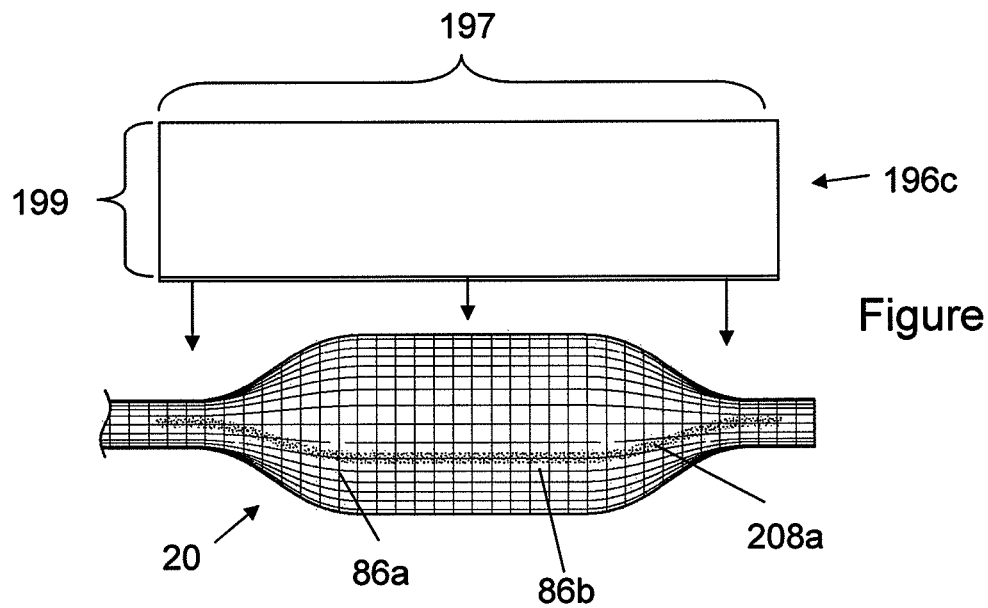
FIGS. 51A through 51F illustrate a method for manufacturing the device

FIG. 51A illustrates that the outer surface of balloon 20 may have a glue or first adhesive 208A. A panel 196c may be positioned over the mandrel. The panel 196c may have a panel length 197 and a panel width 199. The panel length 197 may be equal to or less than twice the balloon length 28. The panel width 199 may be equal to or less than 4 times the balloon diameter 50. The panel 196c may be a single layer or multiple layers. For instance, the panel could be a layer of film and meltable adhesive 208. The panel 196c can be positioned with adhesive on the side that touches the reinforcing fibers with the film facing radially outwards. The panel 196c may be perforated as described supra. The panel 196c may not be capable of sustaining pressure between the top and bottom of the panel 196c.

Figure 51B:
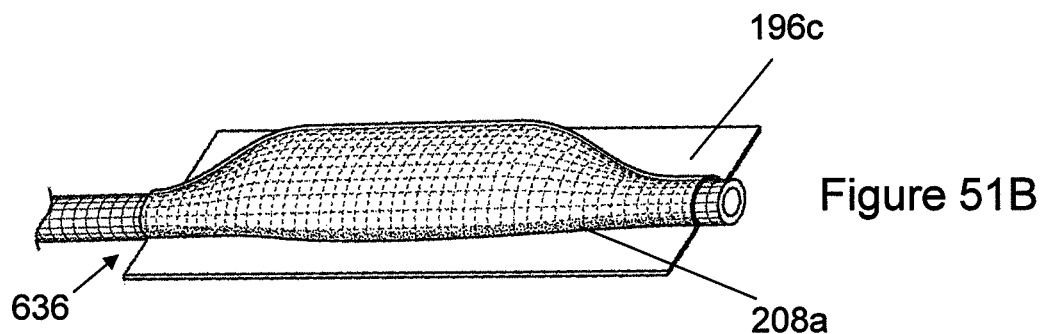

FIG. 51B illustrates that a positive pressure can be applied to the top 220a of the pressure chamber (e.g., through the case top port 222) and/or a negative pressure or suction or vacuum applied to the bottom 220b of the pressure chamber (e.g., through the case bottom port). The panel 196c can get sucked and/or pressed down onto the balloon 20. The first panel can be smoothly fitted to the partially built balloon and adhered at the first adhesive 208A.

Panel 196c and/or 196d may be adhered to balloon 20 by melting an adhesive in or on panel 196c and/or 196d. This melting can be accomplished with light (for example, infrared), with hot air, with a laser, with UV light, via an RF welding process or by using a hot metal part to iron the panel 196c and/or 196d into place. The panel 196c and/or 196d can be mounted into a trimming jig and trimmed as described supra.

Figure 51C:
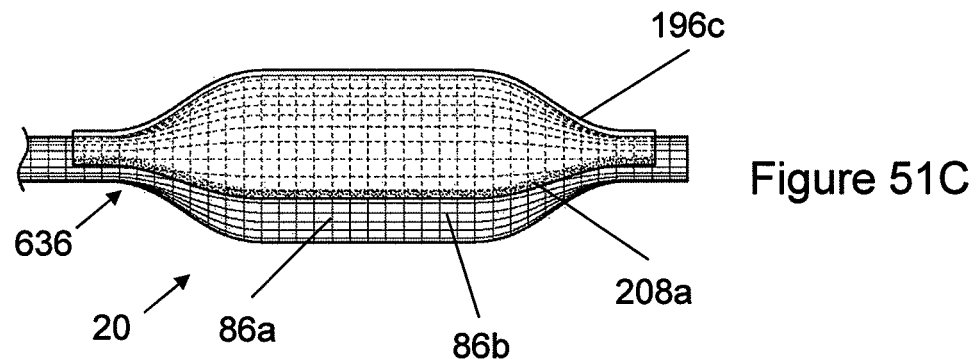

FIG. 51C illustrates that the balloon can have the excess area or the first panel 196c removed in preparation for attachment to the second panel 196d.

Figure 51D:
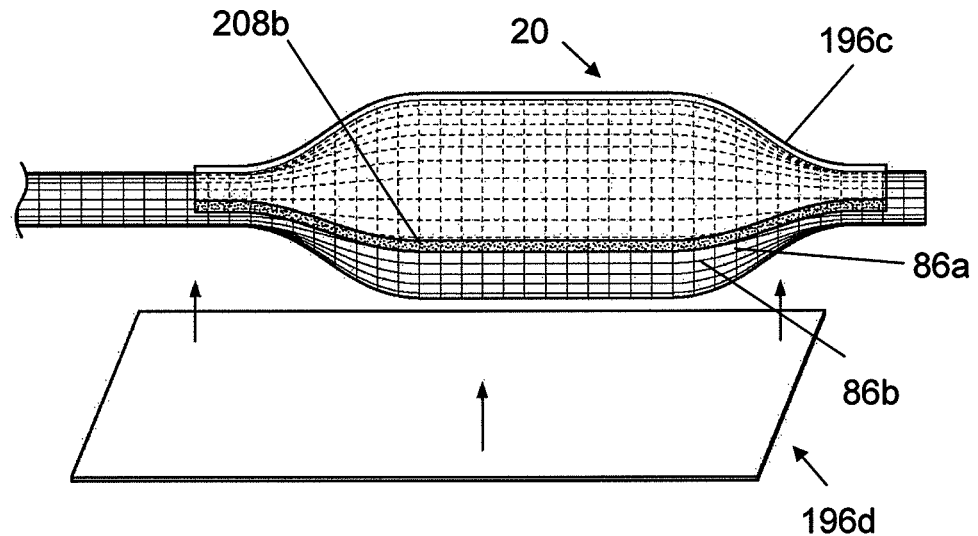

FIG. 51D illustrates that a second adhesive 208b can be applied to the first panel around the perimeter of the second panel's contact area with the first panel. The second adhesive can be an epoxy, urethane, a thermoplastic, a cyanoacrylate, a UV cure, or combinations thereof. The mandrel can be seated in the mandrel seat with the first panel in the mandrel seat. The second panel 196d can be placed on the mandrel as shown (upside down relative to the FIGS. 30A and 30B for illustrative purposes).

Figure 51E:
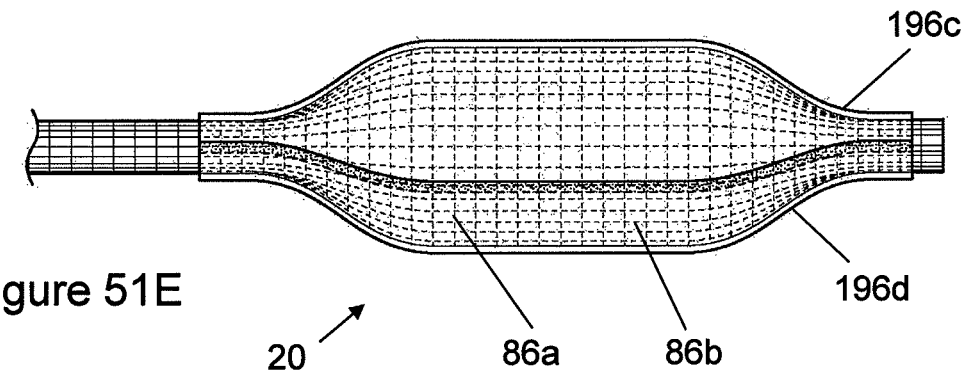

FIG. 51E illustrates that after the case top 220a is secured to the case bottom 220b, the positive and/or negative pressures can be applied to the pressure chamber as described infra (for example, in the descriptions of FIGS. 32A and 32B). The second panel 196d can be smoothly fitted or pressure formed to or against the balloon 20 and adhered to the first panel 196c at the second adhesive 208b. The first and second panels (196c and 196d) can form the outer layer 72a of the balloon wall. The outer layer may be leak-tight. The outer layer may be capable of sustaining pressure.

Figure 51F:
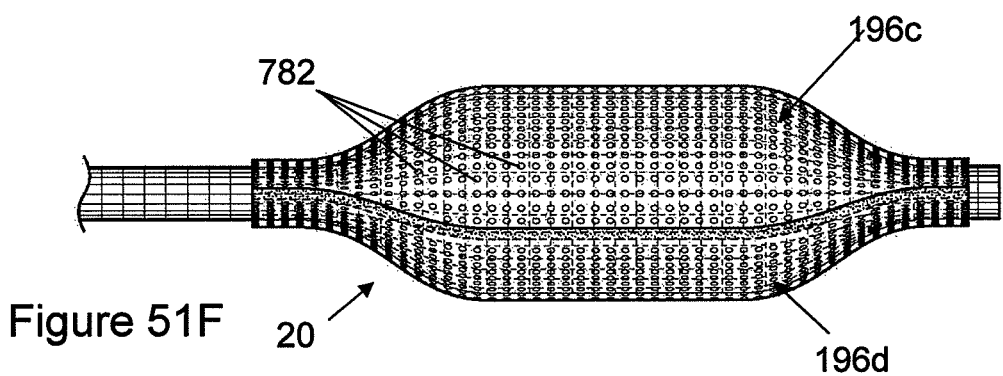

FIG. 51F illustrates that a perforated panel 196 may be applied to the balloon 20. Perforations 782 may have been formed on the panel 196 before it was formed onto balloon 20 after it was formed onto balloon 20. Perforations 782 may have changed size during a forming operation. A perforated panel may have been formed with a second leaktight panel 196e to maintain differential pressure or suction or vacuum during forming. Panel 196e may be not become part of the balloon wall 22.

Panels 196 may be made from films that are highly permeable. By "highly permeable" it is meant that the panel has a nitrogen transmission rate of greater than 60 and a CO2 transmission rate of greater than 1000. More narrowly, Panels 196 may be made from films in which the panel has a nitrogen transmission rate of greater than 200 and a CO2 transmission rate of greater than 2000. Still more narrowly, Panels 196 may be made from films in which the panel has a nitrogen transmission rate of greater than 500 and a CO2 transmission rate of greater than 5000. The units of transmission rate are cc (at STP)/sq. meter atm-day (for example, cubic centimeters at STP per square meter atmosphere-day). STP is 0 Centigrade and 1 atm. Normalized thickness is 0.5 mm (0.02" in.).

The outer layer 72a may be substantially smooth and homogenous. The outer layer may completely encapsulate reinforcement fibers 85 and/or 86 and/or 87b and provide protection from catching or pulling or abrasion or damage of these fibers when in the body.

The outer layer 72a may be formed by vapor deposition, for example by vapor deposition of Parylene, as described herein.

Any layer (for example, layer 72a) may perfuse a chemical, such as a drug. The drug may be trapped in the layer until the balloon 20 expands and/or is heated by the body.

A balloon 20 can be formed with no longitudinal fibers 86b such that, when inflated, the balloon 20 has a significantly higher longitudinal compliance than radial compliance.

Any methods of adding a layer to the mandrel or previous layer can be repeated to add additional layers, such as an outer layer of an MMA-resistant film.

The mandrel and the layers, including the panels, strips, wires or fibers, rosette, or combinations thereof, can be adhered, heated and/or pressurized, for example, to melt solvate, or otherwise bond the layers, for example by creating molecular bonds and decreasing the viscosity and modulus of the layers.

FIGS. 66A-66E illustrate that a medical inflatable device 2, for example the balloon 20 shown in FIGS. 2A and 2B, can be formed using the methods described supra and in, for example, FIGS. 32A and/or 32B and/or 32C and/or 32D and/or 32E and/or 32F and/or 32G and/or 32H.

In addition, FIGS. 66F and 66G illustrate that a panel 196, for example a "0-90" panel as described supra, can be heated and formed into a spherical reinforcement cap 1060 which may be bonded to the distal end 233 of the mandrel 230 over panels 196a and 196b. Cap 1060 may be sized and shaped to fit tightly or snugly over the distal end 233 of mandrel 230. Cap 1060 may closely match the radius of curvature of the distal end 233 of mandrel 230. Reinforcement cap 1060 may have a spherical reinforcement cap edge 1061. As shown in FIG. 26I, edge 1061 may partly define a spherical cap coverage angle 1065. Coverage angle 1065 may be from 20-90°, more narrowly from 30-65°. Edge 1601 may be a circular edge. Reinforcement cap 1060 may comprise one, two, three or more layers 72 of fiber 86, for example the materials listed in FIG. 28. Layers 72 of fiber 86 comprising cap 1060 may be unidirectional and form an angle of about 30° or 45° or 60° or 90° or 120° or 150° with each previous and/or subsequent layer 72. For example, cap 1060 may comprise a first layer 72c comprising fiber, a second layer 72d comprising fiber and a third layer 72e comprising fiber with angles of 0°, 60°, and 120° respectively. For example, cap 1060 may comprise a first layer 72c comprising fiber and a second layer 72d comprising fiber with angles of 0° and 90° respectively. Layers 72 may be a fiber tape.

FIGS. 66F and 66G further illustrate that a radiopaque marker 1064 may be bonded to the distal end of mandrel 230 over panels 196a and 196b. The radiopaque marker 1064 may be comprised of a radiopaque material such as those listed herein.

Referring to FIGS. 67A-67D, strips 192 can be used to form a layer on any of the balloons described herein. Strips 192 can be an elongated element of polymer film, metal foil or fiber tape or combinations thereof cut into a shape that may be useful in constructing a medical inflatable device 2. The strip 192 may be cut by hand, with a high pressure water jet or with a laser or combinations thereof.

FIG. 167A illustrates that the strip 192 can have a strip first narrow section 396a, a strip first taper 397a, a strip first wide section 398a, a strip first central narrowing 399a, a strip central section 400, a strip second central narrowing 399*b*, a strip second wide section 398*b*, a strip second taper 397*b*, a strip second narrow section 396*b* and strip longitudinal axis 194. The strip central section 400 can be approximately circular. The strip 192 can have one or more reinforcement fibers 86. The reinforcement fibers can be substantially aligned with the strip longitudinal axis 194. For example, the strip 192 can have uni-tape. The strip 192 can have one or more layers 72. The reinforcement fibers 86 can extend the entire length of the strip 192. A polymer film (not shown) can be on one side or both sides of the strip 192. The strip 192 can be flexible before and after consolidation.

FIG. 67B illustrates that the strip 192 can be substantially rectangular.

FIG. 67C illustrates that the strip 192 can have a central section 400 that is substantially narrower than strip first wide section 398*a*. For instance, section 400 may be about 10-90% the width of section 398*a*, more narrowly 10-50%, more narrowly still 10%-30%.

FIG. 67D illustrates that a first, second and third strip 192*a*, 192*b*, and 192*c* can be aligned at equal strip angles 404 to each other to form a rosette. The strip angle 404 can be the angle from the first strip longitudinal axis 194*a* to the adjacent strip longitudinal axis 194*b*. The circular sections 400 for each strip 192 can be aligned substantially concentric to each other (as shown) and for a rosette 402. The rosette 402 may be applied to form a medical inflatable device 2. Strip 192 can have no reinforcement fibers. Strip 192 may be made of a radiopaque material, such as a metal foil.

FIG. 66H illustrates that a strip 192*a* can be applied to the inner layer 72*b* or the mandrel 230. Strip 192*a* can be placed around the distal end 233 of the mandrel 230. The strip central section 400 may be centered on the distal end 233 of the mandrel 230. The strip 192*a* may be adhered to the mandrel 230 using an adhesive 208 or by melting the adhesive such that it bonds to the underlying layer 72*b*.

FIG. 66I illustrates that a first strip 192*a*, second strip 192*b* and third strip 192*c* can be placed onto a mandrel 230. For example, the strips 192 can be placed on the layer 72*b* or on any layer 72 or panel 196 or strip 192 disclosed herein. The longitudinal ends of the strips 192 can be on the proximal taper 34 or proximal stem 30. The strips 192 may partially or completely cover the spherical reinforcement dap 1060.

The strip central sections 400 may overlap to form a circular cap over mandrel distal end 233. A marker wire 190 or fiber 86 can be helically wrapped around the mandrel 230, for example as shown in FIG. 47A and described supra. A marker wire 190 or fiber 86 may be bonded to strips 192.

FIGS. 66J and 66K show that a helical wound fiber 86 can have a helical wind overlap distance 1062 with the spherical reinforcement cap 1060. The distance 1062 can be from about 0 to about 4 mm, more narrowly from about 0.5 to about 2 mm. The overlap between fiber 86 and cap 1060 can form a helical wind overlap angle 1066 as shown in FIG. 362*b*. Angle 1066 can be from about 0° to about 25°, more narrowly from about 5° to about 15°. Fiber 86 can cover spherical reinforcement cap edge 1061.

Figure 66A:
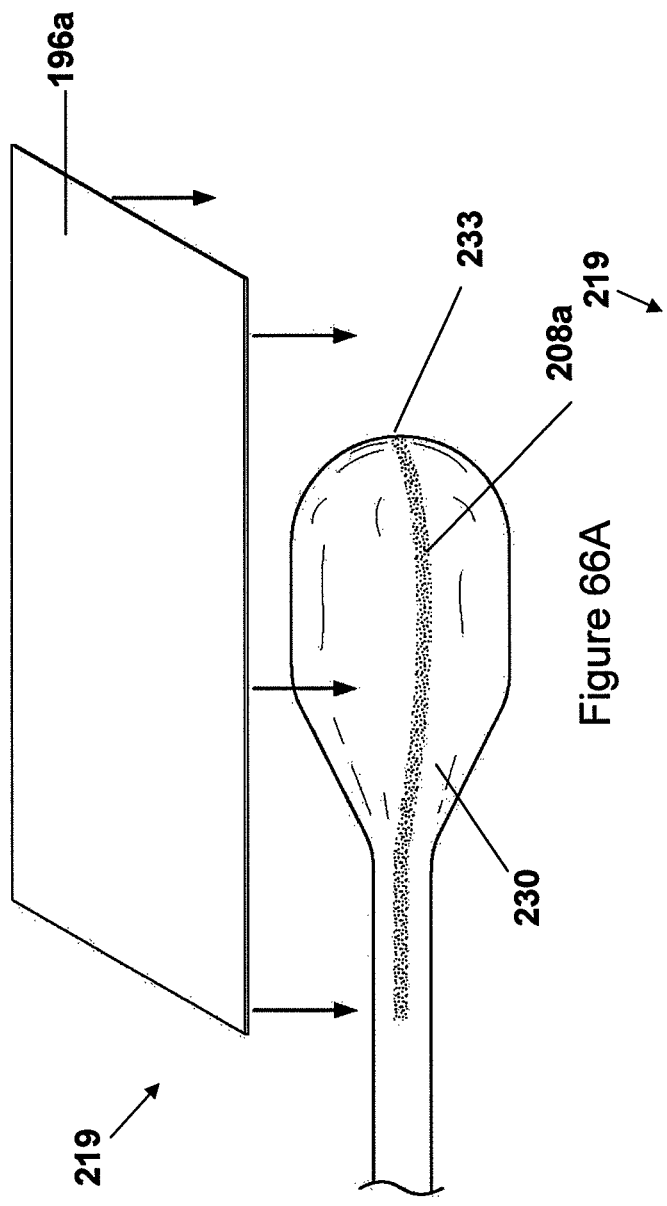
FIGS. 66A-66N illustrate a method of manufacturing a medical inflatable device.
Figure 66B:
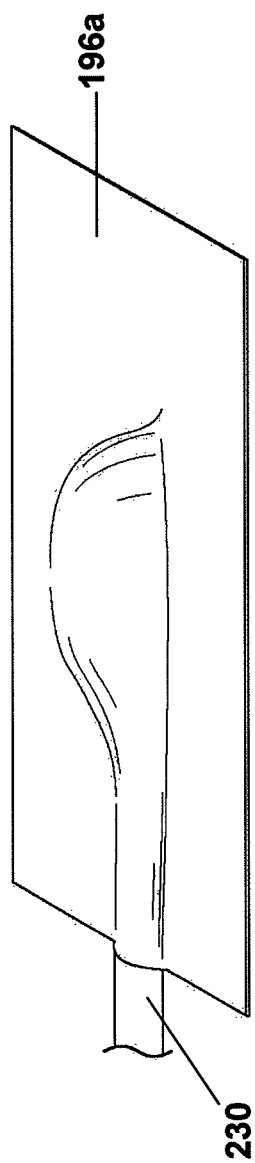
Figure 66C:
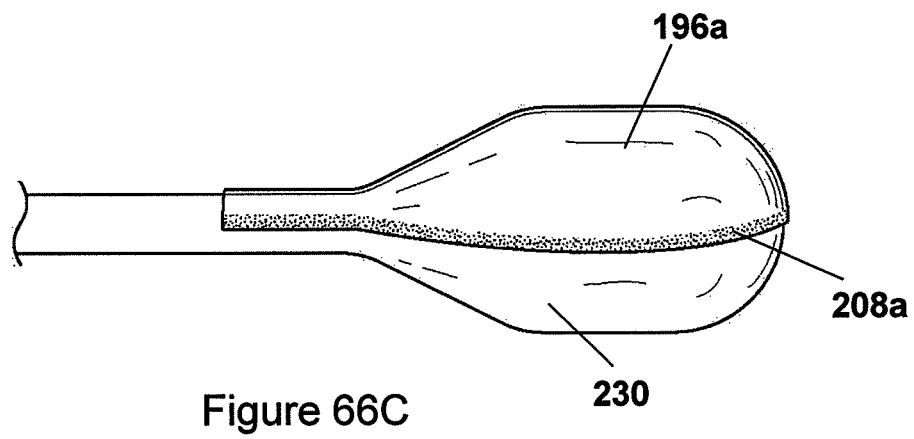
Figure 66D:
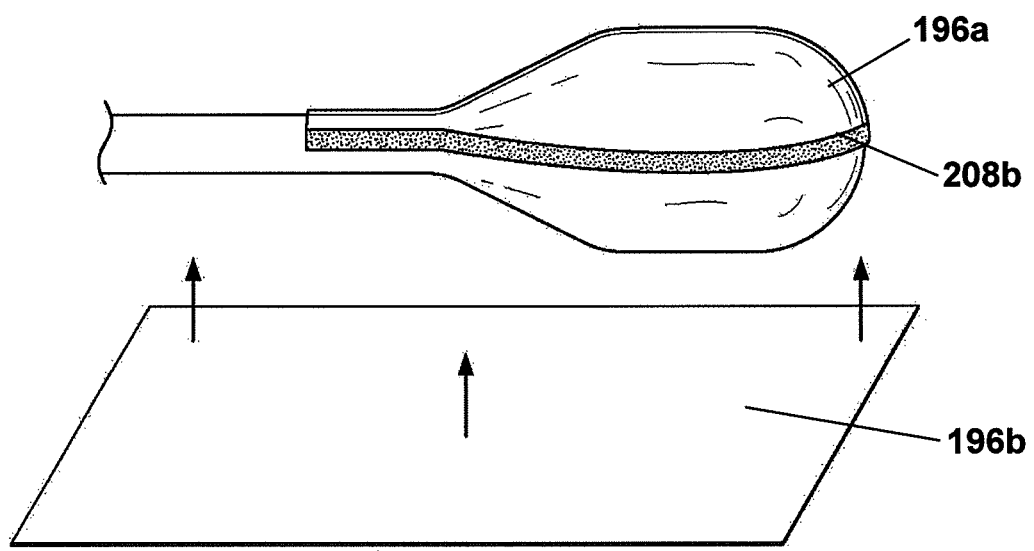
Figure 66E:
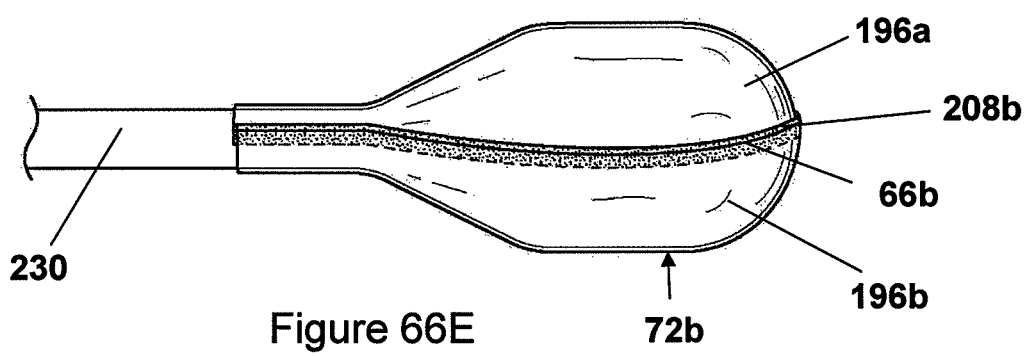
Figure 66L:
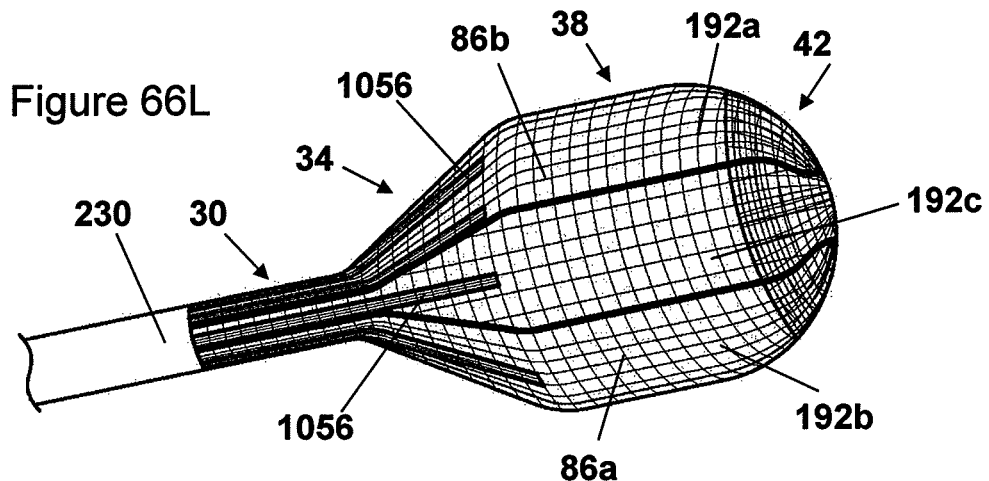

FIG. 66L illustrates that longitudinal reinforcing strips 1056, as described above with respect to FIGS. 49C and 49D, can partially or fully cover the balloon proximal taper 34 and the balloon proximal stem 30. The longitudinal reinforcing strips 1056 may be placed over and bonded to latitudinal fibers 86*a*, such through adhesive and/or a thermally weldable material.

Figure 66M:
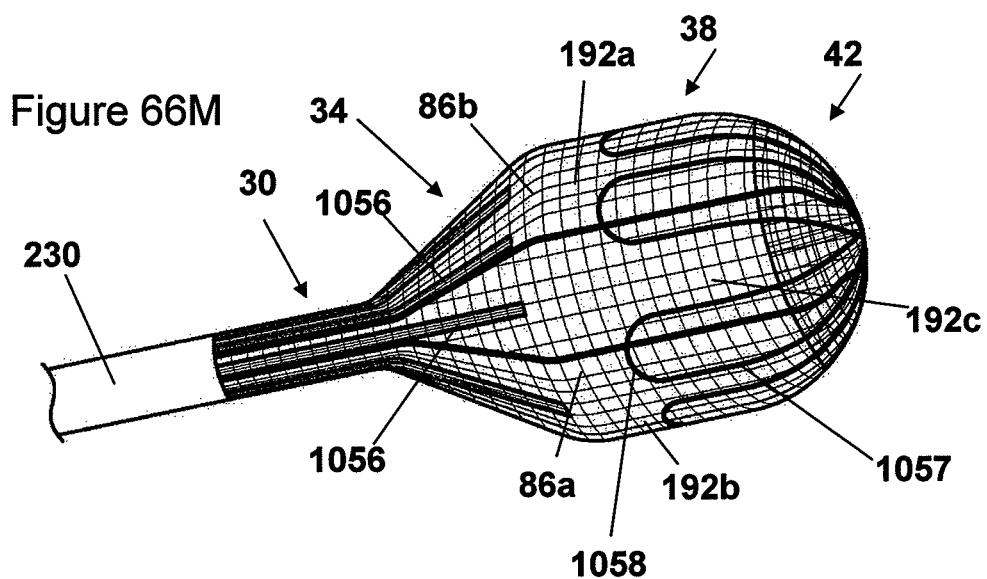

FIG. 66M illustrates that spherical cap reinforcement 1057 may be adhered over the balloon distal taper 42. Reinforcement 1057 may be, for example, a continuous fiber 86 or several fiber 86 pieces. Reinforcement 1057 may pass over itself on the distal taper 42. Reinforcement 1057 may have spherical cap reinforcement loops 1058. A balloon 20 may contain 0 to 50 loops 1058, more narrowly 4-10 loops 1058.

Figure 66N:
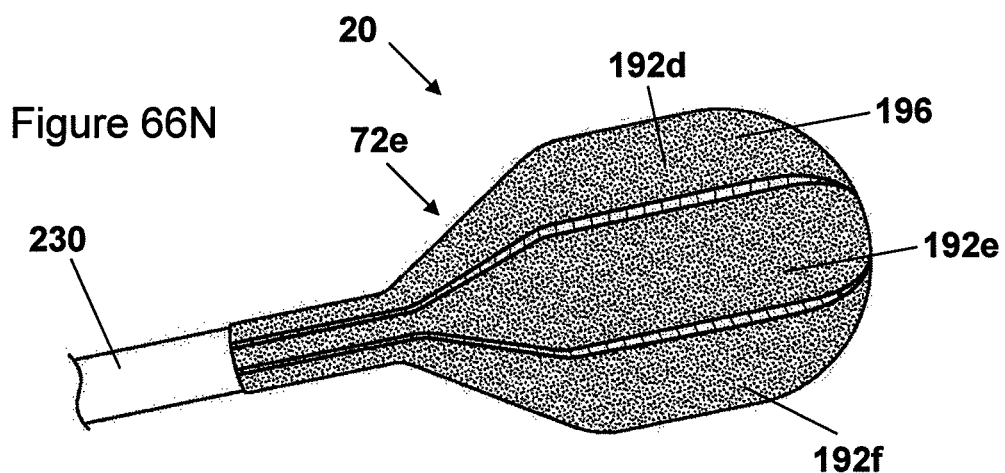

FIG. 66N illustrates that a rosette (as shown in FIG. 124) and/or strips 192 and/or panels 196 panel can be placed onto the balloon 20. The strips 192 and/or panel 196 can be made from a metal foil. The strips 192 and/or panel 196 may provide radiopacity to the balloon 20. The strips 192 and/or panel 196 may strengthen the balloon. The strips 192 and/or panel 196 may make the balloon significantly more resistant to puncture.

Any methods of adding a layer to the mandrel or previous layer can be repeated to add additional layers, such as an outer layer of an MMA-resistant film. The methods shown in FIGS. 66A-66E may be used to attach a panel (for example, a film) or panels (for example, films) to the balloon 20 to form an outer layer 72*a*.

The mandrel and the layers, including the panels, strips, wires or fibers, rosette, or combinations thereof, can be adhered, heated and/or pressurized, for example, to melt solvate, or otherwise bond the layers, for example by creating molecular bonds and decreasing the viscosity and modulus of the layers.

FIG. 52 illustrates that a panel 196 may be applied to a balloon 20 to form an outer layer 72*a*. The panel 196 may be a film, such as those listed in FIG. 27. The panel 196 may applied in a manner similar to that shown in FIGS. 45A-45D.

Methods described supra for forming bladders 52 can also be used to form the outer layer 72*a*. For example, FIGS. 33A-33D, FIGS. 34A-34I, FIG. 35, FIG. 36 and FIG. 37 disclose methods for applying a bladder 52 to a mandrel 230. These same methods may be used for applying an outer film 72*a* to a balloon 20.

A outer layer 72*a* may be formed by deposition. For example, a metal such as gold (or other materials listed herein) may be deposited to form outer layer 72*a*. For example, a material such as parylene may be deposited to outer layer 72*a*.

A outer layer 72*a* may be formed from a heat shrink tube. The tube may be formed in manufacture to fit the balloon 20, blown out to size, then placed over the balloon 20 and shrunk to fit the balloon. Shrinking may be accomplished by the application of heat.

FIG. 53A illustrates that after the layers 72 of the balloon have been assembled on the mandrel 230, a distal caul 260*a* can be placed over the distal end of the balloon. A proximal caul 260*b* can be slid over the mandrel and the proximal end of the balloon. The proximal caul 260*b* can be sealed to the distal caul 260*a*. The cauls 260 can be made from a flouro-polymer. The cauls 260 can have thermoformed FEP with a 0.005 in (127 μm) initial thickness.

FIG. 53B illustrates that the assembly in FIG. 53A can be placed between top and bottom vacuum sheets 238*a* and 238*b*. Sheets 238 may be sealed to each other with vacuum seal tape 240 to form a vacuum bag. The interior of the vacuum bag can be heated. The vacuum bag can be inserted inside of an oven or autoclave. The layers of the balloon on the mandrel can be thermally cured or melted, for example under from about 15 psi (103 kPa) to about 450 psi (3100 kPa) of pressure. The suction tube 242 can suction the interior of the vacuum bag. For example the pressure in the vacuum bag can be less than about 1.5 psi (10 kPa).

FIG. 54 illustrates that a wash tube 264 can be inserted into a mandrel washout port 262. A dissolving or solvating fluid can be delivered through the wash tube and into the washout port 262. The mandrel can be removed by delivery of a fluid solvent such as water, alcohol or a ketone. The solvent may be applied during the consolidation process such that the solvent melts or partially softens the mandrel and concurrently pressurizes the bladder. The mandrel 230 can be removed by raising the mandrel to a melting temperature for the mandrel. The mandrel 230 can be removed by deflating the mandrel or by collapsing an internal structure.

FIG. 55A illustrates that the balloon 20 may be placed in a balloon mold 622 containing a balloon pocket 624. The balloon mold 622 may be porous such that substantial amounts of gas may be drawn from balloon pocket 624 thru the wall of balloon mold 622 and out into the surrounding atmosphere. The balloon 20 may have a tube (not shown) placed in its inner volume that may extend out either end of the balloon 20. The tube may be thin and very flexible. The tube may be a silicone rubber.

A coating may be sprayed into mold 622 that bonds to the balloon during cure and forms an outer layer 72a on the balloon 20.

FIG. 55B illustrates that the balloon mold may be closed around the balloon 20. Pressure may be applied thru balloon second fluid port 56b such that the balloon expands to contact the inside of balloon pocket 624. Alternately, the tube (not shown) extending out either end of the balloon may be pressurized to force the balloon into contact with pocket 624.

FIG. 55C shows Pressure P inside the balloon volume 24 pressing the balloon wall 22 outwards. Mold 622 may be placed in an oven and heated. Mold 622 may have built in heaters. The balloon mold may be placed under vacuum (as per FIG. 53B) or placed in a vacuum chamber during heating.

Heating the balloon under pressure may cause one or more layers 72 to melt and fuse with adjoining layers. The melting under pressure may remove voids in the balloon wall 22. The inner layer 72b and outer film layer 72a may not melt. Heating the balloon 20 under pressure may cause the balloon wall 22 to fuse or laminate into one continuous structure. The balloon outer wall 22b and/or outer layer 72a may be substantially smoothed by being heated with pressure in balloon volume 24. The balloon outer wall 22b and/or outer layer 72a may be permeable or perforated such that gas or other material trapped in the balloon wall 22 during manufacture may escape when the balloon is heated under pressure.

The final balloon outer diameter 50 may be very accurate and repeatable. For instance, at a given pressure, the outer diameter of a group of parts may all fall within about 2% (+/−1%) of each other. For instance, if the nominal dimension of the outer diameter 50 of the balloon is about 24 mm (0.945 in) at about 60 psi (414 kPa) all parts may have an outer diameter of about 23.76 mm (0.935 in) to about 24.24 mm (0.954 in).

FIG. 56A illustrates that a pleated balloon 20 in an expanded or inflated configuration can be substantially circular in cross-section.

FIG. 56B illustrates that a balloon can be clamped in a pleating tool 266 with two, three, four, five or more removable pleating blocks 268. Heating the pleating blocks 268 to about 80 C and then pressing them against the balloon for about 1 minute causes the balloon to become pleated or fluted. Commercial pleating machines such as balloon folding machinery from Interface Associates (Laguna Niguel, Calif.) can also be used. A small amount of wax may be used to hold the pleated and folded balloon into its desired shape.

FIG. 56C illustrates that a pleated balloon in a deflated or contracted configuration can have one or more pleats or flutes 84. The balloon 20 may reform these pleat after inflation when vacuum is applied to balloon volume 24.

Additional laminates can be added to areas of a balloon that might require extra strength for certain procedures or uses. A balloon may have different amounts of fiber, adhesive or polymer film in different portions of the balloon wall. A balloon may have different number of fiber layers in different portions of the balloon wall.

Method of Use

The device 2, for example including the balloon 20, can be used for Kyphoplasty, angioplasty including CTO dilation, stent delivery, sinuplasty, valvuloplasty, drug or other fluid delivery through the balloon, radiopaque marking, incising the inside of a vessel (e.g., to open or expand a vessel), brachytherapy, intentionally obstruct a vessel, or combinations thereof. The device 2 can be used to deliver one or more stents and/valves and/or emboli filters to the coronary blood vessels (e.g., arteries or veins), carotid artery, peripheral blood vessels, the GI tract, the biliary ducts, the urinary tract, the gynecologic tract, and combinations thereof. The device 2 can be used to prepare a cardiac annulus and/or the leaflets of a natural heart valve for open or percutaneous (minimally invasive) valve replacement. The device 2 can expand and deploy a percutaenously delivered heart valve FIG. 57A illustrates a cross section of a balloon wall 22 taken thru balloon central section 38. The balloon 20 can be in a substantially inflated condition and has balloon central section outer diameter 50. The balloon wall 22 can have a balloon wall area 432 shown as the crosshatched area in FIG. 57A.

FIG. 57B illustrates a cross section of balloon wall 22 taken thru balloon central section 38 wherein the balloon 20 is in a substantially deflated and folded configuration. The balloon 20 is shown in a delivery tube 428 or cannula with a delivery tube inside diameter 436 and a delivery tube inside diameter cross sectional area 434. The delivery tube cross sectional area 434 is about equal to diameter 436 divided by 2, the product of that calculation squared and the product of that calculation multiplied by 3.1415. The delivery tube cross sectional area 434 is defined as:

$$\text{Area } 434 = (\text{delivery tube inside diameter } 436/2)^2 * pi.$$

The compression ratio of the balloon can be from about 3:1 to about 10:1, more narrowly from about 5:1 to about 8:1, still more narrowly about 6:1 to about 7:1. The compression ratio can be the ratio between the outside diameter 50 of the substantially inflated balloon (e.g., as shown in FIG. 57a) and the tube inside diameter 436 (e.g., the tube as shown in FIG. 57B). For instance, a balloon 20 with balloon outer diameter 50 equal to 24 mm (0.945 in) may be folded to fit in a delivery tube inside diameter 436 of about 3.6 mm (0.142 in).

The balloon can have a packing density equal to or greater than about 40%, more narrowly greater than or equal to about 55%, yet more narrowly equal to or greater than about 70%. The packing density can be the percentage ratio between the cross sectional area 432 of the walls of the balloon and the delivery tube inside diameter cross sectional area 434.

The packing density and compression ratios for the balloon can remain substantially constant and the wall strength of the balloon can remain substantially constant with repeated packing and unpackings, and/or compressings and uncompressings.

The balloon can be folded into the cannula and expanded about eight times or more while not significantly degrading the strength of the balloon wall.

Figure 58:
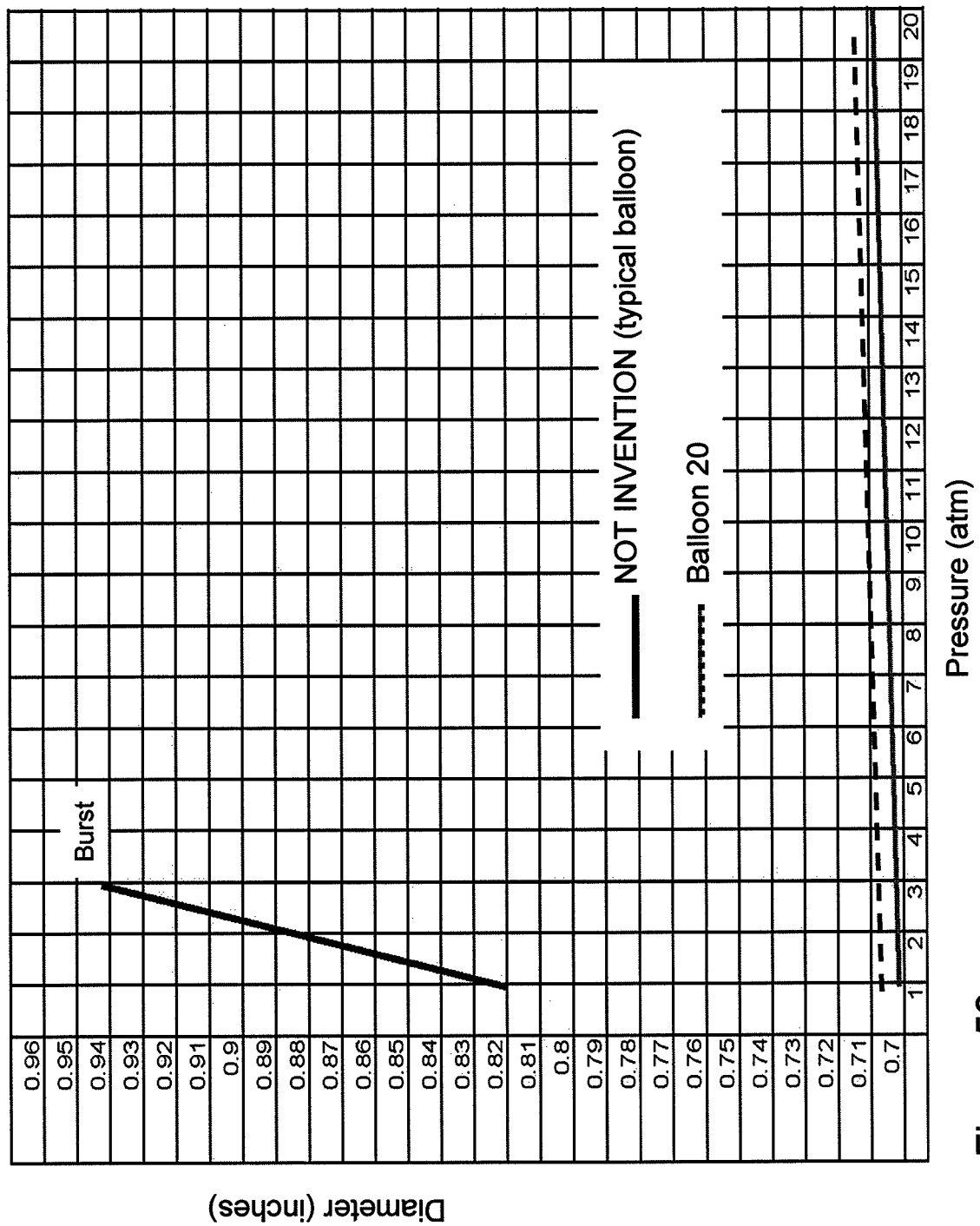
FIG. 58 is a graph of compliance of the variation of the balloon compared with a typical compliant balloon.

FIG. 58 illustrates that the diametric elasticity of existing medical inflatable devices can be approximately 0.06 in./ATM and a typical burst pressure is about 3 atm. The medical inflatable device 2 can have an exemplary diametric elasticity of 0.0004 in./ATM and a burst pressure above 20 atm. Medical inflatable device 2 and balloon 20 can be substantially inelastic.

Figure 59:
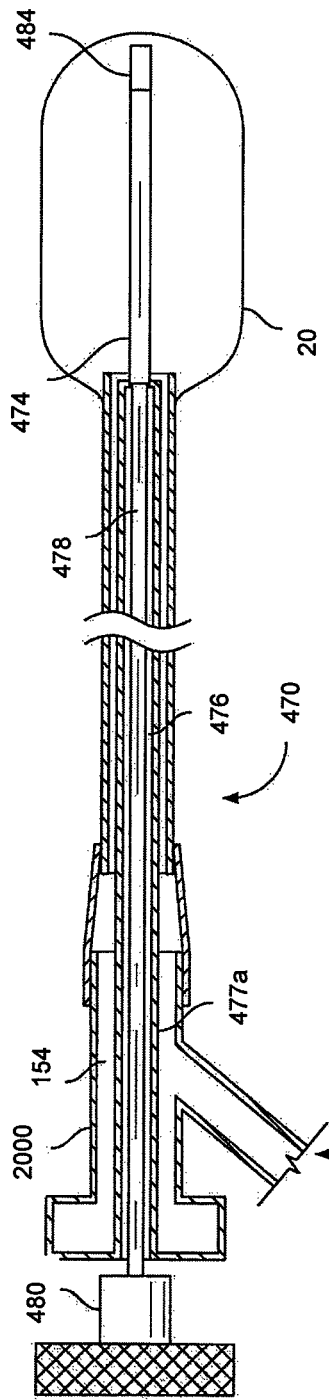
FIGS. 59 and 60A illustrate variations of a deployment tool with the device.

FIG. 59 illustrates that the inflation system 470 can be attachable to a syringe 472 or other source of flow and pressure. The inflation system 470 can include part or all of the hollow shaft 2000, an inner shaft 477a, a stiffening shaft 476, a hollow shaft lumen 154, a stiffening shaft lumen 478, an inflation port 482 and a stiffening rod control 480. The distal end of the stiffening shaft 476 can have a stiffening rod tip 484.

The syringe 472 can be detachable or non-detachable from the remainder of the inflation system 470. The balloon 20 may be inflated by pushing inflation fluid, such as water or dye, from the syringe 472, into the inflation port 482, through the hollow shaft lumen 154 and into the balloon 20. The removable stiffening shaft 476 may be left in place to stiffen the inflation system 470 while positioning the balloon 20 in the body. Once the balloon 20 is in place, the removable shaft stiffener 476 can be removed to allow the hollow shaft 2000 additional freedom of motion outside the body.

The stiffening shaft 476 can be integral with or removably attached to the stiffening rod 474. The stiffening rod tip 484 can have atraumatic geometry, or a soft plastic or elastomeric tip that will minimize puncture or damage the distal end of the balloon. The stiffener 476 can be withdrawn manually automatically.

A flexible tether (not shown) may be attached near or at where balloon 20 bonds to hollow shaft 2000. The flexible tether may pass thru the inside of hollow shaft 2000 and be anchored to the proximal end of hollow shaft 2000. The flexible tether may act as a safety strap. The safety strap may act as an emergency retrieval tool in case the balloon becomes detached in the patient. The flexible tether may be made of one or more of the materials listed in FIG. 28.

Figure 60A:
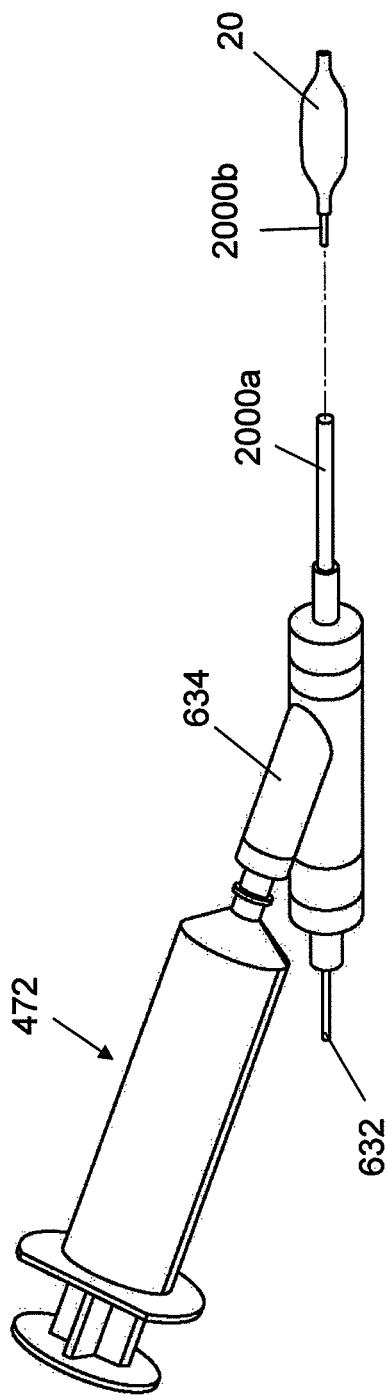

FIG. 60A shows that inflation fluid may be provided by detachable syringe 472 thru catheter Y-fitting 634. Inflation fluid may flow between in the inside wall of the outer catheter tube 2000a and the outside wall of the inner catheter tube 2000b. Inflation fluid may flow into balloon volume 24 to inflate the balloon. A guide wire may be inserted at guidewire port 632 and pass thru the inside of the inner catheter tube 630.

FIG. 60B shows a cutaway of an alternate embodiment of the distal end of a balloon catheter. Second hollow shaft 2000b may be in fluid communication with balloon volume 24 and may form inner lumen 154a. Second hollow shaft 2000b may be used to inflate and deflate balloon 20. Distal and proximal ends of balloon 20 may be attached to the radially outside surface of first hollow shaft 2000a. First hollow shaft 2000a may be connected to catheter tip 838. First hollow shaft 2000a may enclose outer lumen 154b. Catheter tip 838 may have one or more catheter tip ports 839 as shown in FIG. 60C. Outer lumen 154b may be in fluid communication with one or more catheter tip ports 839. With the balloon 20 inflated during a medical procedure, fluid, such as air, may freely travel through catheter tip port 839 and outer lumen 154b. For instance, a patient may be able to breathe through catheter tip port 839 and outer lumen 154b if the balloon 20 is inflated in said patient's airway.

First hollow shaft 2000a may have a first hollow shaft outer diameter 2001a and a second first hollow shaft outer diameter 2001b. Diameter 2001a may pass thru the balloon 20. Diameter 2001a may be distal to diameter 2001b. Diameter 2001a may be substantially smaller than diameter 2001b. Making diameter 2001b as large as possible may maximize the flow of fluid, such as air, through outer lumen 154b during a procedure. Holes (not shown) may be placed proximal to balloon 20 in first hollow shaft 2000a to connect lumen 154b to the air radially outside of first hollow shaft 2000a. Said holes may allow easier flow of air, through lumen 154b during a medical procedure.

FIG. 61 shows a cross section of the heart 562. The heart 562 has an aorta 568, a left ventricle 570 and an aortic valve 564

FIG. 62A shows a folded balloon 20 with a prosthetic heart valve 626 crimped over it. In FIG. 62B expansion of balloon 20 from a deflated state to an inflated state may cause prosthetic heart valve 626 to deploy to a larger size. Balloon 20 may be substantially non-compliant as described herein. Non-compliance may allow the heart valve to deploy to a very precise inner diameter regardless of pressure applied.

FIGS. 63A, 63B and 63C illustrate that a guidewire 572 can be inserted through the aorta 568 and positioned in the left ventricle 570 of the heart 562. The device 2 can be slidably inserted over the guidewire through the aorta 568. The device 2 may be in a deflated state when first placed in the aortic valve 564. The device 2 can be positioned to align along the guidewire the balloon 20 with the aortic valve leaflets 566. The device 2 can also be rotated about the balloon longitudinal axis to align with the aortic valve 564, for example when cutting apart attached leaflets 566 in a bicuspid aortic valve with a flange, vane, blade, other cutting element described herein, or combinations thereof.

FIG. 63D shows the balloon 20 in an expanded configuration. The device 20 can be non-compliant and open the aortic valve 564 to a precise dimension (for example, about 20 mm (0.787 in) or about 24 mm (0.945 in)). The balloon 20 can fixedly reconfigure and press the aortic valve leaflets 566 against the outer wall or annulus 582 of the aortic valve 564. The balloon 20 can radially expand the aortic valve annulus 582.

The balloon can have an annular lumen 160, as shown in FIGS. 16 through 20. Natural blood flow through the aortic valve can flow through the annular lumen 160 when the balloon 20 is in an inflated or expanded configuration in the aortic valve. The device can have a device valve 178. The device valve 178 can open and close, for example depending on the ventricular pressure against the device valve.

FIG. 63E illustrates that the balloon 20 can be deflated, contracted and withdrawn from the aortic valve 564.

FIG. 63F shows the aortic valve 564 in an opened configuration at a larger dimension than before the procedure.

The method described supra can be performed on an aortic, mitral, pulmonary, tricuspid or vascular valve.

Figure 64A:
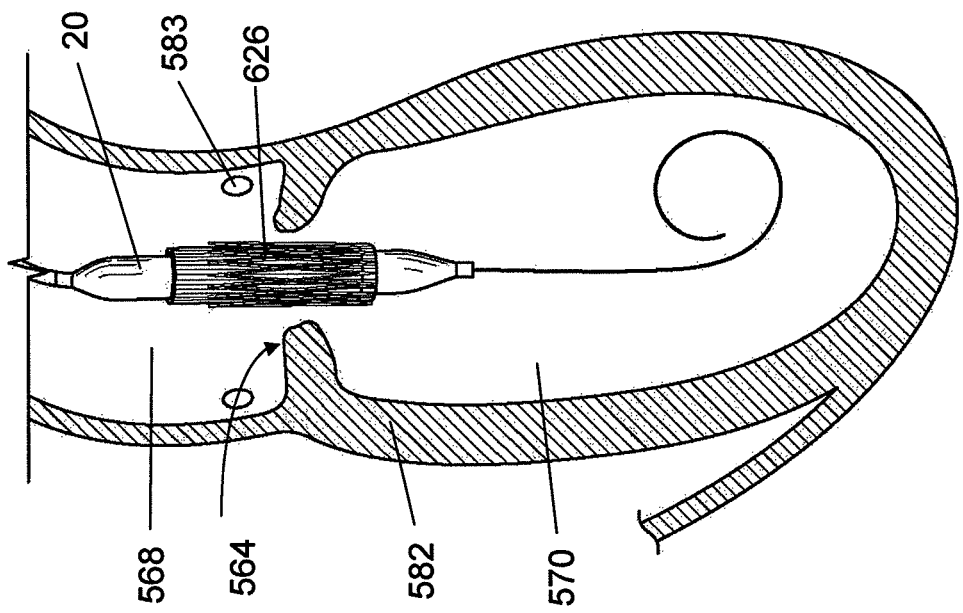
FIGS. 64A through 64F illustrate a variation of a method for using the device.
Figure 64B:
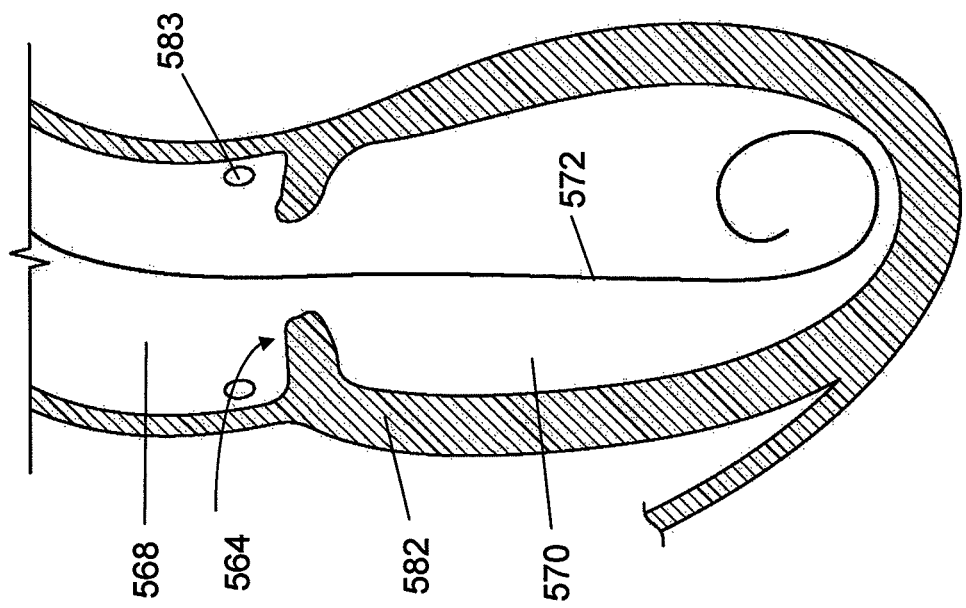
Figure 64C:
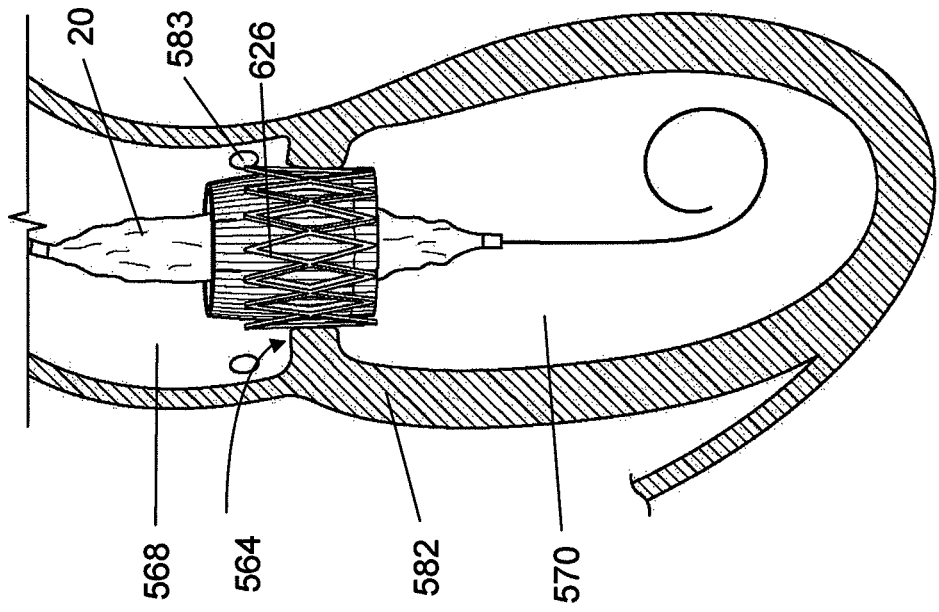
Figure 64D:
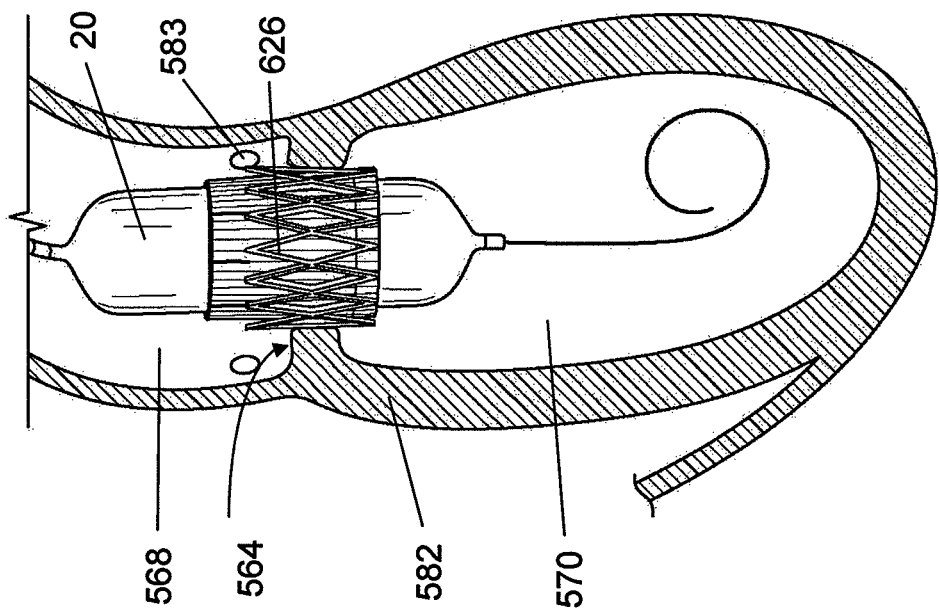
Figure 64F:
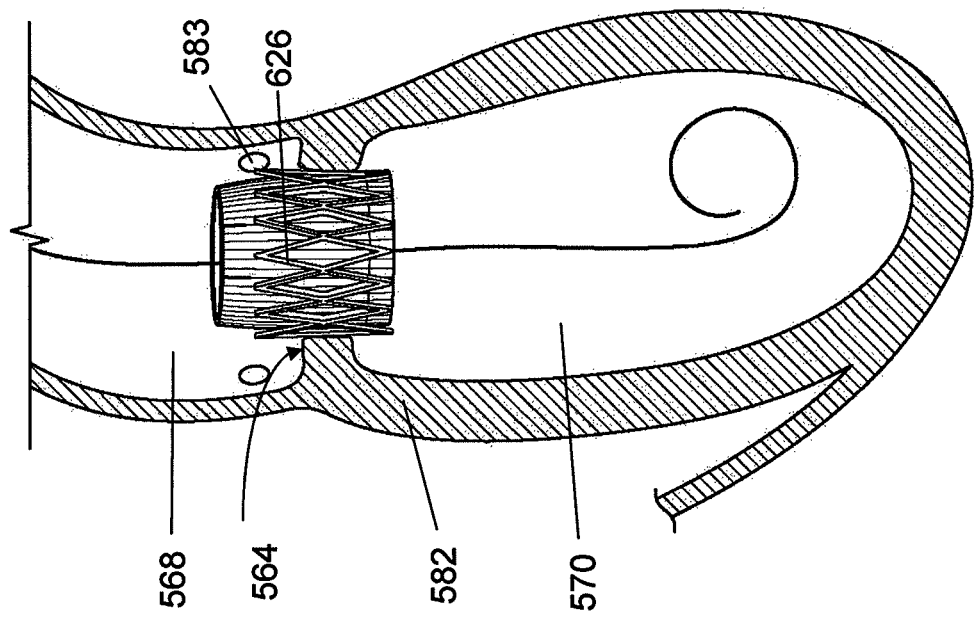
Figure 64E:
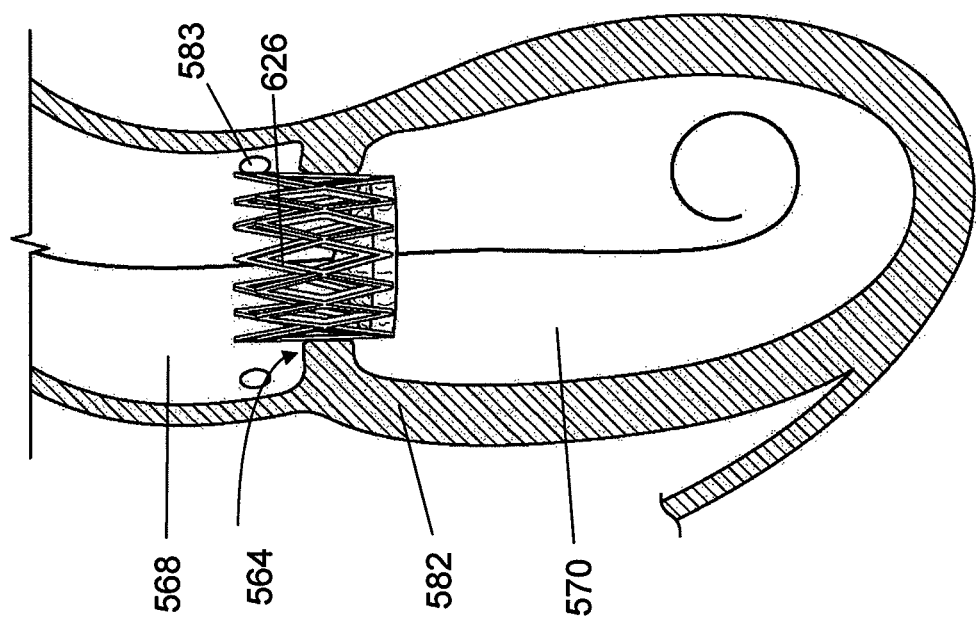

Referring now to FIGS. 64A-64F, The balloon 20 can be used to deploy a prosthetic valve 626 in, for instance, the aortic valve 564 near the coronary ostia 583. A guidewire 572 may first be introduced thru the aorta 568 into the left ventricle 570. Next, as shown in FIG. 64B, a balloon catheter carrying prosthetic heart valve 626 and deflated balloon 20 may be introduced over guidewire 572 into aortic valve 564. In FIG. 64C, balloon 20 is quickly inflated to expand the prosthetic heart valve into the aortic valve 564. The inflation is performed quickly as, when balloon 20 is fully inflated, cardiac output may be zero. If a balloon 20 with an annular lumen 160 is used (not shown), blood may continue to flow from the heart 562 and into the aorta 568 even with the balloon expanded and balloon inflation and deflation may not be quick. In FIG. 64D, the balloon is quickly deflated, leaving the valve prosthesis 626 behind in the aortic valve. FIG. 64E show the prosthetic valve closing (64E) and opening (64F) immediately after the balloon 20 is withdrawn FIG. 65A illustrates that the balloon can be positioned in a narrowed, atherosclerotic length of a blood vessel 574 having atherosclerotic plaque 576 on the interior of the vessel wall 578. The vessel 574 can have a vessel lumen 580 through which blood can flow.

FIG. 65B illustrates that the balloon 20 can be inflated and expanded. The balloon 20 can remodel the vessel, pushing the sclerotic plaque 576 radially away from the balloon longitudinal axis. The balloon 20 can deploy a vascular stent to the sclerotic length of the vessel.

FIG. 65C illustrates that the balloon 20 can be deflated, contracted and removed from the narrowed length of the vessel 574. The vessel lumen 574 can remain patent after the balloon is removed, for example restoring blood flow past the treated atherosclerotic length.

The balloon 20 can be implanted in the body semipermanently or permanently. The balloon 20 can have one, two or more openings for fluid entry and/or exit.

Figures 68A, 68B:
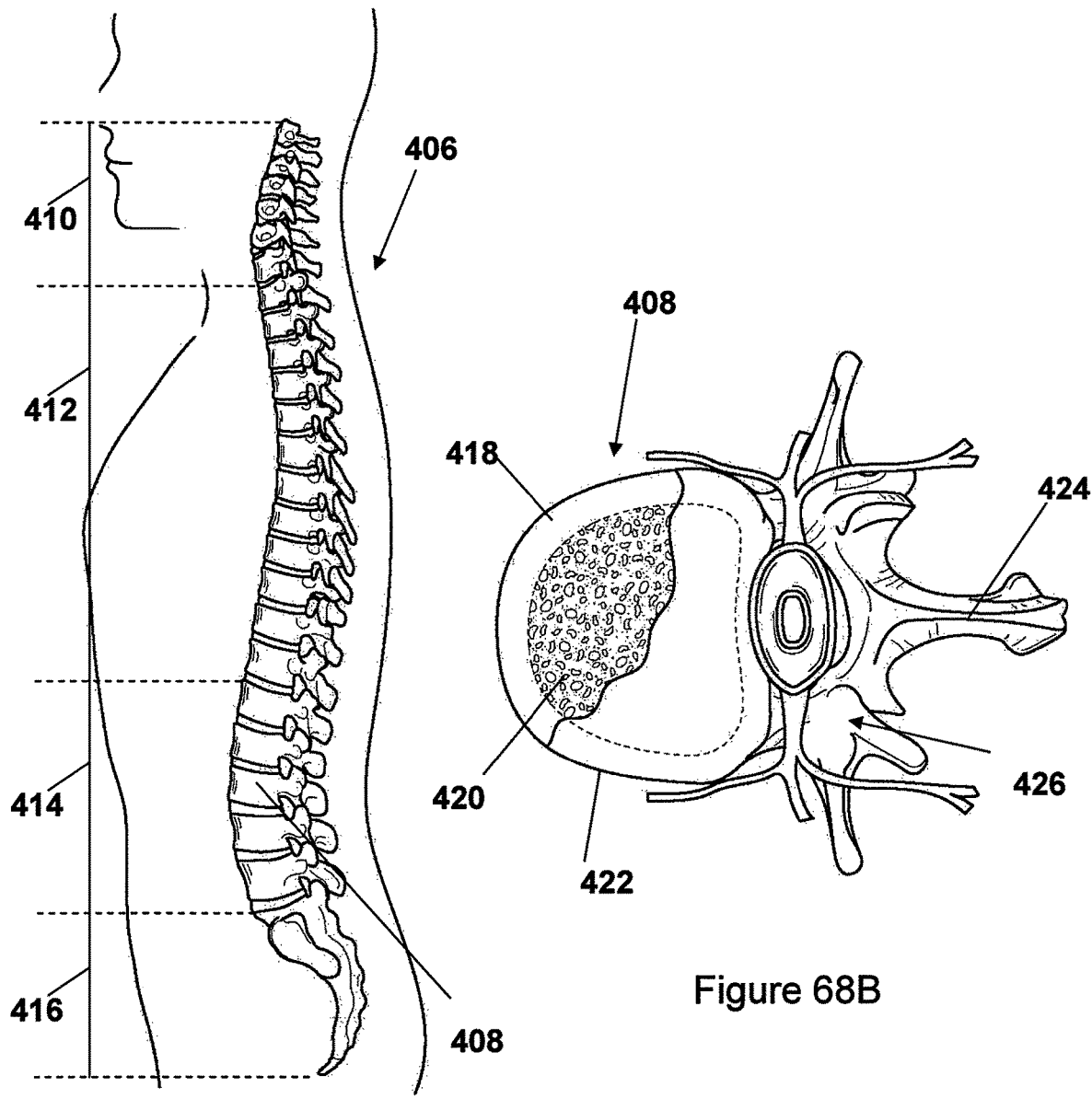
FIG. 68A illustrates a sagittal view of a patient and a spine.
FIG. 68B illustrates a vertebra.

FIG. 68A illustrates a sagittal view of a patient and the spine 406. The spine 406 can have vertebrae 408 and cervical, thoracic, lumbar and sacral regions 410, 412, 414, and 416. The device 470 and 996 can be used in or between vertebrae 408 in any region of the spine 406.

FIG. 68B illustrates a vertebra 408 that can have cortical bone 418 and cancellous bone 420. The vertebrae 408 can have a vertebral body 422 a vertebral process 424 and pedicles 426.

FIGS. 69A through 69I illustrate a method for deploying balloons 20 bilaterally, for example including one balloon inserted through each of opposing pedicles 426a and 426b.

FIG. 69A illustrates that a first delivery tube 428a, such as a cannula, can be placed through the left pedicle 426a. The delivery tube 428 may have an inside diameter of less than about 6 mm, more narrowly from about 2 mm to about 4.5 mm. A bone drill can be passed through the delivery tube to form a first drill void 430a on the left side of the vertebral body. A second delivery tube 428b can be through the right pedicle 426b. A second drill void 430b can be formed on the left side of the vertebral body.

FIG. 69B illustrates that a first balloon 20a can be inserted into the left side of the vertebral body through the first delivery tube 428a. A second balloon 20b can be inserted into the right side of the vertebral body through the second delivery tube 428b. The balloons 20a and 20b may be part of an inflation system 470, such as that shown in FIG. 59.

FIG. 69C illustrates that fluid pressure can be delivered, as shown by arrow 438, through the hollow shafts 2000 to the balloons 20. The balloons 20 can inflate and expand, as shown by arrows 440a and 440b. The expanding balloon can compress the cancellous bone surrounding the drill void, creating a larger balloon void 442. The first and second balloons can form a first void segment 454a and a second void segment 454b, respectively, of the balloon void 442. The void segments 454 may overlap, as shown. The void segments 454 may be separate.

FIG. 69D illustrates that the second balloon 20b can be deflated, contracted and removed from the balloon void.

FIG. 69E illustrates that a second cement conduit 444b can be inserted through the second delivery tube 428b and into the second void segment 454b. Bone cement 445 can be delivered through the second cement conduit 444b and into the second void segment 454b. Cement conduits 444a and 444b may each be equivalent to outer assembly tube 1002.

FIG. 69F illustrates that the bone cement 445 can fill the second void segment 454b and/or contact the first balloon 20a. The second cement conduit 444b can be removed from the balloon void. The bone cement delivered to the second void segment can cure. The first balloon 20a may not erode, decay or bond to the cement.

Figure 69I:
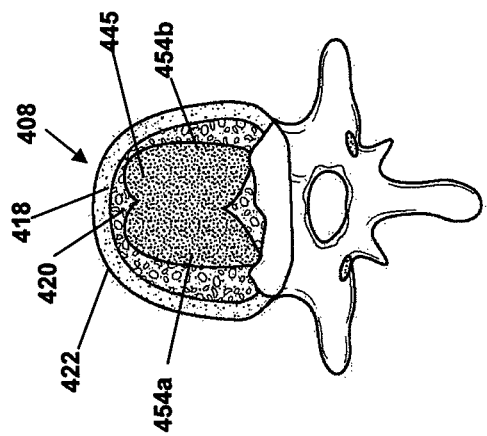
Figure 69H:
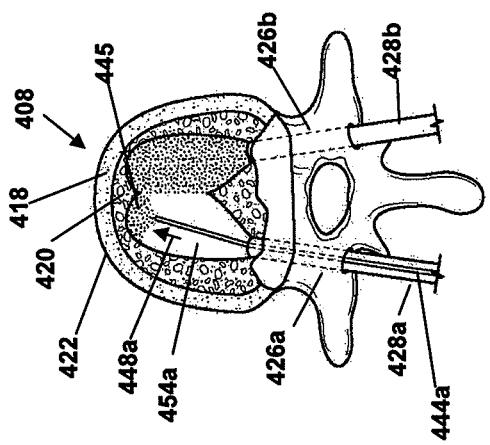
Figure 69G:
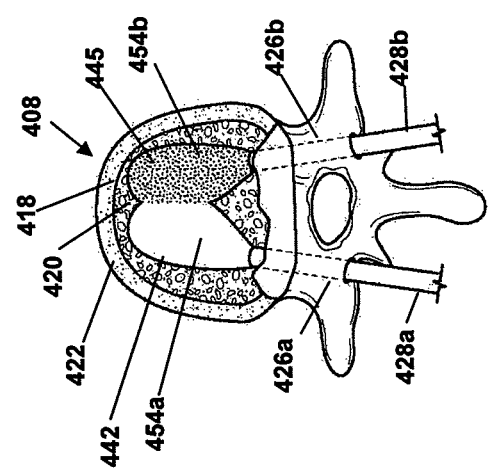

FIG. 69G illustrates that the first balloon 20a can be deflated, contracted and withdrawn from the first void segment 454a.

FIG. 69H illustrates that a first cement conduit 444a can be inserted through the first delivery tube 428a and into the first void segment 454a. Bone cement 445 can be delivered through the first cement conduit 444a and into the first void segment 454a.

FIG. 69I illustrates that the first and second delivery tubes 428 can be removed from the patient. The balloon voids 454a and 454b can be substantially filled with bone cement 445. The bone cement 445 can cure.

FIG. 58 illustrates that the diametric elasticity of existing medical inflatable devices can be approximately 0.06 in./ATM and that a typical burst pressure can be about 3 ATM. In contrast, balloon 20 can advantageously have an exemplary diametric elasticity of 0.0004 in./ATM and a burst pressure above 20 ATM (290 psi). For example, the burst pressure can be from about 290 psi to about 1500 psi. More narrowly, the burst pressure can be from about 500 psi to about 1000 psi. For example, the burst pressure can be about 500 psi, about 750 psi, about 1000 psi, about 1500 psi, or higher than 1500 psi. For example, the burst pressure can be greater than 4 ATM with a diameter of greater than 20 mm, with a diametric compliance of less than about 15%, or less than about 10% or less than 5%.

The procedure described in FIGS. 69A to 69I and FIG. 58 may also be performed with the omission of one of the two delivery tubes 428 and wherein only a single void 454 is created with one balloon 20 using access through the remaining tube 428.

U.S. patent application Ser. No. 13/293,058, filed 9 Nov. 2011; and PCT International Application No. PCT/US2011/043925, filed 13 Jul. 2011, are incorporated by reference herein in their entireties.

Any elements described herein as singular can be pluralized (i.e., anything described as "one" can be more than one), and plural elements can be used individually. Characteristics disclosed of a single variation of an element, the device, the methods, or combinations thereof can be used or apply for other variations, for example, dimensions, burst pressures, shapes, materials, or combinations thereof. Any species element of a genus element can have the characteristics or elements of any other species element of that genus. The term "comprising" is not meant to be limiting. The above-described configurations, elements or complete assemblies and methods and their elements for carrying out the invention, and variations of aspects of the invention can be combined and modified with each other in any combination.

The invention claimed is:

1. An inflatable balloon comprising:
   a balloon having a cylindrical section and a conical section;
   a plurality of non-woven fibers extending along or around the conical section; and
   a plurality of longitudinally extending reinforcing strips in the conical section over the plurality of non-woven fibers.

2. The inflatable balloon of claim 1, wherein each reinforcing strip includes a plurality of fibers extending at an angle relative to the at least one fiber, and wherein each reinforcing strip is positioned a set circumferential distance away from a neighboring reinforcing strip.

3. The inflatable balloon of claim 2, wherein the angle between the plurality of fibers of the reinforcing strip and the at least one fiber is approximately 90 degrees.

4. The inflatable balloon of claim 2, wherein the plurality of fibers of the reinforcing strip extend substantially parallel to a longitudinal axis of the balloon.

5. The inflatable balloon of claim 1, wherein the at least one fiber is a circumferential fiber, and further comprising a plurality of longitudinal fibers extending at an angle to the at least one circumferential fiber, wherein the at least one circumferential fiber extends over the plurality of longitudinal fibers.

6. The inflatable balloon of claim 5, wherein the angle between the plurality of longitudinal fibers and the at least one circumferential fiber is approximately 90 degrees.

7. The inflatable balloon of claim 5, wherein the plurality of longitudinal fibers extend substantially parallel to the longitudinal axis of the balloon.

8. The inflatable balloon of claim 1, wherein each of the reinforcing strips comprises a fiber tape.

9. The inflatable balloon of claim 1, wherein the reinforcing strips are arranged to radiate from an end of the balloon towards a central portion of the balloon.

10. The inflatable balloon of claim 1, wherein each reinforcing strip includes only a single layer in a radial direction.

11. The inflatable balloon of claim 1, wherein each reinforcing strip includes a tapered region.

12. The inflatable balloon of claim 1, wherein the balloon includes a cylindrical end section, the conical section located between the cylindrical end section and the cylindrical section.

13. The inflatable balloon of claim 12, wherein the reinforcing strips overlap within the cylindrical end section.

14. The inflatable balloon of claim 12, wherein the plurality of reinforcing strips are connected together within the cylindrical end section.

15. The inflatable balloon of claim 1, wherein the reinforcing strips extend part way into the cylindrical section and end within the cylindrical section.

16. An inflatable balloon comprising:
    a balloon having a cylindrical section and a conical section;
    at least one fiber on the conical section; and
    at least one reinforcing strip in the conical section extending longitudinally over the at least one fiber, the reinforcing strip extending only along the conical section of the balloon.

17. The inflatable balloon of claim 16, wherein the at least one fiber is a circumferential fiber, and further comprising a plurality of longitudinal fibers extending at an angle to the at least one circumferential fiber, wherein the at least one circumferential fiber extends over the plurality of longitudinal fibers.

18. An inflatable balloon comprising:
    a balloon having a cylindrical section and a conical section;
    at least one fiber on the conical section; and
    at least one reinforcing strip extending longitudinally over the at least one fiber, the at least one reinforcing strip extending along the conical section and ending within the cylindrical section of the balloon.

19. The inflatable balloon of claim 18, wherein the at least one fiber is a circumferential fiber, and further comprising a plurality of longitudinal fibers extending at an angle to the at least one circumferential fiber, wherein the at least one circumferential fiber extends over the plurality of longitudinal fibers.

20. The inflatable balloon of claim 1, wherein a plurality of longitudinally the plurality of longitudinally extending reinforcing strips are not covered by any fibers.

21. An inflatable balloon comprising:
    a balloon having a cylindrical section and a conical section;
    at least one longitudinal fiber extending along the conical section; and
    a plurality of longitudinally extending reinforcing strips in the conical section over the at least one longitudinal fiber.

* * * * *